(12) United States Patent
Hirao et al.

(10) Patent No.: US 9,540,650 B2
(45) Date of Patent: Jan. 10, 2017

(54) NUCLEIC ACID FRAGMENT BINDING TO TARGET PROTEIN

(71) Applicant: TAGCYX BIOTECHNOLOGIES, Yokohama-shi, Kanagawa (JP)

(72) Inventors: Ichiro Hirao, Tokyo (JP); Michiko Hirao, Tokyo (JP); Rie Yamashige, Saitama (JP); Shigeyuki Yokoyama, Saitama (JP)

(73) Assignee: TAGCYX BIOTECHNOLOGIES, Yokohama-shi, Kanagawa (JP)

( * ) Notice: Subject to any disclaimer, the term of this patent is extended or adjusted under 35 U.S.C. 154(b) by 4 days.

(21) Appl. No.: 14/358,895

(22) PCT Filed: Nov. 15, 2012

(86) PCT No.: PCT/JP2012/079611
§ 371 (c)(1),
(2) Date: May 16, 2014

(87) PCT Pub. No.: WO2013/073602
PCT Pub. Date: May 23, 2013

(65) Prior Publication Data
US 2015/0119254 A1    Apr. 30, 2015

(30) Foreign Application Priority Data

Nov. 18, 2011 (JP) .................................. 2011-253357
Jul. 2, 2012 (JP) .................................. 2012-148962

(51) Int. Cl.
*C12N 15/115* (2010.01)
*A61K 48/00* (2006.01)
(Continued)

(52) U.S. Cl.
CPC ............. *C12N 15/115* (2013.01); *A61K 48/00* (2013.01); *C12N 15/1048* (2013.01);
(Continued)

(58) Field of Classification Search
CPC .................................................. C12N 15/115
See application file for complete search history.

(56) References Cited

U.S. PATENT DOCUMENTS 5,861,254 A * 1/1999 Schneider .......... C12N 15/1048
435/6.11
2010/0036111 A1 2/2010 Hirao et al.
2011/0087015 A1 4/2011 Hirano et al.

FOREIGN PATENT DOCUMENTS

EP    1970445 A1    9/2008
JP    09-502354 A   3/1997
(Continued)

OTHER PUBLICATIONS

Gold et al., "Aptamer-Based Multiplexed Proteomic Technology for Biomarker Discovery," PLoS One, Dec. 7, 2010, 5(12):e15004, 1-17.
(Continued)

*Primary Examiner* — Jon E Angell
(74) *Attorney, Agent, or Firm* — Foley & Lardner LLP

(57) ABSTRACT

An object of the present invention is to develop and provide a method for efficiently producing a nucleic acid aptamer, particularly, a DNA aptamer, having higher specificity and binding activity against a target substance than those of nucleic acid aptamers obtained by conventional methods. The present invention provides a transcribable or replicable nucleic acid aptamer comprising a natural nucleotide and a non-natural nucleotide having an artificial base-pairable artificial base. The present invention also provides a method for sequencing a non-natural nucleotide-containing single-stranded nucleic acid molecule selected from a single-stranded nucleic acid library.

7 Claims, 27 Drawing Sheets

(51) Int. Cl.
C12N 15/10 (2006.01)
C12Q 1/68 (2006.01)
C12N 15/11 (2006.01)
C12N 15/113 (2010.01)
G01N 33/53 (2006.01)

(52) U.S. Cl.
CPC .......... *C12N 15/111* (2013.01); *C12N 15/113* (2013.01); *C12Q 1/6869* (2013.01); *G01N 33/5308* (2013.01); *C12N 2310/12* (2013.01); *C12N 2310/16* (2013.01); *C12N 2310/33* (2013.01); *C12N 2310/331* (2013.01); *C12N 2320/13* (2013.01)

(56) References Cited

FOREIGN PATENT DOCUMENTS

| | | |
|---|---|---|
| WO | WO 92/14842 A1 | 9/1992 |
| WO | WO 95/07364 A1 | 3/1995 |
| WO | WO 2007/066737 A1 | 6/2007 |

OTHER PUBLICATIONS

Hirao et al., "An unnatural hydrophobic base pair system: site-specific incorporation of nucleotide analogs into DNA and RNA," Nat. Methods, Sep. 2006, 3(9):729-735, abstract only.
Hirao, Ichiro, "Shinki Aptamer Sosei eno Challenge—Jinki Enkitsui Gijutsu (A Challenge of Production of Novel Aptamers—Technology Using Artificial Base Pairs)," Gene & Medicine MOOK, 2009, 15:167-173, with partial English translation.
Hirao, Ichiro, "Synthetic biology for the development of novel nucleic acid aptamers," Cytometry Research, 2009, 19(2):9-17, with English abstract on first page.
Kimoto et al., "Site-Specific Incorporation of Extra Components into RNA by Transcription Using Unnatural Base Pair Systems," Methods in Molecular Biology, 2010, 634:355-369.
Kimoto et al., "An unnatural base pair system for efficient PCR amplification and functionalization of DNA molecules," Nucleic Acids Research, 2009, 37(2):e14, 9 pages.
Min et al., "A simple and direct electrochemical detection of interferon-γ using its RNA and DNA aptamers," Biosensors and Bioelectronics, 2008, 23:1819-1824.
Ng et al., "Pegaptanib, a targeted anti-VEGF aptamer for ocular vascular disease," Nat. Rev. Drug. Disc., Feb. 2006, 5(2):123-132, Abstract only.

Nimjee et al., "Aptamers: An Emerging Class of Therapeutics," Annu. Rev. Med., 2005, 56:555-583.
Shoji et al., "Modified DNA Aptamer That Binds the (R)-Isomer of a Thalidomide Derivative with High Emantioselectivity," J. Am. Chem. Soc., 2007, 129:1456-1464.
Tuleuova et al., "Development of an Aptamer Beacon for Detection of Interferon-Gamma," Anal Chem., 2010, 82: 1851-1857.
Vaught et al., "Expanding the Chemistry of DNA for in Vitro Selection," J. Am. Chem. Soc., 2010, 132:4141-4151.
Supplementary European Search Report dated May 19, 2015, in EP 12850348.9.
Balasubramanian et al., "Interferon-γ-Inhibitory Oligodeoxynucleotides Alter the Conformation of Interferon-γ," Molecular Pharmacology, May 1998, 53(5):926-932.
Endo et al., "Unnatural base pairs mediate the site-specific incorporation of an unnatural hydrophobic component into RNA transcripts," Bioorganic & Medicinal Chemistry Letters, May 17, 2004, 14(10):2593-2596.
Hirao, Ichiro, "Placing Extra Components into RNA by Specific Transcription Using Unnatural Base Pair Systems," BioTechniques, Jun. 1, 2006, 40(6):711-717.
Kawai et al., "Site-Specific Fluorescent Labeling of RNA Molecules by Specific Transcription Using Unnatural Base Pairs," J. Am. Chem. Soc., Dec. 1, 2005, 127(49):17286-17295.
Kawai et al., "Supporting Information: Site-Specific Fluorescent Labeling of RNA Molecules by Specific Transcription Using Unnatural Base Pairs," J. Am. Chem. Soc., Dec. 1, 2005, 127(49):18 pages.
Kimoto et al., "Site-Specific Incorporation of a Photo-Crosslinking Component into RNA by T7 Transcription Mediated by Unnatural Base Pairs," Chemistry & Biology, Jan. 2004, 11(1):47-55.
Kimoto et al., "Supplementary Information for: DNA amplification and functionalization PCR by an unnatural base pair system," Feb. 1, 2009, 1-14, URL:http://nar.oxfordjournals.org/content/suppl/2008/11/16/gkn956.DC1/nar-02079-met-g-2008-File008.pdf.
Majumder et al., "Aptamers: from bench side research towards patented molecules with therapeutic applications," Expert Opin. Ther. Patents, Nov. 1, 2009, 19(11):1603-1613.
Moriyama et al., "Site-specific biotinylation of RNA molecules by transcription using unnatural base pairs," Nucleic Acids Research, Aug. 19, 2005, 33(15):e129, 8 pages.
Moriyama et al., "Supplementary Material: Site-specific biotinylation of RNA molecules by transcription using unnatural base pairs," Nucleic Acids Research, Aug. 19, 2005, 33(15):4 pages.

* cited by examiner

Fig. 6-1

| Library | Sequence in randamized 43 nucleotide region with tag | SEQ ID NO | Number of clones | DNA name | Same clones identified by the cloning method |
|---|---|---|---|---|---|
| N43Ds-01 | AAGTGTTCTGGAGACnCTTAGGATGCGCGAGGGGTGCGCCTT | 25 | 602 | N43Ds-01-1 | cN43Ds-01-44 |
| | AAAAATGCGGGGGTCnGTGCGTAGGTTCGGAAATTTGTTATGT | 27 | 445 | N43Ds-01-2 | cN43Ds-01-43 |
| | AACGGGCGTGGGCGnCGGGCAGTATTGGGTCCCGTTGTGGGCC | 39 | 179 | N43Ds-01-3 | |
| | AAGGCTCTGGGGATAnCGTAGCTACGGTCGAGGTGTCACCTTGGG | 40 | 138 | N43Ds-01-4 | |
| N43Ds-02 | ATGGAATTGTGGGGCCGAATCTGTTATGTnTGCCAGGAAGGAGC | 28 | 1456 | N43Ds-02-1 | cN43Ds-02-01 |
| | ATCTTCACTATAACGTACGTTCGCTCATCTnTGGTGGTCGGTTGGA | 41 | 711 | N43Ds-02-2 | |
| | ATCTTGCACGCGGGGGGTTCTGGTGTAGGAnCGGAGGGAAAGTGC | 30 | 63 | N43Ds-02-3 | cN43Ds-02-26 |
| N43Ds-03 | AGGCGCGGGGGTTTTGGnGCAGCCAACGGAGCCnGGGGGCAACA | 42 | 4 | N43Ds-03-1 | |
| N43Ds-04 | TAATGAGGCAGCnGAGTCCCAGGATGAnACGGGATTGAnAATAGCGGTGTTGCTT | 43 | 52 | N43Ds-04-1 | |
| N43Ds-05 | TTATATTTTCCAnGCCAGAAnCGGGATTGGTGGGGAGTCGCCGGG | 44 | 6 | N43Ds-05-1 | |
| N43Ds-06 | TGCCCCCGGGGTTTTGGGTGCAGGCAnCGGAGCCnGGGGCAACA | 45 | 40 | N43Ds-06-1 | |
| N43Ds-07 | TCTTTCGTAGGGnTTAGGCGGGnTGTATCGGTGnTGGGACAGG | 46 | 702 | N43Ds-07-1 | |
| N43Ds-08 | GAGGAATGTCCAGCGCTGGGnTTGGAGGGGnGTCGGAnTGGGCTC | 31 | 914 | N43Ds-08-1 | cN43Ds-08-07 |
| | GACAGATTATGTGGACTCCAnTCAGAGGATnTCCCCGnATGGGCC | 47 | 49 | N43Ds-08-2 | |
| | GAGGGAGCAGGTGCTAAGGGnCTGGTGGGGnGTCGGTnTCAAGCA | 48 | 21 | N43Ds-08-3 | |
| | GAGATGGATGGTAGTGCCGnACCGGGGGGnTGGAGAnGCTGGCT | 49 | 19 | N43Ds-08-4 | |
| | GAGCCAGTGATCGCTATGGGnTTGGTGGGGnGTCGGAnGGCTGTC | 50 | 17 | N43Ds-08-5 | |
| | GAGGGCGGCTTAAACAAGGGnTTGGGCGGGnGTCGGTnGTAAGGC | 32 | 4 | N43Ds-08-6 | cN43Ds-08-37 |
| N43Ds-09 | GTCTAAGTAnGCTGGGnTTGGCGGGnTGTCGGATATACTTTGAC | 34 | 299 | N43Ds-09-1 | cN43Ds-09-11 |
| | GTGAGTAAAnTTAGGGnTTGGAGGGGnGTCGGTAGTAGGATACTC | 51 | 100 | N43Ds-09-2 | |
| | GTATGGCCAnTCAGGGnTTGGCGCGGnGTCGGTAGTAGTCTAGAG | 52 | 40 | N43Ds-09-3 | |
| | GTAGAGCnGTGGGnTTGGAGGGGnGTCGGCCGCCACCGCCAGTG | 53 | 18 | N43Ds-09-4 | |
| | GTTGTTATGnGAGGGGnTTGGTGGGGnGTCGGCTAGCATCAATGG | 54 | 15 | N43Ds-09-5 | |
| | GTTTATAGCnTATGGGnTTGGGCGGGnGTCGGATACTCTACCGTG | 55 | 6 | N43Ds-09-6 | |

Fig. 6-2

| Library | Sequence in randomized 43 nucleotide region with tag | SEQ ID NO | Number of clones | DNA name | Same clones identified by the cloning method |
|---|---|---|---|---|---|
| N43Ds-10 | CACAATATTCGGnTTGGAGGGnGTCGGGTGGATAGnTGGTGCT | 35 | 324 | N43Ds-10-1 | cN43Ds-10-13 |
| | CAGCGCAGGGGnTTGGAGGGnGTCGGCTGCTGTGnGATGGTG | 56 | 60 | N43Ds-10-2 | |
| | CAGATTGCCGGGnTTGGAGGGnGTCGGCCAGCTGAnTATCTGC | 57 | 46 | N43Ds-10-3 | |
| | CATAATATTAGGGnTTGGAGGGnGTCGGTATTCTCnTGGATGG | 58 | 16 | N43Ds-10-4 | |
| | CATGATCATTGGGnTTGGAGGGnGTCGGAAGATGCAnTGGTGGC | 59 | 8 | N43Ds-10-5 | |
| | CATGGTTCTGGGnTTGGGGGGnGTCGGCTTTACTAnTATGGTG | 60 | 3 | N43Ds-10-6 | |
| N43Ds-11 | CTATAGTTGGTCCnAGTCGTGTGTGGGnTTGGAGGGnGTCGGGA | 61 | 86 | N43Ds-11-1 | |
| N43Ds-12 | CAGCGGGGTAnGGGTGTAGGGTGCGGAnTGGAGnACGTTAGGC | 62 | 143 | N43Ds-12-1 | |
| N43Ds-15 | TTATATTTCCATGCCAGAnTCGGGnTTGGTGGGnGTCGGGCGG | 63 | 104 | N43Ds-15-1 | |
| | TTAAAACGTCGAGTCAGACnGGAGGGnTTGGAGGGnGTCGGGGCG | 64 | 31 | N43Ds-15-2 | |
| | TTATGGCTGCGGGATGTGCnATGGGGnTTGGGGGGGnGCCGGCTAT | 65 | 9 | N43Ds-15-3 | |
| N43Ds-18 | CCTGTGAGCTCTGATGGTCTGGnGTAAGGnGATAGCGCACACAA | 66 | 18 | N43Ds-18-1 | |
| N43Ds-19 | GGAGGCTGCGCTATTTTCGCCTAnGCCGCGnGGGGTGCGGCCAGG | 67 | 497 | N43Ds-19-1 | |
| | GGAGGTCGCTGGTCGCTTGGnTATGGGnTGCAGGCCGGCG | 68 | 6 | N43Ds-19-2 | |
| N43Ds-20 | GGTAGGGTAAGTAGGTATTGCCnGTCGnTGGATGGCTGCCG | 36 | 2056 | N43Ds-20-1 | cN43Ds-20-21 |
| | GGTGGGGAGCGGCCAGCTGATTnACGTTAAGnTTAATTAGGCGGG | 69 | 15 | N43Ds-20-2 | |
| N43Ds-21 | CGATTCCTTATCCTAGGACTTnTTTCCGCGnCACGTGCTCAGATT | 37 | 2959 | N43Ds-21-1 | cN43Ds-21-04 |
| | CGAGGAGTCGTGCTGCGGGnTTGGAGGGGnGCCGGCGAAAAGCA | 70 | 37 | N43Ds-21-2 | |
| | CGATATGGTAGGGTTGTAGGGnTTGGTGGGnGCCCGGTGGAAACCC | 71 | 37 | N43Ds-21-3 | |
| | CGAGTTTGGTTAGTGGTCTGnTTAGGGAGAnCCCTCGTGAAATGA | 72 | 13 | N43Ds-21-4 | |
| N43Ds-22 | CGTCGGCGGAATCTGGCAGTnTGCCGCGACCnTTCACCTGTAAGT | 73 | 36 | N43D-s22-1 | |

Fig. 7

| Sample | Sequence of the tag and the following randomized region | SEQ ID NO |
|---|---|---|
| N43Ds-09-1 (299) | G̲T̲CTAAGTADsGGT*GGC*Ds*TT-GCCGGGC*Ds*TGTCGG*ATATACTTGAC | 34 |
| N43Ds-08-1 (914) | GAGGAATGTCCAGCGCT*GGC*Ds*TT-GGAGGGC*Ds-*GTCGG*ADsTGGGCTC | 31 |
| N43Ds-09-2 (100) | GTGAGTAAADsTTA*GGC*Ds*TT-GGAGGGC*Ds-*GTCGG*TAGGATACTC | 51 |
| N43Ds-15-1 (104) | T̲T̲ATATTTTCCATGCCAGADsTCG*GGGC*Ds*TT-GGTGGGC*Ds-*GTCGGC*GGG | 63 |
| N43Ds-07-1 (702) | TCTTTCGTA*GGC*DsTTA*GCCGGGC*Ds*TGT*ATCGGT*GDs*TGGG*AGAGG | 46 |
| N43Ds-10-1 (324) | CACAATATTC*GGGC*Ds*TT-GGAGGGC*Ds-*GTCGG*TGGATAGDsTGGTGCT | 35 |
| N43Ds-10-2 (60) | CAGCGCAGGG*GGC*Ds*TT-GGAGGGGC*Ds-*GTCGGC*TGTGTGDsGATGGTG | 56 |
| N43Ds-11-1 (86) | C̲T̲ATAGTTGGTCCDsAGTCGTGT*GGC*Ds*TT-GGAGGGC*Ds-*GTCGG*A | 61 |
| N43Ds-12-1 (143) | C̲A̲GCGGGGGGGTADsGGGTGTAGGGTGC*GG*ADs*T—GGAGG—*DsACGTTAGGC | 62 |
| N43Ds-21-1 (2959) | C̲G̲ATTCCTTATCCTAGGACTDsTTTCCGCGCDsCACGTGCTCAGATT | 37 |
| N43Ds-20-1 (2056) | G̲G̲TAGGGTAAGTAGGTATTGCGDsGTCGTAGCDsTGGATGGCGTGCCG | 36 |
| N43Ds-19-1 (497) | G̲G̲AGGCTGCGCTATTTTCGCCTADsGCCGCGGDsGGGGTGCGGCCAGG | 67 |
| N43Ds-04-1 (52) | T̲A̲ATGAGGCAGCDsGAGTCCCAGGATGADsAATAGCGGGTGTTGCTT | 43 |

Fig. 8

| Sample | Length (mer) | Sequence | SEQ ID NO |
|---|---|---|---|
| N43Ds-08-1 (Ds) | 98 | T*ctgtcaatcgatcgtatcgatcagtccaGAGGAATGTCCAGGCGTGGGDsGTCGGA DsTGGGCTCgcatgactcgaacggattagtgactac | 331 |
| N43Ds-08-1 (AT) | 98 | T*ctgtcaatcgatcgtatcgatcagtccaGAGGAATGTCCAGCCGCTGGGATTGGAGGGGTGTCGGAA TGGGCTCgcatgactcgaacggattagtgactac | 74 |
| N43Ds-09-1 (Ds) | 98 | T*ctgtcaatcgatcgtatcgatcagtccaGTCTAAGTADsGGTGGGDsTTGGCGGGGDsTGTCGGATA TACTTTGACgcatgactcgaacggattagtgactac | 332 |
| N43Ds-09-1 (AT) | 98 | T*ctgtcaatcgatcgtatcgatcagtccaGTCTAAGTAAGGTGGGTTTGGCGGGATGTCGGATATAC TTTGACgcatgactcgaacggattagtgactac | 75 |
| N43Ds-09-1 (G) | 98 | T*ctgtcaatcgatcgtatcgatcagtccaGTCTAAGTAGGGTGGGGTTGGCGGGGTGTCGGATATAC TTTGACgcatgactcgaacggattagtgactac | 76 |
| N43Ds-20-1 (Ds) | 99 | T*ctgtcaatcgatcgtatcgatcagtccaCGTAGGGTAAGTAGGTATTGCCDsGTCGTAGDsTGGAT GGGCGCCgcatgactcgaacggattagtgactac | 333 |
| N43Ds-20-1 (A) | 99 | T*ctgtcaatcgatcgtatcgatcagtccaCGTAGGGTAAGTAGGTATTGCCAGTCGTAGCATGGATGG CGTGCCGgcatgactcgaacggattagtgactac | 77 |
| N43Ds-21-1 (Ds) | 99 | T*ctgtcaatcgatcgtatcgatcagtccaCGATTCCTTATCCTAGACTDsTTTCCGCGDsCACCCT GCTCAGATTgcatgactcgaacggattagtgactac | 334 |
| N43Ds-21-1 (AT) | 99 | T*ctgtcaatcgatcgtatcgatcagtccaCGATTCCTTATCCTAGGACTTTTTTCCGCGCACACGTGC TCAGATTgcatgactcgaacggattagtgactac | 78 |
| VEGF binding DNA 64 | 64 | T*ATACCAGTCTATTCAATTGCACTCTGTGGGGGTGGACGGGGCCCGGGTACAGTATGTGCAATC | 79 |

Fig. 10

5'-CTGTCAATCATCGTATCAGTCCAC-(N)₄₅-GCATGACTCGAACGGATTAGTGACTAC-3'
(SEQ ID NO:1) (SEQ ID NO:2)

| N43Ds-09-1 (Ds) | GTCTAAGTANGGTGGGNTTGGCGGGGNTGTCGGATATACTTTGAC | | SEQ ID NO |
|---|---|---|---|
| | GTCTAAGTANGGTGGGNTTGGaGGGGNTGTCGGATgaACTTTGAC | (1) | 34 |
| | GTaTAAGTANGGTGGGNTTGGCGGGGNTGTCGGATATACTTgtAC | (1) | 80 |
| | GTCaAAGaANtGTGGGNTTGGaGGGGNTGTCGGATATACTTTGAC | (1) | 81 |
| | GaCTAAAGTANtGTGGGNTTGGaGGGGNTGTCGGATAtgCTTTGtC | (2) | 82 |
| | GTCaAAGTANtGTGGGNTGGaGGGGNTGTCGGAgATACTTTGgg | (1) | 83 |
| | GTCgAAGgANtGTGGGNTTGGaGGGGNTGTCGGATgTACTTTGAC | (1) | 84 |
| | GgtTAAGTANtCTGGGNTTGGaGGGGNTGTCGGAgATACTTTGAa | (2) | 85 |
| | GgCTAAGTANtGTGGGNTTGGaGGGGNTGTCGGAggTACTTACAC | (1) | 86 |
| | GTtaAAGTANcaTGGGNTTGGaGGGGNTGTCGGATATACTTTGAT | (1) | 87 |
| | GTCTgAGTANGGTGGGNTTGGCGGGGNTGTCGGATACACTcTGcg | (1) | 88 |
| | GTCTAAaTANtGTGGGNTTGGaGGGGNTGTCGGAgTACTTTGAC | (1) | 89 |
| | GTCTAAGTANtGTGGGNTTGGaGGGGNcGTCGGAagTACTTTGAt | (1) | 90 |
| | GgCagAGTANGtTGGGNTTGGaGGGGNTGTCGGATtTACTaTGAC | (1) | 91 |
| | GTCgAAGTANtaTGGGNTTGGaGGGGNTGTCGGAagTACTTTGAt | (1) | 92 |
| | GctTtAGTANGggGGGNTTGGaGGGGNTGTCGCGgTcTACTTTGgC | (1) | 93 |
| | GTaTtAGTANtGGGGGNTTGGaGGGGNTGTCGGAgATACTaTGtC | (2) | 94 |
| | GyCggAGTANtGaGGGNTTGGaGGGGNTGTCGGtTATACTggGAC | (1) | 95 |
| | GcCTAAaTANtaTGGGNTTGGaGGGGNTGTCGGAggTAgTTTGgC | (1) | 96 |
| | GTCaAAGTANcaaGGGNTTGGaGGGGNTGTCGGtaATtCTTTGAG | (1) | 97 |
| | GTCTAAtTANtaTGGGNTTGGaGGGGNTGTCGGAaATAaTggGAt | (1) | 98 |
| | aTgggAGTANtaTGGGNTTGGaGGGGNTGTCGGAgATACTTcaAt | (1) | 99 |
| | tTCgAAGgANcaTGGGNTTGGgGGGGNTGTCGGAgAgcCTTaGAa | (1) | 100 |
| | GcggAgGTANtaTGGGNTTGGaGGGGNTGTCGGAaATACTTatgC | (1) | 101 |
| | aTgCAAGaANttaGGGNTTGGaGGGGNTGTCGGtTATAtTTTaAa | (1) | 102 |
| | GTgTtAaTANtaTGGGNTTGGgGGGGNTGTCGGAaATgtTaaGcC | (1) | 103 |
| | | | 104 |

Fig. 14

| DNA library [n= Ds 6% / N(A,G,C,T) 94%] | ACGCATGAACAAACTTGCTTG | nnnnnnnnnnnnnnnnnnnnnnnnnnn | GGAGTACGCAGAAGTTTCATTGT | SEQ ID NO 114 |
|---|---|---|---|---|
| | | *ACCCTTGTAACCTAAAGTCTAAGT*:Bio24-8R08 | | |
| 08(5) | ACGCATGAACAAACTTGCTTG | CGTACGCCGGAGGGGGCGGCCT | GGAGTACGCAGAAGTTTCATTGT | 115 |
| 11(9) | ACGCATGAACAAACTTGCTTG | CGTACGCGGTGGGGGGTCGGCCT | GGAATTCAGATTCA GGAGTACGCAGAAGTTTCATTGT | 120 |
| 18(1) | ACGCATGAACAAACTTGCTTG | CGTACGCGGTGGGGGGCCTGGGAACATT | GGATTCAGATTCA GGAGTACGCAGAAGTTTCATTGT | 121 |
| | ACGCATGAACAAACTTGCTTG | CGTACGCGGTGGGGGGCCTGGGAACATT | GGATTCAGATTCC GGAGTACGCAGAAGTTTCATTGT | 122 |
| | | *GAAC CTTGGCGTTGCACCGACCAT*:Bio24-8R03 | | |
| 03(1) | ACGCATGAACAAACTTGCTTG | GAACCGCATGTGGCTGTAGTGCCGCAATGGGGGT | GGTGAGCG GGAGTACGCAGAAGTTTCATTGT | 116 |
| 26(1) | ACGCATGAACAAACTTGCTTG | GAACCGCAACGTGGCTGTAGCGGCCGAATGGGGG | TGGTGAGCG GGAGTACGCAGAAGTTTCATTGT | 123 |
| 65(1) | ACGCATGAACAAACTTGCTTG | GAACCGCAACGTGGCTCGTAGTGCCGAATGGGGCGT | CGTGAGCG GGAGTACGCAGAAGTTTCATTGT | 124 |
| | ACGCATGAACAAACTTGCTTG | GAACCGCAACGTGGCTGGTAGTGCCGAATGGGCGG | TGTGACCG GGAGTACGCAGAAGTTTCATTGT | 125 |
| | | *GAAC TTCCCAATTTTGTTACTCCA*:Bio24-8R01 | | |
| 01(8) | ACGCATGAACAAACTTGCTTG | AAGGGTTAAAACAATGAGGTACGCGGGGGGGTGGGTGT | AGGTGTC GGAGTACGCAGAAGTTTCATTGT | 117 |
| 47(2) | ACGCATGAACAAACTTGCTTG | AAGGGTTAAAACTATCGAGGTACGCGGGGGGTGGGTGT | AGGTGTC GGAGTACGCAGAAGTTTCATTGT | 126 |
| 59(1) | ACGCATGAACAAACTTGCTTG | AAGGGTTGAAACTATGAGGTACGCGGGGGGGTGGCTG | TAGGTCTC GGAGTACGCAGAAGTTTCATTGT | 127 |
| 66(1) | ACGCATGAACAAACTTGCTTG | AAGGGTTGAAACTATGAGGTACGCGGGGGGTGGCTG | TAGGTCTC CTAGTACGCAGAAGTTTCATTGT | 128 |
| | ACGCATGAACAAACTTGCTTG | GAGGGTTAAAACTATGAGGTACGCGGGGGGTGGCTG | TAGGTGTC GGAGTACGCAGAAGTTTCATTGT | 129 |
| | | *GAAC ACTTGTTATGAATGTCTTCATG*:Bio24-8R02 | | |
| 02(4) | ACGCATGAACAAACTTGCTTG | TGAACATGCTTACTGACTACGCCGGGGTCGGTGGGTCGTAGGTGGC | GGAGTACGCAGAAGTTTCATTGT | 118 |
| 39(2) | ACGCATGAACAAACTTGCTTG | TGAACATGCTTACTGAGTACGCCGGGGTCCGAGGGTCGTAGCTGCC | GGAGTACGCAGAAGTTTCATTGT | 130 |
| 04(1) | ACGCATGAACAAACTTGCTTG | TGAACATGCTTACAGAGTACGCCGGGGTCGGGTCGTAGGTGGC | GGAGTACGCAGAAGTTTCATTGT | 131 |
| 10(1) | ACGCATGAACAAACTTGCTTG | TGAACATGCTTACAGAGTACGCCGGGGTCGGGTCGTAGGTGGC | CTAGTACGCAGAAGTTTCATTGT | 132 |
| 72(1) | ACGCATGAACAAACTTGCTTG | TGAACATGCTTACAGAGTACGCCGGGGTCGGGTCGTAGGTGGC | GGAGTACGCAGAAGTTTCATTGT | 133 |
| | ACGCATGAACAAACTTGCTTG | TGAACATTCTTACAGAGTACGCCGGGGTCGGGTCGTAGGTGGC | AGAGTACGCAGAAGTTTCATTGT | 134 |
| | | *GAAC TCAACTATTACACAACCATG*:Bio24-8R15 | | |
| 15(1) | ACGCATGAACAAACTTGCTTG | AGTTGATAATGTGTTGCTACGCCGGGGGTTGAGGTGTAGGTTC | GGAGTACGCAGAAGTTTCATTGT | 119 |
| 35(2) | ACGCATGAACAAACTTGCTTG | AGTTGATTATGTGTTGCTACGCCGGGGGTGGAGGTGTAGGTTC | GGAGTACGCAGAAGTTTCATTGT | 135 |
| | | | | 136 |
| 34(1) | ACGCATGAACAAACTTGCTTG | ATACTAAGATAACCGCGGGGGGGGAGGTGTAGTCGGAGGATC | GGAGTACGCAGAAGTTTCATTGT | 137 |
| 30(4) | ACGCATGAACAAACTTGCTTG | CATGTTGACTTCAAAAGTACGCCGGGGTTTCGGCCTGCAGGTGCC | GGAGTACGCAGAAGTTTCATTGT | 138 |
| 57(2) | ACGCATGAACAAACTTGCTTG | CATGTTGACTTCAAAAGTACGCCGGGGTGGAGGTGAGGTTC | GGAGTACGCAGAAGTTTCATTGT | 139 |
| 54(1) | ACGCATGAACAAACTTGCTTG | TAACTACATGTACACTAGTACGCCGGGGGTGGAGGTGAGGTTC | GGAGTACGCAGAAGTTTCATTGT | 140 |
| 49(1) | ACGCATGAACAAACTTGCTTG | CAATCGGTGAACTTAAGTTACGCGGGGGTATAGGGTGTAGGTTAC | GGAGTACGCAGAAGTTTCATTGT | 141 |
| 22(2) | ACGCATGAACAAACTTGCTTG | CTACATTGGGTGGTTGTCCGGCGGGGGTAAGTATGTAGGATT | GGAGTACGCAGAAGTTTCATTGT | 142 |
| 61(1) | ACGCATGAACAAACTTGCTTG | TGGACGGGCAAGGGGTGGGGTTCCAAAGGGGGGCAGGATGCGTT | GGAGTACGCAGAAGTTTCATTGT | 143 |
| 23(3) | ACGCATGAACAAACTTGCTTG | TAGTCCCGCTTTGCGGGGGTTTGGGTCGCAGGTTCGGATAAGTG | GGAGTACGCAGAAGTTTCATTGT | 144 |
| 21(1) | ACGCATGAACAAACTTGCTTG | GATGGTAGTTGCCGAAGGGGGGTAATATATTAAGTTGGGGATTG | GGAGTACGCAGAAGTTTCATTGT | 145 |
| 05(1) | ACGCATGAACAAACTTGCTTG | AGGGGCATTTACGCGGGGGGGTGGGTATGCAGGTATCGGATGTGAAT | GGAGTACGCAGAAGTTTCATTGT | 146 |

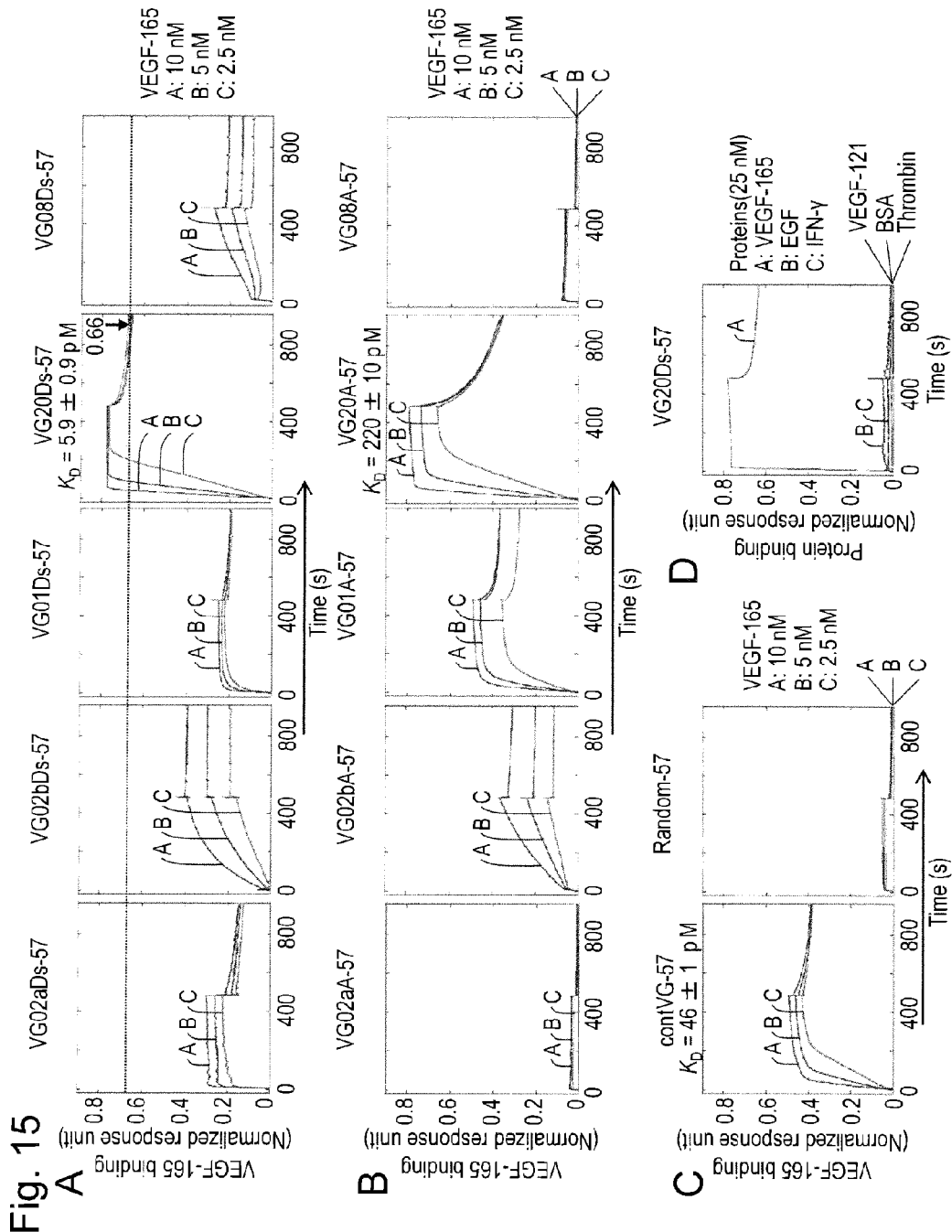

Fig. 16A

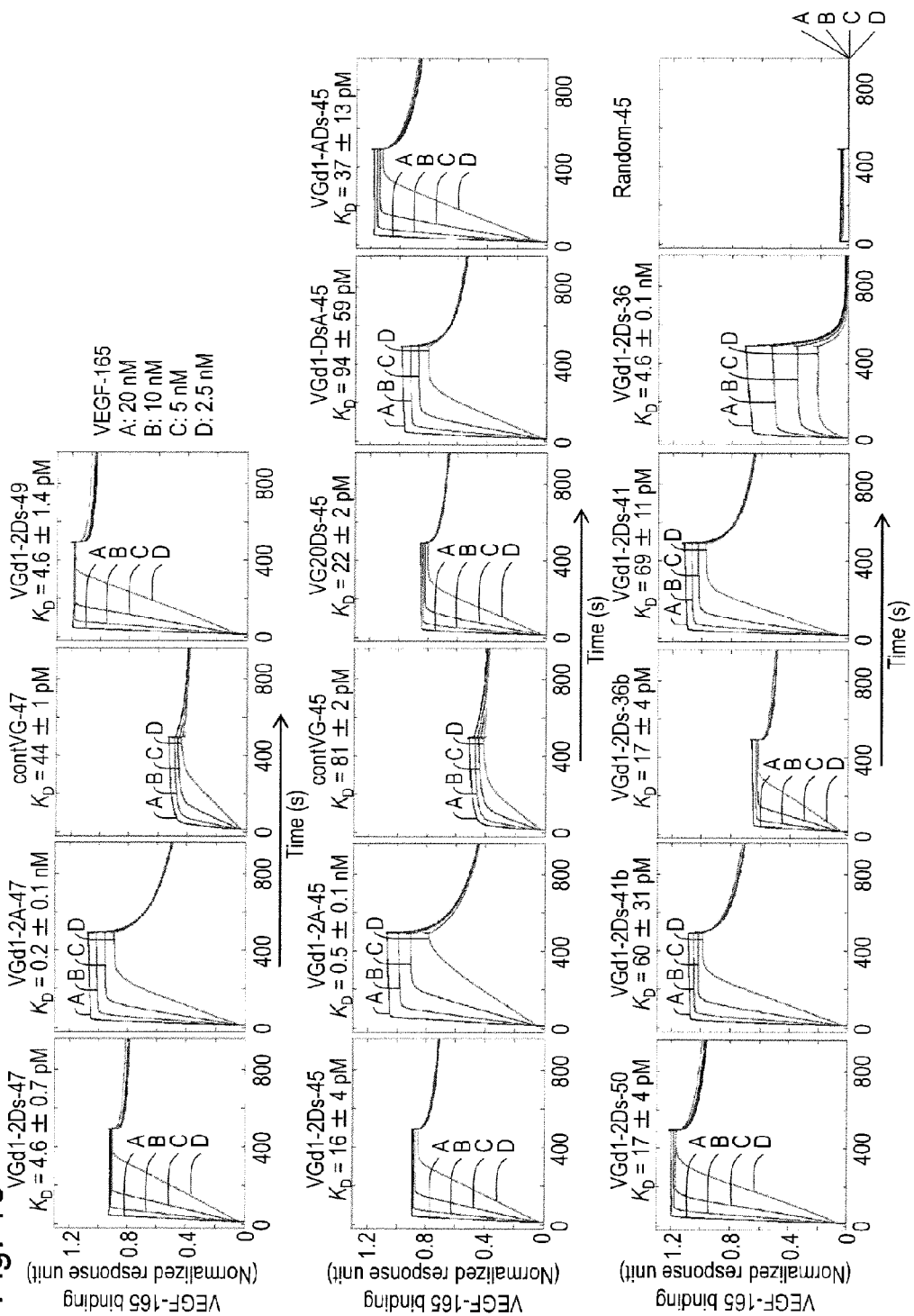

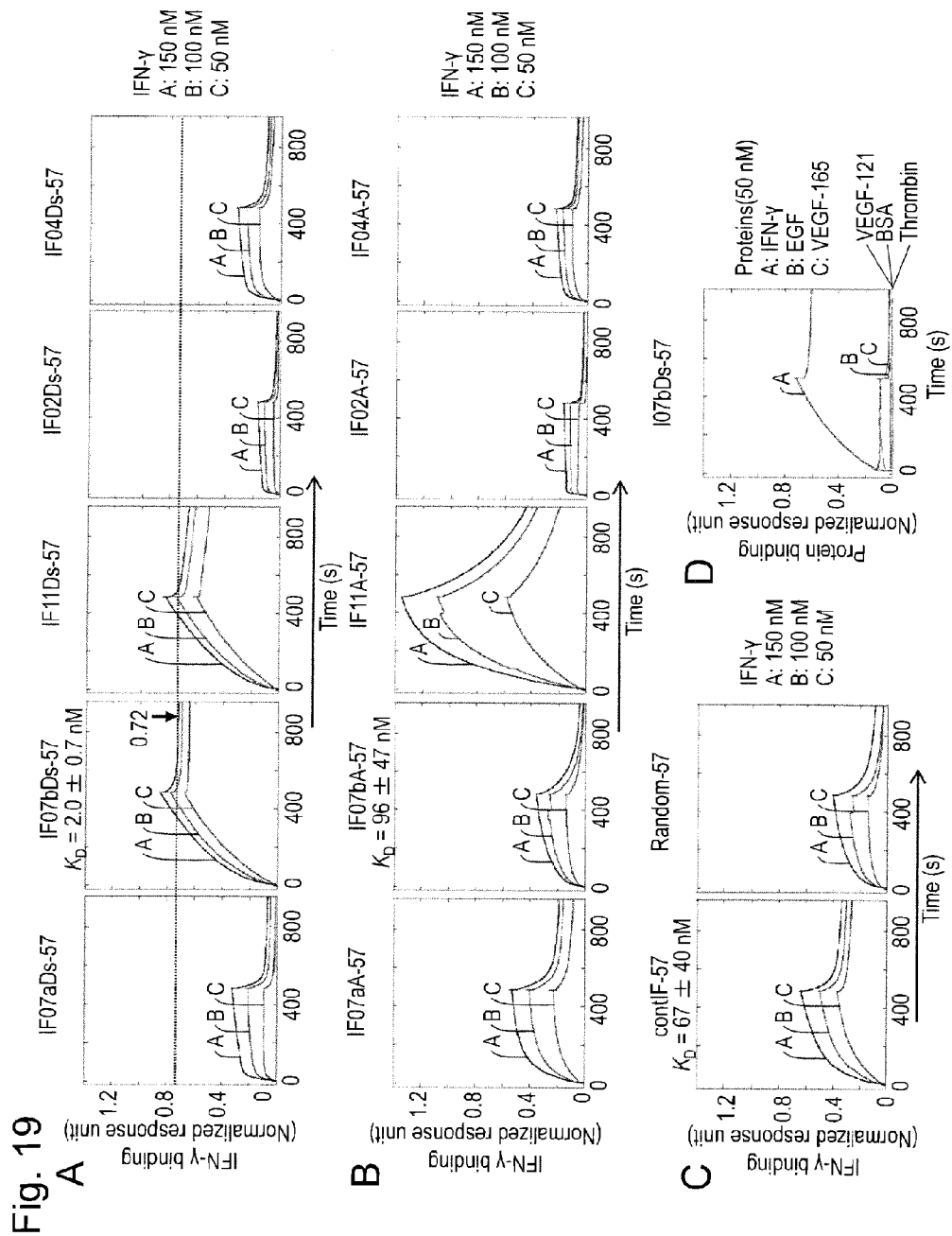

Fig. 20A

NUCLEIC ACID FRAGMENT BINDING TO TARGET PROTEIN

TECHNICAL FIELD

The present invention relates to a method for efficiently producing a functional nucleic acid, particularly, a nucleic acid aptamer (especially, a DNA aptamer), using artificial bases-containing nucleic acid library.

The instant application contains a Sequence Listing which has been submitted electronically in ASCII format and is hereby incorporated by reference in its entirety. Said ASCII copy, created on Nov. 26, 2014, is named 081356-0431_SL.txt and is 151,903 bytes in size.

BACKGROUND ART

In recent years, nucleic acid aptamers, as with other functional nucleic acids such as siRNAs, have received attention as novel active ingredients for pharmaceutical drugs or diagnostic drugs in place of low-molecular-weight compounds and are under research and development in various ways around the world with the aim of medically applying the aptamers.

These nucleic acid aptamers are functional nucleic acids capable of strongly and specifically binding, through their own conformations, to target substances such as proteins to inhibit or suppress the functions of the target substances. A vascular endothelial growth factor (VEGF)-targeting modified RNA aptamer for treatment of age-related macular degeneration (Macugen) approved by FDA in 2004 is known as a typical example of the nucleic acid aptamer pharmaceutically used.

Such nucleic acid aptamers are constituted by only 4 kinds of bases in comparison with antibodies which are proteins composed of 20 kinds of amino acids. In addition, these 4 kines of bases are very similar in chemical or physical properties. For these reasons, the nucleic acid aptamers are disadvantageously limited by variations and performance.

In order to solve this problem, previously reported methods employ one or two types of modified natural bases composed of natural bases bound with substituents via linkers in a nucleic acid library for nucleic acid aptamer separation (Patent Literatures 1 and 2 and Non Patent Literatures 1 to 3). DNA aptamers that are intended for application to nucleic acid chips capable of detecting proteins and may be used in the diagnostic field are also known as modified nucleic acid aptamers comprising such modified natural bases (Non Patent Literature 3). However, one or two types of modified natural bases introduced in the modified nucleic acid aptamers result in the replacement of approximately 25% or more of bases in the whole nucleic acid aptamer with the modified natural bases. This raises another issue of reduced selectivity or cytotoxicity of the aptamers, though enhancing the production efficiency of the aptamers. Hence, use of the modified nucleic acid aptamers having the modified natural bases is currently limited to diagnosis, and none of such aptamers have been approved as therapeutic drugs (Non Patent Literature 3).

CITATION LIST

Patent Literature

Patent Literature 1: JP Patent Publication (Kohyo) No. 09-502354 A (1997)
Patent Literature 2: WO1992014842

Non Patent Literature

Non Patent Literature 1: Shoji A., et al., J. Am. Chem. Soc., 129, 1456-1464 (2007)

Non Patent Literature 2: Vaught J. D., et al., J. Am. Chem. Soc., 132, 4141-4151 (2010)
Non Patent Literature 3: Gold L., et al., PLoS One, 5, e15004 (2010)

SUMMARY OF INVENTION

Technical Problem

An object of the present invention is to develop and provide a method for efficiently producing a nucleic acid aptamer, particularly, a DNA aptamer, having higher specificity and binding activity against a target substance than those of nucleic acid aptamers obtained by conventional methods.

Another object of the present invention is to provide a pharmaceutical composition comprising the nucleic acid molecule as an active ingredient.

Solution to Problem

The present inventors have conducted diligent studies to attain the objects and consequently found that a nucleic acid aptamer having higher target substance-binding ability than that of a nucleic acid aptamer constituted only by natural nucleotides can be obtained by the introduction of a non-natural nucleotide having an artificial base into a single-stranded nucleic acid molecule constituted by natural nucleotides. This artificial base is pairable with another artificial base through complementarity and as such, can also function in nucleic acid replication or transcription. This allows a nucleic acid library to be amplified by a conventional nucleic acid amplification method such as PCR. Although such an artificial base capable of functioning in nucleic acid replication or transcription has already been known (Hirao I., et al., Nature Methods, 3, 729-735 (2006); Hirao I., et al., J. Am. Chem. Soc., 129, 15549-15555 (2007); Kimoto M., et al., Nucleic Acids Res., 37, e14 (2009); Kimoto M., et al., J. Am. Chem. Soc., 132, 15418-15426 (2010); Kimoto M., et al., Expert Rev. Mol. Diagn., 11, 321-331 (2011); Malyshev D. A., et al., J. Am. Chem. Soc., 131, 14620-14621 (2009); Malyshev D. A., et al., Chemistry, 16, 12650-12659 (2010); Yang Z., et al., Nucleic Acids Res., 35, 4238-4249, (2007); and Yang Z., et al., J. Am. Chem. Soc., 133, 15105-15112 (2011)), a nucleic acid aptamer comprising a non-natural nucleotide having the artificial base has been totally unknown so far. This is partly because no method has been established for sequencing a nucleic acid aptamer comprising a non-natural nucleotide in a nucleic acid library. Thus, the present inventors have also developed a novel method for determining individual nucleotide sequences in a library including nucleic acid molecules comprising a non-natural nucleotide.

The present invention is based on the development results and specifically provides the following aspects:

(1) A transcribable or replicable nucleic acid aptamer comprising natural nucleotides and non-natural nucleotides having an artificial base-pairable artificial base.

(2) The nucleic acid aptamer according to (1), wherein the artificial base is selected from the group consisting of Ds, Pn, and Pa.

(3) The nucleic acid aptamer according to (2), wherein the artificial base includes an artificial base-pairable derivative of the artificial base.

(4) The nucleic acid aptamer according to any of (1) to (3), wherein the content of the non-natural nucleotide is 20% or less of the total number of nucleotides.

(5) The nucleic acid aptamer according to any of (1) to (4), wherein the nucleic acid is a DNA or an RNA.

(6) The nucleic acid aptamer according to (1), wherein the nucleic acid aptamer is directed against a vascular endothelial growth factor as a target substance.

(7) The nucleic acid aptamer according to (6), wherein the nucleic acid aptamer comprises any one nucleotide sequence selected from the group consisting of SEQ ID NOs: 25 to 73, 80 to 104, 106 to 109, 111, and 155 to 166 (provided that "n" in the sequences represents Ds), 175, 177, 179, 181, 183, 198, 201, 202, 205 to 209, 211, 212, and 229 to 278.

(8) The nucleic acid aptamer according to (7), wherein the nucleic acid aptamer consists of any one nucleotide sequence according to (7) that is 5' flanked by the nucleotide sequence represented by SEQ ID NO: 1 and 3' flanked by the nucleotide sequence represented by SEQ ID NO: 2.

(9) The nucleic acid aptamer according to (1), wherein the nucleic acid aptamer is directed against interferon γ as a target substance.

(10) The nucleic acid aptamer according to (9), wherein the nucleic acid aptamer comprises any one nucleotide sequence selected from the group consisting of SEQ ID NOs: 167 to 174 (provided that "n" in the sequences represents Ds), 186, 188, 190, 192, 194, 214 to 222, and 279 to 328.

(11) The nucleic acid aptamer according to (10), wherein the nucleic acid aptamer consists of any one nucleotide sequence according to (10) that is 5' flanked by the nucleotide sequence represented by SEQ ID NO: 1 and 3' flanked by the nucleotide sequence represented by SEQ ID NO: 2.

(12) A single-stranded nucleic acid library including a transcribable or replicable, non-natural nucleotide-containing single-stranded nucleic acid molecule comprising natural nucleotides and non-natural nucleotides having an artificial base-pairable artificial base.

(13) The single-stranded nucleic acid library according to (12), wherein the content of the non-natural nucleotide in the non-natural nucleotide-containing single-stranded nucleic acid molecule is 20% or less of the total number of nucleotides.

(14) The single-stranded nucleic acid library according to (12) or (13), wherein the single-stranded nucleic acid molecule comprises 5'-terminal and 3'-terminal primer-binding regions each consisting of a known nucleotide sequence common in the library, and a central region located between the primer-binding regions.

(15) The single-stranded nucleic acid library according to (14), wherein the library comprises non-natural nucleotide-containing single-stranded nucleic acid molecules further comprising an identification site that is disposed at at least one end of the central region so as to flank the primer-binding region and is constituted by natural nucleotides related to positional information about one or more artificial bases disposed at a particular position on the nucleotide sequence of the central region.

(16) A method for producing a nucleic acid aptamer, comprising: a complex formation step of mixing a single-stranded nucleic acid library according to any of (12) to (15) with a target substance in a solution to form a complex of a single-stranded nucleic acid molecule and the target substance; a complex recovery step of recovering the complex; a single-stranded nucleic acid molecule recovery step of recovering the single-stranded nucleic acid molecule from the recovered complex; an amplification step of amplifying the recovered single-stranded nucleic acid molecule by a nucleic acid amplification method; and a nucleic acid aptamer preparation step of preparing a nucleic acid aptamer from a nucleic acid molecule obtained by the amplification step.

(17) The method according to (16), further comprising a repetitive step of repeating one or more times a fresh round from the complex formation step to the nucleic acid aptamer preparation step using a fresh single-stranded nucleic acid library of nucleic acid aptamers prepared in the nucleic acid aptamer preparation step.

(18) The method according to (17), wherein the number of repetitions is 15 or less.

(19) The method according to any of (16) to (18), wherein the nucleic acid aptamer is a DNA aptamer or an RNA aptamer.

(20) The method according to (19), wherein when the nucleic acid aptamer is an RNA aptamer, the amplification step comprises a reverse transcription substep, a DNA amplification substep, and a transcription substep.

(21) The method according to any of (16) to (20), wherein the artificial base is selected from Ds, Pn, and Pa.

(22) The method according to (21), wherein the artificial base includes an artificial base-pairable derivative of the artificial base.

(23) A method for sequencing a non-natural nucleotide-containing single-stranded nucleic acid molecule selected from a single-stranded nucleic acid library according to (14), comprising: a first amplification step of amplifying the selected single-stranded nucleic acid molecule by a nucleic acid amplification method with natural nucleotides as substrates using a primer set binding to the primer-binding regions; a cloning step of obtaining a single clone from amplification products constituted only by natural nucleotides obtained by the first amplification step; a second amplification step of amplifying the selected single-stranded nucleic acid molecule by a nucleic acid amplification method with natural nucleotides and non-natural nucleotides as substrates using the primer set binding to the primer-binding regions; a single-stranded nucleic acid molecule isolation step of using the single clone obtained in the cloning step as a probe to isolate a single clone-derived single-stranded nucleic acid molecule from amplification products obtained by the second amplification step; and a sequencing step of sequencing the single clone-derived single-stranded nucleic acid molecule isolated in the single-stranded nucleic acid molecule isolation step.

(24) The method according to (23), wherein the probe used in the single-stranded nucleic acid molecule isolation step is immobilized on a solid-phase carrier.

(25) The method according to (23) or (24), wherein the single clone-derived single-stranded nucleic acid molecule isolated in the single-stranded nucleic acid molecule isolation step comprises a non-natural nucleotide.

(26) A method for sequencing a non-natural nucleotide-containing single-stranded nucleic acid molecule selected from a single-stranded nucleic acid library according to (15), comprising: a third amplification step of amplifying the selected single-stranded nucleic acid molecule by a nucleic acid amplification method with natural nucleotides as substrates using a primer set binding to the primer-binding regions; a cloning step of obtaining a single clone from amplification products constituted only by natural nucleotides obtained by the amplification step; a sequencing step of sequencing the single clone obtained by the cloning step; and an artificial base position determination step of determining the position of an artificial base on the nucleotide sequence of the single-stranded nucleic acid molecule templated for the single clone, on the basis of the nucleotide sequence of the identification site in the nucleotide sequence of the single clone.

(27) The method according to any one of (23) to (26), wherein the artificial base is selected from the group consisting of Ds, Pn, and Pa.

(28) The method according to (27), wherein the artificial base includes an artificial base-pairable derivative of the artificial base.

(29) The method according to any of (23) to (28), wherein the single-stranded nucleic acid molecule constituting the single-stranded nucleic acid library is a DNA or an RNA.

(30) The method according to any of (26) to (29), wherein when the single-stranded nucleic acid molecule is an RNA, the amplification step or the first to third amplification steps comprise a reverse transcription substep, a DNA amplification substep, and a transcription substep.

(31) A pharmaceutical composition which comprises a nucleic acid aptamer according to any of (1) to (5) and/or a nucleic acid aptamer obtained by a method according to any of (16) to (22) as an active ingredient and functionally inhibits a target substance of the nucleic acid aptamer.

(32) A pharmaceutical composition for functional inhibition of a vascular endothelial growth factor, comprising a nucleic acid aptamer according to any of (6) to (8) as an active ingredient.

(33) A pharmaceutical composition for functional inhibition of interferon γ, comprising a nucleic acid aptamer according to any of (9) to (11) as an active ingredient.

(34) A method comprising using a nucleic acid aptamer according to any of (1) to (5) and/or a nucleic acid aptamer obtained by a method according to any of (16) to (22) to detect a target substance in a sample to which the nucleic acid aptamer binds.

(35) A replicable deoxyribozyme or a transcribable ribozyme comprising unmodified natural ribonucleotides and non-natural ribonucleotides having an artificial base-pairable artificial base.

(36) The ribozyme according to (35), wherein the artificial base is selected from the group consisting of Ds, Pn, and Pa.

(37) The ribozyme according to (35), wherein the artificial base includes an artificial base-pairable derivative of the artificial base.

(38) A kit for nucleic acid aptamer, deoxyribozyme, or ribozyme production comprising a single-stranded nucleic acid library according to any of (12) to (15) and a primer set binding to the primer-binding regions.

The present specification encompasses the contents described in the specifications and/or drawings of Japanese Patent Application Nos. 2011-253357 and 2012-148%2 on which the priority of the present application is based.

Advantageous Effects of Invention

The method for producing a nucleic acid aptamer according to the present invention can efficiently produce a nucleic acid aptamer, particularly, a DNA aptamer, having high specificity and binding activity against a target substance.

The sequencing method of the present invention can sequence a single-stranded nucleic acid molecule that may comprise a non-natural nucleotide, selected from a single-stranded nucleic acid library, though such sequencing has not been achieved so far.

BRIEF DESCRIPTION OF DRAWINGS

FIG. 6-1 shows a breakdown of clones analyzed by Ion Torrent PGM and the numbers thereof. In the diagram, the underlined boldface represents an identification site. The position of Ds predicted from the identification site is indicated with lower-case letter "n".

FIG. 6-2 shows a breakdown of clones analyzed by Ion Torrent PGM and the numbers thereof. In the diagram, the underlined boldface represents an identification site. The position of Ds predicted from the identification site is indicated with lower-case letter "n".

FIG. 7 shows motif alignment among clones obtained by Ion Torrent PGM. The numeral within parentheses in the "Sample" column represents the number of reads (the number of clones). An identification site is underlined. The position of Ds predicted from the identification site is indicated with boldface Ds. A sequence homologous to GGGDsTTGGNGGGGDsGTCGG (SEQ ID NO: 335) (N represents an arbitrary natural base) in 9 sequences is indicated in italic.

FIG. 8 shows full-length DNA aptamers and a control sequence (VEGF binding DNA 64) used in SPR analysis in Example 2. The underlined boldface represents an identification sequence. The lower-case letter represents a primer-binding region. The boldface represents the site of Ds or Ds replaced with a natural base, T*=Biotin-dT. VEGF binding DNA 64 corresponds to a control sequence. The sequence region indicated in bold italic corresponds to a sequence used as Competitor in selection.

FIG. 10 shows the nucleotide sequences of 28 clones obtained by doped selection after 5 rounds, wherein the nucleotide sequences were determined by a cloning method using E. coli. In each nucleotide sequence, "D" represents "Ds".

FIG. 14 shows the nucleotide sequences of 59 clones obtained by random selection after 8 rounds, wherein the nucleotide sequences were determined by a cloning method using E. coli. The numeral within parentheses represents the number of identical clones. In the random region of each clone sequence, the base indicated in boldface represents a site found to have a single-nucleotide mutation among homologous bases. The diagram also shows 5 types of biotinylated probes (3'-probe sequence-5') used in the position identification of the artificial base Ds.

FIG. 15 shows SPR sensorgrams showing the VEGF-165 binding of each clone obtained by the first round of SELEX for VEGF-165 described in Example 8. FIGS. 15A to 15C show the SPR sensorgrams wherein 2.5 nM, 5 nM, or 10 nM VEGF-165 was injected. FIG. 15D shows analysis on the binding of VG20Ds-57 to various proteins. Each sensorgram was normalized to the molecular weight of a DNA fragment bound with SPR, the molecular weight of an injected protein, and the amount of the SPR-bound DNA fragment immobilized (RU). The injection time is 480 seconds. The dissociation time is 480 seconds. Values obtained 930 seconds after injection (after a lapse of 450 seconds as dissociation time) are shown in Table 9.

FIG. 16A shows sequences obtained by the second round of doped SELEX for VEGF-165. 45 base portions were doped in the selection of top 50 sequences among sequences obtained by 4 rounds of doped SELEX, and are shown in the diagram. The boldface represents a base portion mutated from the sequence of VG20.

FIG. 18 shows SPR sensorgrams showing the VEGF-165 binding of various VGd1-2Ds-47 variants, wherein 2.5 nM (A), 5 nM (B), 10 nM (C), or 20 nM (D) VEGF-165 was injected.

FIG. 19 shows SPR sensorgrams showing the IFN-γ binding of each clone obtained by the first round of SELEX for IFN-γ described in Example 11. FIGS. 19A to 19C show the SPR sensorgrams wherein 50 nM, 100 nM, or 150 nM IFN-γ was injected. FIG. 19D shows analysis on the binding of IF07bDs-57 to various proteins. Each sensorgram was normalized to the molecular weight of a DNA fragment bound with SPR, the molecular weight of an injected protein, and the amount of the SPR-bound DNA fragment immobilized (RU). The injection time is 480 seconds. The dissociation time is 480 seconds. Values obtained 930 seconds after injection (after a lapse of 450 seconds as dissociation time) are shown in Table 9.

FIG. 20A shows sequences obtained by the second round of doped SELEX for IFN-γ. 45 base portions were doped in the selection of top 50 sequences among sequences obtained by 4 rounds of doped SELEX, and are shown in the diagram. The boldface represents a base portion mutated from the sequence of IF07b.

DESCRIPTION OF EMBODIMENTS

1. Nucleic acid aptamer 1-1. Outline

Figure 1:
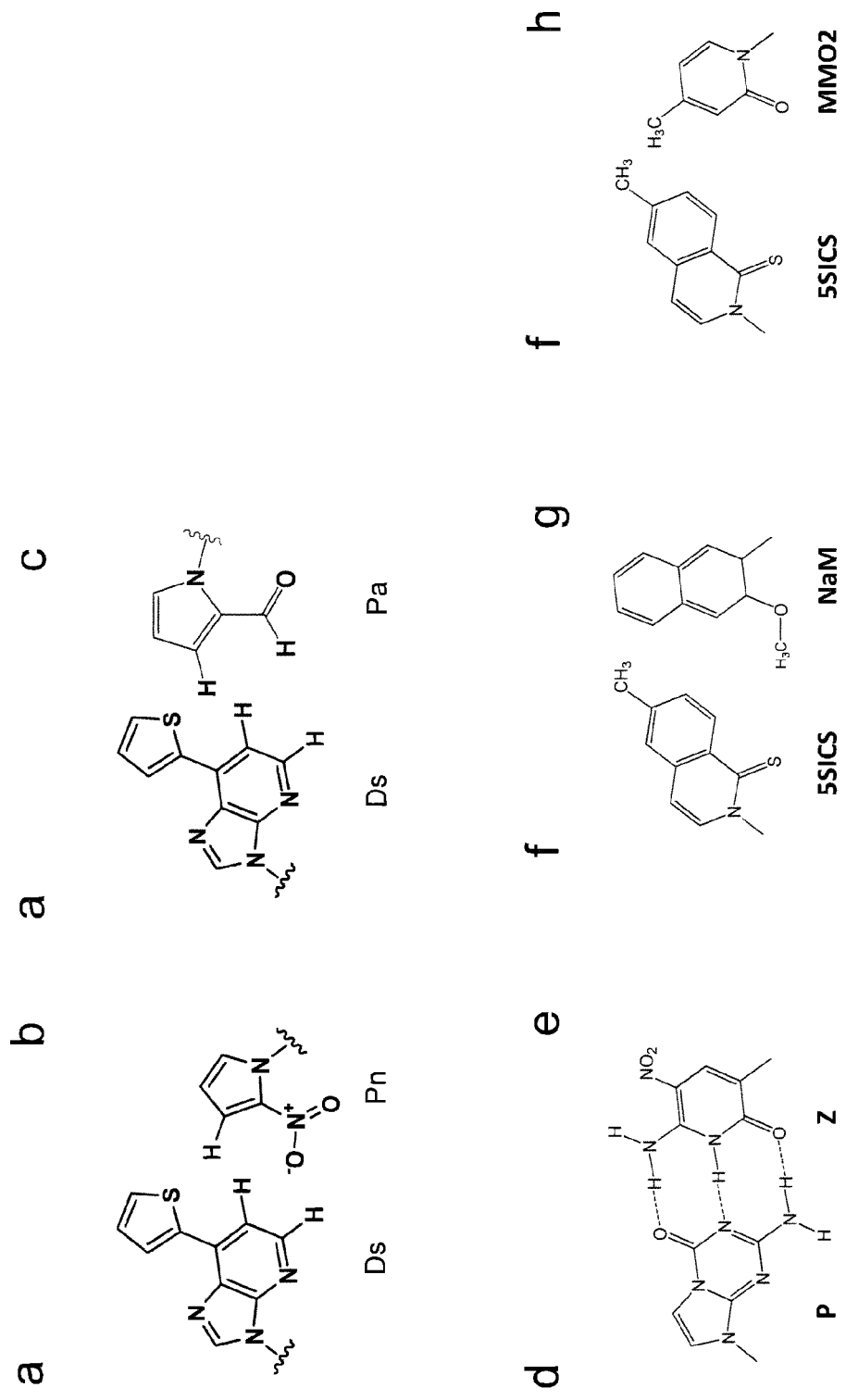
FIG. 1 is a diagram showing specific examples of artificial bases.

The first embodiment of the present invention relates to a nucleic acid aptamer. The nucleic acid aptamer of the present invention comprises a natural nucleotide and a non-natural nucleotide and can have characteristically higher specificity and binding activity against a target substance than those of nucleic acid aptamers obtained by conventional methods.

1-2. Definition

The general terms used in the present specification are defined as follows:

In the present specification, the "nucleic acid" or the "nucleic acid molecule" refers to a biological polymer that is constituted by nucleotide units linked through phosphodiester bonds, as a rule.

In the present specification, the "natural nucleotide" refers to a naturally occurring nucleotide. Examples thereof include DNAs composed of deoxyribonucleotides having any of the natural bases adenine, guanine, cytosine, and thymine, RNAs composed of ribonucleotides having any of the natural bases adenine, guanine, cytosine, and uracil, and combinations thereof. A nucleic acid (molecule) constituted only by natural nucleotides is referred to as a natural nucleic acid (molecule) in the present specification.

In the present specification, the "non-natural nucleotide" refers to a non-naturally occurring nucleotide constituted by an artificial base. A phosphate group and a sugar constituting the non-natural nucleotide according to the present invention are structurally identical to those of the natural nucleotide.

In the present specification, the "artificial base" refers to an artificially constructed base analog having properties similar to those of the natural base constituting the natural nucleotide and can form artificial base pairing with its partner base analog (hereinafter, referred to as a "complementary artificial base" in the present specification), as in the natural base. In the present specification, the "artificial base pairing" refers to base pairing formed between a pair of complementary artificial bases, as in a pair of complementary natural bases adenine and thymine, adenine and uracil, or guanine and cytosine. The artificial base pairing includes a chemical bond via a hydrogen bond found in the base pairing between natural bases, a physical bond via the molecular structure-based association between artificial bases, and stacking effects via hydrophobic interaction.

The "properties similar to those of the natural base" possessed by the artificial base include properties that permit nucleic acid replication or transcription (including reverse transcription) through the complementarity of artificial base pairing. The artificial base has exclusive selectivity in artificial base pairing, as in the natural base. Thus, even a nucleic acid molecule comprising a non-natural nucleotide, as with the natural nucleotide, can be replicated or transcribed accurately through the complementarity between artificial bases, if non-natural nucleotides respectively having a pair of complementary artificial bases are present among substrate nucleotides. This allows a DNA molecule to be amplified by a nucleic acid amplification method such as PCR or an RNA molecule to be amplified by an in vitro transcription method, while the molecule comprises a non-natural nucleotide.

Specific examples of the artificial base are shown in FIG. 1. FIG. 1a shows Ds (7-(2-thienyl)-3H-imidazo[4,5-b]pyridin-3-yl; referred to as "Ds" in the present specification). FIG. 1b shows Pn (2-nitropyrrol-1-yl; referred to as "Pn" in the present specification). FIG. 1c shows Pa (2-formyl-1H-pyrrol-1-yl; referred to as "Pa" in the present specification). FIG. 1d shows P (2-amino-imidazo[1,2-a]-1,3,5-triazin-4 (8H)-one; referred to as "P" in the present specification). FIG. 1e shows Z (6-amino-5-nitro-2(1H)-pyridone; referred to as "Z" in the present specification). FIG. 1f shows 5SICS (6-methylisoquinoline-1(2H)-thione; referred to as "5SICS" in the present specification). FIG. 1g shows NaM (3-methoxynaphthalen-2-yl; referred to as "NaM" in the present specification). FIG. 1h shows MMO2 (2-methoxy-4-methylphenyl; referred to as "MMO2" in the present specification). The complementary artificial base of the artificial base Ds is Pn and Pa. The complementary artificial base of P is Z. The complementary artificial base of 5SICS is NaM and MMO2.

In the absence of a non-natural nucleotide having a complementary artificial base in substrates, the artificial base can instead pair with a natural base similar in structure and/or properties to the complementary artificial base during replication or transcription. In this case, the non-natural nucleotide in the templated nucleic acid molecule is replaced with a natural nucleotide after replication or transcription. For example, Ds is known to be replaced with A or T.

In the present specification, the "nucleic acid aptamer" refers to an aptamer constituted by a nucleic acid and refers to a ligand molecule that is able to strongly and specifically bind to a target substance through the secondary structure of a single-stranded nucleic acid molecule via a hydrogen bond or the like and further the conformation formed on the basis of a tertiary structure, thereby specifically inhibiting or suppressing the functions (e.g., biological activity) of the target substance. Thus, the nucleic acid aptamer can serve as an inhibitor of target substance function. In the present specification, the "functional inhibition of a target substance" refers to inhibition or suppression of the catalytic function or gene expression control function (including control of transcription, translation, transport, etc.) and/or biological function such as apoptosis control function of the target substance.

The nucleic acid aptamer is generally known as RNA aptamers constituted only by RNAs and DNA aptamers constituted only by DNAs. In the present specification, the nucleic acid constituting the nucleic acid aptamer is not particularly limited. The nucleic acid aptamer includes, for example, DNA aptamers, RNA aptamers, and aptamers constituted by DNAs and RNAs in combination. A DNA aptamer is more preferred in consideration of stability, production cost required for chemical synthesis, and the number of steps in aptamer production.

In the present specification, the "target substance" refers to a substance that can serve as a target to which the nucleic acid aptamer, a deoxyribozyme, or a ribozyme binds. The target substance is not particularly limited by its type as long as the target substance is a substance to which the nucleic acid molecule can bind. Examples thereof include peptides (oligopeptides and polypeptides), nucleic acids, lipids, sugars (including sugar chains), and low-molecular-weight compounds. The target substance is preferably a peptide, more preferably a polypeptide, i.e., a protein. Alternatively, the target substance may be any of naturally derived substances, chemically synthesized substances, recombinant substances, and the like.

1-3. Constitution

The nucleic acid aptamer of the present invention comprises a natural nucleotide and a non-natural nucleotide and is constituted by a transcribable or replicable polynucleotide.

The non-natural nucleotide contained in the nucleic acid aptamer of the present invention is constituted by an artificial base. The artificial base is not particularly limited by its type as long as the artificial base has the properties described above. Examples thereof include artificial bases listed as specific examples of the above artificial base and derivatives of the artificial base described later.

The content of the non-natural nucleotide in the nucleic acid aptamer of the present invention can be 20% or less, preferably 15% or less, more preferably 10% or less, of the total number of nucleotides constituting the nucleic acid aptamer. Usually, a nucleic acid aptamer of 100 or less bases in full length can produce the effect of the present invention, if having 1 to 20 non-natural nucleotides per nucleic acid aptamer.

When a plurality of non-natural nucleotides are contained per nucleic acid aptamer, the artificial bases of these non-natural nucleotides may be the same and/or different. When these artificial bases are different, it should be noted that two or more artificial bases having an identical complementary artificial base do not coexist with each other in one nucleic acid aptamer. This is because the original artificial base might be replaced with another artificial base via the complementary artificial base during the replication or transcription process. For example, in a nucleic acid aptamer comprising nonspecific nucleotides respectively having Pn and Pa, the positions of Pn and Pa might be replaced with the other via their complementary artificial base Ds during the replication process.

The base of the non-natural nucleotide constituting the nucleic acid aptamer of the present invention may be a derivative of the artificial base exemplified above. The "derivative of the artificial base" refers to a base analog derived from the artificial base by partial substitution by a different atomic group or a different functional group and retains the complementarity of the artificial base to the complementary artificial base.

Examples of the derivative of the artificial base Ds include Ds derivatives represented by the following formula (1):

[Formula 1]

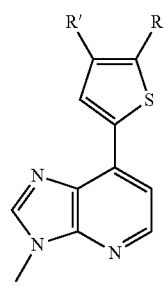

(1)

wherein R and R' each independently represent any moiety represented by the following formula (2):

[Formula 2]

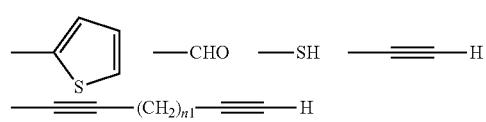

(2)

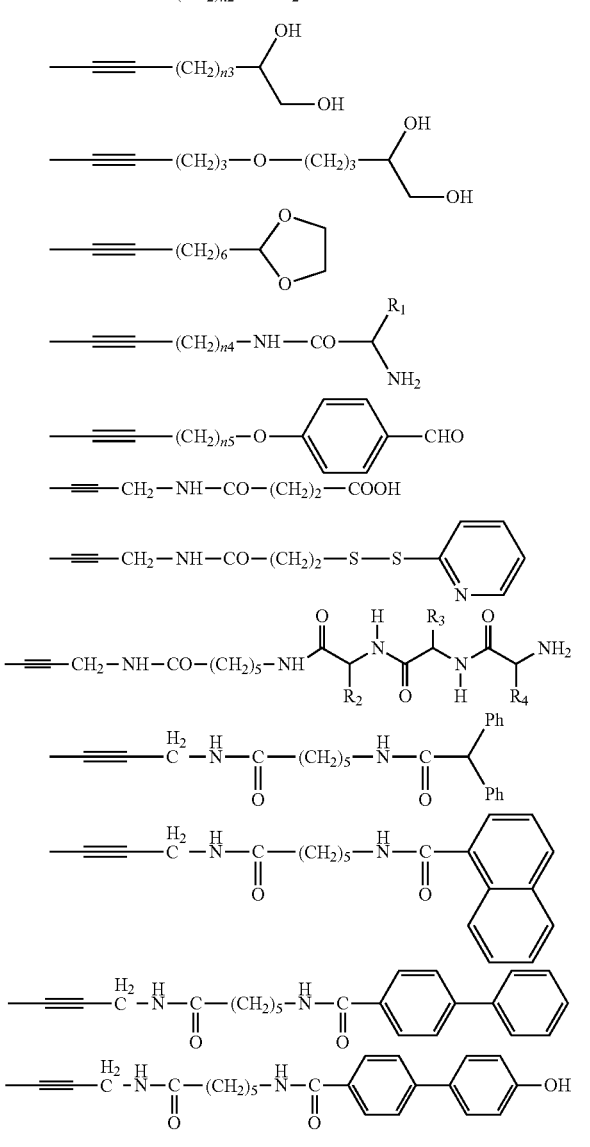

wherein n1=2 to 10; n2=1 or 3; n3=1, 6, or 9; n4=1 or 3; n5=3 or 6; R1=Phe (phenylalanine), Tyr (tyrosine), Trp (tryptophan), His (histidine), Ser (serine), or Lys (lysine); and R2, R3, and R4=Leu (leucine), Leu, and Leu, respectively, or Trp, Phe, and Pro (proline), respectively.

Examples of the derivative of Pn include artificial base derivatives represented by the following formula (3):

[Formula 3]

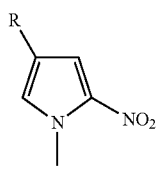

(3)

wherein R represents any moiety represented by the following formula (4):

[Formula 4]

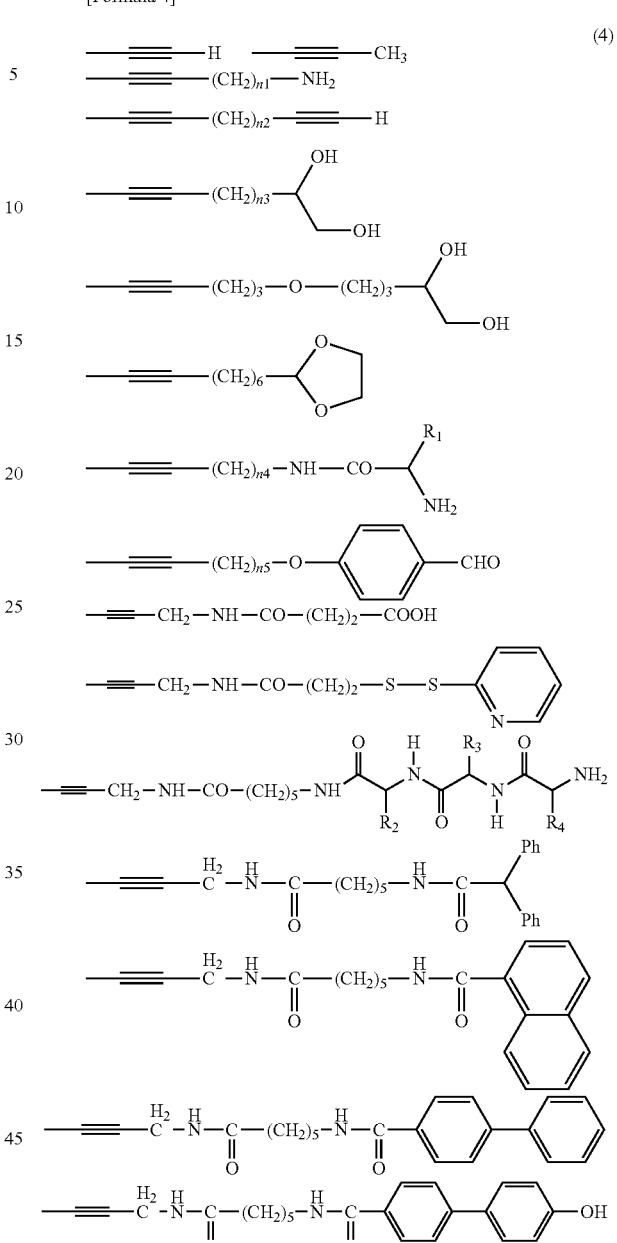

(4)

wherein n1=1 or 3; n2=2 to 10; n3=1, 6, or 9; n4=1 or 3; n5=3 or 6; R1=Phe, Tyr, Trp, His, Ser, or Lys; and R2, R3, and R4=Leu, Leu, and Leu, respectively, or Trp, Phe, and Pro, respectively.

Examples of the derivative of Pa include artificial base derivatives represented by the following formula (5):

[Formula 5]

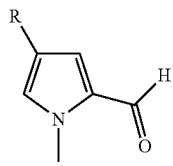

(5)

wherein R represents any moiety represented by the following formula (6):

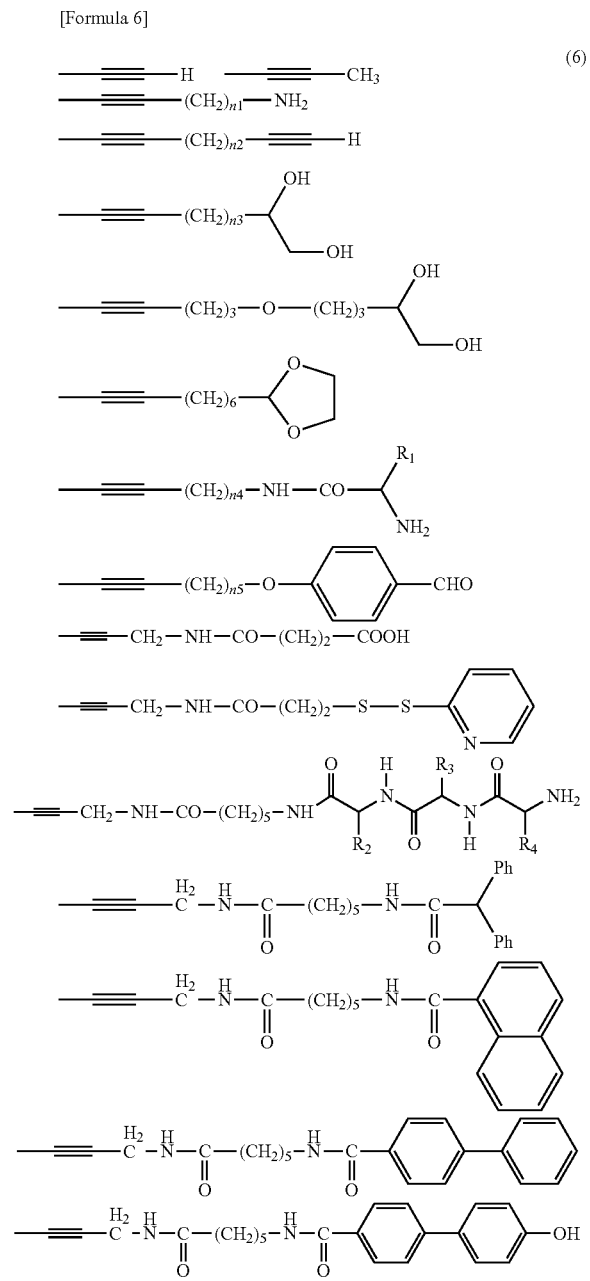

wherein n1=1 or 3; n2=2 to 10; n3=1, 6, or 9; n4=1 or 3; n5=3 or 6; R1=Phe, Tyr, Trp, His, Ser, or Lys; and R2, R3, and R4=Leu, Leu, and Leu, respectively, or Trp, Phe, and Pro, respectively.

The derivative is artificial base-pairable with the complementary artificial base to achieve nucleic acid replication or transcription (including reverse transcription).

Some of natural nucleotides constituting the nucleic acid aptamer of the present invention may be modified. In this context, the "modification" refers to the substitution of some or all of nucleotide units constituting the nucleic acid or their component nucleosides by a different atomic group or a different functional group. Specific examples thereof include sugar modification, base modification, and phosphate modification.

The sugar modification refers to modification of a ribose portion constituting nucleoside. Examples thereof include modification of a ribose portion constituting ribonucleoside, which is substitution of a 2'-hydroxy group. Specifically, such modification corresponds to, for example, substitution of the hydroxy group by a methoxy group that results in 2'-O-methylribose, substitution of the hydroxy group by an ethoxy group that results in 2'-O-ethylribose, substitution of the hydroxy group by a propoxy group that results in 2'-O-propylribose, substitution of the hydroxy group by a butoxy group that results in 2'-O-butylribose, substitution of the hydroxy group by a fluoro group that results in 2'-deoxy-2'-fluororibose, or substitution of the hydroxy group by a 2'-O-methoxy-ethyl group that results in 2'-O-methoxyethylribose. Alternative examples thereof include substitution of a (deoxy)ribose portion of nucleoside by a different sugar. Specifically, such substitution corresponds to, for example, substitution of the ribose portion by arabinose, 2'-fluoro-β-D-arabinose, a ribose derivative in which a 2'-hydroxy group and a 4'-carbon atom of ribose are cross-linked by methylene, or a ribose derivative in which 4'-oxygen in the ribose ring is substituted by sulfur. Alternatively, such substitution includes substitution of an oxygen atom (4'-oxygen atom of ribose) on the ribofuranose ring by sulfur.

The "base modification" refers to modification of a base portion constituting nucleoside. Examples thereof include substitution of the base portion by a functional group, addition of a functional group to the base portion, and substitution of the base portion by a base analogue. Specifically, such a modified base corresponds to, for example, modified pyrimidines such as 5-methylcytosine resulting from substitution at position 5 of cytosine by a methyl group, 5-hydroxycytosine resulting from substitution at position 5 of cytosine by a hydroxy group, 5-fluorouracil resulting from substitution at position 5 of uracil by a fluoro group, 4-thiouracil resulting from substitution of a 4-oxygen atom of uracil by a thio group, 5-methyluracil resulting from substitution at position 5 of uracil by a methyl group, and 2-thiouracil resulting from substitution of a 2-oxygen atom of uracil by a thio group, modified purines such as 6-methyladenine resulting from substitution at position 6 of adenine by a methyl group, and 6-thioguanine resulting from substitution at position 6 of guanine by a thio group, or other heterocyclic bases.

The base length of the aptamer of the present invention is not limited and is preferably within the range of 10 to 100 bases, more preferably within the range of 15 to 80 bases.

The nucleic acid aptamer of the present invention is constituted by natural and non-natural nucleotides and can be replicated or transcribed (or reverse-transcribed), as in a polynucleotide constituted only by natural nucleotides. This is because, as mentioned above, the artificial base carried by the non-natural nucleotide can exert functions similar to those of the natural base in the replication or transcription of the nucleic acid aptamer through its complementarity of artificial base pairing with the complementary artificial base. Thus, the nucleic acid aptamer can be cloned by a conventional nucleic acid amplification method or in vitro transcription method.

1-4. Production Method

The nucleic acid aptamer of the present invention, which comprises a non-natural nucleotide, can be produced through predetermined production steps from a single-stranded nucleic acid library by the addition of non-natural nucleotides respectively having a pair of complementary artificial bases to substrate nucleotides in a nucleic acid amplification step, because the artificial base carried by the non-natural nucleotide has the properties mentioned above. Hereinafter, the method for producing a nucleic acid aptamer according to the present invention will be described.

1-4-1. Single-Stranded Nucleic Acid Library

In the present specification, the "single-stranded nucleic acid library" refers to a pool constituted by a plurality of identical and/or different single-stranded nucleic acid molecules including candidate molecules of nucleic acid aptamers. The single-stranded nucleic acid library, however, may comprise a double-stranded molecule formed by the pairing of all or some bases in the single-stranded nucleic acid molecule with those in another single-stranded nucleic acid molecule.

The single-stranded nucleic acid library of the present invention is completely or partially constituted by non-natural nucleotide-containing single-stranded nucleic acid molecules.

In the present specification, the "non-natural nucleotide-containing single-stranded nucleic acid molecule" refers to a single-stranded nucleic acid molecule comprising a natural nucleotide and a non-natural nucleotide. The non-natural nucleotide may be the aforementioned derivative of the artificial base that retains the complementarity of the artificial base to the complementary artificial base.

The content of the non-natural nucleotide in the non-natural nucleotide-containing single-stranded nucleic acid molecule is 20% or less, preferably 15% or less, more preferably 10% or less, of the total number of nucleotides constituting the nucleic acid molecule. When the non-natural nucleotide-containing single-stranded nucleic acid molecule comprises a plurality of non-natural nucleotides, the artificial bases of these non-natural nucleotides may be the same and/or different. The non-natural nucleotide-containing single-stranded nucleic acid molecule can contain, for example, non-natural nucleotides respectively having a pair of different artificial bases complementary to each other such as Ds and Pn, a Ds derivative and Pn, a Ds derivative and a Pn derivative, Ds and Pa, a Ds derivative and Pa, or a Ds derivative and a Pa derivative. When these artificial bases are different, it should be noted that two or more artificial bases having an identical complementary artificial base do not coexist with each other in one nucleic acid molecule. This is because the original artificial base might be replaced with another artificial base via the complementary artificial base during the replication or transcription process. For example, in a non-natural nucleotide-containing single-stranded nucleic acid molecule comprising non-specific nucleotides respectively having Pa and Pn, the positions of Pa and Pn might be replaced with the other via their complementary artificial base Ds during the replication process.

The single-stranded nucleic acid molecule constituting the single-stranded nucleic acid library may be a single-stranded DNA molecule or a single-stranded RNA molecule. A single-stranded nucleic acid library constituted by single-stranded DNA molecules is used for producing a DNA aptamer by the method for producing a nucleic acid aptamer according to the present invention, whereas a single-stranded nucleic acid library constituted by single-stranded RNA molecules is used for producing an RNA aptamer by the method according to the present invention.

Figure 2:
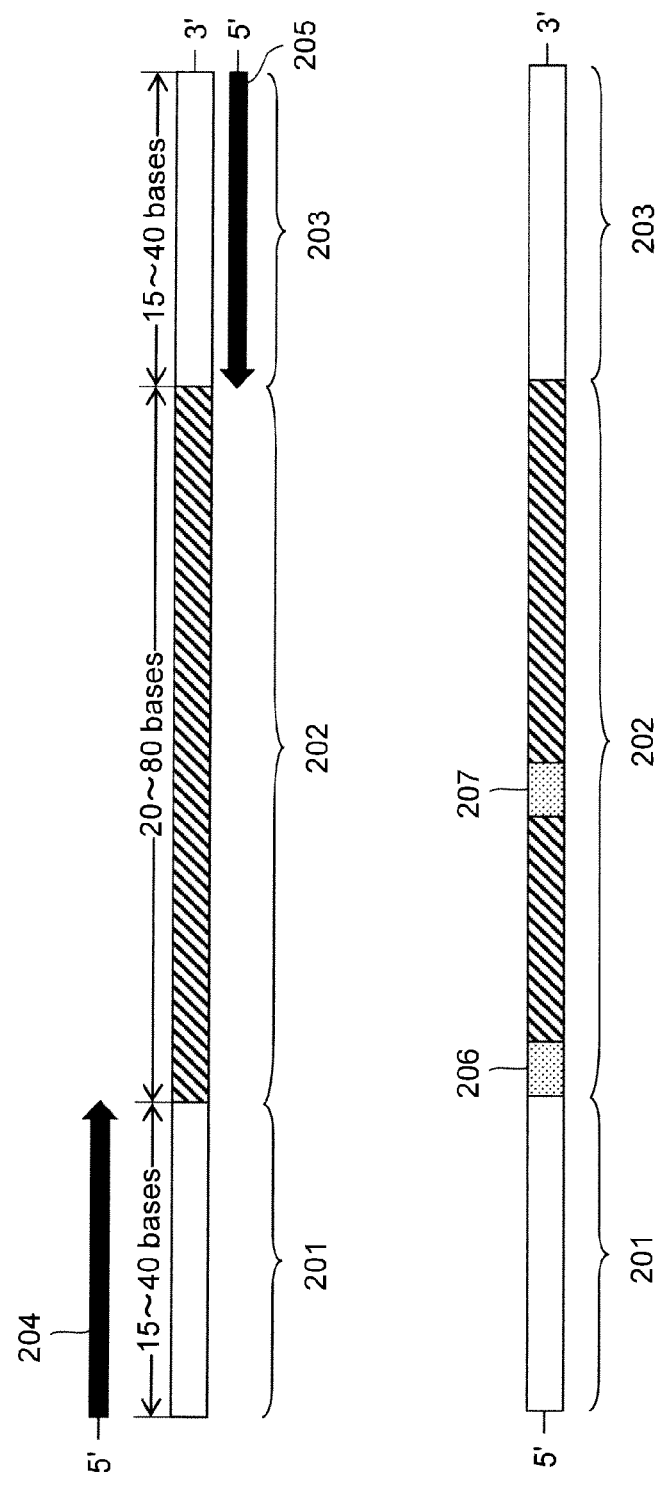
FIG. 2 is a schematic diagram showing the structure of a single-stranded nucleic acid molecule constituting a single-stranded nucleic acid library.

The single-stranded nucleic acid molecule constituting the single-stranded nucleic acid library can have a primary structure shown in FIG. 2. As shown in FIGS. 2A and 2B, all single-stranded nucleic acid molecules each comprise 5'-terminal and 3'-terminal primer-binding regions (201 and 203) to which primers bind, and a central region (202) located between these two primer-binding regions.

The primer-binding regions are constituted by natural nucleotides, non-natural nucleotides, or combinations thereof.

The primer-binding regions are each 15 to 40 bases long. The central region is 20 to 80 bases long. Thus, the single-stranded nucleic acid molecule constituting the single-stranded nucleic acid library has a base length ranging from 50 to 160 bases.

The 5'-terminal and 3'-terminal primer-binding regions each consist of a known nucleotide sequence common among the single-stranded nucleic acid molecules constituting the single-stranded nucleic acid library. The 5'-terminal primer-binding region (201) comprises a nucleotide sequence matched to a forward primer (204), while the 3'-terminal primer-binding region (203) comprises a nucleotide sequence complementary to a reverse primer (205). It is preferred that: the nucleotide sequence of each primer should be a sequence that hardly forms a secondary structure in the molecule of the primer and/or a sequence that does not form a consecutive double-stranded region by the base pairing between the forward primer and the reverse primer; each primer should have a Tm value within the range of 40 to 80° C., 45 to 75° C., or 50 to 65° C.; both the primers should not largely differ in Tm value; and each primer should have a GC content of 40 to 60% or 45 to 55%.

The central region (202) completely or partially consists of a random nucleotide sequence or a particular nucleotide sequence.

The whole nucleotide sequence of the central region is a random nucleotide sequence (202 indicated with an oblique line), as a rule. Particularly, for use of the single-stranded nucleic acid library in the first round in the method for producing a nucleic acid aptamer according to the present invention, a random nucleotide sequence is preferred also for expanding a choice of the nucleic acid aptamer. In this case, the single-stranded nucleic acid library may include a single-stranded nucleic acid molecule having no non-natural nucleotide in the central region. This is because such a single-stranded nucleic acid library including the non-natural nucleotide-containing single-stranded nucleic acid molecule and further including a non-natural nucleotide-free single-stranded nucleic acid molecule makes a greater contribution to the goal of the method for producing a nucleic acid aptamer, because use of the library in the method for producing a nucleic acid aptamer according to the present invention may produce a nucleic acid aptamer constituted only by natural nucleotides that binds more strongly to a target substance than the nucleic acid aptamer of the present invention comprising a non-natural nucleotide.

The central region may consist of a "particular nucleotide sequence". The particular nucleotide sequence refers to, for example, the nucleotide sequence of a single-stranded nucleic acid molecule placed under a predetermined selective pressure. In this context, the "single-stranded nucleic acid molecule placed under a predetermined selective pressure" corresponds to, for example, a single-stranded nucleic acid molecule constituting a single-stranded nucleic acid library after a repetitive step (which will be described later) in the production method of the present invention comprising the repetitive step.

One form of the single-stranded nucleic acid library may comprise a single-stranded nucleic acid molecule having a central region partially consisting of a random nucleotide sequence. Examples of the single-stranded nucleic acid molecule having a "central region partially consisting of a random nucleotide sequence" include a single-stranded nucleic acid molecule in which a particular nucleotide sequence is positioned at a predetermined site in the nucleotide sequence of the central region and the other bases are random and/or a single-stranded nucleic acid molecule in which bases at a predetermined site are constituted by artificial bases and the other bases are random. Specific examples thereof include a non-natural nucleotide-containing single-stranded nucleic acid molecule comprising an identification site (206) at at least one end of the central region as shown in FIG. 2B. The "identification site" (206) refers to a site that is disposed in the central region so as to flank the primer-binding region and has a predetermined nucleotide sequence. This identification site is constituted by 1 to 10, preferably 1 to 8, more preferably 1 to 5 natural nucleotides having natural bases. The nucleotide sequence of the identification site is related to positional information about one or more artificial bases (207) disposed in advance at a particular position on the nucleotide sequence of the central region. The phrase "related to positional information about artificial base(s)" refers to functioning as a tag sequence that indicates the position of the artificial base(s) introduced to the predetermined position in the central region. For example, when the identification site disposed at the 5' end of the central region has a nucleotide sequence AG, this identification site may indicate that the 10th base counted from the 5' end of the central region is Ds. Since the identification site is constituted by natural nucleotides and comprises a known nucleotide sequence flanking the primer-binding region as described above, its nucleotide sequence is maintained even after an amplification step and can function as a tag sequence. The positional information about artificial bases can be infinitely set according to the number of bases in the identification site, the nucleotide sequence thereof, the position of the identification site disposed at the 5' end and/or at the 3' end, or a combination thereof. Thus, 1 or 2 or more artificial bases may be disposed in the central region. A single-stranded nucleic acid library comprising such a non-natural nucleotide-containing single-stranded nucleic acid molecule is useful in one form of a method for sequencing a single-stranded nucleic acid molecule described later.

The single-stranded nucleic acid library can be appropriately prepared according to a method known in the art. Examples thereof include a method for preparing the single-stranded nucleic acid library by chemical synthesis using, for example, a nucleic acid synthesizer. Specifically, a single-stranded DNA library can be prepared using a DNA synthesizer. In this case, designed nucleotide sequences can be input into a synthesis program to obtain the single-stranded nucleic acid library of interest according to the program. For example, predetermined nucleotide sequences can be input thereinto for the primer-binding regions, while a random nucleotide sequence can be programmed for the central region. In this regard, one or more non-natural nucleotides can be added to four natural nucleotides as substrates for nucleic acid synthesis to obtain a single-stranded nucleic acid library comprising non-natural nucleotide-containing (non-natural nucleotide-introduced) single-stranded nucleic acid molecules.

Also, the single-stranded nucleic acid library comprising the single-stranded nucleic acid molecule having a central region partially consisting of a random nucleotide sequence can be prepared in the same way as above by inputting predetermined bases at predetermined positions (e.g., the identification site and the artificial base introduction position related thereto) in the primer-binding regions and the central region into the program and inputting a random nucleotide sequence at the other site of the central region into the synthesis program.

The synthesis of each nucleic acid molecule constituting the single-stranded nucleic acid library may be outsourced to each life science manufacturer.

In the method for producing a nucleic acid aptamer, comprising the repetitive step described later, the single-stranded nucleic acid library for use in round 2 or later can be prepared on the basis of single-stranded nucleic acid molecules obtained in a round immediately before the repetitive step.

Since the single-stranded nucleic acid library is a library including nucleic acid aptamer candidates, each single-stranded nucleic acid molecule constituting the single-stranded nucleic acid library has a conformation formed by self folding, as a rule.

1-4-2. Production Steps

Figure 3:
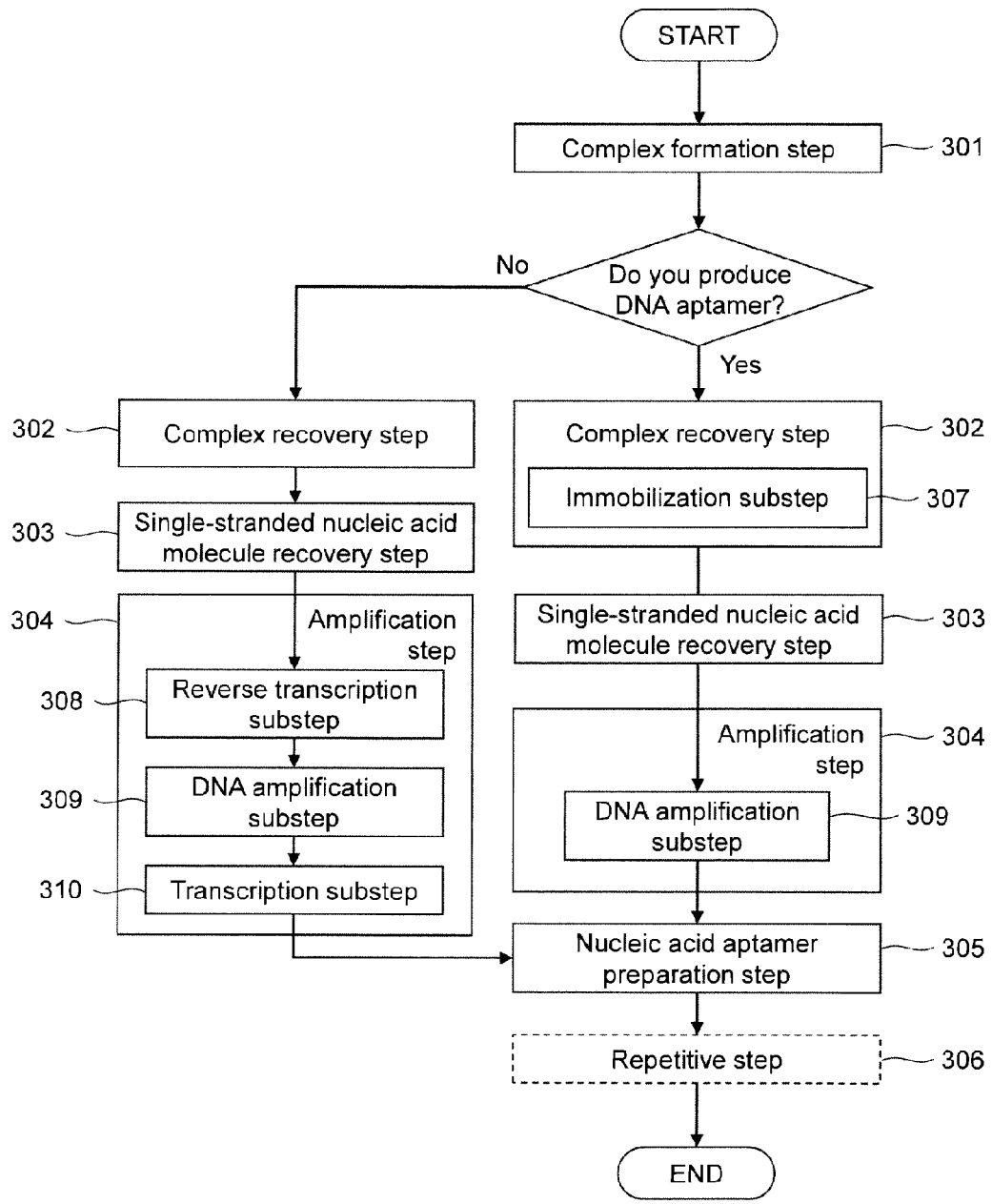
FIG. 3 shows a process flow of a method for producing a nucleic acid aptamer.

FIG. 3 shows a process flow of the method for producing a nucleic acid aptamer according to the present invention. As shown in this diagram, the method for producing a nucleic acid aptamer according to the present invention comprises a complex formation step (301), a complex recovery step (302), a single-stranded nucleic acid molecule recovery step (303), an amplification step (304), and a nucleic acid aptamer preparation step (305) as essential steps. The method for producing a nucleic acid aptamer according to the present invention may also comprise a repetitive step (306) as an optional step. In the case of producing a DNA aptamer as the nucleic acid aptamer, the complex recovery step (302) comprises an immobilization substep (307). In the case of producing an RNA aptamer as the nucleic acid aptamer, the amplification step (304) comprises a reverse transcription substep (308), a DNA amplification substep (309), and a transcription substep (310).

In principle, the method for producing a nucleic acid aptamer is based on a conventional in vitro selection method called SELEX (systematic evolution of ligands by exponential enrichment) (WO1991019813; WO1994008050; Lauhon C. T. and Szostak J. W., 1995, J. Am. Chem. Soc., 117: 1246-1257; Zhao X., et al., 2006, Nucleic Acids Res., 34: 3755-3761; Fan X., et al., 2004, J. T. Lis, 101: 6934-6939; and Jeong S., et al., 2010, Oligonucleotides, 20: 155-161). Particularly, an RNA aptamer can be produced according to the conventional SELEX method. The conventional SELEX method, however, adopts, as a method for recovering a complex in the complex recovery step, (1) a method which involves trapping proteins as target substances onto a nitrocellulose filter through the use of hydrophobic interaction to thereby recover the complex, (2) a method which involves recovering the complex on the basis of mobility shift on a gel during gel electrophoresis, or (3) a method which involves immobilizing in advance target substances onto a carrier or the like and mixing the resulting carrier with a DNA library. In the production of DNA aptamers, therefore, the problem of the method (1) is that DNAs, which are more hydrophobic than RNAs, are non-specifically adsorbed in themselves onto the nitrocellulose filter; the problem of the method (2) is that a DNA library consisting of plural types of different sequences tends to produce disturbed bands; and the problem of the method (3) is that even a DNA bound with only the solid-phase carrier is obtained.

Thus, a modified version of SELEX developed by the present inventors is used in the method for producing a nucleic acid aptamer according to the present invention. This enables minimization of background attributed to nonspecific adsorption as well as production of a nucleic acid aptamer, particularly, a DNA aptamer, very strongly and specifically binding to a target substance.

Hereinafter, each of the above steps and the substeps will be described specifically.

(1) Complex Formation Step

The "complex formation step" (301) refers to the step of mixing a single-stranded nucleic acid library with a target substance in a solution to form a complex of a single-stranded nucleic acid molecule and the target substance.

In this step, the "complex" refers to a nucleic acid-target substance complex formed by the binding between each single-stranded nucleic acid molecule constituting the single-stranded nucleic acid library, specifically, a single-stranded nucleic acid molecule as a nucleic acid aptamer candidate, and the target substance.

The solution used in this step is not particularly limited by its type or properties as long as the solution permits formation of the complex between the nucleic acid and the target substance. Water or an aqueous solution is preferred. The aqueous solution can have a pH ranging from 5.0 to 9.0, preferably 6.0 to 8.0, more preferably 6.5 to 7.6. Its salt concentration can be in the range of 20 to 500 mM, preferably 50 to 300 mM, more preferably 90 to 180 mM, in terms of the final concentration. The aqueous solution is preferably a buffer. The buffer is, for example, a pH buffer solution that is applicable to the above pH range (e.g., a phosphate buffer, a citrate-phosphate buffer, a tris-HCl buffer, or a HEPES buffer) and contains an appropriate salt (e.g., NaCl or $CH_3COOK$) added at a final salt concentration within the above range. Specific examples thereof include a PBS buffer (1.1 mM $KH_2PO_4$, 155 mM NaCl, and 3 mM $Na_2HPO_4$, pH 7.4). The composition of the pH buffer can be finely adjusted according to the need on the basis of composition known in the art described in, for example, Sambrook, J. et al., (2001) Molecular Cloning: A Laboratory Manual Third Ed., Cold Spring Harbor Laboratory Press, Cold Spring Harbor, N.Y.

The solution may further contain a reducing agent or a surfactant, if necessary.

Examples of the reducing agent include dithiothreitol (DTT) and 2-mercaptoethanol. The reducing agent in the solution can have a final concentration ranging from 0.5 to 10 mM, preferably 1 to 5 mM.

The surfactant is preferably a nonionic surfactant. Examples thereof include Nonidet P40 (NO-40), Triton X-100, Triton X-114, Brij-35, Brij-58, Tween-20, Tween-40, Tween-60, Tween-80, n-octyl-β-glucoside, MEGA-8, MEGA-9, and MEGA-10. The surfactant in the solution can have a final concentration ranging from 0.005% to 0.1%, preferably 0.01% to 0.08%, in terms of volume/volume (V/V).

The solution used in this step may further contain a competitive substance. In the present specification, the "competitive substance" refers to a substance that competes with the single-stranded nucleic acid molecule as a nucleic acid aptamer candidate for binding to the target substance. The solution containing the competitive substance permits production of a nucleic acid aptamer more strongly binding to the target substance. The competitive substance is not particularly limited by its type as long as the substance can compete with the single-stranded nucleic acid molecule for binding to the target substance. Examples thereof include nucleic acids, peptides, lipids, sugars, and low-molecular-weight compounds. The competitive substance is preferably a substance similar in properties to the single-stranded nucleic acid molecule serving as the nucleic acid aptamer of interest, for example, a substance binding to the same site on the target substance as that to which the single-stranded nucleic acid molecule binds. Such a substance corresponds to a nucleic acid molecule (single-stranded nucleic acid molecule and/or double-stranded nucleic acid molecule) having a nucleotide sequence analogous to that of the single-stranded nucleic acid molecule of interest. Specifically, when the target substance is, for example, a transcriptional regulator, the competitive substance corresponds to, for example, a nucleotide sequence on the genomic sequence to which the transcriptional regulator originally binds. This nucleic acid molecule used as the competitive substance is designed so as not to have the primer-binding regions (201 and 203) common to the single-stranded nucleic acid molecule constituting the single-stranded nucleic acid library, and the nucleic acid molecule thus prepared cannot be amplified in the amplification step (304) described later and can therefore be removed from the sample even if the competitive substance forms a complex with the target substance.

In order to form the complex, the single-stranded nucleic acid library and the target substance can be mixed at a ratio of 9:1 to 1:9, preferably 1:1 (volume:volume) and incubated at a temperature ranging from 4 to 40° C., preferably 15 to 37° C., for 5 minutes to 30 minutes or longer, for example, approximately 10 minutes to approximately 1 hour, preferably approximately 20 minutes to approximately 40 minutes.

The formed complex may be washed before the subsequent complex recovery step (302). This is because a single-stranded nucleic acid molecule in a free state, which is uncomplexed with the target substance in the solution, can be removed or reduced by washing to thereby further reduce a background attributed to the nonspecific binding of the free single-stranded nucleic acid molecule. The washing of the complex can be performed using a method known in the art on the basis of the type of the target substance and the molecular size or characteristics of the complex. When the target substance is, for example, a protein, the complex can be separated from the free single-stranded nucleic acid using an ultrafiltration membrane that permits passage of only a nucleic acid according to molecular size. A buffer for washing may have the same composition as that of the buffer used in the complex formation. The buffer for washing, as with the buffer used in the complex formation, may also contain a reducing agent or a surfactant. The concentration or composition of the reducing agent or the surfactant may be the same as that of the buffer used in the complex formation. Of course, the remaining free single-stranded nucleic acid can also be removed by washing operation in the subsequent complex recovery step (302) or the single-stranded nucleic acid molecule recovery step (303) even if the free single-stranded nucleic acid is not removed or cannot be completely removed at this stage. Thus, the washing may be performed, if necessary.

(2) Complex Recovery Step

The "complex recovery step" (302) refers to the step of recovering the complex from the solution after the preceding step.

For the production of an RNA aptamer, recovery in this step can be performed according to the conventional SELEX method (WO1991019813; WO1994008050; Lauhon C. T. and Szostak J. W., supra; Zhao X., et al., supra; Fan X., et al., supra; and Jeong S., et al., supra). The convention SELEX method, however, presents the above problems associated with this step in the production of a DNA aptamer. Thus, in the method for producing a nucleic acid aptamer according to the present invention, the complex is preferably recovered by a complex recovery step based on the modified version of SELEX developed by the present inventors.

The complex recovery step based on the modified version of SELEX comprises an immobilization substep (307) of mixing the solution after the complex formation step with a solid-phase carrier to immobilize the complex onto the solid-phase carrier.

(2-1) Immobilization Substep

The "immobilization substep" (307) refers to the substep of mixing the solution after the complex formation step with a solid-phase carrier to immobilize the complex onto the solid-phase carrier.

In the present invention, the "solid-phase carrier" refers to a carrier in a solid state and includes, for example, magnetic beads, high-molecular-weight polysaccharide supports, silica, glass, metals, plastics, ceramics, natural or synthetic resins, and combinations thereof. The solid-phase carrier preferably has hydrophilic surface. In this case, the solid-phase carrier itself may be hydrophilic or may be a hydrophobic carrier with its surface treated by hydrophilic coating. The carrier is not particularly limited by its shape. Particles having a spherical or nearly spherical shape, such as beads, have a large binding surface area and also high operability and as such, are particularly preferred as the shape of the solid-phase carrier in this substep.

In this substep, the "immobilization" refers to the coupling of the complex to the solid-phase carrier. The complex is immobilized onto the solid-phase carrier via connector(s) adsorbed on the target substance and/or the solid-phase carrier.

In the present specification, the "connector" refers to a molecule that mediates the coupling of the target substance to the solid-phase carrier. The connector can include single molecules as well as two or more different molecules linked to each other as long as the connector can mediate the coupling between the target substance and the solid-phase carrier as a result. Specific examples of the connector(s) include biotin and avidin or streptavidin connectors, lectin-biotin (lectin bound with the biotin) and avidin, streptavidin, or NeutrAvidin connectors, a connector consisting of at least one antibody alone, and connector(s) consisting of an antibody and protein A, G, or L.

The connector(s) is adsorbed on the target substance or the solid-phase carrier, or both. In this context, the "adsorption" refers to the immobilization of the connector onto the target substance or the solid-phase carrier through chemical adsorption, physical adsorption, and/or affinity. In this context, the chemical adsorption includes chemical bonds such as covalent bonds, ionic bonds, and hydrogen bonds. The physical adsorption includes coulombic interaction, van der Waals interaction, hydrophobic interaction, or CH-π interaction.

When the connector is adsorbed on only either the target substance or the solid-phase carrier, this connector is capable of specifically recognizing and binding to a substance of the other side on which the connector is not adsorbed. For example, the connector adsorbed on the solid-phase carrier specifically recognizes and binds to the target substance. More specifically, when an antibody or an antibody-bound protein A, for example, is adsorbed as the connector on the solid-phase carrier, the antibody specifically recognizes and binds to the target substance. Hence, the target substance and the solid-phase carrier are mixed in a solution to thereby couple the target substance to the solid-phase carrier via the connector. Some or all target substances after the complex formation step have been complexed with single-stranded nucleic acid molecules as nucleic acid aptamer candidates. Thus, this step can immobilize the complex onto the solid-phase carrier.

When the connector is adsorbed on each of the target substance and the solid-phase carrier, their connectors (hereinafter, the connector adsorbed on the target substance is referred to as a "first connector", while the connector adsorbed on the solid-phase carrier is referred to as a "second connector", for the sake of convenience) are capable of specifically binding to each other. For example, biotin may be adsorbed as the first connector on the target substance, while avidin, streptavidin, or NeutrAvidin may be adsorbed as the second connector on the solid-phase carrier. In this case, the target substance and the solid-phase carrier are mixed in a solution to thereby allow biotin and avidin, streptavidin, or NeutrAvidin to specifically bind to each other. As a result, the target substance is coupled to the solid-phase carrier via the binding between biotin and avidin, streptavidin, or NeutrAvidin.

The connector can be adsorbed onto the target substance or the solid-phase carrier by a method differing depending on the types of the target substance, the solid-phase carrier, and/or the connector. The connector can be appropriately adsorbed by a method known in the art according to their types or the purpose. The adsorption of the connector onto any of the target substance and the solid-phase carrier is preferably carried out by a method that prevents the complex from being easily dissociated due to operation in this substep and the subsequent recovery step.

When the target substance or the solid-phase carrier has a functional group, an exemplary adsorption method can involve, for example, using a connector having an active functional group (e.g., an aldehyde group, a carboxyl group, a sulfo group, an amino group, a thiol group, a cyano group, or a nitro group) capable of covalently binding to the functional group or a connector having such an active functional group introduced therein to adsorb the connector onto the target substance or the solid-phase carrier via a covalent bond formed through chemical reaction such as nucleophilic addition reaction, nucleophilic substitution reaction, or electrophilic substitution reaction between both the functional groups. The method for allowing functional groups to covalently bind to each other through chemical reaction is a technique well known in the art. In the case of adsorbing, for example, a target protein, onto a biotin connector, an active ester group is introduced to biotin using N-hydroxysuccinimide ester (NHS) or the like. Then, an amide bond can be formed between an amino group in the protein and the ester group to thereby adsorb the protein onto the biotin. Various biotinylating reagents are commercially available from each manufacturer and may be used for adsorbing biotin onto the target substance.

When the target substance is an antigen and the first connector is an antibody specifically recognizing and binding to an epitope in the antigen, the antigen and the antibody can be contacted with each other in an appropriate solution to thereby adsorb the first connector onto the target substance through affinity binding.

The connector is adsorbed onto the target substance at an appropriate time after the complex formation step and before this substep and can be adsorbed onto the target substance by any of the adsorption methods described above using, for example, the complex-containing solution obtained after the complex formation step. Alternatively, the connector can be adsorbed onto the solid-phase carrier by any of the adsorption methods at least before the mixing of the complex-containing solution with the solid-phase carrier in this substep.

Specifically, in the case of adsorbing, for example, biotin as the first connector onto a protein as the target substance and streptavidin as the second connector onto magnetic beads as the solid-phase carrier, biotin can be adsorbed onto the protein using, for example, a commercially available biotinylating reagent according to the protocol attached thereto and also using the complex-containing solution obtained after the complex formation step. Also, streptavidin can be adsorbed onto the magnetic beads in advance using a method known in the art, independently of the complex formation step. For example, magnetic beads having a tosyl group or an epoxy group can be merely mixed with streptavidin to thereby directly adsorb the streptavidin thereon via the covalent bond between the group and the primary amino group in the streptavidin. Alternatively, magnetic beads having a carboxyl group can be activated by carbodiimide to thereby adsorb the streptavidin thereon via the covalent bond between the activated carboxyl group and the primary amino group in the streptavidin. These methods are well known in the art.

After the immobilization substep, the formed complex can be recovered in the form of a complex-immobilized solid-phase carrier from the solution using a method based on the characteristics of the solid-phase carrier. The characteristics of the solid-phase carrier refer to properties unique to the solid-phase carrier, such as magnetic force, specific gravity, fluorescence, luminescence, or affinity. When the solid-phase carrier is, for example, magnetic beads, the complex-immobilized solid-phase carrier is recovered using a magnet from the solution and then washed with a buffer having the same composition as that of the buffer used in the complex formation step to wash off target substances or single-stranded nucleic acids nonspecifically adsorbed on the solid-phase carrier. In this way, the complex-immobilized solid-phase carrier can be recovered. Alternatively, when the solid-phase carrier is a high-molecular-weight polysaccharide support, silica, a metal, or glass, the complex-immobilized solid-phase carrier is precipitated by centrifugation. After removal of the supernatant, the precipitates can also be washed with a buffer to thereby recover the complex-immobilized solid-phase carrier. When the solid-phase carrier is, for example, a high-molecular-weight polysaccharide support carrying a fluorescent material, the complex-immobilized solid-phase carrier can be recovered using a fluorescence detector such as FACS.

An uncomplexed target substance in a free state may be immobilized onto the solid-phase carrier in this substep. However, such an uncomplexed target substance is also removed in the amplification step described later which involves removing the target substance from the complex to recover the single-stranded nucleic acid and thus, does not particularly matter.

(3) Single-Stranded Nucleic Acid Molecule Recovery Step

The "single-stranded nucleic acid molecule recovery step" (303) refers to the step of recovering the single-stranded nucleic acid molecule from the recovered complex.

The single-stranded nucleic acid molecule can be recovered according to a method known in the art for recovering nucleic acids from complexes. This method usually differs depending on the type of the target substance complexed therewith. When the target substance is, for example, a peptide such as a protein, the single-stranded nucleic acid molecule of interest can be recovered by the clotting and removal of the protein according to a protein denaturation method such as an alkali method or a phenol/chloroform method. Alternatively, when the target substance is a lipid or a low-molecular-weight compound, for example, an elution buffer is added to the complex, which is then heat-treated to disrupt the structure of the nucleic acid or heat-treated with the elution buffer supplemented with a chelating agent or with the elution buffer pH shifted to that of a binding buffer to disrupt the structure of the nucleic acid. The single-stranded nucleic acid molecule thus obtained by the dissociation of the binding between the target substance and the nucleic acid can be recovered by an alcohol precipitation method or the like.

When the complex recovery step (302) involves the immobilization substep, the complex is recovered in the form of a complex-immobilized solid-phase carrier and therefore eluted, if necessary. The elution method differs depending on the type of the connector(s). When the connector is, for example, an antibody, the complex-immobilized solid-phase carrier can be dissociated by acid treatment or the like and then neutralized, if necessary, by the addition of an alkali to thereby elute the complex from the complex-immobilized solid-phase carrier. Alternatively, when the connectors are biotin and avidin, streptavidin, or NeutrAvidin, the complex-immobilized solid-phase carrier can be heat-treated in a solution containing 7 M or higher urea and/or 2 M or higher β-mercaptoethanol to dissociate the binding between biotin and avidin, streptavidin, or NeutrAvidin and thereby elute the complex therefrom. When the target substance is a glycosylated substance and the connector is lectin, the complex can be eluted by the addition of a sugar such as glucose. These methods can be appropriately performed according to methods known in the art. The subsequent recovery of the single-stranded nucleic acid molecule from the eluted complex is performed by the method as mentioned above.

The buffer for use in washing in this step can have the same composition as that of the buffer used in the complex formation step. The buffer may further contain a reducing agent such as DTT or 2-mercaptoethanol or a nonionic surfactant such as Nonidet P40 (NO-40), Triton X-100, or Tween-20, if necessary. The surfactant in the buffer can have a final concentration ranging from 0.005% to 0.1% or 0.01% to 0.08% in terms of volume/volume (V/V). The washing can be performed one to several times using the buffer and is preferably performed 2 to 3 times. The washing temperature and the washing time are not particularly limited and can be 15 to 50° C. or 20 to 40° C. for 10 minutes to 1 hour.

(4) Amplification Step

The "amplification step" (304) refers to the step of amplifying, by a nucleic acid amplification method, the single-stranded nucleic acid molecule recovered in the single-stranded nucleic acid molecule recovery step.

The "nucleic acid amplification method" refers to a method by which a template nucleic acid is amplified using primers and an enzyme such as polymerase.

This step differs somewhat between a DNA aptamer and an RNA aptamer to be produced as the nucleic acid aptamer. Specifically, only the DNA amplification substep (309) suffices for the DNA aptamer, whereas the DNA amplification substep (309) as well as the reverse transcription substep (308) and the transcription substep (310) are required for the RNA aptamer.

(4-1) DNA Amplification Substep

The "DNA amplification substep" (309) refers to a substep common between the amplification steps of the method for producing a DNA aptamer and the method for producing an RNA aptamer. This substep is of replicating and amplifying a particular region in a template DNA (including cDNA) using primers and an enzyme such as DNA polymerase. The DNA amplification method used in this substep can be any method known in the art. Examples thereof include polymerase chain reaction (PCR) and isothermal and chimeric primer-initiated amplification of nucleic acids (ICAN). PCR is preferred.

The DNA polymerase for use in the reaction is appropriately determined depending on the nucleic acid amplification method used. Usually, thermostable DNA polymerase is used. Such thermostable nucleic acid polymerase is commercially available as various types from each manufacturer such as Takara Bio Inc., New England Biolabs Inc., Life Technologies Corp., F. Hoffmann-La Roche Ltd., or Promega Corp. and may be used in the present invention.

The reaction conditions of the DNA amplification method can be determined in consideration of the length of a polynucleotide to be amplified, the amount of the DNA for template, the Tm values of the primers, the optimum reaction temperature and optimum pH of the DNA polymerase used, etc. For example, for PCR, a sequence matched to the 5'-terminal primer-binding region (201) constituting the single-stranded nucleic acid molecule can be used as the forward primer (204), while a sequence complementary to the 3'-terminal primer-binding region (203) can be used as the reverse primer (205). In this case, the reverse primer labeled with a label is convenient because a double-stranded nucleic acid can be selectively separated and purified as each amplification product on the basis of the label from the reaction solution after the amplification reaction and another single-stranded nucleic acid complementary to the single-stranded nucleic acid of interest in the double-stranded nucleic acid can then be separated and removed on the basis of the label.

For this substep, the point to be noted is the composition of substrates for use in the DNA amplification, i.e., the DNA replication. In the ordinary DNA amplification method, 4 natural deoxyribonucleotides (dATP, dGTP, dCTP, and dTTP; hereinafter, these are collectively referred to as "dNTPs") are used as substrates. In this substep, however, these dNTPs as well as a non-natural deoxyribonucleotide and a non-natural deoxyribonucleotide having a complementary artificial base of the artificial base carried by the nucleotide are used as substrates. The non-natural deoxyribonucleotides used depend on a non-natural nucleotide contained in the non-natural nucleotide-containing single-stranded nucleic acid molecule included in the single-stranded nucleic acid library used in this production method. When the single-stranded nucleic acid library includes, for example, a non-natural nucleotide-containing single-stranded DNA molecule having Ds, the substrates used in this substep are non-natural deoxyribonucleotides respectively having Ds and its complementary artificial base Pn or Pa, in addition to the dNTPs. As mentioned above, the artificial base used herein has properties similar to those of the natural base and thereby permits nucleic acid replication or transcription (including reverse transcription) through the complementarity of artificial base pairing. Hence, the addition of non-natural nucleotides respectively having a pair of complementary artificial bases to substrate nucleotides allows even a DNA molecule comprising a non-natural nucleotide to be amplified by the DNA amplification method.

For PCR involving 3 steps (denaturation, annealing, and extension), the temperature and reaction time of each step can be, for example, 90° C. to 98° C. for approximately 30 seconds to approximately 1 minute for the thermal denaturation step, 50° C. to 60° C. for approximately 30 seconds to approximately 1 minute for the annealing step, and 70° C. to 75° C. for approximately 40 seconds to approximately 2 minutes for the extension step. The number of cycles can usually be 10 cycles to 40 cycles. 15 cycles to 20 cycles are preferred.

The amplified DNAs obtained by this substep may be purified, if necessary. The purification method may be any method known in the art. Examples thereof include an ethanol precipitation method and a purification method using a spin-type gel filtration column.

(4-2) Reverse Transcription Substep

The "reverse transcription substep" (308) is a substep distinctive of the amplification step of the method for producing an RNA aptamer. This substep is of forming cDNAs using primers and an enzyme such as reverse transcription polymerase with RNAs as a template. In the method for producing an RNA aptamer, this substep is carried out before the DNA amplification substep (309).

The reverse transcription method used in this substep can be any method known in the art. This reverse transcription may be performed according to a reverse transcription method described in, for example, Sambrook, J. et al., 1989, Molecular Cloning: A Laboratory Manual Second Ed., Cold Spring Harbor Laboratory Press, Cold Spring Harbor, N.Y.

In this substep, the point to be noted is the composition of substrates for use in the reverse transcription reaction. In the ordinary reverse transcription reaction, dNTPs are used as substrates, as in the DNA amplification substep. In this substep, however, these dNTPs as well as a non-natural deoxyribonucleotide having the artificial base carried by a non-natural ribonucleotide contained in the template RNA molecule and a non-natural deoxyribonucleotide having its complementary artificial base are used as substrates. The non-natural deoxyribonucleotides used depend on a non-natural nucleotide contained in the non-natural nucleotide-containing single-stranded nucleic acid molecule included in the single-stranded nucleic acid library used in this production method. When the single-stranded nucleic acid library includes, for example, a non-natural nucleotide-containing single-stranded RNA molecule having Ds, the substrates used in this substep are non-natural deoxyribonucleotides respectively having Ds and its complementary artificial base Pn or Pa, in addition to the dNTPs. As mentioned above, the artificial base used herein permits nucleic acid reverse transcription through the complementarity of artificial base pairing. Hence, the addition of non-natural nucleotides respectively having a pair of complementary artificial bases to substrate nucleotides allows a cDNA molecule to be formed even from an RNA molecule comprising a non-natural nucleotide.

The cDNA obtained by this substep is subjected to the DNA amplification substep (309).

(4-3) Transcription Substep

The "transcription substep" (310) is a substep distinctive of the amplification step of the method for producing an RNA aptamer. This substep is of transcribing RNAs from DNAs using primers and an enzyme such as an RNA polymerase. In the method for producing an RNA aptamer, this substep is carried out after the DNA amplification substep.

The transcription method used in this substep can be any method known in the art. Examples thereof include an in vitro RNA transcription method. Alternatively, expression induction treatment may be performed by a technique known in the art using transformants of *E. coli* or the like transformed with the DNA, and the RNA of interest can be recovered from the transformants. These transcription methods can be specifically performed according to transcription methods descried in, for example, Sambrook, J. et al., 1989, Molecular Cloning: A Laboratory Manual Second Ed., Cold Spring Harbor Laboratory Press, Cold Spring Harbor, N.Y.

For this substep, the point to be noted is the composition of substrates for use in the transcription reaction. In the ordinary transcription reaction, 4 natural ribonucleotides (ATP, GTP, CTP, and UTP; hereinafter, these are collectively referred to as "NTPs") are used as substrates. In this substep, however, these NTPs as well as a non-natural ribonucleotide having the artificial base carried by the non-natural deoxyribonucleotide contained in the DNA molecule and a non-natural ribonucleotide having its complementary artificial base are used as substrates. The non-natural ribonucleotides used depend on a non-natural nucleotide contained in the non-natural nucleotide-containing single-stranded nucleic acid molecule included in the single-stranded nucleic acid library used in this production method. When the single-stranded nucleic acid library includes, for example, a non-natural nucleotide-containing single-stranded DNA molecule having Ds, the substrates used in this substep are non-natural ribonucleotides respectively having Pn or Pa (complementary artificial base of Ds), in addition to the NTPs. As mentioned above, the artificial base used herein permits nucleic acid reverse transcription through the complementarity of artificial base pairing. Hence, the addition of non-natural nucleotides respectively having a pair of complementary artificial bases to substrate nucleotides allows an RNA molecule to be transcribed even from a DNA molecule comprising a non-natural nucleotide.

(5) Nucleic Acid Aptamer Preparation Step

The "nucleic acid aptamer preparation step" (305) refers to the step of preparing a nucleic acid aptamer from a nucleic acid molecule obtained by the amplification step.

When the nucleic acid molecule after the amplification step is a DNA, this nucleic acid molecule is usually found in the form of a double-stranded nucleic acid resulting from the base pairing of the single-stranded nucleic acid molecule (nucleic acid aptamer) specifically binding to a target substance with another single-stranded nucleic acid molecule having a nucleotide sequence complementary thereto. When the nucleic acid molecule is an RNA, this nucleic acid molecule is obtained as a single-stranded nucleic acid molecule, but does not always form the structure of the nucleic acid aptamer of the present invention. Thus, in this step, a single strand prepared from the double-stranded nucleic acid (when the nucleic acid molecule is a DNA) or the obtained single-stranded nucleic acid molecule (when the nucleic acid molecule is an RNA) is self-folded to prepare the nucleic acid aptamer of the present invention having binding activity against the target substance.

When the nucleic acid molecule is a DNA, the double-stranded nucleic acid is generally made into single strands by thermal denaturation. The thermal denaturation can be performed at a temperature ranging from 60 to 90° C. The solution for use in this denaturation may contain 1 to 7 M urea. Then, electrophoresis is performed using a denaturing gel. A band having the size of interest is eluted from the gel to purify the single strand. Such a method known in the art or a method equivalent thereto can achieve the preparation of single strands from double strands and the purification thereof.

The single-stranded nucleic acids thus prepared from the double-stranded nucleic acid are a mixture of a single-stranded nucleic acid molecule capable of forming the nucleic acid aptamer of interest and its partner single-stranded nucleic acid molecule having a nucleotide sequence complementary thereto. Thus, in this step, the unnecessary single-stranded nucleic acid molecule having a complementary nucleotide sequence may be separated and removed before self folding of the single-stranded nucleic acid molecule forming the nucleic acid aptamer of interest. The selective isolation of the single-stranded nucleic acid molecule of interest can be achieved by use of, for example, the reverse primer labeled with a label as mentioned above. Specifically, after PCR using, for example, a biotin-labeled reverse primer, each amplified double-stranded nucleic acid in the reaction solution is recovered by an ethanol precipitation method or the like. Then, streptavidin is added to the suspension to form a biotin-streptavidin complex through which the double-stranded nucleic acid is then separated and purified. Then, the purified double-stranded nucleic acid is denatured into single strands, which are in turn fractionated by denaturing gel electrophoresis depending on the difference in mobility between the strands. The single-stranded nucleic acid molecule of interest can be isolated and purified from the gel.

In order to self-fold the single-stranded nucleic acid molecule, for example, the single-stranded nucleic acid molecule can be subjected to heating-cooling treatment. As a specific example, the single-stranded nucleic acid molecule can be dissolved in the buffer (e.g., PBS buffer) used in the complex formation step, then thermally denatured at 80 to 98° C., preferably 85 to 95° C., for 30 seconds to 5 minutes, preferably 30 seconds to 3 minutes, and then left, for example, at room temperature for slow cooling or cooled in stages to form an intramolecular conformation. The cooling in stages can be performed, for example, temporal cooling at 50 to 70° C. for approximately 1 minute to approximately 20 minutes after thermal denaturation and then further cooling with the temperature decreased to 15 to 35° C.

This step can produce the nucleic acid aptamer of the present invention specifically binding to the target substance.

(6) Repetitive Step

The "repetitive step" (306) refers to the step of freshly repeating one or more times the procedures from the complex formation step to the nucleic acid aptamer preparation step (hereinafter, this series of steps is referred to as a "round" in the present specification) using a fresh single-stranded nucleic acid library of nucleic acid aptamers prepared in the nucleic acid aptamer preparation step or single-stranded nucleic acid molecules serving as candidates thereof.

This step is an optional step. One or more rounds of this step, however, are preferably performed for narrowing down a nucleic acid aptamer having higher specificity for the target substance after the nucleic acid aptamer preparation step. Specifically, for example, one or more rounds, preferably 1 to 15 rounds, 1 to 8 rounds, or 1 to 5 rounds are performed.

In each round of this step, a pool of the single-stranded nucleic acid molecules obtained in the nucleic acid aptamer preparation step of the immediately preceding round is used as a fresh single-stranded nucleic acid library for use in the complex formation step, as a rule. The single-stranded nucleic acid library for use in each round may be placed under the same or different conditions of the individual steps, i.e., the complex formation step to the nucleic acid aptamer preparation step, as or from the initial conditions according to the need. Examples of the different conditions among the rounds include change in the composition of the solution or the buffer used in each round. Specifically, in the early rounds, a larger number of nucleic acid aptamer candidates are acquired under mild washing conditions using the buffer. In the later rounds, a single-stranded nucleic acid molecule more strongly binding to the target substance can be isolated under strict washing conditions using the buffer mixed with approximately 3 M urea. Alternatively, the concentrations of the target substance and the single-stranded nucleic acid library in the complex formation step may be changed among the rounds. For example, the concentrations of the target substance and the single-stranded nucleic acid library can be decreased with each round to render complex formation conditions stricter. As a result, the nucleic acid aptamer more strongly binding to the target substance can be isolated.

2. Sequencing Method

The second embodiment of the present invention relates to a method for sequencing a single-stranded nucleic acid molecule selected from a single-stranded nucleic acid library.

Nucleic acid aptamers obtained by the method for producing a nucleic acid aptamer according to the first embodiment require sequencing for their large-scale production through chemical synthesis. Single clones having an identical nucleotide sequence are necessary for the sequencing. The nucleic acid aptamers obtained by the production steps, however, may include a plurality of different nucleic acid aptamer clones. Such single clones must therefore be prepared from the produced nucleic acid aptamers. Conventional nucleic acid aptamers constituted by natural nucleotides can be prepared into single clones by an ordinary nucleic acid cloning technique known in the art, and then sequenced, even if the obtained nucleic acid aptamers are a plurality of different clones. Specifically, an exemplary method involves inserting each clone of the obtained nucleic acid aptamer into an appropriate cloning vector, which is then transferred to E. coli or the like, isolating single clones as transformants, and then sequencing the single clones through cycle sequencing reaction or the like.

The nucleic acid aptamer of the present invention comprises a non-natural nucleotide having an artificial base. The method for sequencing a nucleic acid molecule comprising a non-natural nucleotide is technically known per se in the art (Hirao I., et al., Nature Methods, 3, 729-735 (2006); and Kimoto M., et al., Nucleic Acids Res., 37, e14 (2009)). This method, however, requires preparing single clones of nucleic acid molecules comprising a non-natural nucleotide, as in the conventional nucleic acid molecules constituted only by natural nucleotides. Nonetheless, the nucleic acid aptamer of the present invention comprising a non-natural nucleotide cannot be prepared into single clones by the conventional cloning technique, because such a non-natural nucleotide is absent in vivo in E. coli or the like. Hence, a method for sequencing a single-stranded nucleic acid molecule that may comprise a non-natural nucleotide, selected from single-stranded nucleic acid library consisting of single clones or a plurality of different clones has not yet been established.

This time, the present inventors have developed two novel methods, i.e., a random library method and a predetermination method, as the method for sequencing a single-stranded nucleic acid molecule that may comprise a non-natural nucleotide, selected from a single-stranded nucleic acid library. Use of these methods can sequence the nucleic acid aptamer obtained by the method for producing a nucleic acid aptamer. Hereinafter, each method will be described.

2-1. Random Library Method

The "random library method" is a method for sequencing a single-stranded nucleic acid molecule selected from the single-stranded nucleic acid library of the present invention. The single-stranded nucleic acid molecule targeted by this method has a central region (202) (shown in FIG. 2A) consisting of a random nucleotide sequence that may comprise a non-natural nucleotide.

Figure 4:
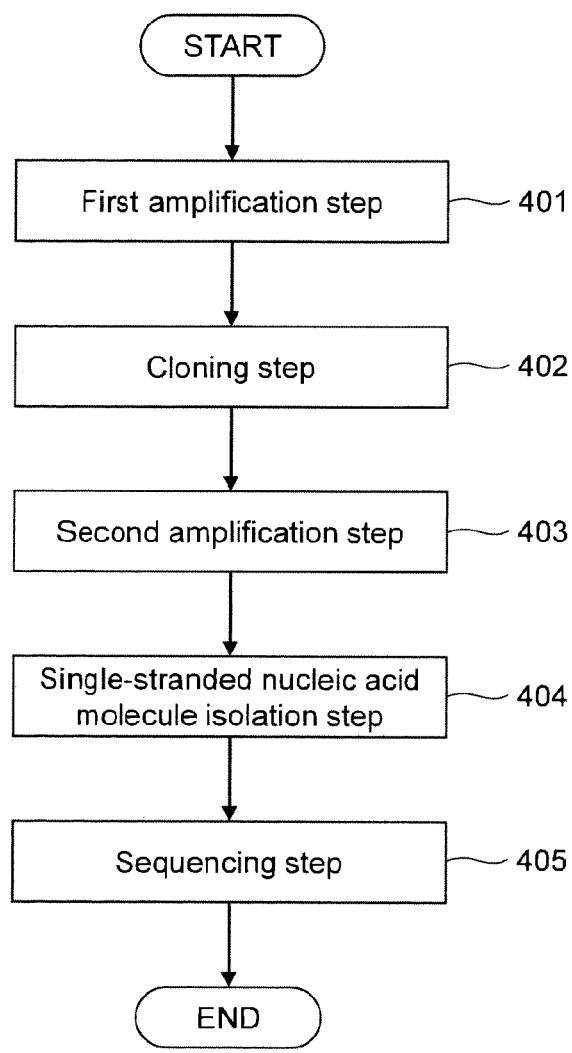
FIG. 4 shows a process flow of a random library method.

FIG. 4 shows a process flow of the random library method. As shown in this diagram, the random library method comprises a first amplification step (401), a cloning step (402), a second amplification step (403), a single-stranded nucleic acid molecule isolation step (404), and a sequencing step (405) as essential steps. Of these steps, the second amplification step (403) is independent of the first amplification step (401) and the cloning step (402). Thus, the second amplification step (403) can be carried out before the first amplification step (401), after the cloning step (402), or in parallel with the first amplification step (401) and the cloning step (402). Hereinafter, each step will be described specifically.

(1) First Amplification Step

The "first amplification step" (401) refers to the step of amplifying the single-stranded nucleic acid molecule selected from the single-stranded nucleic acid library, by a nucleic acid amplification method with natural nucleotides as substrates.

The basic procedures of this step follow the procedures described in "1-4-2. Production steps (4) Amplification step" in "1-4. Production method" of the first embodiment. Specifically, in this step, the single-stranded nucleic acid molecule selected from the single-stranded nucleic acid library is amplified by a nucleic acid amplification method known in the art. This step comprises only the DNA amplification substep when the single-stranded nucleic acid molecule to be sequenced is a DNA, and comprises the reverse transcription substep, the DNA amplification substep, and the transcription substep in the case of an RNA to be sequenced.

Here, the description about the same methods as in "1-4-2. Production steps (4) Amplification step" of the first embodiment mentioned above will be omitted, and only different points will be described specifically.

The single-stranded nucleic acid molecule selected from the single-stranded nucleic acid library of the present invention has the structure shown in FIG. 2, as mentioned above. Since the 5'-terminal and 3'-terminal primer-binding regions (201 and 203) each consist of a known nucleotide sequence, the single-stranded nucleic acid molecule can be amplified by a nucleic acid amplification method using a primer set composed of a forward primer (204) and a reverse primer (205).

A feature of this step is that only natural nucleotides are used as substrates in the nucleic acid amplification method even if the single-stranded nucleic acid molecule to be sequenced comprises a non-natural nucleotide. This means that: only dNTPs are used as substrates for DNA replication in the DNA amplification substep; only dNTPs are used as substrates for reverse transcription from RNAs in the reverse transcription substep; and only NTPs are used as substrates for RNA transcription from DNAs in the transcription substep. In the absence of a non-natural nucleotide having a complementary artificial base in substrates, the artificial base can instead pair with a natural base similar in structure and/or properties to the complementary artificial base during replication or transcription so that the non-natural nucleotide is replaced with a natural nucleotide, as mentioned above. Hence, this step yields single-stranded nucleic acid molecules constituted only by natural nucleotides as amplification products, even if the single-stranded nucleic acid molecule to be sequenced is a non-natural nucleotide-containing single-stranded nucleic acid molecule.

(2) Cloning Step

The "cloning step" (402) refers to the step of obtaining a single clone from amplification products obtained by the first amplification step.

Each amplification product obtained by the first amplification step is constituted only by natural nucleotides, as mentioned above. Thus, even a plurality of different clones of single-stranded nucleic acid molecules selected from the single-stranded nucleic acid library can be prepared into single clones by an ordinary nucleic acid cloning technique known in the art. An exemplary method involves inserting each clone of the obtained nucleic acid aptamer into an appropriate cloning vector, which is then transferred to *E. coli* or the like, and isolating single clones as transformants. Such a cloning method may be performed according to a method described in, for example. Sambrook, J. et al., 1989, Molecular Cloning: A Laboratory Manual Second Ed. Cold Spring Harbor Laboratory Press, Cold Spring Harbor, N.Y. Alternatively, various cloning kits or the like are commercially available from each manufacturer and may be used in the present invention.

(3) Second Amplification Step

The "second amplification step" (403) refers to the step of amplifying the selected single-stranded nucleic acid molecule by a nucleic acid amplification method with natural nucleotides and non-natural nucleotides as substrates using the primer set binding to the primer-binding regions.

The basic procedures of this step, as with the first amplification step, also follow the procedures described in "1-4-2. Production steps (4) Amplification step" in "1-4. Production method" of the first embodiment. Specifically, in this step, the single-stranded nucleic acid molecule selected from the single-stranded nucleic acid library is amplified by a nucleic acid amplification method known in the art. This step comprises only the DNA amplification substep when the single-stranded nucleic acid molecule to be sequenced is a DNA, and comprises the reverse transcription substep, the DNA amplification substep, and the transcription substep in the case of an RNA to be sequenced.

The second amplification step differs from the first amplification step in that only natural nucleotides are used as substrates in the nucleic acid amplification method of the first amplification step, whereas in this step, natural nucleotides and the non-natural nucleotides are used as substrates to amplify the selected single-stranded nucleic acid molecule. Thus, this step can be regarded as an approach closer to the procedures described in "1-4-2. Production steps (4) Amplification step" of the first embodiment.

According to a non-natural nucleotide contained in the non-natural nucleotide-containing single-stranded nucleic acid molecule included in the single-stranded nucleic acid library of the present invention, this non-natural nucleotide and its partner non-natural nucleotide are used as substrates, together with natural nucleotides. Thus, when the single-stranded nucleic acid molecule is a non-natural nucleotide-containing single-stranded nucleic acid molecule, this step yields the non-natural nucleotide-containing single-stranded nucleic acid molecule as amplification products.

(4) Single-Stranded Nucleic Acid Molecule Isolation Step

The "single-stranded nucleic acid molecule isolation step" (404) refers to the step of using the single clone obtained in the cloning step as a probe to isolate a single single-stranded nucleic acid molecule from amplification products obtained by the second amplification step.

This step first involves preparing the single clone obtained in the cloning step into a probe.

When the single-stranded nucleic acid library is a DNA library, the single clone is usually obtained as a double-stranded DNA. Thus, this double-stranded DNA is prepared into single strands. The preparation of the double-stranded DNA into single strands is generally performed by thermal denaturation. The thermal denaturation can be performed at a temperature ranging from 60 to 90° C. The solution for use in this denaturation may contain 1 to 7 M urea. Then, electrophoresis is performed using a denaturing gel. A band having the size of interest is eluted from the gel to purify the single strand. Such a method known in the art or a method equivalent thereto can achieve the preparation of single strands from the double-stranded DNA and the purification thereof.

Subsequently, one of the two DNA strands is separated as a probe. Either of a sense strand encoding the nucleic acid aptamer or an antisense strand having a nucleotide sequence complementary thereto may be used. An antisense strand is preferred. The method mentioned above can be used for separating one of the two DNA strands. Specific examples thereof include a method which involves labeling any one of the forward primer and the reverse primer with a label and separating and purifying one of the DNA strands as a probe on the basis of the label. Specifically, in order to separate, for example, the antisense strand, each amplified double-stranded DNA in the reaction solution after PCR using a biotin-labeled reverse primer is recovered by an ethanol precipitation method or the like. Then, streptavidin is added to the suspension to form a biotin-streptavidin complex through which the double-stranded nucleic acid is then separated and purified. Then, the purified double-stranded nucleic acid is denatured into single strands, which are in turn fractionated by denaturing gel electrophoresis depending on the difference in mobility between the strands. The antisense strand of interest can be separated and purified from the gel.

When the single-stranded nucleic acid library is an RNA library, the single clone is obtained as a single-stranded RNA. Nonetheless, this single-stranded RNA cannot be used as a probe, because the amplification product obtained by the second amplification step is also a single-stranded RNA that does not form a complementary relationship therewith. In addition, another problem emerges that the RNA itself is unstable and susceptible to degradation. Thus, the RNA obtained as the single clone in the cloning step may be temporarily reverse-transcribed into a double-stranded DNA, which is in turn made into single strands and purified in the same way as above. The reverse transcription reaction can be performed according to the method described in the reverse transcription substep.

Subsequently, the single clone-derived single-stranded nucleic acid thus prepared is used as a probe to isolate a single single-stranded nucleic acid molecule from amplification products obtained by the second amplification step. The amplification products obtained by the first amplification step and the second amplification step using the same single-stranded nucleic acid library as a template may include amplification products derived from the same single-stranded nucleic acid molecule. These amplification products derived from the same molecule have an identical nucleotide sequence, as a rule. In the case of a non-natural nucleotide-containing single-stranded nucleic acid molecule, however, the amplification product of the first amplification step has a natural nucleotide in place of the non-natural nucleotide. Accordingly, the amplification products, albeit derived from the same single-stranded nucleic acid molecule, differ in nucleotide sequence. The amplification products, however, are very highly homologous in their nucleotide sequences as a whole. Hence, single clones can be isolated in sufficient amounts as sequencing samples by using, as a probe, the single clone obtained by the cloning step from the amplification product of the first amplification step, even if the single-stranded nucleic acid library includes a plurality of different single-stranded nucleic acid molecules that are non-natural nucleotide-containing single-stranded nucleic acid molecules. This step is based on such principles.

The single single-stranded nucleic acid molecule can be isolated from the amplification products of the second amplification step by a method known in the art using the prepared probe. This isolation may be performed according to a method described in, for example, Sambrook, J. et al., 1989, Molecular Cloning: A Laboratory Manual Second Ed., Cold Spring Harbor Laboratory Press, Cold Spring Harbor, N.Y. For more efficient isolation, the probe may be immobilized onto a solid-phase carrier and hybridized with the single-stranded nucleic acid molecule of interest among the amplification products of the second amplification step, followed by isolation. The immobilization of the probe onto the solid-phase carrier and the isolation of the single-stranded nucleic acid molecule of interest may be performed using the method described in "1-4-2. Production steps (2) Complex recovery step" in "1-4. Production method" of the first embodiment.

This step can isolate the single-stranded nucleic acid molecule to be sequenced as a single clone, regardless of the single-stranded nucleic acid molecule constituted only by natural nucleotides or the non-natural nucleotide-containing single-stranded nucleotide.

(5) Sequencing Step

The "sequencing step" (405) refers to the step of sequencing the single clone-derived single-stranded nucleic acid molecule isolated by the single-stranded nucleic acid molecule isolation step.

A sequencing method known in the art can be used in this step. The method for sequencing a DNA comprising a non-natural nucleotide having an artificial base is technically known in the art. This sequencing may be performed according to a method described in, for example, Hirao I., et al., Nature Methods, 3, 729-735 (2006); and Kimoto M., et al., Nucleic Acids Res., 37, e14 (2009). This sequencing method can also determine the nucleotide sequences of conventional DNA molecules consisting only of natural nucleotides and as such, can determine the sequence of the single clone-derived single-stranded nucleic acid molecule isolated by the single-stranded nucleic acid molecule isolation step, regardless of the non-natural nucleotide-containing single-stranded nucleic acid molecule or the nucleic acid aptamer consisting only of natural nucleotides.

The single-stranded nucleic acid molecule that may comprise a non-natural nucleotide, selected from the single-stranded nucleic acid library, can be sequenced through these steps, though such sequencing means has not been achieved so far.

2-2. Predetermination Method

The "predetermination method" refers to a method for sequencing single-stranded nucleic acid molecule selected from a single-stranded nucleic acid library constituted by non-natural nucleotide-containing single-stranded nucleic acid molecules that each have an identification site and comprise a non-natural nucleotide only at a predetermined particular position. The identification site in each non-natural nucleotide-containing single-stranded nucleic acid molecule constituting this single-stranded nucleic acid library is constituted by natural nucleotide(s). The nucleotide sequence of the identification site is related to positional information about artificial base(s) predetermined on the nucleotide sequence of the central region in the single-stranded nucleic acid molecule. This method involves replacing the non-natural nucleotide-containing single-stranded nucleic acid molecule with a single-stranded nucleic acid molecule constituted only by natural nucleotides, preparing a single clone by a conventional technique, sequencing the single clone, and then determining the position of the natural nucleotide-replaced non-natural nucleotide having an artificial base on the basis of the nucleotide sequence of the identification site to sequence the non-natural nucleotide-containing single-stranded nucleic acid molecule of interest.

Figure 5:
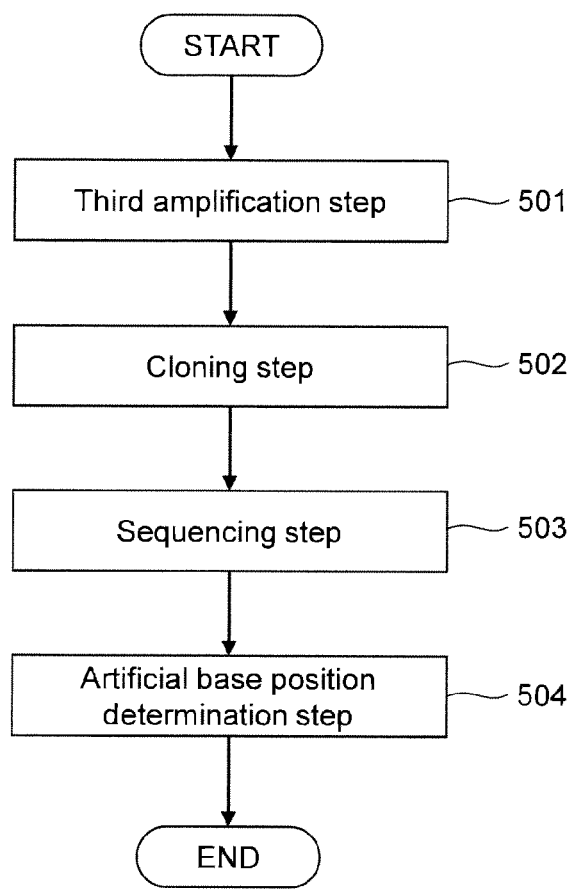
FIG. 5 shows a process flow of a predetermination method.

FIG. 5 shows a process flow of the predetermination method. As shown in this diagram, the predetermination method comprises a third amplification step (501), a cloning step (502), a sequencing step (503), and an artificial base position determination step (504) as essential steps. Hereinafter, each step will be described specifically.

(1) Third Amplification Step

The "third amplification step" (501) refers to the step of amplifying the selected non-natural nucleotide-containing single-stranded nucleic acid molecule by a nucleic acid amplification method with natural nucleotides as substrates using a primer set binding to the primer-binding regions.

The basic procedures of this step follow the procedures described in "1-4-2. Production steps (4) Amplification step" in "1-4. Production method" of the first embodiment. Specifically, in this step, the non-natural nucleotide-containing single-stranded nucleic acid molecule selected from the single-stranded nucleic acid library is amplified by a nucleic acid amplification method known in the art. This step comprises only the DNA amplification substep when the single-stranded nucleic acid molecule to be sequenced is a DNA, and can comprise the reverse transcription substep, the DNA amplification substep, and the transcription substep in the case of an RNA to be sequenced.

All single-stranded nucleic acid molecules to be sequenced in this method are non-natural nucleotide-containing single-stranded nucleic acid molecules. In this step, however, only natural nucleotides are used as substrates in the nucleic acid amplification method, as in the first amplification step of the random library method. This means that only dNTPs are used as substrates for DNA replication in the DNA amplification substep; only dNTPs are used as substrates for reverse transcription from RNAs in the reverse transcription substep; and only NTPs are used as substrates for RNA transcription from DNAs in the transcription substep. As a result, the non-natural nucleotide is replaced with a natural nucleotide during the amplification reaction process so that single-stranded nucleic acid molecules constituted only by natural nucleotides are obtained as amplification products, even if the single-stranded nucleic acid molecule to be sequenced is a non-natural nucleotide-containing single-stranded nucleic acid molecule.

(2) Cloning Step

The "cloning step" (502) refers to the step of obtaining a single clone from amplification products constituted only by natural nucleotides obtained by the amplification step.

Each amplification product obtained by the third amplification step is constituted only by natural nucleotides, as mentioned above. Thus, even a plurality of different clones of non-natural nucleotide-containing single-stranded nucleic acid molecules selected from the single-stranded nucleic acid library can be prepared into single clones by an ordinary nucleic acid cloning technique known in the art as a result of replacement with a natural nucleotide. An exemplary method involves inserting each clone of the obtained nucleic acid aptamer into an appropriate cloning vector, which is then transferred to *E. coli* or the like, and isolating single clones as transformants. Such a cloning method may be performed according to a method described in, for example, Sambrook, J. et al., 1989, Molecular Cloning: A Laboratory Manual Second Ed., Cold Spring Harbor Laboratory Press, Cold Spring Harbor, N.Y. Alternatively, various cloning kits or the like are commercially available from each manufacturer and may be used in the present invention.

(3) Sequencing Step

The "sequencing step" (503) refers to the step of sequencing the single clone obtained by the cloning step. This step can be performed according to a technique known in the art. For example, single clones prepared from the transformants of the single clones can be sequenced by a technique known in the art via cycle sequencing reaction or the like. Specifically, an exemplary method can involve preparing DNAs from the transformants of the single clones by a technique known in the art such as a mini-preparation method, followed by sequencing using a commercially available kit such as Big Dye Terminator Cycle Sequencing Kit (Applied Biosystems Inc.) and a sequencer.

(4) Artificial Base Position Determination Step

The "artificial base position determination step" (504) refers to the step of determining the position of an artificial base on the nucleotide sequence of the single-stranded nucleic acid molecule templated for the single clone, on the basis of the nucleotide sequence of the identification site in the nucleotide sequence of the single clone.

The nucleotide sequence of the single-stranded nucleic acid molecule determined by the sequencing step is a nucleotide sequence constituted only by 4 natural bases (A, T, G, and C). Since all single-stranded nucleic acid molecules sequenced in the third amplification step of this method are non-natural nucleotide-containing single-stranded nucleic acid molecules, an artificial base is disposed at the particular position of the central region in the actual nucleotide sequence. In this step, the base replaced with the natural base in the third amplification step on the nucleotide sequence is modified to the original artificial base on the basis of the nucleotide sequence of the identification site in the nucleotide sequence of the single-stranded nucleic acid molecule after the sequencing step to determine the actual nucleotide sequence of the sequenced non-natural nucleotide-containing single-stranded nucleic acid molecule.

The identification site is disposed at the terminal site of the central region so as to flank the 5'-terminal and/or 3'-terminal primer-binding regions of the non-natural nucleotide-containing single-stranded nucleic acid molecule, and has a predetermined nucleotide sequence. Also, its nucleotide sequence, which is constituted by natural nucleotide(s), is maintained without change from the third amplification step to the sequencing step. In addition, the nucleotide sequence of the identification site is related to positional information about an artificial base predetermined on the nucleotide sequence of the central region. Thus, the determination of the nucleotide sequence of the identification site can inevitably reveal at what position the artificial base is disposed or has been disposed in the central region of the single-stranded nucleic acid molecule.

3. Anti-Vascular Endothelial Growth Factor Nucleic Acid Aptamer

The third embodiment of the present invention relates to an anti-vascular endothelial growth factor (hereinafter, abbreviated to "VEGF") nucleic acid aptamer.

VEGF functions as an angiogenic factor. This growth factor is known as a causative agent of age-related macular degeneration (AMD). The age-related macular degeneration is a progressive retinal disease that raises serious symptoms such as decreased visual performance or acquired blindness in adults. This disease has been found to become severe as its clinical condition is worsen with the progress of angiogenesis in the retina (Martin A. et al., 2003, Medicinal Research Reviews, Vol. 23, No. 2: 117-145; and Ferris III, F. L. et al., 1984, Archives of Ophthalmology, Vol. 102, Issue 11: 1640-1642).

The anti-VEGF nucleic acid aptamer of the present invention is a DNA aptamer comprising a non-natural nucleotide-containing single-stranded DNA molecule that strongly and specifically binds to VEGF as a target substance to suppress the angiogenic function of VEGF (hereinafter, this DNA aptamer is referred to as an "anti-VEGF DNA aptamer"). The anti-VEGF DNA aptamer of the present invention is produced by the method for producing a nucleic acid aptamer according to the first embodiment and sequenced by the random library method or the predetermination method according to the second embodiment.

The anti-VEGF DNA aptamer of the present invention comprises any one nucleotide sequence selected from the group consisting of SEQ ID NOs: 25 to 73, 80 to 104, 106 to 109, 111, and 155 to 166 (provided that "n" in the sequences represents Ds), 175, 177, 179, 181, 183, 198, 201, 202, 205 to 209, 211, 212, and 229 to 278. This region represented by any of SEQ ID NOs: 25 to 73, 80 to 104, 106 to 109, 111, and 155 to 166 (provided that "n" in the sequences represents Ds), 198, 201, 202, 205 to 209, 211, and 212 mainly corresponds to the central region (202) in the nucleic acid aptamer of the present invention shown in FIG. 2. Hence, a nucleic acid aptamer comprising each of these nucleotide sequences that is 5' flanked by the nucleotide sequence represented by SEQ ID NO: 1 and 3' flanked by the nucleotide sequence represented by SEQ ID NO: 2 is also preferred as the anti-VEGF DNA aptamer of the present invention.

4. Anti-Interferon-γ Nucleic Acid Aptamer

The fourth embodiment of the present invention relates to an anti-interferon-γ (hereinafter, abbreviated to "IFN-γ") nucleic acid aptamer.

The anti-IFN-γ nucleic acid aptamer of the present invention is a DNA aptamer comprising a non-natural nucleotide-containing single-stranded DNA molecule that strongly and specifically binds to an IFN-γ as a target substance to suppress the cytotoxic T cell-inducing activity of IFN-γ (hereinafter, this DNA aptamer is referred to as an "anti-IFN-γ DNA aptamer"). The anti-IFN-γ DNA aptamer of the present invention is produced by the method for producing a nucleic acid aptamer according to the first embodiment and sequenced by the predetermination method according to the second embodiment.

The anti-IFN-γ DNA aptamer of the present invention comprises any one nucleotide sequence selected from the group consisting of SEQ ID NOs: 167 to 174 (provided that "n" in the sequences represents Ds), 186, 188, 190, 192, 194, 214 to 222, and 279 to 328.

5. Pharmaceutical Composition

The fifth embodiment of the present invention relates to a pharmaceutical composition.

5-1. Constitution

The pharmaceutical composition of the present invention comprises at least one inhibitor of target substance function described in the third embodiment. The pharmaceutical composition of the present invention can also contain a pharmaceutically acceptable carrier. The "pharmaceutically acceptable carrier" refers to a substance that is usually used in the pharmaceutical formulating art and added without inhibiting or suppressing the effect of the pharmaceutical composition in order to facilitate the formulation of the pharmaceutical composition or its application to organisms and maintain the effect of the inhibitor of target substance function. Examples of the carrier include excipients, binders, disintegrants, fillers, emulsifiers, flow control additives, lubricants, and surfactants.

Examples of the "excipients" include sugars such as monosaccharides, disaccharides, cyclodextrin, and polysaccharides (specifically including, but not limited to, glucose, sucrose, lactose, raffinose, mannitol, sorbitol, inositol, dextrin, maltodextrin, starch, and cellulose), metal salts (e.g., sodium phosphate or calcium phosphate, calcium sulfate, and magnesium sulfate), citric acid, tartaric acid, glycine, low-, middle-, or high-molecular-weight polyethylene glycol (PEG), Pluronic, and combinations thereof.

Examples of the "binders" include starch glues composed of corn, wheat, rice, or potato starch, gelatin, tragacanth, methylcellulose, hydroxypropylmethylcellulose, sodium carboxymethylcellulose, polyvinylpyrrolidone, and combinations thereof.

Examples of the "disintegrants" include the starches described above, carboxymethyl starch, cross-linked polyvinylpyrrolidone, agar, alginic acid or sodium alginate, and salts thereof.

Examples of the "fillers" include the sugars described above, calcium phosphate (e.g., tricalcium phosphate or calcium hydrogen phosphate), and combinations thereof.

Examples of the "emulsifiers" include sorbitan fatty acid ester, glycerin fatty acid ester, sucrose fatty acid ester, and propylene glycol fatty acid ester.

Examples of the "flow control additives" and the "lubricants" include silicate, talc, stearate, and polyethylene glycol.

Such carriers can be used appropriately according to the need. The pharmaceutical composition of the present invention may also contain, in addition to the additives described above, optional additives such as corrigents, solubilizers, suspending agents, diluents, surfactants, stabilizers, absorption promoters (e.g., quaternary ammonium salts and sodium lauryl sulfate), expanders, wetting agents, humectants (e.g., glycerin and starch), adsorbents (e.g., starch, lactose, kaolin, bentonite, and colloidal silicic acid), disintegration inhibitors (e.g., saccharose, stearin, cacao butter, and hydrogenated oil), coating agents, coloring agents, preservatives, antioxidants, fragrances, flavors, sweeteners, and buffers.

The "surfactants" correspond to, for example, alkali metal salts, alkaline earth metal salts, and ammonium salts of lignosulfonic acid, naphthalenesulfonic acid, phenolsulfonic acid, or dibutylnaphthalenesulfonic acid, alkylaryl sulfonate, alkyl sulfate, alkyl sulfonate, fatty alcohol sulfate, fatty acid and sulfated fatty alcohol glycol ether, condensates of sulfonated naphthalene or naphthalene derivatives and formaldehyde, condensates of naphthalene or naphthalenesulfonic acid, phenol, and formaldehyde, polyoxyethylene octylphenyl ether, ethoxylated isooctylphenol, octylphenol, nonylphenol, alkylphenyl polyglycol ether, tributylphenyl polyglycol ether, tristearylphenyl polyglycol ether, alkylaryl polyether alcohol, alcohol and fatty alcohol/ethylene oxide condensates, ethoxylated castor oil, polyoxyethylene alkyl ether, ethoxylated polyoxypropylene, lauryl alcohol polyglycol ether acetal, sorbitol ester, lignosulfite waste liquors, and methylcellulose.

The pharmaceutical composition of this embodiment may contain one or more of these carriers per pharmaceutical composition.

The pharmaceutical composition of the present invention can further contain an additional drug without canceling the pharmacological effect of the nucleic acid of the present invention. The pharmaceutical composition of the present invention may contain, for example, a predetermined amount of an antibiotic.

The pharmaceutical composition of the present invention is not particularly limited by its dosage form as long as the form does not deactivate the active ingredient and can exert the pharmacological effect in vivo after administration. The dosage form usually differs depending on an administration method and/or prescription conditions.

Examples of dosage forms suitable for oral administration can include solid preparations (including tablets, pills, sublingual preparations, capsules, drops, and troches), granules, dusts, powders, and liquid preparations. The solid preparations can be prepared, if necessary, in coated dosage forms known in the art, for example, as sugar-coated tablets, gelatin-coated tablets, enteric coated tablets, film-coated tablets, bilayer tablets, or multilayer tablets.

Parenteral administration is subdivided into systemic administration and local administration. The local administration is further subdivided into interstitial administration, transepidermal administration, transmucosal administration, and transrectal administration. The pharmaceutical composition can also be prepared in a dosage form suitable for each administration method. Examples of dosage forms suitable for systemic or interstitial administration include injections which are liquid preparations. Examples of dosage forms suitable for transepidermal administration or transmucosal administration can include liquid preparations (including liniments, eye drops, nasal drops, and inhalants), suspensions (including emulsions and creams), dusts (including nasal drops and inhalants), pastes, gels, ointments, and plasters. Examples of dosage forms suitable for transrectal administration can include suppositories.

In the case of drug administration to plants, examples of the dosage form of the pharmaceutical composition include liquids, solids (including semi-solids), and combinations thereof. In this case, the pharmaceutical composition can be prepared as solutions, oil dispersions, emulsions, suspensions, dusts, powders, pastes, gels, pellets, tablets, and granules.

These dosage forms are not particularly limited by their specific shapes or sizes and can have any shape or size that falls within ranges accepted for each dosage form known in the art.

5-2. Production Method

The pharmaceutical composition of the present invention can be produced by the application of a formulation method known in the art, as a rule. See a method described in, for example, Remington's Pharmaceutical Sciences (Merck Publishing Co., Easton, Pa.).

For example, the injection can be produced by a method routinely used in the art which involves dissolving the nucleic acid molecule of the second embodiment in a pharmaceutically acceptable solvent and adding, if necessary, a pharmaceutically acceptable carrier to the resulting solution.

Examples of the "pharmaceutically acceptable solvent" include water, ethanol, propylene glycol, ethoxylated isostearyl alcohol, polyoxygenated isostearyl alcohol, and polyoxyethylene sorbitan fatty acid esters. Desirably, such a solvent is sterilized and preferably adjusted, if necessary, to be isotonic to blood.

5-3. Administration Method

The pharmaceutical composition of this embodiment can be administered to an organism in a pharmaceutically effective amount for the treatment or prevention of the disease of interest or the like. The recipient organism is a vertebrate, preferably a mammal, more preferably a human.

The pharmaceutical composition of the present invention may be administered systemically or locally. An appropriate route can be selected according to, for example, the type, site of onset, or degree of progression of the disease. For a disease whose onset is localized to a site, local administration is preferred in which the pharmaceutical composition of the present invention is directly administered to the site of onset and its neighborhood through injection or the like. This is because the nucleic acid molecule of the present invention can be delivered in sufficient amounts to the site (tissue or organ) to be treated with little influence on the other tissues. For a disease whose site to be treated cannot be identified or a disease whose onset is systemic, systemic administration through intravenous injection or the like is preferred, though the administration route is not limited thereto. This is because the nucleic acid molecule of the present invention can be distributed throughout the body via blood flow and thereby delivered even to a lesion that cannot be found by diagnosis.

The pharmaceutical composition of the present invention can be administered by any appropriate method without deactivating the active ingredient. For example, any of parenteral (e.g., injection, aerosol, application, eye drop, and nasal drop) and oral administrations can be performed. Injection is preferred.

In the case of administration through injection, an injection site is not particularly limited. The injection site may be any site at which the nucleic acid molecule serving as an active ingredient can bind to the target substance to thereby suppress its functions. Examples thereof include intravenous, intraarterial, intrahepatic, intramuscular, intraarticular, intramedullary, intraspinal, intraventricular, transpulmonary, transdermal, hypodermic, intradermal, intraperitoneal, intranasal, enteral, and sublingual injections. Intravascular injection such as intravenous injection or intraarterial injection is preferred. This is because, as mentioned above, the pharmaceutical composition of the present invention can be distributed throughout the body via blood flow and also because this injection is relatively low invasive.

6. Method for Detecting Target Substance

The sixth embodiment of the present invention relates to a method for detecting a target substance using the nucleic acid aptamer according to the first embodiment.

6-1. Constitution

The nucleic acid aptamer according to the first embodiment is capable of very strongly and specifically binding to a target substance of the nucleic acid molecule. The target substance present in a sample can therefore be detected by use of this property of the nucleic acid molecule.

The detection method itself can be any detection method known in the art as long as the method is based on the binding between the nucleic acid aptamer according to the first embodiment and the target substance. For example, a SPR method, a quartz crystal microbalance method, turbidimetry, colorimetry, or fluorometry can be used.

SPR (surface plasmon resonance) refers to a phenomenon in which as a thin metal film is irradiated with laser beam, reflected light intensity remarkably attenuates at a particular angle of incidence (resonance angle). The SPR method is an assay method based on this phenomenon and is capable of highly sensitively assaying a substance adsorbed on the surface of the thin metal film serving as a sensor portion. In the present invention, for example, the nucleic acid aptamer of the first embodiment is immobilized in advance onto the surface of a thin metal film. A sample is flowed on the thin metal film surface to allow the target substance to bind to the nucleic acid molecule. The resulting difference in the substance adsorbed on the metal surface between before and after the sample flowing can be detected to thereby detect the target substance in the sample. SPR methods such as a displacement method and an indirect competitive method are known, any of which may be used in the present invention.

The quartz crystal microbalance (QCM) method refers to a method using a phenomenon in which the resonance frequency of a quartz crystal decreases according to the mass of the substance adsorbed onto the surface of electrodes attached to the quartz crystal. A QCM sensor based on this method can quantitatively capture a trace amount of the adsorbed substance according to the amount of change in the resonance frequency of a quartz crystal. In the present invention, the nucleic acid molecule is immobilized in advance, as in the SPR method, onto the electrode surface. A sample is contacted with the electrode surface. The target substance in the sample can be quantitatively detected from the amount of change in the resonance frequency of a quartz crystal caused by the binding between the nucleic acid molecule and the target substance. This technique is well known in the art. See, for example, Christopher J., et al. (2005), Self-Assembled Monolayers of a Form of Nanotechnology, Chemical Review, 105: 1103-1169.

The turbidimetry refers to a method which involves irradiating a solution with light and optically measuring the attenuation of light scattered by a substance floating in the solution or light transmitted through the solution using a colorimeter or the like to determine the amount of the substance in the solution. In the present invention, absorbance can be measured before and after addition of the nucleic acid aptamer of the first embodiment into a sample to thereby quantitatively detect the target substance in the sample.

Alternatively, the target substance may be detected by combined use with an antibody against the target substance. For example, a method based on sandwich ELISA may be used. This method involves first immobilizing the nucleic acid aptamer of the first embodiment onto a solid-phase carrier and next adding a sample thereto to allow the nucleic acid molecule to bind to the target substance present in the sample. Subsequently, the sample is washed off. Then, the anti-target substance antibody is added thereto and allowed to bind to the target substance. After washing, the anti-target substance antibody can be detected using an appropriately labeled secondary antibody to thereby detect the target substance in the sample. An insoluble carrier in the form of, for example, beads, a microplate, a test tube, a stick, or a test piece made of a material such as polystyrene, polycarbonate, polyvinyltoluene, polypropylene, polyethylene, polyvinyl chloride, nylon, polymethacrylate, latex, gelatin, agarose, cellulose, Sepharose, glass, a metal, a ceramic, or a magnetic material can be used as the solid-phase carrier.

7. Catalyzing Enzyme (Deoxyribozyme or Ribozyme)

The seventh embodiment of the present invention relates to a catalyzing enzyme.

7-1. Constitution

The "deoxyribozyme" refers to a DNA molecule having catalytic activity and is also called a DNA catalyst. The "ribozyme" refers to an RNA molecule having catalytic activity and is also called a ribonucleic acid enzyme. These enzymes specifically bind to target substances such as RNA molecules or low-molecular-weight compounds as substrates to cleave or ligate the target RNA molecules or function to catalyze chemical reaction such as oxidation or reduction.

The deoxyribozyme of the present invention comprises a natural deoxyribonucleotide and a non-natural deoxyribonucleotide and is constituted by a replicable polynucleotide.

The ribozyme of the present invention comprises a natural ribonucleotide and a non-natural ribonucleotide and is constituted by a transcribable or replicable polynucleotide.

The non-natural nucleotide contained in the deoxyribozyme or the ribozyme of the present invention (hereinafter, also referred to as a "(deoxy)ribozyme" in the present specification) is constituted by an artificial base. The artificial base is not particularly limited by its type as long as the artificial base has the properties of the artificial base described in the first embodiment. Examples thereof include artificial bases listed as specific examples of the above artificial base and derivatives of the artificial base described later.

The content of the non-natural nucleotide in the (deoxy) ribozyme of the present invention can be 20% or less, preferably 15% or less, more preferably 10% or less, of the total number of nucleotides constituting the (deoxy)ribozyme. Usually, a (deoxy)ribozyme of 100 or less bases in full length can produce the effect of the present invention, if having 1 to 4 non-natural nucleotides per (deoxy)ribozyme.

When a plurality of non-natural nucleotides are contained per (deoxy)ribozyme, the artificial bases of these non-natural nucleotides may be the same and/or different. When these artificial bases are different, it should be noted that two or more artificial bases having an identical complementary artificial base do not coexist with each other in one (deoxy) ribozyme. This is because the original artificial base might be replaced with another artificial base via the complementary artificial base during the replication or transcription process. For example, in a (deoxy)ribozyme comprising nonspecific nucleotides respectively having Pn and Pa, the positions of Pn and Pa might be replaced with the other via their complementary artificial base Ds during the replication process.

The base of the non-natural nucleotide constituting the (deoxy)ribozyme of the present invention may be the derivative of the artificial base exemplified in the first embodiment.

7-2. Method for Producing (Deoxy)Ribozyme

The method for producing the deoxyribozyme of the present invention comprises a complex formation step, a complex recovery step, a single-stranded nucleic acid molecule recovery step, a DNA amplification step, a deoxyribozyme preparation step, and a catalytic activity confirmation step as essential steps. The method for producing the deoxyribozyme of the present invention may comprise a repetitive step as an optional step.

The method for producing the ribozyme of the present invention comprises a complex formation step, a complex recovery step, a single-stranded nucleic acid molecule recovery step, a reverse transcription step, a DNA amplification step, a transcription step, a ribozyme preparation step, and a catalytic activity confirmation step as essential steps. The method for producing the ribozyme of the present invention may comprise a repetitive step as an optional step.

Of these steps, the complex formation step, the complex recovery step, the single-stranded nucleic acid molecule recovery step, and the repetitive step can be performed according to the complex formation step, the complex recovery step, the single-stranded nucleic acid molecule recovery step, and the repetitive step, respectively, in the method for producing a nucleic acid aptamer. Also, the reverse transcription step, the DNA amplification step, and the transcription step can be performed according to the reverse transcription substep, the DNA amplification substep, and the transcription substep, respectively, in the amplification step of the method for producing a nucleic acid aptamer. The (deoxy)ribozyme preparation step, as with the nucleic acid aptamer preparation step in the method for producing a nucleic acid aptamer, can involve self-folding the obtained single-stranded nucleic acid molecule to prepare the (deoxy)ribozyme of the present invention having binding activity against a target substance and enzymatic activity. The catalytic activity confirmation step refers to the step of confirming the catalytic activity of the (deoxy) ribozyme and can involve confirming whether or not the (deoxy)ribozyme catalyzes a substrate serving as its target substance on the basis of the state of the substrate as a reaction product by a technique known in the art.

8. Kit for Nucleic Acid Aptamer, Deoxyribozyme, or Ribozyme Production

The eighth embodiment of the present invention relates to a kit for producing the nucleic acid aptamer according to the first embodiment or the ribozyme according to the seventh embodiment.

The kit of the present invention comprises the single-stranded nucleic acid library comprising a non-natural nucleotide-containing single-stranded nucleic acid molecule according to the first embodiment, and a primer set having sequences complementary to the primer-binding regions of the single-stranded nucleic acid molecule constituting the single-stranded nucleic acid library. The kit may further comprise an instruction manual of the kit.

EXAMPLES

Example 1

Production of DNA Aptamer Binding to VEGF-165—(1)

(1) Preparation of Library of Single-Stranded DNAs Each Comprising Artificial Base Ds at Particular Site of Central Region For libraries of single-stranded DNAs (97 bases or 98 bases in full length) each comprising the artificial base Ds at a particular site of the central region, first, 22 types of DNA library sequences (see below) each having the artificial base Ds assigned to 1 to 3 arbitrary particular positions in the central region were each chemically synthesized and gel-purified. Then, these various DNA libraries were mixed in equal amounts and used as the first libraries for the method for producing a nucleic acid aptamer according to the present invention. In order to identify at what position Ds was disposed in the central region even in a mixed state of these various single-stranded DNAs, a 2-base or 3-base tag sequence was incorporated as an identification site in the central region, immediately downstream of the 5'-terminal PCR primer-binding region. As a result, the library from which a DNA fragment is derived and the position at which the artificial base is incorporated can be determined by sequence analysis even after replacement of the artificial base in the DNA fragment with a natural base by PCR.

The chemically synthesized 22 types of DNA library sequences will be shown below.

N43Ds-01:
SEQ ID NO: 3
5'-CTGTCAATCGATCGTATCAGTCCAC(AA)NNNNNNNNNNNNNDsN
NNNNNNNNNNNNNNNNNNNNNNNNNNNNGCATGACTCGAACGGATTAG
TGACTAC-3';

N43Ds-02:
SEQ ID NO: 4
5'-CTGTCAATCGATCGTATCAGTCCAC(AT)NNNNNNNNNNNNNNNN
NNNNNNNNNNDsNNNNNNNNNNNNNNNNGCATGACTCGAACGGATTAG
TGACTAC-3';

N43Ds-03:
SEQ ID NO: 5
5'-CTGTCAATCGATCGTATCAGTCCAC(AG)NNNNNNNNNNNNNNNN
DsNNNNNNNNNNNNNNNNNDsNNNNNNNNNNNNGCATGACTCGAACGGATTA
GTGACTAC-3';

N43Ds-04:
SEQ ID NO: 6
5'-CTGTCAATCGATCGTATCAGTCCAC(TA)NNNNNNNNNNNDsNNNN
NNNNNNNNNNDsNNNNNNNNNNNNNNNNNNGCATGACTCGAACGGATTA
GTGACTAC-3';

N43Ds-05:
SEQ ID NO: 7
5'-CTGTCAATCGATCGTATCAGTCCAC(TT)NNNNNNNNNNNDsNNNN
NNNDsNNNNNNNNNNNNNNNNNNNNNNNNGCATGACTCGAACGGATTA
GTGACTAC-3';

N43Ds-06:
SEQ ID NO: 8
5'-CTGTCAATCGATCGTATCAGTCCAC(TG)NNNNNNNNNNNNNNNN
NNNNNNNNDsNNNNNNNDsNNNNNNNNNNNGCATGACTCGAACGGATTA
GTGACTAC-3';

N43Ds-07:
SEQ ID NO: 9
5'-CTGTCAATCGATCGTATCAGTCCAC(TC)NNNNNNNNNNNDsNNNN
NNNNNNDsNNNNNNNNNNNDsNNNNNNNNNNNGCATGACTCGAACGGATT
AGTGACTAC-3';

N43Ds-08:
SEQ ID NO: 10
5'-CTGTCAATCGATCGTATCAGTCCAC(GA)NNNNNNNNNNNNNNNN
NNDsNNNNNNNNNDsNNNNNNNDsNNNNNNNNNGCATGACTCGAACGGATT
AGTGACTAC-3';

N43Ds-09:
SEQ ID NO: 11
5'-CTGTCAATCGATCGTATCAGTCCAC(GT)NNNNNNNNDsNNNNNNNDs
NNNNNNNNNNNDsNNNNNNNNNNNNNNNNNNNNGCATGACTCGAACGGATTA
GTGACTAC-3';

N43Ds-10:
SEQ ID NO: 12
5'-CTGTCAATCGATCGTATCAGTCCAC(CA)NNNNNNNNNNNNDsNNN
NNNNNNDsNNNNNNNNNNNNNNDsNNNNNNNNGCATGACTCGAACGGATT
AGTGACTAC-3';

N43Ds-11:
SEQ ID NO: 13
5'-CTGTCAATCGATCGTATCAGTCCAC(CT)NNNNNNNNNNNNDsNNN
NNNNNNNNDsNNNNNNNNNNNDsNNNNNNNNGCATGACTCGAACGGATT
AGTGACTAC-3';

N43Ds-12:
SEQ ID NO: 14
5'-CTGTCAATCGATCGTATCAGTCCAC(CAG)NNNNNNNNNNDsNNNN
NNNNNNNNNNNNDSNNNNNNNDsNNNNNNNNNGCATGACTCGAACGGAT
TAGTGACTAC-3';

N43Ds-13:

SEQ ID NO: 15

5'-CTGTCAATCGATCGTATCAGTCCAC(CAT)NNNNNNNNNDsNNNN
NNDsNNNNNNDsNNNNNNNNNNNNNNNNNNNGCATGACTCGAACGGAT
TAGTGACTAC-3';

N43Ds-14:

SEQ ID NO: 16

5'-CTGTCAATCGATCGTATCAGTCCAC(TAT)NNNNNNNNNNNNNNN
NDsNNNNNNDsNNNNNNDsNNNNNNNNNNNNNGCATGACTCGAACGGAT
TAGTGACTAC-3';

N43Ds-15:

SEQ ID NO: 17

5'-CTGTCAATCGATCGTATCAGTCCAC(TTA)NNNNNNNNNNNNNNN
NDsNNNNNNDsNNNNNNNNNDsNNNNNNNNNGCATGACTCGAACGGAT
TAGTGACTAC-3';

N43Ds-16:

SEQ ID NO: 18

5'-CTGTCAATCGATCGTATCAGTCCAC(GCT)NNNNNNNNNNNNNNN
NNNNNNNNDsNNNNNDsNNNNNNNNNNNNNNNGCATGACTCGAACGGATT
AGTGACTAC-3';

N43Ds-17:

SEQ ID NO: 19

5'-CTGTCAATCGATCGTATCAGTCCAC(CCA)NNNNNNNNNNNNNNN
NNNNNNNDsNNNNNNDsNNNNNNNNNNNNNNNGCATGACTCGAACGGATT
AGTGACTAC-3';

N43Ds-18:

SEQ ID NO: 20

5'-CTGTCAATCGATCGTATCAGTCCAC(CCT)NNNNNNNNNNNNNNN
NNNNNNDsNNNNNNNDsNNNNNNNNNNNNNNNGCATGACTCGAACGGATT
AGTGACTAC-3';

N43Ds-19:

SEQ ID NO: 21

5'-CTGTCAATCGATCGTATCAGTCCAC(GGA)NNNNNNNNNNNNNN
NNNNNNNDsNNNNNNNDsNNNNNNNNNNNNNNGCATGACTCGAACGGA
TTAGTGACTAC-3';

N43Ds-20:

SEQ ID NO: 22

5'-CTGTCAATCGATCGTATCAGTCCAC(GGT)NNNNNNNNNNNNNN
NNNNDsNNNNNNNNDsNNNNNNNNNNNNNNNGCATGACTCGAACGGATT
AGTGACTAC-3';

N43Ds-21:

SEQ ID NO: 23

5'-CTGTCAATCGATCGTATCAGTCCAC(CGA)NNNNNNNNNNNNNN
NNNNDsNNNNNNNNNDsNNNNNNNNNNNNNNNGCATGACTCGAACGGA
TTAGTGACTAC-3';

N43Ds-22:

SEQ ID NO: 24

5'-CTGTCAATCGATCGTATCAGTCCAC(CGT)NNNNNNNNNNNNNN
NNNDsNNNNNNNNNNDsNNNNNNNNNNNNNNNGCATGACTCGAACGGATT
AGTGACTAC-3';

In these sequences, N=A, G, C, or T; the 5' fixed sequence (corresponding to a 5'-PCR primer sequence) represents CTGTCAATCGATCGTATCAGTCCAC (SEQ ID NO: 1); the 3' fixed sequence (corresponding to a sequence complementary to a 3' PCR primer sequence represented by SEQ ID NO: 149) represents GCATGACTCGAACGGATTAGTGACTAC (SEQ ID NO: 2); and the sequence within parentheses represents an identification site.

(2) Production of VEGF-165-Binding Single-Stranded DNA Aptamer Comprising Ds

VEGF-165-binding DNA aptamers were isolated by procedures described below according to a nucleic acid-protein complex immobilization method using each single-stranded DNA library prepared in the preceding paragraph (1), the target protein human VEGF-165 (PeproTech, Inc.), and magnetic beads.

A. Operation of 1 Selection Round (i) Binding Between Target Protein and DNA Library Each single-stranded DNA library was dissolved in a PBS solution (1.1 mM $KH_2PO_4$, 155 mM NaCl, and 3 mM $Na_2HPO_4$, pH 7.4) and subjected to folding treatment (90° C. for 3 min→60° C. for 3 min→25° C.) for forming a conformation in the DNA molecules. Then, the library solution was mixed with a PBS solution containing Nonidet P-40 to adjust the final concentration of Nonidet P-40 to 0.05%. In order to exclude nucleic acid fragments that were nonspecifically adsorbed onto magnetic beads from the library, the resulting nucleic acid solution was mixed with 0.2 mg of streptavidin-coupled magnetic beads (Hydrophilic Streptavidin Magnetic Beads, New England Biolabs Inc.), and the mixture was inverted and mixed at room temperature for 30 minutes. After removal of the magnetic beads using a magnetic stand and centrifugation operation, the supernatant was mixed with the target protein VEGF-165 and incubated at 25° C. for 30 minutes to form DNA-protein complexes.

(ii) Screening for DNA Sequence Bound with Target Protein

An aqueous solution of 9% (vol) 10 mM EZ-link Sulfo-NHS-LC-Biotin (Thermo Fischer Scientific Inc.) was added (final concentration: 0.83 mM) into the mixed solution thus obtained, and the mixture was incubated at 25° C. for 15 minutes for protein biotinylation. Unreacted biotinylating reagents were removed by ultrafiltration using Microcon 50 (Millipore Corp.). Then, the resulting solution was mixed with streptavidin-coupled magnetic beads and incubated at room temperature for 10 minutes to immobilize the DNA-protein complexes onto the magnetic beads. In order to wash off unbound proteins or nucleic acids nonspecifically adsorbed on magnetic beads, the operation of suspending the magnetic beads in 40 ml of a PBS solution containing 0.05% Nonidet P-40 (buffer solution A), and incubating the suspension at 37° C. for 30 minutes was then repeated 2 to 3 times. To the magnetic beads thus washed, 400 µl of an eluting solution (100 mM sodium citrate (pH 5.0), 7 M urea, and 3 mM EDTA) was added, and the mixture was heated at 90° C. for 5 minutes to dissociate the protein-DNA complexes. Then, the DNAs thus dissociated from the proteins were recovered from the eluate by phenol-chloroform extraction and isopropyl alcohol precipitation operation and used as PCR templates in library preparation for the subsequent selection round.

(iii) Preparation (Amplification) of Single-Stranded DNA Library

Each single-stranded DNA library for use in the subsequent round was prepared by: performing PCR amplification using the template DNAs obtained by the preceding selection round and biotin-modified primers; then separating single strands of DNA fragments comprising Ds on the basis of a gel shift using the binding with streptavidin; and eluting and recovering the DNA fragments from the gel. PCR was performed (volume: 400 μl) using AccuPrime Pfx DNA polymerase (Invitrogen Corp.). The reaction composition was 1× AccuPrime Pfx reaction mix (containing 0.3 mM dNTPs and 1 mM MgSO$_4$), 1 μM 5'-primer (sequence: see below), 1 μM 3'-primer (sequence: see below), 0.1 mM dNTPs (N=A, G, C, and T) (final concentration: 0.4 mM), 0.5 mM MgSO$_4$ (final concentration: 1.5 mM), 50 μM dDsTP, 50 μM Diol1-dPxTP, and 0.05 U/μl AccuPrime Pfx DNA polymerase. The PCR cycle conditions involved (94° C. for 30 sec→50° C. for 30 sec→65° C. for 2 min)×13 to 19 cycles.

```
                                       (SEQ ID NO: 1)
5'-primer:    5'-CTGTCAATCGATCGTATCAGTCCAC-3'

(SEQ ID NO: 148; B = biotin-modified T)
3'-primer:    5'-BGTAGTCACTAATCCGTTCGAGTCATGC-3'
```

DNAs were recovered from the PCR solution by ethanol precipitation and then dissolved by the addition of 5 μl of SA buffer solution (10 mM Tris-HCl (pH 7.6), 50 mM NaCl, and 1 mM EDTA) per 0.1 ml of the PCR solution. The solution was heated at 75° C. for 3 minutes to denature the DNAs into single strands. To this solution, 12.5 μg of streptavidin (5 mg/ml SA buffer solution, 2.5 μl) per 0.1 ml of the PCR solution was added, and the mixture was incubated at 25° C. for 30 minutes to form biotin-avidin complexes. To this complex-containing solution, the same volume of 10 M urea-1×TBE solution was added, and the amplified single-stranded DNA library was then separated using a 6% polyaramide denaturing gel containing 7 M urea, eluted and recovered from the gel, and used as a library for the subsequent round.

B. Condition of Selection Round in Repetitive Step

The selection conditions of each round are shown in Table 1.

species was 300 pmol, i.e., approximately 2×10$^{14}$ molecules. In order to render the protein-DNA complex formation conditions stricter, protein and DNA concentrations were gradually decreased, while an excessive amount of a DNA fragment (5'-TGTGGGGGTGGACGGGCCGGGTAGA-3') (SEQ ID NO: 147) previously reported as a VEGF-binding DNA aptamer was added as a competitive DNA molecule (Competitor) during protein-DNA library mixing in round 8. In round 7, washing with 40 ml of buffer solution A was performed twice, followed by additional operation of inverting and mixing using buffer solution A (1 ml, at room temperature for 15 min) containing 3 M urea to render the washing conditions further stricter. In round 8, the washing operation in the presence of urea was repeated twice.

(3) Sequencing of DNA Aptamer Obtained by Selection

The DNA aptamers obtained by selection were sequenced using two methods described below.

(i) Sequencing of DNA Aptamer by Cloning Method Using E. coli

Aliquots of the single-stranded DNAs recovered in the selection after the final round (round 8) were used as templates in PCR to replace the artificial base Ds with a natural base. The PCR products were cloned by a conventional method. Specifically, 5 cycles of PCR (volume: 20 μl) were performed in the presence of 1 μM each primer (5'-primer: 5'-CTGTCAATCGATCGTATCAGTCCAC-3' (SEQ ID NO: 1) and 3'-primer: 5'-GTAGTCACTAATC-CGTTCGAGTCATGC-3' (SEQ ID NO: 149)) and 20 nM template single-stranded DNA with the reaction composition of 0.3 mM dNTPs (N=A, G, C, and T), 50 μM dPa'TP, and 1× Titanium Taq in 1× Titanium Taq PCR buffer (Clontech Laboratories, Inc.). In this PCR, dPa'TP was intentionally added. This is because the artificial base Ds, depending on its flanking sequence, may be difficult to amplify using only natural base substrates, and Pa', which is susceptible to replacement with a natural base, is incorporated instead of Ds, at a position complementary to Ds in the first cycle of PCR in order to reduce variations in the efficiency of replacement with a natural base. The PCR cycle conditions involved 94° C. for 1 min→(94° C. for 30 sec→68° C. for 2 min)×5 cycles→75° C. for 10 min. A portion (4 μl) of the PCR products was cloned into E. coli (Top10) using TOPO TA cloning kit (Invitrogen Corp.). A plasmid derived from each clone was recovered, and each clone was sequenced. Of the determined sequences of the clones, the nucleotide sequences (14 types) of 35 clones

TABLE 1

Condition of selection by predetermination method in preparation of DNA aptamer binding to VEGF-165

| Selection Round | ssDNA | | VEGF-165 | | Competitor | | volume | Number of washing | | PCR cycles |
|---|---|---|---|---|---|---|---|---|---|---|
| | pmol | nM | pmol | nM | pmol | nM | μl | A | B | |
| 1 | 300 | 1000 | 150 | 500 | | | 300 | 2* | | 13 |
| 2 | 40 | 500 | 40 | 500 | | | 80 | 2 | | 14 |
| 3 | 10 | 250 | 10 | 250 | | | 40 | 2 | | 17 |
| 4 | 10 | 62.5 | 40 | 250 | | | 160 | 2 | | 16 |
| 5 | 5 | 15.2 | 20 | 60.6 | | | 330 | 2 | | 18 |
| 6 | 5 | 15.2 | 20 | 60.6 | | | 330 | 3 | | 13 |
| 7 | 10 | 10 | 5 | 5 | | | 1000 | 2 | 1 | 18 |
| 8 | 10 | 10 | 5 | 5 | 1000 | 1000 | 1000 | 2 | 2 | 19 |

For the first round, the mixture of equal amounts of 22 types of DNA library sequences prepared by chemical synthesis was directly used. The total number of molecular each having 45 or 46 bases between the primer sequences and having the tag sequence are shown in Table 2.

TABLE 2

Nucleotide sequences of 35 clones obtained by selection after 8 rounds (determined by cloning method using E. coli) (Primers disclosed as SEQ ID NOS 1 and 2, respectively) 5'-CTGTCAATCGATCGTATCAGTCCAC-(Tag sequence)$_{2-3}$-(N)$_{43}$-GCATGACTCGAACGGATTAGTGACTAC-3'

| Clone | (Tag sequence)$_{2-3}$-(N)$_{43}$ | | SEQ ID NO. |
|---|---|---|---|
| cN43Ds-01-44 | (1) | AAGTGTTCTGGAGACnCTTAGGATGTCGCGGAGGGGTGCGGCCTT | 25 |
| cN43Ds-01-46 | (1) | AAAAATGCGAGGGTCnGTGGCGTAGGTTCGGAAATTTTGTTATGT | 26 |
| cN43Ds-01-43 | (1) | AAAAATGCGGGGGTCnGTGGCGTAGGTTCGGAAATTTTGTTATGT | 27 |
| cN43Ds-02-01 | (2) | ATGGAATTGTGGGGCCGGAATCTGTTATGTnTGCCAGGAAGGAGC | 28 |
| cN43Ds-02-18 | (2) | ATGGAAATGTGGGGCCGGAATCTGTTATGTnTGCCAGGAAGGAGC | 29 |
| cN43Ds-02-26 | (1) | ATCTTGCACGCGGGGGGTTCTGGTGTAGGAnCGGAGGGAAAGTGC | 30 |
| cN43Ds-08-07 | (2) | GAGGAATGTCCAGCGCTGGGnTTGGAGGGGnGTCGGAnTGGGCTC | 31 |
| cN43Ds-08-37 | (1) | GAGGGCGGCTTAAACAAGGGnTTGGGGGGGnGTCGGTnGTAAGGC | 32 |
| cN43Ds-08-24 | (1) | GATGAAGAGGGTGGCGTCCGnACGGGGGGGnAGGTATnCACGTAG | 33 |
| cN43Ds-09-11 | (3) | GTCTAAGTAnGGTGGGnTTGGCGGGGnTGTCGGATATACTTTGAC | 34 |
| cN43Ds-10-13 | (4) | CACAATATTCGGGnTTGGAGGGGnGTCGGGTGGATAGnTGGTGCT | 35 |
| cN43Ds-20-21 | (4) | GGTAGGGTAAGTAGGTATTGCCnGTCGTAGCnTGGATGGCGTGCCG | 36 |
| cN43Ds-21-04 | (11) | CGATTCCTTATCCTAGGACTTnTTTCCGCGCnCACGTGCTCAGATT | 37 |
| cN43Ds-21-33 | (1) | CGATTCCTTTTCCTAGGACTTnTTTCCGCGCnCACGTGCTCAGATT | 38 |

The position of the artificial base Ds was determined on the basis of the sequences of the DNA libraries classified according to the tag sequence. The largest number of clones was the cN43Ds-21-04 sequence, whereas a motif analogous to the sequence GGGDsTTGGAGGGGDsGTCGG (SEQ ID NO: 336) contained in cN43Ds-08-07 was shown to be conservatively contained in other clones. Also, the nucleotide sequence at the position of the artificial base Ds predicted from the tag sequence was shown to be replaced with A or T in most clones. The A or T mutation of the sequence at the position corresponding to the artificial base Ds strongly suggests that the artificial base is retained even during PCR through selection.

(ii) Sequencing of DNA Aptamer Using Next-Generation Sequencer (Life Technologies Corp.; Ion Torrent the Personal Genome Machine™ (PGM™))

PCR for replacement of the artificial base with a natural base shown in the preceding paragraph (i) was performed at a volume of 100 µl. The obtained PCR products were purified using Wizard® SV Gel and PCR Clean-Up System (Promega Corp.). A library was prepared from the DNAs thus purified using Ion Fragment Library Kit (Life Technologies Corp.) according to a method described in the manual attached thereto. The obtained DNA library was quantified using Ion Library Quantification Kit (Life Technologies Corp.), diluted to a predetermined concentration, and then treated with Ion Xpress™ Template Kit v2.0 (Life Technologies Corp.) to prepare template DNAs for analysis with The Personal Genome Machine™ (PGM™) from Life Technologies Corp. Then, Ion Torrent PGM™ sequencing was performed using Ion Sequencing Kit (Life Technologies Corp.). The total number of reads thus obtained was analyzed using CLC Genomics Workbench (version 4.7.2) from CLC bio Japan, Inc. Specifically, the Ds-containing library sequences were screened for analyte sequences consecutively comprising 25-base 5'-primer—tag sequence (varying)—43-base sequence—6-base partial sequence (GCATGA) of the 3'-primer with the number of reads of 2 or more for identical sequences, while complementary sequences of the Ds-containing library sequences were screened for analyte sequences consecutively comprising 27-base 3'-primer—43-base sequence—tag sequence (varying)—6-base partial sequence (GTGGAC) of the 5'-primer with the number of reads of 2 or more for identical sequences. A total of 14094 read sequences were further analyzed. FIGS. 6-1 and 6-2 show the number of analyzed reads satisfying the above conditions for each library, and the selected sequences in which the number of reads of identical sequences except for sites corresponding to the artificial base Ds was 3 or more.

As a result, the clone sequences analyzed with Ion Torrent PGM™ and the clone sequences analyzed by cloning were both shown to exhibit similar tendency. Most sequences confirmed by the cloning method were also able to be confirmed from the Ion Torrent PGM™ analysis results of the clones. Of the sequences analyzed with Ion Torrent PGM™, the largest number of clones was N43Ds-21-1, which had the same sequence as that of the clone cN43Ds-21-04 obtained at the largest number by the cloning method. Many sequences comprising the motif GGGDsTTG-GNGGGGDsGTCGG (SEQ ID NO: 335) (N=arbitrary natural base) were also confirmed. Of them, 13 types of sequences were able to be confirmed with the number of reads of 50 or more (FIG. 7).

Example 2

Binding Analysis of DNA Aptamer Binding to VEGF-165—(1)

In this Example, N43Ds-08-1, N43Ds-09-1, N43Ds-20-1, and N43Ds-21-1 were selected as typical clones from the clones obtained in Example 1 and analyzed for their VEGF-165-binding ability as full-length DNA fragments (DNA aptamers) by surface plasmon resonance (SPR) assay using BIACORE 3000 (GE Healthcare Japan Corp.).

First, Ds-containing single-stranded DNA fragments each having biotinylated T added to the 5' end (98-mer or 99-mer in full length), and DNA fragments with Ds replaced with the natural base A, T, or G were prepared by chemical synthesis and gel purification, on the basis of each clone sequence obtained by the method for producing a nucleic acid aptamer according to the present invention. Their sequences are shown in FIG. 8. The SPR sensor chip used was a streptavidin-coated (SA) chip (GE Healthcare Japan Corp.). Each DNA fragment was irreversibly immobilized onto the chip and then analyzed for its binding to VEGF. A DNA fragment reported as a VEGF-binding DNA aptamer (VEGF binding DNA 64, 64 mer) was also prepared as a control and similarly analyzed for its binding. The SPR assay conditions involved: running buffer: buffer solution A and set temperature: 25° C.

Figure 9:
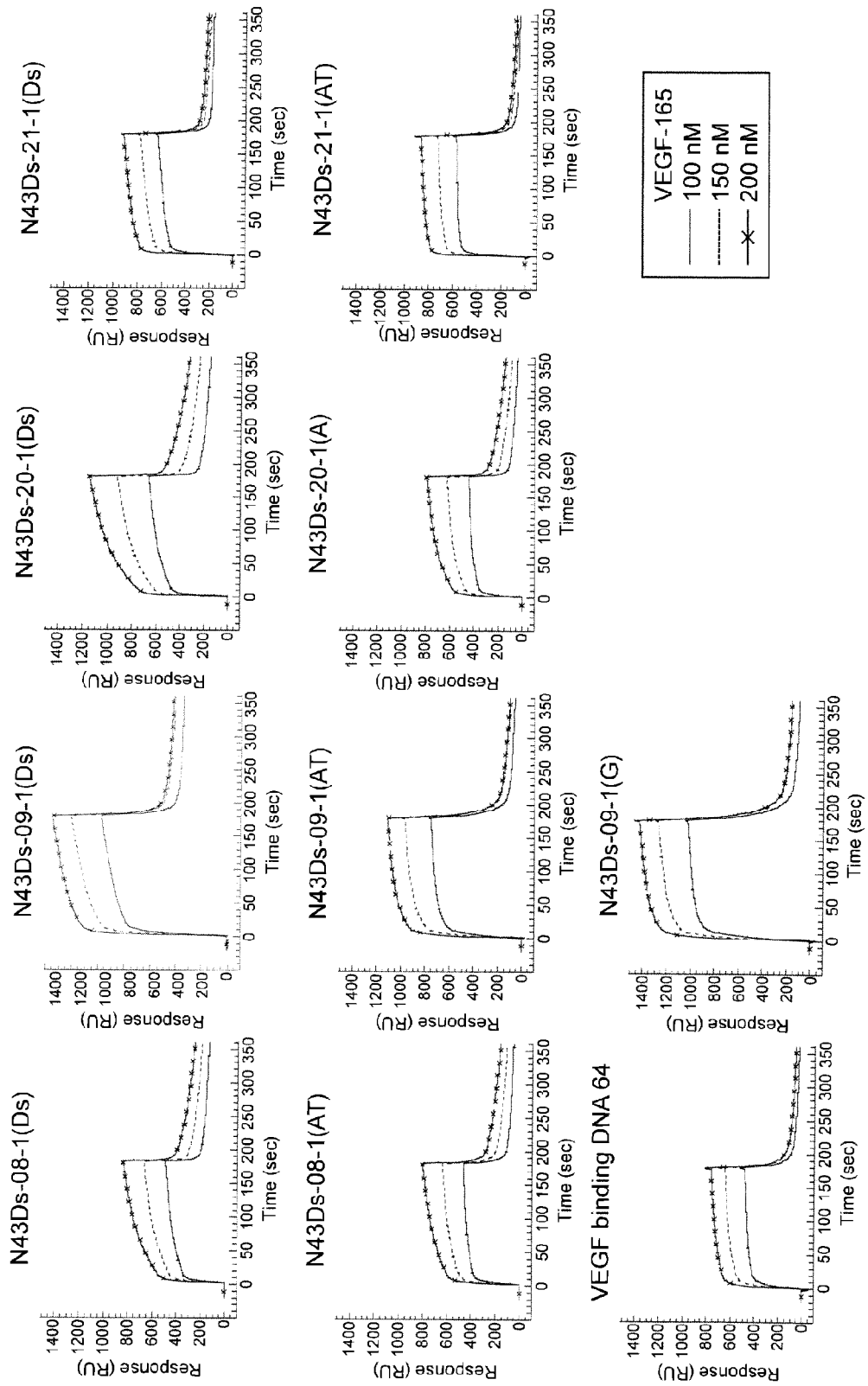
FIG. 9 shows the sensorgrams of full-length DNA aptamers.

For the immobilization of each DNA fragment onto the sensor chip, a DNA solution diluted with a PBS solution to 50 nM was subjected to folding treatment (90° C. for 3 min→60° C. for 3 min→25° C.), and Nonidet P-40 was then added thereto at a final concentration of 0.05%. The resulting DNA solution (10 µl; corresponding to 2 min) was injected to the SA chip at a flow rate of 5 µl/min to immobilize the DNA fragment onto the chip. After the immobilization, DNA fragments nonspecifically adsorbed on the SA chip were washed off by the injection (5 µl×5) of a 50 mM NaOH solution at a flow rate of 20 µl/min. The interaction between the immobilized DNA fragment and VEGF-165 was detected under monitoring by the injection of 100 nM, 150 nM, and 200 nM VEGF-165 solutions (diluted with buffer solution A; in terms of dimer) at the Kinetic Injection mode. The assay conditions involved a flow rate of 20 µl/min and protein injection for 3 minutes. The regeneration of the chip (dissociation of bound proteins and DNA refolding) was performed by the injection of 5 µl (corresponding to 15 sec) of a 50 mM NaOH solution followed by the priming treatment of the chip and the injection of buffer solution A in large amounts. In order to cancel bulk effect on the sensor chip or response values attributed to nonspecific adsorption, the response value of a DNA-unimmobilized cell used as a reference cell was subtracted from the sensorgram of each DNA fragment. The results are shown in FIG. 9.

As a result of this assay, the waveform of the sensorgram showed weak nonspecific binding, in addition to the specific binding between the DNA fragment and VEGF-165. In this case, the dissociation constant (Kd=kd/ka) based on association rate (ka) and dissociation rate (kd) was judged as being difficult to calculate by curve fitting. Thus, the binding intensity of each DNA fragment was evaluated by comparison using, as an index, the degree of non-dissociability at the stage of protein dissociation after the completion of protein injection. Specifically, the response value (RU) obtained 23 seconds after the completion of injection was defined as 100%, and the degree of binding retention was determined from the response value (RU) obtained after a lapse of further 200 seconds. The degrees obtained for 100 nM, 150 nM, and 200 nM proteins were averaged to calculate the rate of binding retention (Retention %). The calculation results are shown in Table 3.

TABLE 3

Comparison of rate of binding retention (non-dissociability) after VEGF-165 binding

| DNA [mer] | | Retention % |
| --- | --- | --- |
| N43Ds-08-1 (Ds) | [98] | 64 ± 4 |
| N43Ds-08-1(AT) | [98] | 49 ± 4 |
| N43Ds-09-1(Ds) | [98] | 83 ± 2 |
| N43Ds-09-1(AT) | [98] | 39 ± 2 |
| N43Ds-09-1(G) | [98] | 37 ± 4 |
| N43Ds-20-1(Ds) | [99] | 60 ± 2 |
| N43Ds-20-1(A) | [99] | 42 ± 4 |
| N43Ds-21-1(Ds) | [99] | 78 ± 3 |
| N43Ds-21-1(AT) | [99] | 45 ± 2 |
| VEGF binding DNA 64 | [64] | 34 ± 5 |

In all clones, the DNA fragment containing the artificial base Ds was shown to have a higher rate of VEGF-165 binding retention than that of the DNA fragment with the artificial base Ds replaced with a natural base. Particularly, N43Ds-09-1 not only exhibited stronger binding compared with the other DNA fragments, but exhibited greater reduction in the rate of binding retention as a result of replacement of Ds with G or A/T compared with the other DNA fragments. These results demonstrated that the binding of N43Ds-09-1 to VEGF-165 depends on the presence or absence of Ds and has a larger dissociation rate (kd) as a result of replacement of Ds with a natural base.

Example 3

Doped Selection Based on Sequence of N43Ds-09-1—(1)

In this Example, doped selection was performed in order to examine a site involved in binding to the target protein as to the 98-mer (full length) DNA fragment N43Ds-09-1 (obtained in Examples 1 and 2) strongly binding to VEGF-165 in a manner dependent on the artificial base Ds.

(1) Preparation of DNA Library Used in Doped Selection

Each DNA library used in doped selection was prepared by chemical synthesis and gel purification so that 3 Ds bases and primer regions in the N43Ds-09-1 sequence were fixed while the other portions constituted by natural nucleotide sequences including the tag sequence contained 62.5% of the original bases and 37.5% of bases different from the original bases (12.5% each of 3 types of bases). The sequences are as follows:

N43Ds-09-1-Dope (SEQ ID NO: 337)
5'-ctgtcaatcgatcgtatcagtccacgtctaagta(Ds)ggtggg (Ds)ttggcgggg(Ds)tgtcggatatactttgacgcatgactcgaa cggattagtgactac-3'

(upper-case letter: fixed sequence, lower-case letter: doped sequence)

a=A: 62.5%; G: 12.5%; C: 12.5%, T: 12.5%
g=A: 12.5%; G: 62.5%; C: 12.5%, T: 12.5%
c=A: 12.5%; G: 12.5%; C: 62.5%, T: 12.5%
t=A: 12.5%; G: 12.5%; C: 12.5%, T: 62.5%

(2) Doped Selection of VEGF-165-Binding ssDNA Aptamer Comprising Ds

VEGF-165-binding DNA aptamers were isolated by the same procedures as in "A. Operation of 1 selection round" shown in Example 1 according to a nucleic acid-protein complex immobilization method using each DNA library prepared in the paragraph (1), the target protein human VEGF-165 (PeproTech, Inc.), and magnetic beads.

A. Conditions of Doped Selection Round

The selection conditions of each round are shown in Table 4.

TABLE 4

Condition of doped selection in preparation of DNA aptamer binding to VEGF-165

| Selection | ssDNA | | VEGF-165 | | Competitor | | volume | Number of washing | | PCR |
|---|---|---|---|---|---|---|---|---|---|---|
| Round | pmol | nM | pmol | nM | pmol | nM | µl | A | B | cycles |
| 1 | 300 | 1000 | 150 | 500 | | | 300 | 2* | | 18 |
| 2 | 50 | 500 | 50 | 500 | | | 100 | 2 | | 12 |
| 3 | 25 | 62.5 | 50 | 125 | 250 | 625 | 400 | 3 | | 13 |
| 4 | 10 | 10 | 5 | 5 | 1000 | 1000 | 1000 | 2 | 1 | 24 |
| 5 | 10 | 10 | 5 | 5 | 1000 | 1000 | 1000 | 2 | 2 | 23 |

The first round was carried out directly using 300 pmol of the DNA library N43Ds-09-1-Dope prepared by chemical synthesis. In order to render the protein-DNA complex formation conditions stricter with each selection round, as in Example 1, protein and DNA concentrations were gradually decreased, while an excessive amount of a DNA fragment (5'-TGTGGGGGTGGACGGGCCGGGTAGA-3'; SEQ ID NO: 147) previously reported as a VEGF-binding DNA aptamer was added as a competitive DNA molecule (Competitor) during protein-DNA library mixing in rounds 3, 4, and 5. In round 4, washing with 40 ml of buffer solution A was performed twice, followed by additional operation of inverting and mixing using buffer solution A (1 ml, at room temperature for 15 min) containing 3 M urea to render the washing conditions further stricter. In round 5, this operation was repeated twice.

(3) Sequencing of DNA Aptamer Obtained by Doped Selection

The DNA aptamers obtained by doped selection were sequenced in the same way as in Example 1 by two methods described below using the DNAs recovered in the selection after the final round (round 5).

(i) Identification of DNA Aptamer Sequence by Cloning Method Using E. coli

Of the sequences of clones determined in the same way as in Example 1, the nucleotide sequences (25 types) of 28 clones each having 45 bases between the primer sequences are shown in FIG. 10.

(ii) Identification of DNA Aptamer Sequence Using Next-Generation Sequencer (Life Technologies Corp.; Ion Torrent the Personal Genome Machine™ (PGM™))

Figure 11:
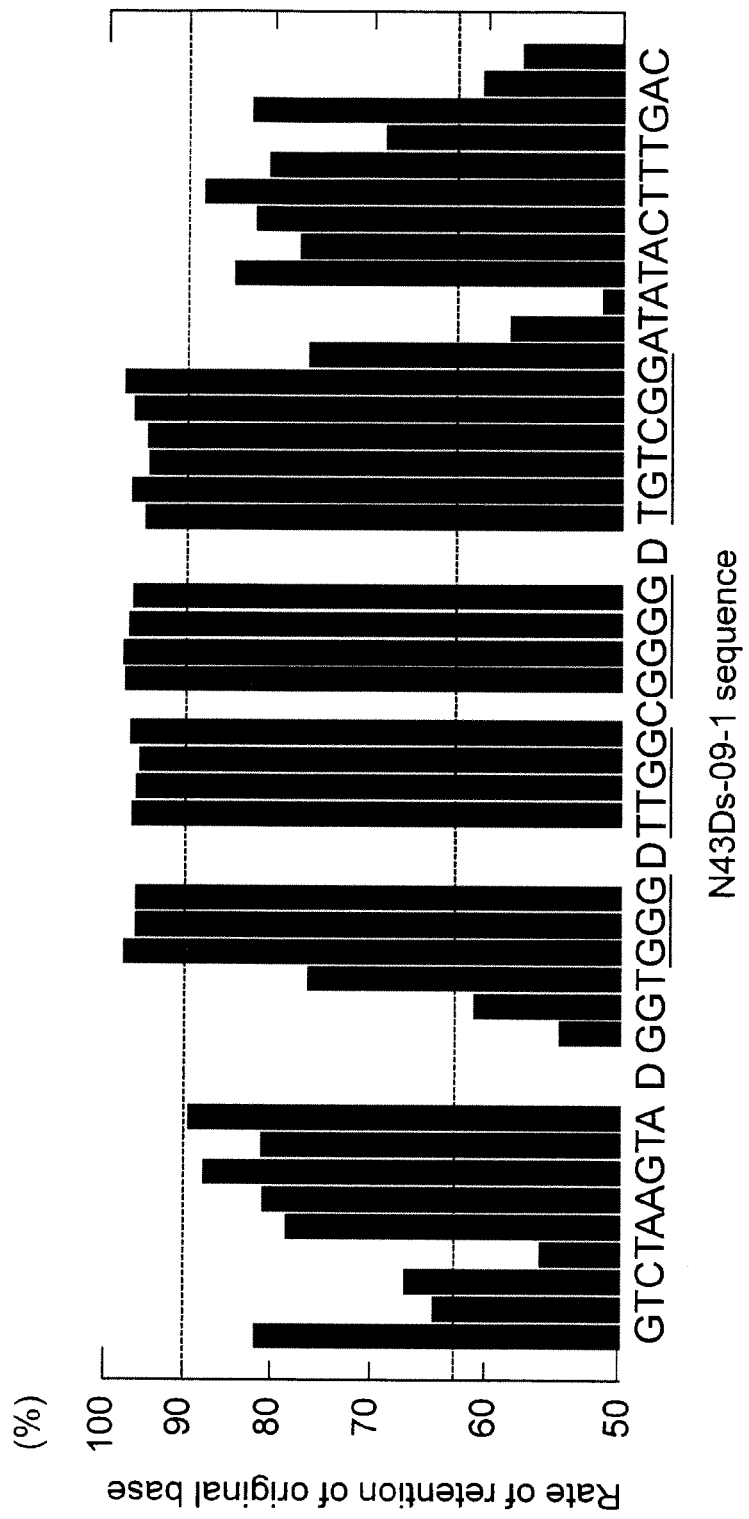
FIG. 11 shows Ion Torrent PGM analysis results of a DNA obtained by doped selection after 5 rounds. In the nucleotide sequence shown in the abscissa, "ID" represents "Ds" (SEQ ID NO: 34).

PGM sequencing was performed in the same way as in Example 1. The total number of reads thus obtained was analyzed using CLC Genomics Workbench (version 4.7.2). Reads (total number: 2474) consecutively comprising 25-base 5'-primer—45-base sequence—6-base partial sequence (GCATGAC) of the 3'-primer were selected for the Ds-containing library sequences, while reads (total number: 2365) consecutively comprising 27-base 3'-primer—45-base sequence—6-base partial sequence (GTGGAC) of the 5'-primer were selected for complementary sequences of the Ds-containing library sequences. A total of 4839 clone sequences were further analyzed. FIG. 11 shows results of calculating the composition of a base at each position among 45 bases.

As a result of analysis by both of the approaches of (i) and (ii), the common sequence (SEQ ID NO: 105) consisting of the motif GGGDsTTGGNGGGGDsTGTCGG (N=A, G, C, or T) in the original sequence of N43Ds-09-1 was shown to be very highly conserved. Many clones comprising a sequence analogous to this motif were also obtained in the selection of Example 1 (FIG. 7), suggesting that this motif is important for the binding to VEGF-165.

Example 4

Binding Analysis of DNA Fragment Comprising Motif Obtained by Doped Selection—(1)

In this Example, a truncated DNA fragment Ds-09-1-DsDsDs (35-mer) of N43Ds-09-1 comprising the motif GGGDsTTGGNGGGGDsTGTCGG (SEQ ID NO: 105) identified in Example 3, and its variant DNA fragments were analyzed for their VEGF-165-binding ability by surface plasmon resonance (SPR) assay using BIACORE 3000 (GE Healthcare Japan Corp.).

A. SPR Analysis on VEGF-165 Binding of Various DNA Fragments

The SPR assay conditions involved: running buffer: buffer solution A and set temperature: 25° C., as in Example 2. Six types of DNA fragments used in the analysis of this Example are shown in Table 5.

TABLE 5

DNA fragment (35-mer) used in SPR analysis

| | Sequence | SEQ ID NO | Retention (%) | Kd (nM) |
|---|---|---|---|---|
| Ds-09-1-DsDsDs | T*GTCTAAGTADsGGTGGGDsTTGGCGGGGDsTGTCGGA | 106 | 92 ± 1 | 4 |
| Ds-09-1-ADsDs | T*GTCTAAGTAA GGTGGGDsTTGGCGGGGDsTGTCGGA | 107 | 94 ± 1 | 1 |
| Ds-09-1-DsADs | T*GTCTAAGTADsGGTGGGA TTGGCGGGGDsTGTCGGA | 108 | 33 ± 3 | >100 |
| Ds-09-1-DsDsA | T*GTCTAAGTADsGGTGGGDsTTGGCGGGGA TGTCGGA | 109 | 32 ± 3 | >100 |
| Ds-09-1-AAA | T*GTCTAAGTAA GGTGGGA TTGGCGGGGA TGTCGGA | 110 | 28 ± 4 | >100 |
| Ds-09-1-mDsDsDs | T*GTCTAAGTADstGTGGGDsTTGGaGGGGDsTGTCGGA | 111 | 90 ± 6 | 50 |
| VEGF binding DNA 35 | T*TGCACTC *TGTGGGGGTGGACGGGCCGGGTAGATA* | 329 | | >100 |

T* = Biotin-dT

Ds-09-1-ADsDs, Ds-09-1-DsADs, Ds-09-1-DsDsA, and Ds-09-1-AAA resulted from the replacement of one or all artificial bases Ds in Ds-09-1-DsDsDs with the natural base A. The variant DNA fragment Ds-09-1-mDsDsDs resulted from the replacement of two base portions conserved in Ds-09-1-DsDsDs at a low in the doped selection with bases having a high frequency of appearance. For comparison, 98-mer (full length) N43Ds-09-1, full-length DNA fragments N43Ds-09-1(AT) and N43Ds-09-1(G) with the artificial base Ds replaced with a natural base, and a control DNA fragment reported as a VEGF-binding DNA aptamer (VEGF binding DNA 35, 35 mer) were also assayed under the same conditions. As in the full length binding analysis of Example 2, each DNA fragment having biotinylated T added to the end for the direct immobilization of the DNA fragment onto an SA chip (GE Healthcare Japan Corp.) was prepared by chemical synthesis and gel purification. For the immobilization of each DNA fragment onto the sensor chip, a DNA solution diluted with a PBS solution to 25 nM was subjected to folding treatment (90° C. for 3 min→60° C. for 3 min→25° C.), and Nonidet P-40 was then added thereto at a final concentration of 0.05%. The resulting DNA solution (5 µl; corresponding to 1 min) was injected to the SA chip at a flow rate of 5 µl/min to immobilize the DNA fragment onto the chip. After the immobilization, DNA fragments nonspecifically adsorbed on the SA chip were washed off by the injection (5 µl×5) of a 50 mM NaOH solution at a flow rate of 20 µl/min.

Figure 12:
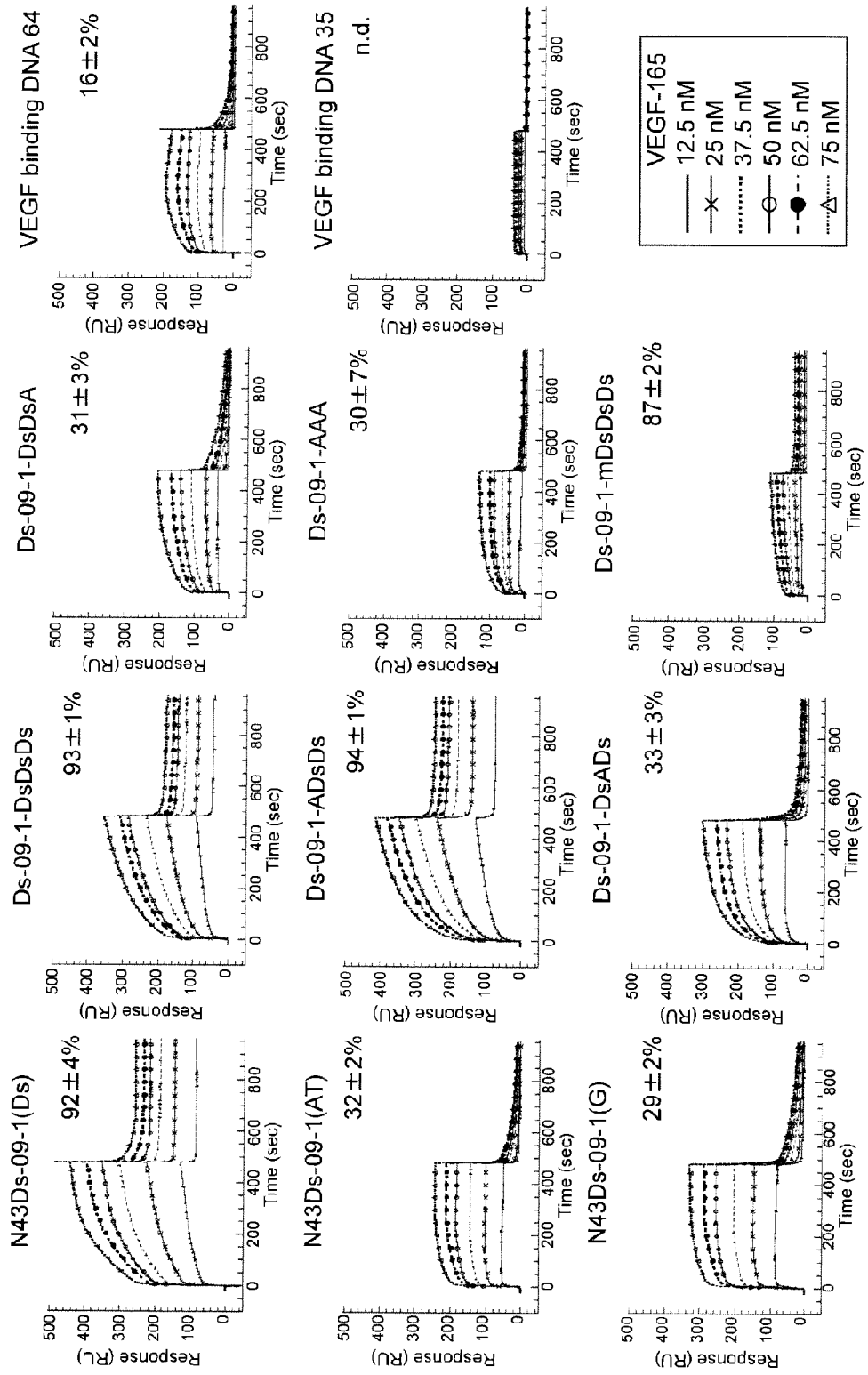
FIG. 12 shows the sensorgrams of full-length and truncated DNA aptamers.

The interaction between the immobilized DNA fragment and VEGF-165 was detected under monitoring by the injection of 12.5 nM, 25 nM, 37.5 nM, 50 nM, 62.5 nM, and 75 nM VEGF-165 solutions (diluted with buffer solution A; in terms of dimer) at the Kinetic Injection mode. The assay conditions involved a flow rate of 20 µl/min and protein injection for 6 minutes. The regeneration of the chip (dissociation of bound proteins and DNA refolding) was achieved by the injection of 5 µl (corresponding to 15 sec) of a 50 mM NaOH solution followed by the priming treatment of the chip and the injection of buffer solution A in large amounts. In order to cancel bulk effect on the sensor chip or response values attributed to nonspecific adsorption, the response value of a DNA-unimmobilized cell used as a reference cell was subtracted from the sensorgram of each DNA fragment. The results are shown in FIG. 12. The 35-mer truncated form Ds-09-1-DsDsDs, as with the full-length N43Ds-09-1(Ds), was shown to strongly bind to VEGF-165. The DNA fragment Ds-09-11-ADsDs resulting from the replacement of 5-terminal Ds of three Ds bases contained in Ds-09-1-DsDsDs with the natural base A was also shown to strongly bind to VEGF-165. By contrast, the DNA fragment Ds-09-1-DsADs or Ds-09-1-DsDsA resulting from the replacement of the 2nd or 3rd Ds counted from the 5' end with A, and the DNA fragment Ds-09-1-AAA resulting from the replacement of all of the artificial bases Ds with A were shown to exhibit faster dissociation and weaker binding against VEGF after VEGF injection, compared with Ds-09-1-DsDsDs and Ds-09-1-ADsDs. The DNA fragment Ds-09-1-mDsDsDs had a lower response (RU) after VEGF injection than that of the other DNA fragments, but was shown to exhibit slower dissociation from VEGF after VEGF injection, as in Ds-09-1-DsDsDs or Ds-09-1-ADsDs.

The SPR assay using short fragments produced weak nonspecific binding only at an ignorable level, compared with the SPR assay using the full-length DNA fragment. Thus, the dissociation constants (Kd) of Ds-09-1-DsDsDs, Ds-09-1-ADsDs, and Ds-09-1-mDsDsDs were successfully calculated by curve fitting using BiaEvaluation software attached to Biacore 3000, and 1:1 binding reaction models. The Kd values were 4 nM for Ds-09-1-DsDsDs, 1 nM for Ds-09-1-ADsDs, and 50 nM for Ds-09-1-mDsDsDs. The Kd values of Ds-09-1-DsADs, Ds-09-1-DsDsA, and Ds-09-1-AAA with weak binding were not accurately calculatable due to difficult fitting, but were shown to be larger than 100 nM (Table 5).

The binding intensity of each DNA fragment was also compared in the same way as in Example 2 using, as an index, the degree of non-dissociability at the stage of protein dissociation after the completion of protein injection. Specifically, the response value (RU) obtained 16 seconds after the completion of injection was defined as 100%, and the degree of binding retention was determined from the response value (RU) obtained after a lapse of further 300 seconds. The degrees obtained for 37.5 nM, 50 nM, 62.5 nM, and 75 nM proteins were averaged to calculate the rate of binding retention (Retention %) (FIG. 10 and Table 5). As a result, the short truncated DNA fragments Ds-09-1-DsDsDs, Ds-09-1-ADsDs, and Ds-09-1-mDsDsDs had 90% or more rate of binding retention, which was almost equivalent to the rate of binding retention of the 98-mer (full length) Ds-09-1.

These results demonstrated that the short truncated DNA fragment (35-mer) comprising GGGDsTTGGNGGGGDsTGTCGG (SEQ ID NO: 105) becomes less dissociable from VEGF and strongly binds to VEGF in a manner dependent on the Ds base in the motif.

B. Analysis of Truncated DNA Fragment for VEGF-165 Binding Selectivity

Figure 13:
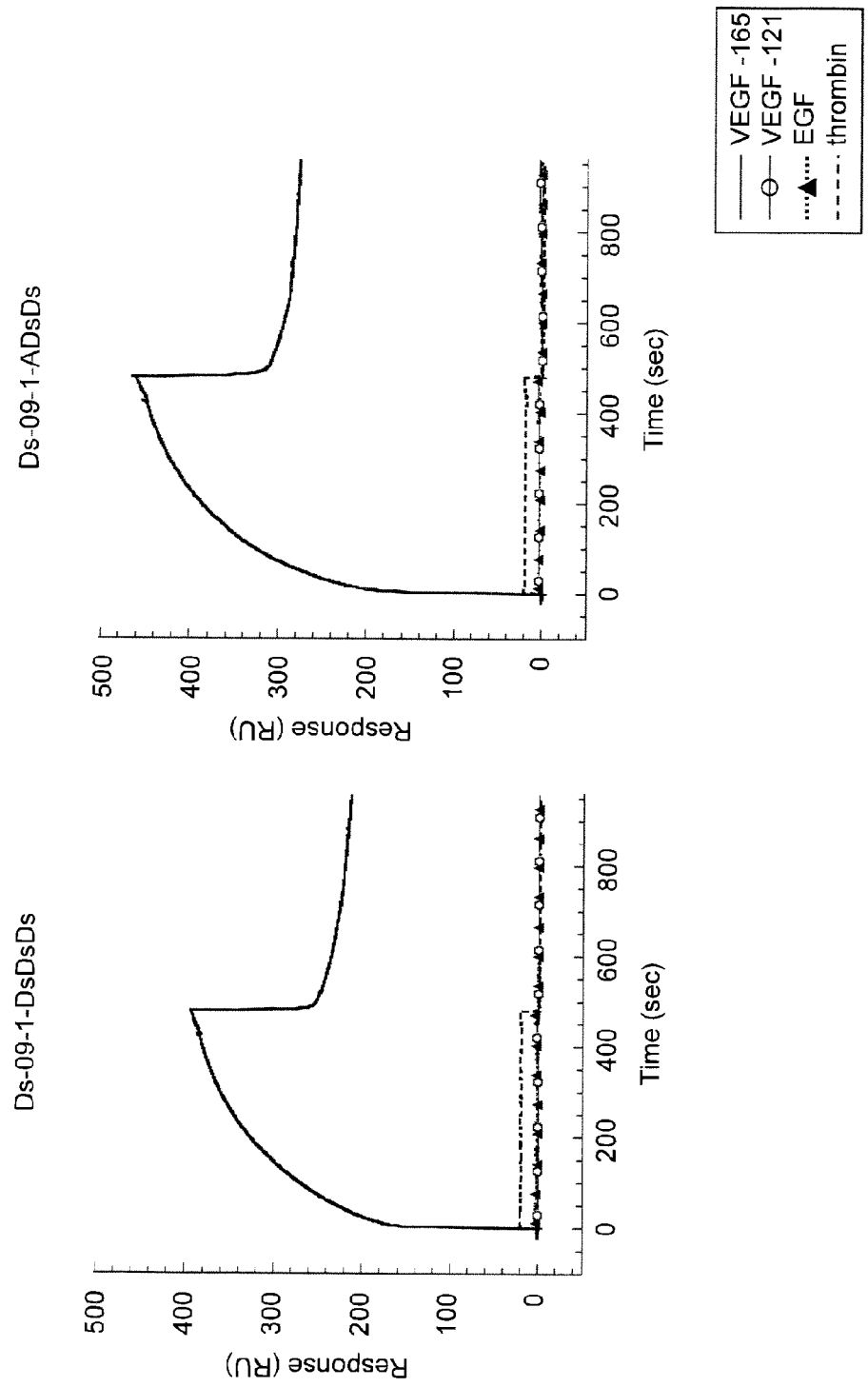
FIG. 13 shows analysis on interactions with VEGF-165 and the other proteins.

In order to examine the 35-mer aptamers obtained by this selection for their VEGF-165 binding selectivity, Ds-09-11-DsDsDs and Ds-09-11-ADsDs were examined for their binding ability against a VEGF-165 subtype VEGF-121 (PeproTech, Inc.), human EGF (PeproTech, Inc.), and human α-thrombin (Enzyme Research Laboratories Ltd.). In the same way as in the VEGF-165 binding analysis, Ds-09-11-DsDsDs and Ds-09-11-ADsDs were each immobilized onto an SA chip, to which each protein (75 nM) was injected. The resulting sensorgrams are shown in FIG. 13. Both Ds-09-11-DsDsDs and Ds-09-11-ADsDs hardly bound to the proteins other than VEGF-165, demonstrating that the artificial base-containing aptamers obtained by selection in this experiment selectively bind to VEGF-165.

Example 5

Selection Using Library of Single-Stranded DNAs Each Randomly Comprising Artificial Base Ds in Central Region (Random Library Method)

In this Example, a random library of single-stranded DNAs each having a randomly incorporated artificial base Ds was used as each artificial base Ds-containing single-stranded DNA library to select DNA aptamers binding to VEGF.

(1) Preparation of Single-Stranded DNA Library with Randomly Incorporated Artificial Base Ds Each single-stranded DNA library (N45.26mixDs-3) with the randomly incorporated artificial base Ds was chemically synthesized using a prepared amidite mixture composed of 6% of amidites of the artificial base Ds and 94% of amidites of 4 natural bases in equal amounts for the 45-base sequence of the central region. As for the theoretical composition of the libraries synthesized under this condition, it was assumed that: libraries of Ds-free DNA fragments consisting of natural bases constituted 6.2% of the total; libraries of DNA fragments each comprising 1 Ds base at an arbitrary position constituted 17.7% of the total; libraries of DNA fragments each comprising 2 Ds bases constituted 24.9% of the total; libraries of DNA fragments each comprising 3 Ds bases constituted 22.8% of the total; libraries of DNA fragments each comprising 4 Ds bases constituted 15.3% of the total; libraries of DNA fragments each comprising 5 Ds bases constituted 8.0% of the total; and libraries of DNA fragments each comprising 6 or more Ds bases constituted the remaining approximately 2%. The sequence (full-length: 89-mer; the region within parentheses represents a fixed sequence for a PCR primer) of N45.26mixDs-3 will be shown below.

```
                                                (SEQ ID NO: 114)
5'-(ACGCATGAACAAACTTGCTTG)NNNNNNNNNNNNNNNNNNNNNNN

NNNNNNNNNNNNNNNNNNNNNN(GGAGTACGCAGAAGTTTCATTGT)-3'
(N = A, G, C, or T (94%) or Ds (6%))
```

(2) Selection of VEGF-165-Binding ssDNA Aptamer Comprising Ds

VEGF-165-binding DNA aptamers were isolated by the same procedures as in <Operation of 1 selection round> shown in Example 1 according to a nucleic acid-protein complex immobilization method using each DNA library prepared in the preceding paragraph (1), the target protein human VEGF-165 (PeproTech, Inc.), and magnetic beads. The PCR cycle conditions for library preparation of (iii) involved (94° C. for 30 sec→50° C. for 30 sec→65° C. for 2 min)×15 to 25 cycles. The following sequences were used as a 5'-primer and a 3'-primer:

```
                                  (SEQ ID NO: 112)
5'-primers:   5'-ACGCATGAACAAACTTGCTTG-3'

(SEQ ID NO: 150)
3'-primers:   5'-BACAATGAAACTTCTGCGTACTCC-3'
(B = biotin-modified T)
```

<Condition of Selection Round>

The selection conditions of each round are shown in Table 6.

TABLE 6

Selection condition for DNA aptamer binding to VEGF-165 (selection in the case where Ds was incorporated at random position)

| Selection Round | ssDNA pmol | ssDNA nM | VEGF-165 pmol | VEGF-165 nM | volume μl | Number of washing A | PCR cycles |
|---|---|---|---|---|---|---|---|
| 1 | 300 | 1000 | 150 | 500 | 300 | 3* | 15 |
| 2 | 20 | 500 | 20 | 500 | 40 | 3 | 15 |
| 3 | 10 | 250 | 10 | 250 | 40 | 3 | 20 |
| 4 | 2.5 | 62.5 | 10 | 250 | 40 | 3 | 17 |
| 5 | 5 | 15.2 | 20 | 60.6 | 330 | 3 | 15 |
| 6 | 5 | 5 | 5 | 5 | 1000 | 4 | 20 |
| 7 | 30 | 50 | 3 | 5 | 600 | 4 | 25 |
| 8 | 40 | 40 | 5 | 5 | 1000 | 5 | 25 |

For the first round, each DNA library prepared by chemical synthesis was directly used. The total number of molecular species was 300 pmol, i.e., approximately $2 \times 10^{14}$ molecules. In order to render the protein-DNA complex formation conditions stricter, protein and DNA concentrations were gradually decreased, while the number of the complex washing step was increased.

(3) Sequence Analysis of Library for Each Selection Round

In the sequence analysis of DNAs comprising the artificial base Ds, the sequencing pattern differs by the addition of ddPa'TP or dPa'TP as a substrate complementary to the artificial base Ds during ordinary dye-terminator sequencing reaction. The presence or absence of the artificial base Ds in each DNA fragment templated in the sequencing can therefore be predicted. Thus, each single-stranded DNA library prepared after each selection round was used as a template in sequence analysis in the presence of ddPa'TP or dPa'TP to analyze the degree of retention of the artificial base Ds through the selection process.

Specifically, for DNA sequencing reaction at a total scale of 10 μl, 1 μl of Sequencing Buffer for v1.1 (×5) attached to commercially available BigDye Terminator v1.1 Cycle Sequencing Kit (Applied Biosystems Inc.), a sequencing primer (2 pmol, 5'-ACAATGAAACTTCTGCGTACTCC-3'; SEQ ID NO: 113), the single-stranded DNA fragments (approximately 0.15 pmol) prepared by PCR amplification after each round, and ddPa'TP or dPa'TP (500 pmol) were added to 2 μl of Cycle Sequencing Mix of the kit, followed by 25 cycles of PCR (96° C. for 10 sec→50° C. for 5 sec→60° C. for 4 min). Unreacted dye terminators were removed from the reaction solution using CentriSep spin column (Applied Biosystems Inc.). The remaining solution was dried under reduced pressure. To the residue, 3 μl of a formamide dilution of Blue-Dextran was added, and a portion of the mixture was analyzed with ABI377 DNA sequencer. The composition of the gel used in the analysis was 6% polyacrylamide-6 M urea gel. The peak pattern of each sequence was analyzed using Applied Biosystems PRISM sequencing analysis v3.2 software. The results of analyzing the sequencing pattern showed that particular sequence groups were being concentrated in round 4 or later. Since the aptamers consisting only of a natural nucleotide sequence were also included in the library, no pattern indicated that the sequencing reaction stopped at the position complementary to the artificial base in the presence of ddPa'TP. However, the sequencing patterns in the presence of ddPa'TP and in the presence of dPa'TP were confirmed to be distinct in all rounds. In the case of a sequence constituted only by natural bases, no significant difference is usually confirmed in sequencing pattern between in the presence of ddPa'TP and in the presence of dPa'TP. Thus, the library obtained by this selection was presumed to have a sequence that retained at least the artificial base Ds.

(4) Identification of DNA Aptamer Sequence Obtained by Selection

The results of sequencing in the paragraph (3) suggested that the aptamers consisting only of a natural nucleotide sequence were also included in the library after 8 rounds. Thus, the operation of concentrating the DNA fragments comprising the artificial base Ds was performed before the approach of Example 1(3)(i). The resulting DNA aptamers comprising Ds were sequenced.

The operation of concentrating the DNA fragments comprising the artificial base Ds was performed in the same way as a method described in Nucleic Acid Research (2009), Kimoto et al. except that Biotin-dPxTP was used instead of FAM-hx-dPxTP in the literature. Specifically, 1 pmol of each single-stranded DNA library amplified after 8 rounds was amplified as a template by 5 cycles of PCR using AccuPrime Pfx DNA polymerase in the presence of 50 µM dDsTP and 50 µM Biotin-dPxTP to prepare Ds-containing single-stranded DNA fragments into double-stranded DNAs comprising the Ds-(Biotin-dPx) base pair. The composition and conditions of PCR were the same as in Example 1(2)(iii) except that: Diol1-dPxTP was replaced with Biotin-dPxTP; and unbiotinylated primers (5'-ACAATGAAACTTCT-GCGTACTCC-3' (SEQ ID NO: 113) and 5'-ACGCAT-GAACAAACTTGCTTG-3' (SEQ ID NO: 112)) were used as PCR primers. Then, the PCR solution was buffer-replaced with 1× binding solution (20 mM Tris-HCl (pH 7.6), 0.5 M NaCl, and 10 mM $MgCl_2$) by ultrafiltration using Microcon 10 (Millipore Corp.) to remove, from the PCR solution, unreacted Biotin-dPxTP that was not incorporated in PCR products. The resulting solution (approximately 45 µl) was incubated at 25° C. for 15 minutes with the streptavidin-coupled magnetic beads (40 µl) used in selection to immobilize the double-stranded DNAs comprising the Ds-(Biotin-dPx) base pair onto the magnetic beads. The beads were washed with 1× binding solution to remove DNA fragments comprising no Ds-(Biotin-dPx) base pair. Then, 12 µl of a 20 mM NaOH solution was added to the recovered magnetic beads, and the mixture was left at room temperature for approximately 5 minutes to thereby make the double-stranded DNAs into single-stranded DNAs and liberate the Ds-containing DNA fragments into the solution. The solution was neutralized by the addition of 3 µl of an 80 mM HCl solution. Then, the DNA fragment-containing solution was recovered using a magnetic stand to prepare template DNAs for the approach of Example 1(3)(i).

(5) Identification of DNA Aptamer Sequence by Cloning Method

A portion of the DNA solution thus obtained was used as template in PCR to replace the artificial base Ds with a natural base. The PCR products were cloned by a conventional method. Specifically, PCR (volume: 20 µl) was performed in the presence of 1 µM each primer (5'-ACAAT-GAAACTTCTGCGTACTCC-3' (SEQ ID NO: 113) and 5'-ACGCATGAACAAACTTGCTTG-3' (SEQ ID NO: 112)) using 4 µl of the DNA solution as a template and 1× ExTaq Premix (Takara Bio Inc.) supplemented with dPa'TP at a final concentration of 50 M. The PCR cycle conditions involved (94° C. for 30 sec→50° C. for 30 sec→65° C. for 2 min)×10 cycles→75° C. for 5 min. A portion (4 µl) of the PCR products was cloned into E. coli (Top10) using TOPO TA cloning kit (Invitrogen Corp.). A plasmid derived from each clone was recovered, and each clone was sequenced. Of the determined sequences of the clones, the nucleotide sequences (27 types) of 59 clones each having 45 bases between the primer sequences were aligned. The results are shown in FIG. 14.

Results of homology analysis on the identified sequences showed 5 types of homologous sequence groups containing 2 or 3 base mutations in the central region and also demonstrated that these base mutations included base mutations presumed to replace the artificial base Ds with the natural base T or A as a result of this cloning method.

Example 6

Identification of Position of Artificial Base Ds in Aptamer Obtained by Production Method In this Example, the presence or absence of the artificial base Ds in the sequences of the 5 types of aptamer groups obtained in Example 5 and the position thereof in these sequences were identified.

A. Isolation of DNA Fragment Complementary to Probe from DNA Library

FIG. 14 shows the probe sequences of 24-base DNA fragments designed to be respectively specific for the sequences of the 5 types of groups. These probes, which were already chemically synthesized (also 5'-terminally biotinylated) and simply purified, were purchased from Invitrogen Corp and used in this experiment. Each single-stranded DNA library prepared by the PCR amplification (using dDsTP and Diol1-dPxTP) of the DNA fragments obtained after 8 rounds was adjusted to 100 nM/1× binding solution. The resulting solution (130 µl) was incubated at room temperature for 10 minutes with streptavidin-coupled magnetic beads (50 &l) to remove streptavidin-bound DNA fragments. Then, 20 µl of the recovered DNA solution was mixed with each biotinylated probe (5 µM, 1 µl), followed by annealing operation (90° C. for 3 min→slow cooling at a rate of 0.1° C./sec→55° C. for 15 min). Then, the reaction solution was mixed with streptavidin-coupled magnetic beads (5 µl) buffer-replaced with 1× binding solution, and the mixture was incubated at 55° C. for 5 minutes to immobilize the biotinylated probes and a DNA fragment complementarily hybridized with each probe onto the magnetic beads. The solution was removed using a magnetic stand to remove redundant DNA fragments unhybridized with probes. Then, the magnetic beads were washed five times with 150 µl of 1× binding solution. Then, 10 µl of sterile water was added to the magnetic beads thus washed, and the mixture was heated at 75° C. for 5 minutes. Then, the resulting solution was recovered to recover a DNA fragment hybridized with each probe.

B. DNA Sequencing of DNA Fragment Recovered Using Probe

The recovered DNA fragments were used in 3 types of DNA sequencing methods of (i) to (iii) described below. These sequencing methods were performed in the same way as the method shown in Example 5(3) except for specified changes.

(i) 4 µl of the recovered DNA solution was directly sequenced in the presence of 0.05 mM dPa'TP.

(ii) 15 cycles of PCR amplification were performed using 2 µl of the recovered DNA solution and AccuPrime Pfx DNA polymerase in the presence of dDsTP and Diol1-dPxTP. Then, fragments were recovered by gel purification and dissolved in 10 µl of water. The solution (1 to 2 µl) was used in sequencing in the presence of 0.05 mM dPa'TP or in the presence of 0.05 mM ddPa'TP (the artificial base Ds is retained during PCR, if the recovered DNA carries Ds).

(iii) 15 cycles of PCR amplification were performed using 2 µl of the recovered DNA solution and ExTaq DNA polymerase in the presence of 0.05 mM dPa'TP. Then, fragments were recovered by gel purification and dissolved in 10 µl of water. The solution (1 to 2 µl) was used in sequencing in the presence of 0.05 mM dPa'TP or in the presence of 0.05 mM ddPa'TP (the artificial base Ds is replaced with A or T after PCR if the recovered DNA carries Ds).

In the methods (ii) and (iii), the strand containing the artificial base Ds was sequenced using a sequencing primer (Sequencing Primer 2: 5'-ACAATGAAACTTCTGCG-TACTCC-3' (SEQ ID NO: 113)), and the strand containing the artificial base Diol1-Px was also sequenced using a sequencing primer (Sequencing Primer 1: 5'-ACGCAT-GAACAAACTTGCTTG-3' (SEQ ID NO: 112)) in the absence of the Pa' substrate. The sequencing patterns of (i) to (iii) demonstrated that at positions found to have A/T base mutations in the aptamer sequences by the cloning method of the DNAs recovered from each library after 8 rounds, (A) Ds is completely conserved or (B) some Ds bases are replaced with the natural base A or T whereas Ds is retained at constant rates. Thus, the approach shown in this Example was able to identify the position of randomly introduced Ds. As shown in Examples 1 and 3, which involved selection using the predetermined Ds introduction positions, most Ds introduction sites were also replaced with A/T in the sequence analysis using a next-generation sequencer. Thus, the results of this Example demonstrated that: the position of Ds that is incorporated in the central region and conserved during the selection process can be identified after selection by the analysis of sequence groups in large amounts using a next-generation sequencer; and the selection is feasible even in the case of using a library of DNAs each having Ds incorporated at a random position.

Example 7

Preparation of Various dPnTP Derivatives

In Examples 1, 3, and 5, Ds was used as the 5th base in the selection library. Since the Pn base is complementary to Ds and functions in PCR, Pn may be used as the 5th base for library preparation and selection. In addition, the propynyl group of the artificial base Pn may be substituted by various substituents. In this Example, the preparation of various dPnTP derivatives shown in the present specification will be described.

(1) Reagent and Solvent

Reagents and solvents were purchased from standard suppliers and used without being further purified. $^1$H-NMR (300 MHz), $^{31}$P-NMR (121 MHz), and $^{13}$C-NMR (75 MHz) spectra were recorded on BRUKER AV300 nuclear magnetic resonance spectrometer. Synthesized nucleoside derivatives and nucleoside 5'-triphosphate were purified using Gilson HPLC system. High-resolution mass spectra (HR-MS, FAB) were recorded on JEOL JM 700 or JEOL GC mate spectrometer. Electron spray-ionized mass spectra (MS, ESI) were recorded on Waters ZMD 4000 mass system or Waters UPLC-MS (H class) system equipped with Waters 2690 LC system.

(2) Synthesis of dPnTP (2-1) Synthesis of 1-(2-deoxy-3-O-acetyl-β-D-ribofuranosyl)-4-propynyl-2-nitropyrrole After azeotropy of 1-(2-deoxy-β-D-ribofuranosyl)-4-propynyl-2-nitropyrrole (200 mg, 0.75 mmol) with pyridine, pyridine (7.5 ml) was added to the residue, then 4,4'-dimethoxytrityl chloride (280 mg, 0.83 mmol) was added thereto, and the mixture was stirred at room temperature for 1 hour. The reaction solution was separated into aqueous and organic layers by the addition of ethyl acetate and a 5% aqueous sodium bicarbonate solution. The organic layer was washed with saturated saline. The organic layer was dried over anhydrous sodium sulfate and then concentrated under reduced pressure. The residue was purified by silica gel column chromatography (methylene chloride:methanol, 200:1, v/v) to obtain 365 mg (86%) of 1-(2-deoxy-5-O-dimethoxytrityl-β-D-ribofuranosyl)-4-propynyl-2-nitropyrrole. After azeotropy of 1-(2-deoxy-5-O-dimethoxytrityl-β-D-ribofuranosyl)-4-propynyl-2-nitropyrrole (160 mg, 0.28 mmol) with pyridine, pyridine (2.8 ml) was added to the residue, then acetic anhydride (53 µl, 0.56 mmol) was added thereto, and the reaction solution was stirred at room temperature for 12 hours. The reaction solution was separated into aqueous and organic layers by the addition of ethyl acetate and a 5% aqueous sodium bicarbonate solution. The organic layer was dried over anhydrous sodium sulfate and then concentrated. After azeotropy of the residue with toluene, the residue was dissolved in 28 ml of methylene chloride. To this reaction solution, dichloroacetic acid (280 µl) was added at 0° C., and the mixture was stirred for 15 minutes under ice cooling. The reaction solution was separated into aqueous and organic layers by the addition of a 5% aqueous sodium bicarbonate solution. The organic layer was washed with a 5% aqueous sodium bicarbonate solution. The organic layer was dried over anhydrous sodium sulfate and concentrated under reduced pressure. Then, the residue was purified on a silica gel column to obtain 78 mg (89%) of 1-(2-deoxy-3-O-acetyl-β-D-ribofuranosyl)-4-propynyl-2-nitropyrrole.

(2-2) Synthesis of 1-(2-deoxy-β-D-ribofuranosyl)-4-propynyl-2-nitropyrrole 5'-triphosphate After azeotropy of 1-(2-deoxy-3-O-acetyl-β-D-ribofuranosyl)-4-propynyl-2-nitropyrrole (31 mg, 0.1 mmol) with pyridine, pyridine (100 µl) and dioxane (300 µl) were added to the residue, then 2-chloro-4H-1,3,2-benzodioxaphosphorin-4-one (110 µl, 1 M dioxane solution) was added thereto, and the mixture was stirred at room temperature for 10 minutes. Tri-n-butylamine (100 µl) and bis(tributylammonium)pyrophosphate (300 μl, 0.5 M DMF solution) were added to the reaction solution, and the mixture was stirred for 10 minutes. Iodine/pyridine (2.0 ml, pyridine-water (98:2 v/v) solution of 1% iodine) was added thereto, and the mixture was stirred for 15 minutes. Then, 5% $NaHSO_3$ (150 μl) was added thereto, and the reaction solution was concentrated. Water (5.0 ml) was added thereto, and the mixture was stirred at room temperature for 30 minutes. Then, 20 ml of 28% ammonia water was added thereto, and the mixture was stirred at room temperature for 2 hours. The reaction solution was concentrated and freeze-dried. Then, the residue was purified by DEAE Sephadex A-25 ion-exchange column chromatography (eluted with 50 mM to 1.0 M TEAB linear gradient) and RP-HPLC to obtain 1-(2-deoxy-β-D-ribofuranosyl)-4-propynyl-2-nitropyrrole 5'-triphosphate (31 μmol, 31%) of interest.

(2-3) Physical Property of Compound (2-3-1) 1-(2-Deoxy-3-O-acetyl-β-D-ribofuranosyl)-4-propynyl-2-nitropyrrole $^1$H NMR (300 MHz, DMSO-d6) δ 7.90 (d, 1H, J=2.1 Hz), 7.30 (d, 1H, J=2.1 Hz), 6.60 (t, 1H, J=6.4 Hz), 5.22 (m, 2H), 4.13 (m, 1H), 3.65 (m, 2H), 2.62 (ddd, 1H, J=3.1, 6.1, 14.3 Hz), 2.43 (m, 1H), 2.08 (s, 3H), 2.00 (s, 3H). HR-MS (FAB, 3-NBA matrix) for $C_{14}H_{17}N_2O_6$ (M+H) calcd. 309.1087. found 309.1066.

(2-3-2) 1-(2-Deoxy-β-D-ribofuranosyl)-4-propynyl-2-nitropyrrole 5'-triphosphate $^1$H NMR (300 MHz, $D_2O$) δ 7.74 (d, 1H, J=2.1 Hz), 7.35 (d, 1H, J=2.1 Hz), 6.76 (t, 1H, J=6.1 Hz), 4.63 (m, 1H), 4.24 (m, 3H), 3.21 (q, 20H, J=7.3 Hz), 2.64 (ddt, 1H, J=5.2, 13.9 Hz), 2.49 (ddt, 1H, J=6.2, 14.0 Hz), 1.99 (s, 3H), 1.28 (t, 29H, J=7.3 Hz). $^{31}$P NMR (121 MHz, $D_2O$) δ −10.16 (d, 1P, J=19.8 Hz), −10.66 (d, 1P, J=20.0 Hz), −22.58 (t, 1P, J=20.0 Hz). MS (ESI) for $C_{12}H_{17}O_{14}N_2P_3$ (M−H)$^-$ calcd. 504.97. found 504.82 (M−H)$^-$. UV (10 mM sodium phosphate buffer, pH 7.0) λmax=373 nm (ε 9500).

(3) Synthesis of $NH_2$—C1-dPnTP (3-1) Synthesis of 1-(2-deoxy-β-D-ribofuranosyl)-4-(3-(trifluomacetamido)-1-propynyl)-2-nitropyrrole (TFA-NH—C1-dPn)

A solution of acetic anhydride (4.6 ml, 33 mmol) in methylene chloride (30 ml) was added to a solution of propargylamine (1.0 ml, 15 mmol) in methylene chloride (30 ml) and pyridine (3.7 ml) at 0° C. The reaction solution was stirred at room temperature for 12 hours. The product was separated into aqueous and organic layers by the addition of methylene chloride and a 5% aqueous sodium bicarbonate solution. The organic layer was washed with 5% sodium bicarbonate and then dried over anhydrous sodium sulfate. The organic layer was concentrated under reduced pressure to obtain TFA-NH linker (925 mg). The TFA-NH linker (227 mg, 1.5 mmol) was added to a solution of 1-(2-deoxy-β-D-ribofuranosyl)-4-iodo-2-nitropyrrole (354 mg, 1.0 mmol), CuI (30 mg, 0.16 mmol), Pd(PPh$_3$)$_4$ (58 mg, 0.05 mmol), and TEA (209 μl, 1.5 mmol) in DMF (5.0 ml). The reaction solution was stirred at room temperature for 12 hours and then concentrated under reduced pressure. TFA-NH—C1-dPn (330 mg, 88%) was obtained by silica gel column chromatography purification (eluted with 10% methanol/methylene chloride solution) and RP-HPLC (35% to 50% $CH_3CN$ in $H_2O$, 12 min).

(3-2) Synthesis of 1-(2-deoxy-β-D-ribofuranosyl)-4-(3-amino-1-propynyl)-2-nitropyrrole 5'-triphosphate ($NH_2$—C1-dPnTP)

After azeotropic drying of TFA-NH—C1-dPn nucleoside (75 mg, 0.2 mmol) with pyridine and toluene, proton sponge (66 mg, 0.3 mmol) was added to the residue, and the mixture was dissolved in $(CH_3O)_3PO$ (1.0 ml). To the solution, $POCl_3$ (26 μl, 0.26 mmol) was added, and the mixture was stirred at 0° C. for 1 hour. Tri-n-butylamine (240 pd) and bis(tri-n-butylammonium) pyrophosphate (2.0 ml, 0.5 M DMF solution) were added to the reaction solution, and the mixture was stirred for 30 minutes. Then, a 0.5 M triethylammonium carbonate buffer solution (TEAB) (1 ml) and water (10 ml) were added thereto. The reaction solution was stirred at room temperature for 1 hour and then freeze-dried. $H_2O$ (10 ml) was added to the residue, then 28% $NH_4OH$ (40 ml) was added thereto, and the mixture was stirred at room temperature for 1 hour. The reaction solution was concentrated under reduced pressure. Then, $NH_2$—C1-dPnTP (54 μmol, 27%) was obtained through purification by DEAE Sephadex A-25 ion-exchange column chromatography (eluted with 50 mM to 1.0 M TEAB linear gradient) and RP-HPLC (28% $CH_3CN$ in 100 mM TEAA, 15 min).

(3-3) Physical Property of Compound (3-3-1) 1-(2-Deoxy-β-D-ribofuranosyl)-4-[3-(trifluoroacetamido)-1-propynyl]-2-nitropyrrole (TFA-NH—C1-dPn)

$^1$H NMR (300 MHz, DMSO-d6) δ10.04 (s, 1H), 7.98 (s, 1H), 7.34 (s, 1H), 6.54 (t, 1H, J=5.5 Hz), 5.27 (d, 1H, J=4.4 Hz), 5.10 (t, 1H, J=4.9 Hz), 4.22 (bs, 3H), 3.84 (m, 1H), 3.67-3.54 (m, 2H), 2.44 (m, 1H), 2.26 (m, 1H). HRMS (FAB, 3-NBA matrix) for $C_{14}H_{15}F_3N_3O_6$ (M+H)$^+$ calcd. 378.0913. found 378.0882.

(3-3-2) 1-(2-Deoxy-β-D-ribofuranosyl)-4-(3-amino-1-propynyl)-2-nitropyrrole 5'-triphosphate ($NH_2$—C1-dPnTP)

$^1$H NMR (300 MHz, $D_2O$) δ 7.96 (d, 1H, J=2.1 Hz), 7.32 (d, 1H, J=2.2 Hz), 6.67 (t, 1H, J=6.4 Hz), 4.55 (m, 1H), 4.24-4.12 (m, 3H), 3.91 (s, 2H), 3.11 (q, 16H, J=7.3 Hz), 2.58 (dt, 1H, J=6.3 and 13.8 Hz), 2.41 (ddd, 1H. J=1.6, 4.8, and 14.0 Hz), 1.19 (t, 24H, J=7.3 Hz). $^{31}$P NMR (121 MHz, $D_2O$) δ −8.51 (bs, 1P), −10.70 (d, 1P, J=19.4 Hz), −22.19 (t, 1P, J=19.9 Hz). MS (ESI) for $C_{12}H_{18}O_{14}N_3P_3$ (M−H)$^-$ calcd. 520.20. found, 520.24. UV (10 mM sodium phosphate buffer, pH 7.0) λmax=364 nm (ε 10, 600).

(4) Synthesis of $NH_2$—C3-dPnTP (4-1) Synthesis of 1-(2-deoxy-β-D-ribofuranosyl)-4-[5-trifluoroacetamido-1-pentynyl]-2-nitropyrrole Copper(I) iodide (32 mg, 168 mol) and tetrakis(triphenylphosphine)palladium(0) (61 mg, 53 μmol) were added to a DMF solution (5.3 ml) of 1-(2-deoxy-β-D-ribofuranosyl)-4-iodo-2-nitropyrrole (373 mg, 1.05 mmol), further triethylamine (220 μl, 1.6 mmol) was added thereto, and the mixture was stirred at room temperature in an argon atmosphere. To this solution, a DMF solution (3.0 ml) of 5-trifluoroacetamido-1-pentyne (283 mg, 1.6 mmol) was added dropwise, and the mixture was stirred at room temperature for 19 hours. After concentration under reduced pressure, the crude product was purified by silica gel column chromatography (developing solvent:dichloromethane:methanol=100: 0-90:10) and C18-HPLC to obtain the compound of interest (355 mg, yield: 83%).

(4-2) Synthesis of 1-(2-deoxy-β-D-ribofuranosyl)-4-[5-amino-1-pentynyl]-2-nitropyrrole 5'-triphosphate ($NH_2$—C3-dPnTP)

1-(2-Deoxy-β-D-ribofuranosyl)-4-(5-trifluoroacetamido-1-pentynyl)-2-nitropyrrole (101 mg, 250 μmol) was subjected to azeotropy twice with anhydrous pyridine and twice with anhydrous toluene. The residue and proton sponge (80 mg, 375 μmol) were dissolved in trimethyl phosphate (1.25 ml). To the solution, phosphorus oxychloride (30 μl, 325 μmol) was added, and the mixture was stirred at 0° C. for 1 hour. Then, tri-n-butylamine (300 μl, 1.25 mmol) and a 0.5 M DMF solution (2.5 ml) of bis(tri-n-butylammonium) pyrophosphate were added thereto, and the mixture was stirred for 30 minutes. The reaction was stopped by the addition of a 0.5 M triethylammonium carbonate buffer solution (TEAB) (1.25 ml) thereto. Water (12.5 ml) was added thereto, and the mixture was stirred at room temperature for 1 hour. To this solution, concentrated ammonia water (50 ml) was added, and the mixture was stirred at room temperature for 1 hour. The solution was concentrated under reduced pressure. Then, the residue was purified by polystyrene column chromatography (1.5×20 cm, 50 mM TEAB solution of 0% to 15% acetonitrile) and DEAE Sephadex A-25 column chromatography (1.5×30 cm, linear concentration gradient; 50 mM to 0.8 M solution of TEAB). A portion (3/5 of synthesized amount) of $NH_2$—C3-dPnTP obtained by the DEAE purification was purified (37.8 μmol) by C8-HPLC (Senshu Pak, concentration gradient; 100 mM triethylammonium acetate buffer solution (pH 7.0) of 2.5% to 50% acetonitrile).

(4-3) Physical Property of Compound (4-3-1) 1-(2-Deoxy-β-D-ribofuranosyl)-4-[5-trifluoroacetamido-1-pentynyl]-2-nitropyrrole $^1$H NMR (300 MHz, DMSO-d6) δ 9.47 (brs, 1H), 7.91 (d, 1H, J=2.2 Hz), 7.27 (d, 1H, J=2.2 Hz), 6.55 (t, 1H, J=5.7 Hz), 5.29 (d, 1H, J=4.5 Hz), 5.10 (t, 1H, J=5.2 Hz), 4.24 (m, 1H), 3.85 (dt, 1H, J=4.1, 3.9 Hz), 3.66 (ddd, 1H, J=12.1, 5.2, 3.7 Hz), 3.57 (ddd, 1H, J=12.1, 4.9, 4.8 Hz), 3.29 (m, 2H), 2.48-2.39 (m, 1H), 2.42 (t, 2H, J=7.0 Hz), 2.23 (ddd, 1H, J=13.4, 5.8, 5.7 Hz), 1.73 (m, 2H). HRMS (FAB, 3-NBA matrix) for $C_{16}H_{19}F_3N_3O_6$ $(M+H)^+$ calcd. 406.1226. found 406.1225.

(4-3-2) 1-(2-Deoxy-β-D-ribofuranosyl)-4-[5-amino-1-pentynyl]-2-nitropyrrole 5'-triphosphate ($NH_2$—C3-dPnTP). $^1$H NMR (300 MHz, $D_2O$) δ 7.87 (d, 1H, J=1.6 Hz), 7.25 (d, 1H, J=2.0 Hz), 6.68 (t, 1H, J=5.8 Hz), 4.56 (m, 1H), 4.24-4.13 (m, 3H), 3.11 (q, J=7.3 Hz, the signals of $NH_2CH_2$— were superimposed), 2.65-2.36 (m, 4H), 1.85 (m, 2H), 1.19 (t, 22H, J=7.4 Hz). $^{31}$P NMR (121 MHz, $D_2O$) δ −9.15 (1P), −11.13 (d, 1P, J=19.4 Hz), −22.61 (t, 1P, J=20.0 Hz). MS (ESI) for $C_{14}H_{21}N_3O_{14}P_3$ $(M-H)^-$ calcd. 548.02. found 548.09. UV (10 mM sodium phosphate buffer, pH 7.0) λmax=374 nm (ε 10, 600).

(5) Synthesis of Diol3o3-dPnTP (5-1) Synthesis of 5-(4-pentynyloxyl)pentane-1,2-diacetate (Di(OAc)3o3 Linker)

A solution of 4-pentyn-1-ol (4.65 ml, 50 mmol), 5-bromo-1-pentene (17.8 ml, 150 mmol), and KOH (12.6 g, 225 mmol) in benzene (50 ml) was heated to reflux for 12 hours. After filtration, the reaction solution was separated into aqueous and organic layers by the addition of ethyl acetate and a 10% aqueous ammonium chloride solution. The organic layer was washed with a 10% aqueous ammonium chloride solution and a saturated aqueous solution of sodium chloride, dried over anhydrous sodium sulfate and then concentrated under reduced pressure. 5-(4-Pentynyloxy)-1-pentene (6.5 g) was partially purified by silica gel column chromatography (eluted with a hexane solution of 10% EtOAc). $OsO_4$ (543 mg, 2.0 mmol) was added to a solution of 5-(4-pentynyloxy)-1-pentene (6.5 g) and N-methylmorpholine-N-oxide (10.0 g, 85.4 mmol) in acetone/$H_2O$/tBuOH (4:1:1, 214 ml), and the mixture was stirred at room temperature for 1 hour. After addition of $NaHSO_3$ (1.5 g), the resulting precipitate was filtered off. The residue was washed with methanol, and the filtrates were concentrated under reduced pressure. The product was partially purified by silica gel column chromatography (eluted with a methylene chloride solution of 3% methanol) to obtain 5-(4-pentynyloxyl)pentane-1,2-diol (2.9 g). After azeotropic drying of 5-(4-pentynyloxyl)pentane-1,2-diol (2.9 g) with pyridine, pyridine (78 ml) was added to the residue, and acetic anhydride (5.9 ml, 62.4 mmol) was added thereto. The reaction solution was stirred at room temperature for 9 hours. The product was extracted with ethyl acetate and a 5% aqueous sodium bicarbonate solution. The organic layer was dried over anhydrous sodium sulfate and concentrated under reduced pressure. 5-(4-Pentynyloxy)pentane-1,2-diacetate (Di(OAc)3o3 linker) (3.27 g, 24%, 3 steps) was obtained by silica gel column chromatography purification (eluted with a methylene chloride solution of 20% hexane).

(5-2) Synthesis of 1-(2-deoxy-β-D-ribofuranosyl)-4-[5-(4-pentynyloxyl)pentane-1,2-diacetato)-1-propynyl]-2-nitropyrrole (Di(OAc)3o3-dPn)

Di(OAc)3o3 linker (180 mg, 0.7 mmol) was added to a solution of 1-(2-deoxy-β-D-ribofuranosyl)-4-iodo-2-nitropyrrole (177 mg, 0.5 mmol), CuI (19 mg, 0.1 mmol), Pd(PPh$_3$)$_4$ (29 mg, 0.025 mmol), and TEA (104 μl, 0.75 mmol) in DMF (2.5 ml). The reaction solution was stirred at room temperature for 13 hours and concentrated under reduced pressure. The product was purified by silica gel column chromatography (eluted with a methylene chloride solution of 5% methanol) and RP-HPLC (eluted with linear gradient of 50% to 55% aqueous acetonitrile solutions over 10 minutes) to obtain Di(OAc)3o3-dPn (60 mg, 24%).

(5-3) Synthesis of 1-(2-deoxy-β-D-ribofuranosyl)-4-[5-(4-pentynyloxyl)pentane-1,2-diol)-1-propynyl]-2-nitropyrrole 5'-triphosphate (Diol3o3-dPnTP)

Di(OAc)3o3-dPn nucleoside (50 mg, 0.1 mmol) was azeotropically dried with pyridine and toluene. Proton sponge (33 mg, 0.15 mmol) was added to the residue, and the mixture was dissolved in $(CH_3O)_3PO$ (500 μl). To this solution, POCl$_3$ (13 µl, 0.13 mmol) was added at 0° C., and the mixture was stirred for 1.5 hours. Tri-n-butylamine (120 µl) and bis-tri-n-butylammonium pyrophosphate (1.0 ml, 0.5 M DMF solution) were added to the reaction solution, and the mixture was stirred for 30 minutes. A 0.5 M triethylammonium carbonate buffer solution (TEAB) (500 µl) and water (5.0 ml) were added to the reaction solution, and the mixture was stirred at 0° C. for 30 minutes. After freeze drying, H$_2$O (2.0 ml) was added to the residue, then 28% NH$_4$OH (20 ml) was added thereto, and the mixture was stirred at room temperature for 1 hour. The reaction solution was concentrated under reduced pressure. Then, the product was purified by DEAE Sephadex A-25 ion-exchange chromatography (eluted with 50 mM to 1.0 M TEAB linear gradient) and RP-HPLC (eluted with 100 mM TEAA solution of 5% to 50% acetonitrile over 12 minutes) to obtain Diol3o3-dPnTP (18 µmol, 18%).

(5-4) Physical Property of Compound (5-4-1) 5-(4-Pentynyloxy)pentane-1,2-diacetate (Di(OAc)3o3 Linker)

$^1$H NMR (300 MHz, DMSO-d6) δ 4.96 (m, 1H), 4.16 (dd, 1H, J=3.3, 12.0 Hz), 4.01 (dd, 1H, J=6.4, 11.9 Hz), 3.39 (t, 2H, J=6.4 Hz), 3.33 (t, 2H, J=6.2 Hz), 2.74 (t 1H, J=2.7 Hz), 2.18 (dt, 2H, J=2.6, 7.2 Hz), 1.66-1.45 (m, 6H). HR-MS (FAB, NBA matrix) for C$_{14}$H$_{23}$O$_5$ (M+H) calcd. 271.1545. found 271.1592.

(5-4-2) 1-(2-Deoxy-β-D-ribofuranosyl)-4-[5-(4-pentynyloxyl)pentane-1,2-diacetato)-1-propynyl]-2-nitropyrrole (Di(OAc)3o3-dPn)

$^1$H NMR (300 MHz, DMSO-d6) δ 7.91 (d, 1H, J=2.2 Hz), 7.28 (d, 1H, J=2.2 Hz), 6.55 (t, 1H, J=5.7 Hz), 5.29 (d, 1H, J=4.5 Hz), 5.10 (t, 1H, J=5.2 Hz), 4.97 (m, 1H), 4.24 (m, 1H), 4.16 (dd, 1H, J=3.3, 12.0 Hz), 4.01 (dd, 1H, J=6.5, 11.9 Hz), 3.85 (m, 1H), 3.70-3.53 (m, 2H), 3.44 (t, 2H, J=6.2 Hz), 3.36 (t, 2H, J=6.1 Hz), 2.45-2.39 (m, 3H), 2.28-2.19 (m, 2H), 2.01, 2.00 (s, s, 3H, 3H), 1.76-1.47 (m, 6H). HR-MS (FAB, NBA matrix) for C$_{23}$H$_{33}$N$_2$O$_{10}$ (M+H)$^+$ calcd. 497.2135. found 497.2110.

(5-4-3) 1-(2-Deoxy-β-D-ribofuranosyl)-4-[5-(4-pentynyloxyl)pentane-1,2-diol)-1-propynyl]-2-nitropyrrole 5'-triphosphate (Diol3o3-dPnTP)

$^1$H NMR (300 MHz, D$_2$O) δ 7.73 (d, 1H, J=2.1 Hz), 7.37 (d, 1H, J=2.1 Hz), 6.76 (t, 1H, J=6.1 Hz), 4.62 (m, 1H), 4.26-4.20 (m, 3H), 3.72-3.42 (m, 7H), 3.20 (q, 22H, J=7.3 Hz), 2.64 (m, 1H), 2.53-2.44 (m, 3H), 1.89-1.41 (m, 6H), 1.28 (t, 32H, J=7.3 Hz). $^{31}$P NMR (121 MHz, D$_2$O) δ −10.07 (d, 1P, J=19.7 Hz), −10.63 (d, 1P, J=20.1 Hz), −22.55 (t, 1P, J=20.0 Hz). MS (ESI) for C$_{19}$H$_{30}$N$_2$O$_{17}$P$_3$ (M−H)$^-$ calcd. 651.37. found 651.39. UV (10 mM sodium phosphate buffer pH 7.0) λmax=374 nm (ε 9, 200).

(6) Synthesis of Diox6-dPnTP (6-1) Synthesis of 2-(7-octynyl)-1,3-dioxolane (Diox6 Linker)

8-Bromo-1-octene (839 µl, 5.0 mmol) was added to a solution of a lithium acetylide-ethylenediamine complex (563 mg, 5.5 mmol) in DMSO (25 ml). The reaction solution was stirred at 10° C. for 2 hours. The product was separated into aqueous and organic layers by the addition of ether and water. Then, the organic layer was washed with water, dried over anhydrous sodium sulfate, and then concentrated under reduced pressure. The product was partially purified by silica gel column chromatography (eluted with a methylene chloride solution of 25% hexane) to obtain dec-1-en-9-yne (457 mg, 67%). OsO$_4$ (42 mg, 0.17 mmol) was added to a solution of dec-1-en-9-yne (450 mg) and N-methylmorpholine-N-oxide (775 mg, 6.6 mmol) in acetone/H$_2$O/tBuOH (4:1:1, 16.5 ml), and the mixture was stirred at room temperature for 30 minutes. After addition of NaHSO$_3$ (115 mg) to the reaction solution, the resulting precipitate was filtered off. The precipitate was washed with methanol, and the filtrates were combined and concentrated under reduced pressure. The product was partially purified by silica gel column chromatography (eluted with a methylene chloride solution of 3% methanol) to obtain dec-9-yne-1,2-diol. NaIO$_4$ (10 mg, 4.8 mmol) was added to a solution of dec-9-yne-1,2-diol in acetone/H$_2$O (7:3, 33 ml), and the mixture was stirred at room temperature for 12 hours. The reaction solution was separated into aqueous and organic layers by the addition of ethyl acetate and water. The organic layer was dried over anhydrous sodium sulfate and then concentrated under reduced pressure to obtain 310 mg of non-8-ynal (2 steps, yield: 68%). A solution of non-8-ynal (310 mg), p-toluenesulfonic acid monohydrate (42 mg, 0.22 mmol), and ethylene glycol (279 mg, 4.5 mmol) in benzene (11 ml) was heated to reflux for 2 hours. The reaction solution was concentrated under reduced pressure. The product was purified by silica gel column chromatography (eluted with methylene chloride) to obtain 2-(7-octynyl)-1,3-dioxolane (310 mg, 76%).

(6-2) Synthesis of 4-(2-(7-octynyl)-1,3-dioxolane)-1-(2-deoxy-β-D-ribofuranosyl)-2-nitropyrrole (Diox-C6CC-dPn)

2-(7-Octynyl)-1,3-dioxolane (137 mg, 0.37 mmol) was added to a solution of 1-(2-deoxy-β-D-ribofuranosyl)-4-iodo-2-nitropyrrole (177 mg, 0.5 mmol), CuI (15 mg, 0.08 mmol), Pd(PPh$_3$)$_4$ (29 mg, 0.025 mmol), and TEA (105 µl, 0.75 mmol) in DMF (2.5 ml), and the mixture was stirred at room temperature for 12 hours. The reaction solution was concentrated under reduced pressure. Then, the product was purified by silica gel column chromatography (eluted with a methylene chloride solution of 2% methanol) and C18 RP-HPLC (54% to 55% aqueous acetonitrile solution) to obtain 180 mg (yield: 88%) of 4-(2-(7-octynyl)-1,3-dioxolane)-1-(2-deoxy-β-D-ribofuranosyl)-2-nitropyrrole (Dio-C6CC-dPn).

(6-3) Synthesis of 4-(2-(7-octynyl)-1,3-dioxolane)-1-(2-deoxy-β-D-ribofuranosyl)-2-nitropyrrole 5'-triphosphate (Diox6-dPnTP)

After azeotropic drying of 4-(2-(7-octynyl)-1,3-dioxolane)-1-(2-deoxy-β-D-ribofuranosyl)-2-nitropyrrole (82 mg, 0.2 mmol) with pyridine and toluene, proton sponge (66 mg, 0.3 mmol) and (CH$_3$O)$_3$PO (1.0 ml) were added to the residue. To this solution, POCl$_3$ (26 µl, 0.26 mmol) was added, and the mixture was stirred at 0° C. for 1.5 hours. To this reaction solution, tri-n-butylamine (240 µl) and bis-tri-n-butylammonium pyrophosphate (2.0 ml, 0.5 M DMF solution) were added, and the mixture was stirred for 30 minutes. A 0.5 M triethylammonium carbonate buffer solution (TEAB) (1 ml) and water (10 ml) were added to the reaction solution, and the mixture was stirred at 0° C. for 30 minutes. The product was purified by DEAE Sephadex A-25 ion-exchange column chromatography (eluted with 50 mM to 1.0 M TEAB linear gradient) and RP-HPLC to obtain 4-(2-(7-octynyl)-1,3-dioxolane)-1-(2-deoxy-β-D-ribofuranosyl)-2-nitropyrrole 5'-triphosphate (Diox6-dPnTP) (yield: 29 μmol).

(6-4) Physical Property of Compound (6-4-1) 2-(7-Octynyl)-1,3-dioxolane (Diox6 Linker)

$^1$H NMR (300 MHz, CDCl$_3$) δ 4.86 (t, 1H, J=4.8 Hz), 3.99-3.86 (m, 4H), 2.20 (dt, 2H, J=2.6, 7.1 Hz), 1.95 (t, 1H, J=2.7 Hz), 1.66 (m, 2H), 1.58-1.39 (m, 8H). HR-MS (FAB, NBA matrix) for $C_{11}H_{19}O_2$ (M+H)$^+$ calcd. 183.1385. found 183.1579.

(6-4-2) 4-(2-(7-Octynyl)-1,3-dioxolane)-1-(2-deoxy-β-D-ribofuranosyl)-2-nitropyrrole (Diox6-dPn)

$^1$H NMR (300 MHz, DMSO-d$_6$) δ 7.90 (d, 1H, J=2.2 Hz), 6.27 (d, 1H, J=5.8 Hz), 5.28 (d, 1H, J=4.5 Hz), 5.10 (t, 1H, J=5.2 Hz), 4.75 (t, 1H, J=4.8 Hz), 4.24 (m, 1H), 3.88-3.53 (m, 7H), 2.43 (m, 1H), 2.36 (t, 2H, J=7.1 Hz), 2.23 (m, 1H), 1.56-1.34 (m, 10H). HR-MS (FAB, NBA matrix) for $C_{20}H_{29}O_7N_2$ (M+H) calcd. 409.1975. found 409.1979.

(6-4-3) 4-(2-(7-Octynyl)-1,3-dioxolane)-1-(2-deoxy-β-D-ribofuranosyl)-2-nitropyrrole 5'-triphosphate (Diox6-dPnTP)

$^1$H NMR (300 MHz, D$_2$O) δ 7.72 (d, 1H, J=2.1 Hz), 7.37 (d, 1H, J=2.1 Hz), 6.77 (t, 1H, J=6.1 Hz), 4.93 (t, 1H, J=5.0 Hz), 4.63 (m, 1H), 4.27-4.18 (m, 3H), 4.08-3.87 (m, 4H), 3.21 (q, 19H, J=7.3 Hz), 2.65 (dt, 1H, J=6.1 Hz), 2.48 (dt, 1H, J=6.2 Hz), 2.40 (t, 2H, J=7.0 Hz), 1.69 (m, 2H), 1.59 (m, 2H), 1.50-1.42 (m, 6H), 1.29 (t, 28H, J=7.3 Hz). $^{31}$P NMR (121 MHz, D$_2$O) 5-10.23 (d, 1P, J=19.6 Hz), −10.63 (d, 1P, J=19.7 Hz), −22.59 (t, 1P, J=19.8 Hz). MS (ESI) for $C_2H_{31}N_2O_{16}P_3$ (M−H)$^+$ calcd. 647.09. found 647.14. UV (10 mM sodium phosphate buffer, pH 7.0) λmax=373 nm (ϵ 9900).

(7) Synthesis of Diol6-dPnTP (7-1) Synthesis of 9-decyne-1,2-diyl diacetate

8-Bromo-1-octene (839 μl, 5.0 mmol) was added to a solution of a lithium acetylide-ethylenediamine complex (563 mg, 5.5 mmol) in DMSO (5 ml), and the mixture was stirred at 10° C. for 2 hours. The reaction solution was separated into aqueous and organic layers by the addition of ether and water. The organic layer was washed with water, dried over anhydrous sodium sulfate, and then concentrated under reduced pressure. The product was purified by silica gel column chromatography (eluted with hexane) to obtain dec-1-en-9-yne (633 mg, 93%). OsO$_4$ (58 mg, 0.23 mmol) was added to a solution of dec-1-en-9-yne (630 mg) and N-methylmorpholine-N-oxide (1.08 g, 9.2 mmol) in acetone/H$_2$O/tBuOH (4:1:1, 23 ml), and the mixture was stirred at room temperature for 1 hour. After addition of NaHSO$_3$ (160 mg), the resulting precipitate was filtered off. The precipitate was washed with methanol, and the filtrates were then combined and concentrated under reduced pressure. The product was purified by silica gel column chromatography (eluted with a methylene chloride solution of 3% methanol) to obtain dec-9-yne-1,2-diol (494 mg). After azeotropy of dec-9-yne-1,2-diol (494 mg) with pyridine, pyridine (10 ml) was added to the residue. Acetic anhydride (2.17 ml, 23 mmol) was added thereto, and the mixture was stirred at room temperature for 13 hours. The reaction solution was separated into aqueous and organic layers by the addition of ethyl acetate and 5% sodium bicarbonate. The organic layer was washed with a 5% aqueous sodium bicarbonate solution, dried over anhydrous sodium sulfate, and then concentrated under reduced pressure. The product was purified by silica gel column chromatography (eluted with a methylene chloride solution of 1% methanol) to obtain 9-decyne-1,2-diyl diacetate (414 mg, 2 steps, yield: 35%).

(7-2) Synthesis of 4-(9-decyne-1,2-diyl diacetato)-1-(2-deoxy-β-D-ribofuranosyl)-2-nitropyrrole (Di-OAc-6-dPn)

9-Decyne-1,2-diyl diacetate (381 mg, 1.5 mmol) was added to a solution of 1-(2-deoxy-β-D-ribofuranosyl)-4-iodo-2-nitropyrrole (354 mg, 1.0 mmol), CuI (38 mg, 0.2 mmol), Pd(PPh$_3$)$_4$ (58 mg, 0.05 mmol), and TEA (208 μl, 1.5 mmol) in DMF (5.0 ml), and the mixture was stirred at room temperature for 20 hours. The reaction solution was separated into aqueous and organic layers by the addition of ethyl acetate and water. The organic layer was washed with water, dried over anhydrous sodium sulfate, and then concentrated under reduced pressure. The product was purified by silica gel column chromatography (eluted with a methylene chloride solution of 3% methanol) and RP-HPLC (55% aqueous acetonitrile solution) to obtain 500 mg (yield: 99%) of 4-(9-decyne-1,2-diyl diacetato)-1-(2-deoxy-β-D-ribofuranosyl)-2-nitropyrrole (Di-OAc-6-dPn).

(7-3) Synthesis of 4-(9-decyne-1,2-diol)-1-(2-deoxy-β-D-ribofuranosyl)-2-nitropyrrole 5'-triphosphate (Diol6-dPnTP)

After azeotropic drying of 4-(9-decyne-1,2-diyl diacetato)-1-(2-deoxy-β-D-ribofuranosyl)-2-nitropyrrole (48 mg, 0.1 mmol) with pyridine and toluene, proton sponge (33 mg, 0.15 mmol) and (CH$_3$O)$_3$PO (500 μl) were added to the residue. To this solution, POCl$_3$ (13 μl, 0.13 mmol) was added at 0° C., and the mixture was stirred for 1.5 hours. Tri-n-butylamine (120 μl) and bis-tri-n-butylammonium pyrophosphate (1.0 ml, 0.5 M DMF solution) were added thereto, and the mixture was stirred for 30 minutes. Then, a 0.5 M triethylammonium carbonate buffer solution (TEAB) (500 μC) and water (5.0 ml) were added thereto, and the mixture was stirred at 0° C. for 30 minutes. After freeze drying, H$_2$O (2.0 ml) and 28% NH$_4$OH (20 ml) were added to the residue, and the mixture was stirred at room temperature for 1 hour. After concentration under reduced pressure, the product was purified by DEAE Sephadex A-25 ion-exchange column chromatography (eluted with 50 mM to 1.0 M TEAB linear gradient) and RP-HPLC (100 mM TEAA solution of 5% to 50% acetonitrile, 12 min) to obtain 18 μmol (yield: 18%) of 4-(9-decyne-1,2-diol)-1-(2-deoxy-β-D-ribofuranosyl)-2-nitropyrrole 5'-triphosphate (Diol6-dPnTP).

(7-4) Physical Property of Compound (7-4-1) 9-Decyne-1,2-diyl diacetate $^1$H NMR (300 MHz, DMSO-d6) 4.94 (m, 1H), 4.07 (ddd, 2H, J=3.2, 6.5, 48.3 Hz), 2.72 (t, 1H, J=2.7 Hz), 2.13 (dt, 2H, J=2.6, 6.8 Hz), 2.00

(s, 3H9, 1.99 (s, 3H), 1.52-1.25 (m, 10H). HR-MS (FAB, NBA matrix) for $C_{14}H_{23}O_4$ $(M+H)^+$ calcd. 255.1596. found 255.1605.

(7-4-2) 4-(9-Decyne-1,2-diyl diacetato)-1-(2-deoxy-β-D-ribofuranosyl)-2-nitropyrrole (Di-OAc-6-dPn) $^1$H NMR (300 MHz, DMSO-$d_6$) δ 7.89 (d, 1H, J=2.2 Hz), 7.26 (d, 1H, J=2.2 Hz), 6.54 (t, 1H, J=5.8 Hz), 5.27 (d, 1H, J=4.5 Hz), 5.09 (t, 1H, J=5.2 Hz), 4.94 (m, 1H), 4.23 (m, 1H), 4.07 (ddd, 2H, J=3.2, 6.5, 48.8 Hz), 3.83 (m, 1H), 3.68-3.52 (m, 2H), 2.42 (m, 1H), 2.35 (t, 2H, J=7.1 Hz), 2.22 (m, 1H), 2.00 (s, 3H), 1.99 (s, 3H), 1.52-1.28 (m, 10H). HR-MS (FAB, NBA matrix) for $C23H_{33}O_9N_2$ $(M+H)^+$ calcd. 481.2186. found 481.2206.

(7-4-3) 4-(9-Decyne-1,2-diol)-1-(2-deoxy-β-D-ribofuranosyl)-2-nitropyrrole 5'-triphosphate (Diol6-dPnTP) $^1$H NMR (300 MHz, $D_2O$) δ 7.72 (d, 1H, J=2.1 Hz), 7.35 (d, 1H, J=2.1 Hz), 6.76 (t, 1H, J=6.1 Hz), 4.62 (m, 1H), 4.26-4.20 (m, 3H), 3.70 (m, 1H), 3.59 (dd, 1H, J=3.8, 11.6 Hz), 3.46 (dd, 1H, J=6.9, 11.6 Hz), 3.20 (q, 20H, J=7.3 Hz), 2.64 (dt, 1H, J=6.2, 13.0 Hz), 2.47 (dt, 1H, J=6.2, 14.0 Hz), 2.40 (t, 2H, J=7.0 Hz), 1.60-1.25 (m, 10H), 1.28 (t, 30H, J=7.3 Hz). $^{31}$P NMR (121 MHz, $D_2O$) δ −10.20 (d, 1P, J=19.9 Hz), −10.64 (d, 1P, J=20.1 Hz), −22.59 (t, 1P, J=20.0 Hz). MS (ESI) for $C_{19}H_{31}N_2O_{16}P_3$ $(M-H)^+$ calcd. 635.08. found. 635.08. UV (10 mM sodium phosphate buffer, pH 7.0) λmax=374 nm (ε 9400).

(8) Synthesis of COOH—C1-dPnTP (8-1) Synthesis of 1-(2-deoxy-β-D-ribofuranosyl)-4-(3-carboxypropanamido-1-propynyl)-2-nitropyrrole 5'-triphosphate (COOH—C1-dPnTP)

A solution of succinic anhydride (4 mg, 40 µmol) in DMSO (500 µL) was added to a 200 mM solution of $NH_2$—C1-dPnTP (10 µmol) in TEAA (pH 7.0, 500 µL), and the mixture was left standing at room temperature for 1 hour. After freeze drying, the residue was purified by HPLC (eluted with 0% to 30% acetonitrile linear gradient in a 100 mM triethylammonium acetate solution over 10 minutes) to obtain 8.4 µmol (yield: 84%) of 1-(2-deoxy-β-D-ribofuranosyl)-4-(3-carboxypropanamido-1-propynyl)-2-nitropyrrole 5'-triphosphate (COOH—C1-dPnTP).

(8-2) Physical Property of Compound (COOH—C1-dPnTP) $^1$H-NMR (300 MHz, $D_2O$) δ (ppm) 7.73 (1H, d, J=2.0 Hz), 7.36 (d, 1H, J=2.0 Hz), 6.70 (t, 1H, J=5.9 and 6.3 Hz), 4.59-4.54 (m, 1H), 4.21-4.15 (m, 3H), 4.10 (s, 2H), 3.15 (q, 24H, J=7.3 Hz), 2.64-2.55 (m, 1H), 2.48-2.39 (m, 5H), 1.23 (t, 36H, J=7.3 Hz). $^{31}$P-NMR (121 MHz, $D_2O$) δ (ppm) −10.66 (d, 1P, J=19.6 Hz), −11.27 (d, 1P, J=19.9 Hz), −23.16 (t, 1P, J=19.8 and 20.1 Hz). MS (ESI) for $C_{16}H_{21}O_{17}N_3P_3$ $(M-H)^+$ calcd. 620.01. found 619.91. UV (10 mM sodium phosphate buffer, pH 7.0) λmax 365 nm (ε9800).

(9) Synthesis of 1-(2-deoxy-β-D-ribofuranosyl)-4-(3-(2-pyridyldithio)propanamido-1-propynyl)-2-nitropyrrole 5'-triphosphate (PDP-C1-dPnTP)

(9-1) Synthesis of PDP-C1-dPnTP

A solution of succinimidyl 3-(2-pyridyldithio)-propionate (PDP-SE, Invitrogen Corp.) (12.5 mg, 40 µmol) in DMF (300 µl) was added to a 0.1 M $NaHCO_3$—$Na_2CO_3$ buffer solution (pH 8.5, 600 µl) of $NH_2$—C1-dPnTP (20 µmol), and the mixture was stirred at room temperature for 3 hours. The reaction was stopped by the addition of 28% ammonia water (1 ml) to the reaction solution, followed by freeze drying. The product was purified by DEAE Sephadex A-25 ion-exchange column chromatography (1.5 cm×30 cm, eluted with 50 mM to 1.0 M TEAB linear gradient) and C18 HPLC to obtain 3.8 µmol of PDP-dPnTP (19%).

(9-2) Physical Property of Compound

PDP-C1-dPnTP: $^1$H NMR (300 MHz, $D_2O$) δ 8.38 (m, 1H), 7.89-7.83 (m, 2H), 7.80 (d, 1H, J=2.1 Hz), 7.38 (d, 1H, J=2.1 Hz), 7.29 (m, 1H), 6.75 (t, 1H, J=6.0 Hz), 4.62 (m, 1H), 4.23 (m, 3H), 4.08 (s, 2H), 3.21 (q, 19H, J=7.3 Hz), 3.12 (t, 2H, J=6.7 Hz), 2.69 (t, 2H, J=6.6 Hz), 2.62 (m, 1H), 2.49 (m, 1H), 1.29 (t, 30H, J=7.3 Hz). $^{31}$P NMR (121 MHz, $D_2O$) δ −10.02 (d, 1P, J=19.9 Hz), −10.68 (d, 1P, J=20.0 Hz), −22.48 (t, 1P, J=19.9 Hz). MS (ESI) for $C_{20}H_{24}N_4O_{15}P_3S_2$ $(M-H)^+$ calcd. 717.00. found 717.08. UV (10 mM sodium phosphate buffer, pH 7.0) λmax 285 nm (ε 7600), 365 nm (ε 10700).

(10) Synthesis of Amino Acid-Bound C1-dPnTP (a.a.-C1-dPnTP)

(10-1) Synthesis of Fmoc-Amino Acid Succinimide Ester (Fmoc-a.a.-SE)

A solution of Fmoc-L-amino acid (0.5 mmol), 1-hydroxy-succinimide (0.6 mmol), and N-(3-dimethylaminopropyl)-N'-ethylcarbodiimide hydrochloride (0.6 mmol) in DMF (1 ml) was stirred at room temperature for 1 hour. The reaction solution was added to 30 ml of water. The resulting precipitate was filtered, washed with water, and dried under reduced pressure. The reaction solutions for Fmoc-His (Fmoc)-SE, Fmoc-Ser(OTBDMS)-SE, and Fmoc-Lys (Fmoc)-SE were each separated into aqueous and organic layers by the addition of ethyl acetate and water. The organic phase was washed twice with water and then dried over sodium sulfate. The organic phase was concentrated under reduced pressure. The residue was purified by silica gel column chromatography (eluted with a methylene chloride solution of 1% methanol) to obtain Fmoc-Phe-SE (195 mg, 81%), Fmoc-Tyr-SE (216 mg, 86%), Fmoc-Trp-SE (219 mg, 84%), Fmoc-His(Fmoc)-SE (200 mg, 57%), Fmoc-Ser(TB-DMS)-SE (222 mg, 82%), and Fmoc-Lys(Fmoc)-SE (278 mg, 81%).

(10-2) Synthesis of Amino Acid-Bound C1-dPnTP (a.a.-C1-dPnTP)

(10-2-1) Phe-, Tyr-, and Trp-C1-dPnTP

A solution of Fmoc-amino acid succinimide ester (Fmoc-a.a.-SE) (29 µmol) in DMF (1 ml) was added to a solution of 1-(2-deoxy-β-D-ribofuranosyl)-4-(3-amino-1-propynyl)-2-nitropyrrole 5'-triphosphate (19 µmol) in DMF (1 ml), and the mixture was left standing at room temperature for 12 hours. Piperidine (100 µl) was added to the reaction solution, and the mixture was stirred at room temperature for 3 minutes. Water (2 ml) was added to the reaction solution, followed by washing three times with ethyl acetate (4 ml). Water (10 ml) and 2 M TEAB (100 µl) were added to the aqueous phase, and the mixture was freeze-dried. The residue was purified on DEAE Sephadex A-25 column (eluted with 50 mM to 1 M TEAB linear gradient) and then purified by HPLC to obtain 1-(2-deoxy-β-D-ribofuranosyl)-4-(3-(L- tyrosinamido)-1-propynyl)-2-nitropyrrole 5'-triphosphate (Tyr-C1-dPnTP, 11.3 μmol, yield: 59%, HPLC: eluted with 0% to 40% acetonitrile linear gradient in a 100 mM triethylamine acetate buffer over 15 minutes), 1-(2-deoxy-β-D-ribofuranosyl)-4-(3-(L-tryptophanamido)-1-propynyl)-2-nitropyrrole 5'-triphosphate (Trp-C1-dPnTP, 12.1 μmol, yield: 64%, HPLC: eluted with 10% to 50% acetonitrile linear gradient in a 100 mM triethylamine acetate buffer over 10 minutes), and 1-(2-deoxy-β-D-ribofuranosyl)-4-(3-(L-phenylalaninamido)-1-propynyl)-2-nitropyrrole 5'-triphosphate (Phe-C1-dPnTP, 11.4 μmol, yield: 60%, HPLC: eluted with 0% to 50% acetonitrile linear gradient in a 100 mM triethylamine acetate buffer over 10 minutes).

(10-2-2) His- and Ser-C1-dPnTP

A solution of Fmoc amino acid succinimide ester (Fmoc-a.a.-SE) (29 μmol) in DMF (1 ml) was added to a solution of 1-(2-deoxy-β-D-ribofuranosyl)-4-(3-amino-1-propynyl)-2-nitropyrrole 5'-triphosphate (19 μmol) in DMF (1 ml), and the mixture was stirred at room temperature for 24 hours. Water (8 ml) was added to the reaction solution, followed by washing once with ethyl acetate (4 ml). The Fmoc group-containing triphosphate contained in the aqueous phase was purified by HPLC (histidine: eluted with 20% to 50% acetonitrile linear gradient in a 100 mM triethylamine acetate buffer over 10 minutes, serine: eluted with 30% acetonitrile in a 100 mM triethylamine acetate buffer over 10 minutes) and then freeze-dried. The residue was dissolved in DMF (2.0 ml), and the solution was treated with piperidine (100 μl) at room temperature for 5 minutes. $H_2O$ (4.0 ml) was added to the reaction solution, followed by washing three times with ethyl acetate (4 ml). $H_2O$ (4 ml) and 2 M TEAB (100 μl) were added to the aqueous phase, and the mixture was freeze-dried. The residue was purified on DEAE Sephadex A-25 column (eluted with 50 mM to 1 M TEAB linear gradient) and then purified by HPLC to obtain 1-(2-deoxy-β-D-ribofuranosyl)-4-(3-(L-histidinamido)-1-propynyl)-2-nitropyrrole 5'-triphosphate (His-C1-dPnTP, 8.8 μmol, yield: 46%, HPLC: eluted with 0%/o to 40% acetonitrile linear gradient in a 100 mM triethylamine acetate buffer over 15 minutes) and 1-(2-deoxy-β-D-ribofuranosyl)-4-(3-(L-serinamido)-1-propynyl)-2-nitropyrrole 5'-triphosphate (Ser-C1-dPnTP, 10.3 μmol, yield: 54%, HPLC: eluted with (0/o to 30% acetonitrile linear gradient in a 100 mM triethylamine acetate buffer over 13 minutes).

(10-3) Physical Property of Compound (10-3-1) Fmoc Amino Acid Succinimide Ester (Fmoc-a.a.-SE)

Fmoc-Phe-SE: $^1$H NMR (300 MHz, DMSO-d6) δ 8.24 (d, 1H, J=8.5 Hz), 7.88 (d, 2H, J=7.5 Hz), 7.62 (dd, 2H, J=2.9 and 7.4 Hz), 7.43-7.21 (m, 9H), 4.73-4.65 (m, 1H), 7.29-4.14 (m, 3H), 3.25 (dd, 1H, J=4.3 and 13.8 Hz), 3.05 (dd, 1H, J=11.0 and 13.8 Hz), 2.84 (s, 4H). Fmoc-Tyr-SE: $^1$H NMR (300 MHz, DMSO-d6) δ 9.23 (s, 1H), 8.19 (d, 1H, J=8.5 Hz), 7.89 (d, 2H. J=7.5 Hz), 7.65-7.60 (m, 2H), 7.44-7.39 (m, 2H), 7.34-7.27 (m, 2H), 7.14 (d, 2H, J=8.4 Hz), 7.68 (d, 2H, J=8.5 Hz), 4.61-4.53 (m, 1H), 4.26-4.15 (m, 3H), 3.12 (dd, 1H, J=4.3 and 13.8 Hz), 2.92 (dd, 1H, J=10.7 and 13.8 Hz), 2.83 (s, 4H). Fmoc-Trp-SE: $^1$H NMR (300 MHz, DMSO-d6) δ 10.95 (s, 1H), 8.24 (d, 1H, J=8.2 Hz), 7.88 (d, 2H, J=7.6 Hz), 7.65-7.57 (m, 3H), 7.44-7.24 (m, 6H), 7.10 (t, 1H, J=7.9 Hz), 7.01 (d, 1H, J=7.5 Hz), 4.70-4.63 (m, 1H), 4.29-4.18 (m, 3H), 3.39 (m, 1H), 3.21 (m, 1H), 2.84 (s, 4H). Fmoc-Ser(OTBDMS)-SE: $^1$H NMR (300 MHz, DMSO-d6) δ 8.11 (d, 1H, J=8.5 Hz), 7.90 (d, 2H, J=7.5 Hz), 7.72 (t, 2H, J=6.6 Hz), 7.42 (t, 2H, J=7.4 Hz), 7.32 (dt, 2H, J=1.0 and 7.4 Hz), 4.63-4.56 (m, 1H), 4.35-4.22 (m, 3H), 4.00-3.88 (m, 2H), 2.81 (s, 4H), 0.86 (s, 9H), 0.07 (s, 3H), 0.06 (s, 3H). Fmoc-His(Fmoc)-SE: $^1$H NMR (300 MHz, DMSO-d6) δ 8.14 (m, 2H), 7.95-7.86 (m, 4H), 7.7 (dd, 2H, J=3.0, 7.3 Hz), 7.62 (d, 2H, J=7.4 Hz), 7.46-7.25 (m, 9H), 4.84-4.76 (m, 1H), 4.69 (d, 2H, J=6.7 Hz), 4.43 (t, 1H, J=6.7 Hz), 4.30 (d, 2H, J=7.0 Hz), 4.20 (t, 1H, J=7.3 Hz), 3.15-3.00 (m, 2H), 2.81 (s, 4H). Fmoc-Lys (Fmoc)-SE: $^1$H NMR (300 MHz, DMSO-d6) δ 8.10 (d, 1H, J=7.8 Hz), 7.89 (d, 4H, J=7.5 Hz), 7.70 (m, 4H), 7.41 (t, 4H, J=7.4 Hz), 7.35-7.26 (m, 5H), 4.44-4.18 (m, 7H), 2.98 (m, 2H), 2.80 (s, 4H), 1.81 (m, 2H), 1.42 (m, 4H).

(10-3-2) Amino Acid-Bound C1-dPnTP (a.a.-C1-dPnTP)

(10-3-2-1) Phe-C1-dPnTP: $^1$H-NMR (300 MHz, $D_2O$) δ 7.83 (d, 1H, J=2.1 Hz), 7.32-7.20 (m, 6H), 7.66 (dd, 1H, J=4.7, 6.3 Hz), 4.54 (m, 1H), 4.22-4.11 (m, 4H), 4.07 (d, 1H, J=17.7 Hz), 3.78 (d, 1H, J=17.7 Hz), 3.11 (q and m, 15H, 2H, J=7.3 Hz), 2.56 (m, 1H), 2.40 (m, 1H), 1.19 (t, 23H, J=7.3 Hz). $^{31}$P-NMR (121 MHz, $D_2O$) δ −8.37 (bs, 1P), −10.67 (d, 1P, J=20.1 Hz), −22.01 (t, 1P, J=20.1 Hz). MS (ESI) for $C_{21}H_{27}O_{15}N_4P_3$ (M–H)$^-$ calcd. 667.06. found 666.66. UV (10 mM sodium phosphate buffer, pH 7.0) λmax 368 nm (9540).

(10-3-2-2) Tyr-C1-dPnTP: $^1$H-NMR (300 MHz, $D_2O$) δ 7.81 (d, 1H, J=2.1 Hz), 7.27 (d, 1H, J=2.1 Hz), 7.08 (d, 2H, J=8.5 Hz), 6.75 (d, 2H, J=8.6 Hz), 6.67 (dd, 1H, J=4.8, 6.2 Hz), 4.53 (m, 1H), 4.21-4.09 (m, 4H), 4.04 (d, 1H, J=17.6 Hz), 3.85 (d, 1H, J=17.7 Hz), 3.11 (q and m, 13H, 1H, J=7.3 Hz), 2.94 (m, 1H), 2.56 (m, 1H), 2.40 (m, 1H), 1.19 (t, 20H, J=7.3 Hz). $^{31}$P-NMR (121 MHz, $D_2O$) δ −9.11 (bs, 1P), −10.71 (d, 1P, J=19.8 Hz), −22.22 (t, 1P, J=19.9 Hz). MS (ESI) for $C_{21}H_{27}O_{16}N_4P_3$ (M–H)$^-$ calcd. 683.06. found, 682.80. UV (10 mM sodium phosphate buffer, pH 7.0) λmax 282 nm (3400), 368 nm (ε 9760).

(10-3-2-3) Trp-C1-dPnTP: $^1$H-NMR (300 MHz, $D_2O$) δ 7.79 (d, 1H, J=2.1 Hz), 7.53 (d, 1H, J=7.6 Hz), 7.38 (d, 1H, J=7.9 Hz), 7.27 (s, 1H), 7.21 (d, 1H, J=2.1 Hz), 7.16-7.04 (m, 2H), 6.66 (dd, 1H, J=4.5, 6.3 Hz), 3.54 (m, 1H), 4.23-4.10 (m, 4H), 3.95 (d, 1H, J=17.7 Hz), 3.68 (d, 1H, J=17.6 Hz), 3.39-3.19 (m, 2H), 3.11 (q, 23H, J=7.3 Hz), 2.55 (m, 1H), 2.41 (m, 1H), 1.19 (t, 35H, J=7.3 Hz). $^{31}$P-NMR (121 MHz, $D_2O$) δ −7.36 (bs, 1P), −10.61 (d, 1P, J=19.8 Hz), −21.79 (t, 1P, J=19.9 Hz, 20.1 Hz). MS (ESI) for $C_{23}H_{28}O_{15}N_5P_3$ (M–H)$^-$ calcd. 706.07. found, 705.84. UV (10 mM sodium phosphate buffer, pH 7.0) λmax 280 nm (7270), 287 nm (ε 6950), 369 nm (ε 9650).

(10-3-2-4) His-C1-dPnTP: $^1$H-NMR (300 MHz, $D_2O$) δ 8.38 (d, 1H, J=1.2 Hz), 7.90 (d, 1H, J=2.1 Hz), 7.22 (s, 1H), 6.67 (dd, 1H, J=4.5, 6.4 Hz), 4.54 (m, 1H), 4.33-4.12 (m, 4H), 4.08 (d, 1H, J=17.7 Hz), 3.94 (d, 1H, J=17.8 Hz), 3.23 (m, 2H), 3.11 (q, 10H, J=7.3 Hz), 2.57 (m, 1H), 2.41 (m, 1H), 1.19 (t, 16H, J=7.3 Hz). $^{31}$P-NMR (121 MHz, $D_2O$) δ −8.29 (d, 1P, J=19.2 Hz), −10.69 (d, 1P, J=19.2 Hz), −21.86 (t, 1P, J=19.4, 19.3 Hz). MS (ESI) for $C_{18}H_{25}O_{15}N_6P_3$ (M–H)$^-$ calcd. 657.05. found 656.93. UV (10 mM sodium phosphate buffer, pH 7.0) λmax 367 nm (ε9890).

(10-3-2-5) Ser-C1-dPnTP: $^1$H-NMR (300 MHz, $D_2O$) δ 7.87 (d, 1H, J=2.0 Hz), 7.27 (d, 1H, J=2.1 Hz), 6.66 (dd, 1H, J=4.5, 6.3 Hz), 4.54 (m, 1H), 4.24-4.09 (m, 5H), 4.0-3.81 (m, 3H), 3.11 (q, 18H, J=7.3 Hz), 2.56 (m, 1H), 2.40 (m, 1H), 1.19 (t, 27H, J=7.3 Hz). $^{31}$P-NMR (121 MHz, $D_2O$) δ

−7.57 (bs, 1P), −10.62 (d, 1P, J=19.6 Hz), −21.88 (t, 1P, J=20.2, 20.0 Hz). MS (ESI) for $C_{15}H_{23}O_{16}N_4P_3$ (M−H)⁻ calcd. 607.02. found 606.81. UV (10 mM sodium phosphate buffer, pH 7.0) λmax 367 nm (ε 9630).

(11) Synthesis of amino acid-bound C3-dPnTP

(11-1) Synthesis of 1-(2-deoxy-β-D-ribofuranosyl)-4-[5-(L-phenylalaninamido)-1-pentynyl]-2-nitropyrrole 5'-triphosphate (Phe-C3-dPnTP)

Fmoc-Phe-SE (13.1 mg, 27 μmol) was added to a DMF solution (4 ml) of $NH_2$—C3-dPnTP (18 μmol), and the mixture was reacted at room temperature for 20 hours. Then, triethylamine was added thereto, and the mixture was further stirred for 5 hours. To this reaction solution, piperidine (100 μl) was added, and the mixture was reacted at room temperature for 30 minutes. To this reaction solution, water (5 ml) was added, and the aqueous layer was washed three times with ethyl acetate and then freeze-dried. The residue was purified by DEAE Sephadex A-25 column chromatography (1.5×30 cm, linear concentration gradient; 50 mM to 1 M solution of TEAB) and C8-HPLC (Senshu Pak, concentration gradient; 100 mM triethylammonium acetate buffer solution (pH 7.0) of 10% to 50% acetonitrile) to obtain the compound of interest (7.4 μmol, 41%).

(11-2) Synthesis of 1-(2-deoxy-β-D-ribofuranosyl)-4-[5-(L-tryptophanamido)-1-pentynyl]-2-nitropyrrole 5'-triphosphate (Trp-C3-dPnTP)

Fmoc-Trp-SE (14.1 mg, 27 mol) was added to a DMF solution (4 ml) of $NH_2$—C3-dPnTP (18 μmol), and the mixture was reacted at room temperature for 20 hours. Then, triethylamine was added thereto, and the mixture was further stirred for 5 hours. To this reaction solution, piperidine (100 μl) was added, and the mixture was reacted at room temperature for 30 minutes. To this reaction solution, water (5 ml) was added, and the aqueous layer was washed three times with ethyl acetate and then freeze-dried. The residue was purified by DEAE Sephadex A-25 column chromatography (1.5×30 cm, linear concentration gradient; 50 mM to 1 M solution of TEAB) and C8-HPLC (Senshu Pak, concentration gradient; 100 mM triethylammonium acetate buffer solution (pH 7.0) of 15% to 50% acetonitrile) to obtain the compound of interest (6.6 μmol, 36%).

(11-3) Synthesis of 1-(2-deoxy-β-D-ribofuranosyl)-4-[5-(L-tyrosinamido)-1-pentynyl]-2-nitropyrrole 5'-triphosphate (Tyr-C3-dPnTP)

Fmoc-Tyr-SE (15.8 mg, 31.5 μmol) was added to a DMF solution (1 ml) of $NH_2$—C3-dPnTP (21 μmol), and the mixture was reacted at room temperature for 60 hours. To this reaction solution, $H_2O$ (8 ml) was added, and the aqueous layer was washed three times with ethyl acetate and then purified by C8 HPLC (Senshu Pak, concentration gradient; 100 mM triethylammonium acetate buffer solution (pH 7.0) of 35% acetonitrile). Piperidine (100 μl) was added to a DMF solution (2 ml) of Fmoc-Tyr-C3-dPnTP, and the mixture was reacted at room temperature for 10 minutes. To this reaction solution, $H_2O$ (8 ml) was added, and the aqueous layer was washed three times with ethyl acetate and then freeze-dried. The residue was purified by DEAE Sephadex A-25 column chromatography (1.5×30 cm, linear concentration gradient; 50 mM to 1 M solution of TEAB) and C8-HPLC (Senshu Pak, concentration gradient; 100 mM triethylammonium acetate buffer solution (pH 7.0) of 10% to 50% acetonitrile) to obtain the compound of interest (9.7 μmol, 46%).

(11-4) Synthesis of 1-(2-deoxy-β-D-ribofuranosyl)-4-[5-(L-serinamido)-1-pentynyl]-2-nitropyrrole 5'-triphosphate (Ser-C3-dPnTP)

Fmoc-(OTBDMS)-Ser-SE (13.0 mg, 28 μmol) was added to a DMF solution (1 ml) of $NH_2$—C3-dPnTP (19 μmol), and the mixture was reacted at room temperature for 60 hours. To this reaction solution, $H_2O$ (8 ml) was added, and the aqueous layer was washed three times with ethyl acetate and then purified by C8 HPLC (Senshu Pak, concentration gradient; 100 mM triethylammonium acetate buffer solution (pH 7.0) of 32% acetonitrile). Piperidine (100 μl) was added to a DMF solution (2 ml) of Fmoc-Ser-C3-dPnTP, and the mixture was reacted at room temperature for 10 minutes. To this reaction solution, $H_2O$ (8 ml) was added, and the aqueous layer was washed three times with ethyl acetate and then freeze-dried. The residue was purified by DEAE Sephadex A-25 column chromatography (1.5×30 cm, linear concentration gradient; 50 mM to 1 M solution of TEAB) and C8-HPLC (Senshu Pak, concentration gradient; 100 mM triethylammonium acetate buffer solution (pH 7.0) of 10% to 50% acetonitrile) to obtain the compound of interest (5.4 μmol, 29%).

(11-5) Synthesis of 1-(2-deoxy-β-D-ribofuranosyl)-4-[5-(L-lysinamido)-1-pentynyl]-2-nitropyrrole 5'-triphosphate (Lys-C3-dPnTP)

Fmoc-Lys(Fmoc)-SE (27.5 mg, 40 μmol) was added to a DMF solution (1 ml.) of $NH_2$—C3-dPnTP (20 μmol), and the mixture was reacted at room temperature for 58 hours. Piperidine (100 μL) was added to the reaction solution, and the mixture was reacted for 3 minutes. Then, $H_2O$ (2 mL) was added thereto. The aqueous layer was washed three times with ethyl acetate (4 mL) and then freeze-dried. The crude product was purified by DEAE Sephadex A-25 column chromatography (1.5×30 cm, linear concentration gradient; 50 mM to 0.8 M solution of TEAB) and C18-HPLC (concentration gradient; 100 mM triethylammonium acetate buffer solution (pH 7.0) of 5% to 50% acetonitrile) to obtain the compound of interest (4.6 μmol, 23%).

(11-6) Physical Property of Compound (11-6-1) Phe-C3-dPnTP: ¹H NMR (300 MHz, $D_2O$) δ 7.71 (d, 1H, J=1.9 Hz), 7.32-7.14 (m, 5H), 7.19 (d, 1H, J=2.0 Hz) 6.61 (t, 1H, J=5.8 Hz), 4.51 (m, 1H), 4.16-4.10 (m, 4H), 3.36 (m, 1H), 3.11 (q, J=7.4 Hz, the signals of Phe-$CH_2$— and one proton of —$CONHCH_2$— were superimposed), 2.51 (m, 1H), 2.31 (m, 1H), 2.19 (m, 1H), 2.05 (m, 1H), 1.55 (m, 2H), 1.19 (t, 18H, J=7.3 Hz). ³¹P NMR (121 MHz, $D_2O$) δ −10.34 (d, 1P, J=18.0 Hz), −11.32 (d, 1P, J=19.7 Hz), −22.99 (t, 1P, J=20.0 Hz). MS (ESI) for $C_{23}H_{30}N_4O_{15}P_3$ (M−H)⁻ calcd, 695.09. found 694.53. UV (10 mM sodium phosphate buffer, pH 7.0) λmax=374 nm (ε 10, 000).

(11-6-2) Trp-C3-dPnTP: ¹H NMR (300 MHz, $D_2O$) δ 7.57 (d, 1H, J=2.0 Hz), 7.38 (d, 2H, J=8.5 Hz), 7.24 (s, 1H), 7.15 (d, 1H, J=2.0 Hz), 7.11 (t, 1H, J=7.8 Hz), 6.99 (t, 1H, J=7.9 Hz), 6.40 (t, 1H, J=5.8 Hz), 4.29 (m, 1H), 4.14-4.07 (m, 4H), 3.39 (m, 1H), 3.24 (t, 2H, J=6.9 Hz), 3.11 (q, J=7.3 Hz, the signal of one proton of —$CONHCH_2$— was superimposed), 3.17-3.01 (m, 1H), 2.32 (m, 1H), 2.14 (m, 1H), 2.01 (m, 1H), 1.84 (m, 1H), 1.49 (m, 2H), 1.19 (t, 18H, J=7.3

Hz). $^{31}$P NMR (121 MHz, D$_2$O) δ −10.45 (d, 1P, J=19.6 Hz), −11.29 (d, 1P, J=19.4 Hz), −23.01 (t, 1P, J=20.0 Hz). MS (ESI) for C$_{25}$H$_{31}$N$_5$O$_{15}$P$_3$ (M−H)$^-$ calcd. 734.10. found 733.64. UV (10 mM sodium phosphate buffer, pH 7.0) λmax=280 nm (ε 8,000), 287 nm (ε 7,600), 375 nm (ε 9,600).

(11-6-3) Tyr-C3-dPnTP: $^1$H NMR (300 MHz, D$_2$O) δ 7.70 (d, 1H, J=2.1 Hz), 7.19 (d, 1H, J=2.1 Hz), 7.02 (d, 2H, J=8.5 Hz), 6.75 (d, 2H, J=8.5 Hz), 6.62 (t, 1H, J=5.9 Hz), 4.51 (m, 1H), 4.16 (m, 3H), 4.06 (m, 1H), 3.39 (m, 1H), 3.11 (q, 13H, J=7.4 Hz), 3.06-2.90 (m, 3H), 2.52 (m, 1H), 2.30 (m, 1H), 2.17 (m, 1H), 2.01 (m, 1H), 1.53 (m, 2H), 1.19 (t, 20H, J=7.3 Hz). $^{31}$P NMR (121 MHz, D$_2$O) δ −9.86 (1P), −11.30 (d, 1P, J=19.8 Hz), −22.89 (t, 1P, J=19.9 Hz). MS (ESI) for C$_{23}$H$_{30}$N$_4$O$_{16}$P$_3$ (M−H)$^-$ calcd. 711.09. found 711.07. UV (10 mM sodiumphosphate buffer, pH 7.0) λmax=282 nm (ε 3,800), 373 nm (ε 10,400).

(11-6-4) Ser-C3-dPnTP: $^1$H NMR (300 MHz, D$_2$O) δ 7.77 (d, 1H, J=2.0 Hz), 7.26 (d, 1H, J=2.0 Hz), 6.68 (t, 1H, J=5.9 Hz), 4.56 (m, 1H), 4.16 (m, 3H), 4.07 (dd, 1H, J=5.4, 4.6 Hz), 3.92 (dd, 1H, J=12.3, 4.2 Hz), 3.82 (dd, 1H, J=12.4, 6.0 Hz), 3.34 (m, 2H), 3.11 (q, 13H, J=7.3 Hz), 2.57 (m, 1H), 2.45-2.36 (m, 3H), 1.72 (m, 2H), 1.19 (t, 20H, J=7.3 Hz). $^{31}$P NMR (121 MHz, D$_2$O) δ −9.83 (1P), −11.29 (d, 1P, J=19.6 Hz), −22.85 (t, 1P, J=19.9 Hz). MS (ESI) for C$_{17}$H$_{26}$N$_4$O$_{16}$P$_3$ (M−H)$^-$ calcd. 635.06. found 634.68. UV (10 mM sodium phosphate buffer, pH 7.0) λmax=373 nm (ε 9,900).

(11-6-5) Lys-C3-dPnTP: $^1$H NMR (300 MHz, D$_2$O) δ 7.80 (d, 1H, J=2.1 Hz), 7.26 (d, 1H, J=2.1 Hz), 6.69 (t, 1H, J=6.0 Hz), 4.55 (m, 1H), 4.23-4.14 (m, 3H), 3.96 (t, 1H, J=6.8 Hz), 3.44 (m, 1H), 3.25 (m, 1H), 3.12 (q, 7H, J=7.3 Hz), 2.90 (t, 2H, J=7.4 Hz), 2.57 (m, 1H), 2.45-2.36 (m, 3H), 1.83 (m, 2H), 1.73 (m, 2H), 1.61 (m, 2H), 1.40 (m, 2H), 1.19 (t, 11H, J=7.3 Hz). $^{31}$P NMR (121 MHz, D$_2$O) δ −9.92 (d, 1P, J=19.3 Hz), −11.34 (d, 1P, J=19.9 Hz), −22.79 (t, 1P, J=19.8 Hz). MS (ESI) for C$_{20}$H$_{33}$N$_5$O$_{15}$P$_3$ (M−H)$^-$ calcd. 676.12. found 675.67.

(12) Synthesis of Diol1-dPnTP (12-1) Synthesis of 4-pentyne-1,2-diacetate

After azeotropy of 4-pentyne-1,2-diol (13.5 mmol) [reference: J. Org. Chem. 2008, 73, 5965-5976] with pyridine, the residue was dissolved in pyridine (27 ml). Then, acetic anhydride (4.8 ml, 50.8 mmol) was added to the solution, and the mixture was reacted at room temperature for 14 hours. The reaction solution was separated into aqueous and organic layers by the addition of ethyl acetate and a 5% aqueous sodium bicarbonate solution. The organic layer was dried over sodium sulfate, filtered, and then concentrated. This residue was purified by silica gel column chromatography to obtain 4-pentyne-1,2-diacetate (800 mg, 4.34 mmol, 32%).

(12-2) Synthesis of 1-(2-deoxy-β-D-ribofuranosyl)-4-(4-pentene-1,2-diacetato)-1-propynyl-2-nitropyrrole DMF (5 ml) was added to 1-(2-deoxy-β-D-ribofuranosyl)-4-iodo-2-nitropyrrole (354 mg, 1 mmol), copper iodide (31 mg, 0.16 mmol), and Pd(PPh$_3$)$_4$ (58 mg, 0.05 mmol). After dissolution of 1-(2-deoxy-β-D-ribofuranosyl)-4-iodo-2-nitropyrrole, triethylamine (208 µl, 1.5 mmol) and 4-pentyne-1,2-diacetate (276 mg, 1.5 mmol) were added thereto, and the mixture was reacted at room temperature for 14 hours. The reaction solution was concentrated. Then, the residue was purified by silica gel column chromatography and HPLC to obtain 1-(2-deoxy-β-D-ribofuranosyl)-4-(4-pentene-1,2-diacetato)-1-propynyl-2-nitropyrrole (400 mg, 0.97 mmol, 97%.).

(12-3) Synthesis of 1-(2-deoxy-β-D-ribofuranosyl)-4-(4-pentene-1,2-diacetato)-1-propynyl-2-nitropyrrole 5'-triphosphate After azeotropy of 1-(2-deoxy-β-D-ribofuranosyl)-4-(4-pentene-1,2-diol)-1-propynyl-2-nitropyrrole (41 mg, 0.1 mmol) twice with pyridine and once with toluene, proton sponge (33 mg, 0.15 mmol) was added to the residue, and the mixture was dissolved in trimethyl phosphate (500 µl). Then, the solution was cooled to 0° C. Phosphoryl chloride (13 µl, 0.13 mmol) was added thereto, and the mixture was stirred at 0° C. for 1 hour. Tri-n-butylamine (120 µl) and bis-tri-n-butylammonium pyrophosphate (1.0 ml, 0.5 M DMF solution) were added thereto, and the mixture was stirred at 0° C. for 30 minutes. Further, 0.5 M TBAF (0.5 ml) and water (5.0 ml) were added thereto, and the mixture was stirred at 0° C. for 30 minutes. Then, the reaction solution was freeze-dried. The residue was dissolved in H$_2$O (4.0 ml). To the solution, 28% ammonia water (20 ml) was added, and the mixture was stirred at room temperature for 90 minutes. This product was purified by DEAE Sephadex A-25 ion-exchange column chromatography and HPLC to obtain 1-(2-deoxy-β-D-ribofuranosyl)-4-(4-pentene-1,2-diacetato)-1-propynyl-2-nitropyrrole 5'-triphosphate (24 mol, 24%).

(12-4) Physical Property of Compound (12-4-1) 4-Pentyne-1,2-diacetate $^1$H NMR (300 MHz, DMSO-d6) δ 5.05-4.98 (m, 1H), 4.24-4.07 (m, 2H), 2.91 (t, 1H, J=2.7 Hz), 2.53 (dd, 1H, J=2.6, 6.4 Hz), 2.01 (s, 6H).

(12-4-2) 1-(2-Deoxy-β-D-ribofuranosyl)-4-(4-pentene-1,2-diol)-1-propynyl-2-nitropyrrole $^1$H NMR (300 MHz, DMSO-d6) δ 7.92 (d, 1H, J=2.2 Hz), 7.28 (d, 1H, J=2.2 Hz), 6.54 (t, 1H, J=5.6 Hz), 5.27 (d, 1H, J=4.5 Hz), 5.11-5.04 (m, 2H), 4.29-4.12 (m, 3H), 3.86-3.82 (m, 1H), 3.69-3.52 (m, 2H), 2.74 (d, 2H, J=6.3 Hz), 2.47-2.38 (m, 1H), 2.27-2.19 (m, 1H), 2.04, 2.02 (s, s, 3H, 3H). HR-MS (FAB, NBA matrix) for C$_{15}$H$_{23}$N$_2$O$_9$ (M+H)$^+$ calcd. 411.1409. found 411.1403.

(12-4-3) 1-(2-Deoxy-β-D-ribofuranosyl)-4-(4-pentene-1,2-diacetato)-1-propynyl-2-nitropyrrole 5'-triphosphate $^1$H NMR (300 MHz, D$_2$O) δ 7.79 (d, 1H, J=2.1 Hz), 7.39 (d, 1H, J=2.1 Hz), 6.77 (t, 1H, J=6.0 Hz), 4.66-4.61 (m, 1H), 4.27-4.22 (m, 3H), 3.98-3.91 (m, 1H), 3.74-3.60 (m, 2H), 3.20 (q, 22H, J=7.3 Hz), 2.72-2.46 (m, 4H), 1.28 (t, 32H, J=7.3 Hz). $^{31}$P NMR (121 MHz, D$_2$O) δ −9.83 (d, 1P, J=19.8 Hz), −10.66 (d, 1P, J=20.0 Hz), −22.53 (t, 1P, J=20.1 Hz). MS (ESI) for C$_{14}$H$_{21}$N$_2$O$_{16}$P$_3$ (M−H)$^-$ calcd. 566.24. found 565.04. UV (10 mM sodium phosphate buffer pH 7.0) λmax=374 nm (ε 9,400).

(13) Synthesis of Diol9-dPnTP

(13-1) Synthesis of Diol9 Linker

A lithium acetylide-ethylenediamine complex (1.69 g, 16.5 mmol) was dissolved in DMSO (75 ml). Then, the solution was cooled to 0 to 10° C. 11-Bromo-1-undecene (3.24 ml, 15 mmol) was added thereto, and the mixture was stirred at room temperature for 2 hours. The reaction solution was separated into aqueous and organic layers by the addition of water and ether. The organic layer was dried over sodium sulfate, filtered, and then concentrated. This residue was purified by silica gel column chromatography (crude, 16.5 mmol). To this crude (8.40 mmol), $OsO_4$ (108 mg, 0.42 mmol), N-methylmorpholine-N-oxide (1.97 g, 20 mmol), and acetone/$H_2O$/tBuOH (4:1:1, 42 ml) were added, and the mixture was stirred at room temperature for 1 hour. $NaHSO_3$ (295 mg) was added to the reaction solution, followed by filtration. The precipitate was washed with methanol, and the filtrates were concentrated. This residue was purified by silica gel column chromatography (crude). After azeotropy of this crude (8.40 mmol) with pyridine, the residue was dissolved in pyridine (15 ml). Then, acetic anhydride (3 ml, 32 mmol) was added to the solution, and the mixture was reacted at room temperature for 14 hours. The reaction solution was separated into aqueous and organic layers by the addition of ethyl acetate and a 5% aqueous sodium bicarbonate solution. The organic layer was dried over sodium sulfate, filtered, and then concentrated. This residue was purified by silica gel column chromatography to obtain Diol9 linker (877 mg, 2.96 mmol, 35%).

(13-2) Synthesis of Diol9-dPn

DMF (5 ml) was added to 1-(2-deoxy-β-D-ribofuranosyl)-4-iodo-2-nitropyrrole (354 mg, 1 mmol), copper iodide (31 mg, 0.16 mmol), and $Pd(PPh_3)_4$ (58 mg, 0.05 mmol). After dissolution of 1-(2-deoxy-β-D-ribofuranosyl)-4-iodo-2-nitropyrrole, triethylamine (208 µl, 1.5 mmol) and Diol9 linker (445 mg, 1.5 mmol) were added thereto, and the mixture was reacted at room temperature for 14 hours. The reaction solution was concentrated. Then, the residue was purified by silica gel column chromatography and HPLC to obtain Diol9-dPn (450 mg, 0.86 mmol, 86%).

(13-3) Synthesis of Diol9-dPnTP

After azeotropy of Diol9-dPn (45 mg, 0.1 mmol) twice with pyridine and once with toluene, proton sponge (33 mg, 0.15 mmol) was added to the residue, and the mixture was dissolved in trimethyl phosphate (500 &l). Then, the solution was cooled to 0° C. Phosphoryl chloride (13 µl, 0.13 mmol) was added thereto, and the mixture was stirred at 0° C. for 1 hour. Tri-n-butylamine (120 µl) and bis-tri-n-butylammonium pyrophosphate (1.0 ml, 0.5 M DMF solution) were added thereto, and the mixture was stirred at 0° C. for 30 minutes. Further, 0.5 M TBAF (0.5 ml) and water (5.0 ml) were added thereto, and the mixture was stirred at 0° C. for 30 minutes. Then, the reaction solution was freeze-dried. The residue was dissolved in $H_2O$ (4.0 ml). To the solution, 28% ammonia water (20 ml) was added, and the mixture was stirred at room temperature for 90 minutes. This product was purified by DEAE Sephadex A-25 ion-exchange column chromatography and HPLC to obtain Diol9-dPnTP (26 µmol, 26%).

(13-4) Physical Property of Compound

(13-4-1) Diol9 Linker $^1$H NMR (300 MHz, DMSO-d6) δ 4.98-4.90 (m, 1H), 4.15 (dd, 1H, J=3.2, 8.7), 3.99 (dd, 1H, J=6.5, 5.4), 2.71 (t, 1H, J=2.7), 2.15-2.10 (m, 8H), 1.99, 1.98 (s, s, 3H, 3H), 1.51-1.23 (m, 16H).

(13-4-2) Diol9-dPn $^1$H NMR (300 MHz, DMSO-d6) δ 7.88 (d, 1H, J=2.2 Hz), 7.25 (d, 1H, J=2.2 Hz), 6.54 (t, 1H, J=5.6 Hz), 5.28 (d, 1H, J=4.4 Hz), 5.09 (t, 1H, J=5.1 Hz), 4.97-4.90 (m, 1H), 4.26-3.95 (m, 3H), 3.85-3.81 (m, 1H), 3.68-3.52 (m, 2H), 2.46-2.18 (m, 4H), 1.99, 1.98 (s, s, 3H, 3H), 1.51-1.24 (m, 16H).

(13-4-3) Diol9-dPnTP $^1$H NMR (300 MHz, $D_2O$) δ 7.71 (d, 1H, J=2.1 Hz), 7.35 (d, 1H, J=2.1 Hz), 6.76 (t, 1H, J=6.1 Hz), 4.65-4.60 (m, 1H), 4.26-4.20 (m, 3H), 3.70-3.41 (m, 3H), 3.20 (q, 22H, J=7.3 Hz), 2.68-2.37 (m, 4H), 1.60-1.25 (m, 50H). $^{31}$P NMR (121 MHz, $D_2O$) δ −10.07 (d, 1P, J=19.7 Hz), −10.63 (d, 1P, J=20.0 Hz), −22.6 (t, 1P, J=20.0 Hz). MS (ESI-Tof) for $C_{22}H_{37}N_2O_{16}P_3 \cdot N (C_2H_5)_3$ (M)$^+$ calcd. 779.26. found 780.26. UV (10 mM sodium phosphate buffer pH 7.0) λmax=374 nm (ε 9, 400).

(14) Synthesis of Bza3-dPnTP

(14-1) Synthesis of Bza3 Linker

Dichloromethane (40 ml) was added to 4-pentyn-1-ol (2.8 ml, 30 mmol) and triphenylphosphine (11.8 g, 45 mmol), and the mixture was cooled to 0° C. Then, carbon tetrabromide (14.9 g, 45 mmol) dissolved in dichloromethane (20 ml) was added thereto. The solution was brought back to room temperature and then separated into aqueous and organic layers by the addition of dichloromethane and a 5% aqueous sodium bicarbonate solution. The organic layer was dried over sodium sulfate, filtered, and then concentrated. This residue was purified by silica gel column chromatography (crude, 30 mmol). This crude (2.2 g, 15 mmol) was added to 4-hydroxybenzaldehyde (1.83 g, 15 mmol), potassium carbonate (2.07 g, 15 mmol), and potassium iodide (250 mg, 1.5 mmol) dissolved in DMF (7.5 ml), and the mixture was stirred overnight at 70° C. The reaction solution was separated into aqueous and organic layers by the addition of ethyl acetate, water, and a few drops of hydrochloric acid. The organic layer was dried over sodium sulfate, filtered, and then concentrated. This residue was purified by silica gel column chromatography to obtain Bza3 linker (453 mg, 2.41 mmol, 16%).

(14-2) Synthesis of Bza3-dPn

DMF (5 ml) was added to 1-(2-deoxy-β-D-ribofuranosyl)-4-iodo-2-nitropyrrole (354 mg, 1 mmol), copper iodide (31 mg, 0.16 mmol), and $Pd(PPh_3)_4$ (58 mg, 0.05 mmol). After dissolution of 1-(2-deoxy-β-D-ribofuranosyl)-4-iodo-2-nitropyrrole, triethylamine (208 µl, 1.5 mmol) and Bza3 linker (282 mg, 1.5 mmol) were added thereto, and the mixture was reacted at room temperature for 14 hours. The reaction solution was concentrated. Then, the residue was purified by silica gel column chromatography and HPLC to obtain Bza3-dPn (236 mg, 0.57 mmol, 57%).

(14-3) Synthesis of Bza3-dPnTP

After azeotropy of Bza3-dPn (41 mg, 0.1 mmol) twice with pyridine and once with toluene, proton sponge (33 mg, 0.15 mmol) was added to the residue, and the mixture was dissolved in trimethyl phosphate (500 μl). Then, the solution was cooled to 0° C. Phosphoryl chloride (13 μl, 0.13 mmol) was added thereto, and the mixture was stirred at 0° C. for 1 hour. Tri-n-butylamine (120 μl) and bis-tri-n-butylammonium pyrophosphate (1.0 ml, 0.5 M DMF solution) were added thereto, and the mixture was stirred at 0° C. for 30 minutes. Further, 0.5 M TBAF (0.5 ml) and water (5.0 ml) were added thereto, and the mixture was stirred at 0° C. for 30 minutes. Then, the reaction solution was freeze-dried. This residue was purified by DEAE Sephadex A-25 ion-exchange column chromatography and HPLC to obtain Bza3-dPnTP (30.5 mol, 30%).

(14-4) Physical Property of Compound (14-4-1) Bza3 Linker $^1$H NMR (300 MHz, DMSO-d6) δ 9.86 (s, 1H), 7.87-7.84 (m, 2H), 7.14-7.10 (m, 2H), 4.15 (t, 2H, J=6.2 Hz), 2.82 (t, 2H. J=2.6 Hz), 2.36-2.31 (m, 2H), 1.96-1.87 (m, 2H)

(14-4-2) Bza3-dPn $^1$H NMR (300 MHz, DMSO-d6) 9.87 (s, 1H), 7.92 (d, 1H, J=2.1 Hz), 7.90-7.84 (m, 2H), 7.28 (d, 1H, J=2.2 Hz), 7.17-7.13 (m, 2H), 6.55 (t, 1H, J=5.6 Hz), 5.29 (d, 1H, J=4.4 Hz), 5.10 (t, 1H, J=5.1 Hz), 4.27-4.18 (m, 3H), 3.87-3.83 (m, 1H), 3.69-3.53 (m, 2H), 2.57 (t, 2H, J=7.1 Hz), 2.47-2.39 (m, 1H), 2.27-2.19 (m, 1H), 2.04-1.95 (m, 2H).

(14-4-3) Bza3-dPnTP $^1$H NMR (300 MHz, D$_2$O) δ 9.77 (s, 1H), 7.95-7.90 (m, 2H), 7.69 (d, 1H, J=2.1 Hz), 7.25 (d, 1H, J=2.1 Hz), 7.21-7.16 (m, 2H), 6.74 (t, 1H, J=6.0 Hz), 4.64-4.59 (m, 1H), 4.36-4.20 (m, 5H), 3.19 (q, 19H, J=7.3 Hz), 2.67-2.42 (m, 4H), 2.14-2.05 (m, 2H), 1.28 (t, 28H, J=7.3 Hz). $^{31}$P NMR (121 MHz, D$_2$O) δ −9.98 (d, 1P, J=19.9 Hz), −10.65 (d, 1P, J=20.1 Hz), −22.55 (t, 1P, J=20.0 Hz). MS (ESI-Tof) for C$_{21}$H$_{25}$N$_2$O$_{16}$P$_3$.N (C$_2$H$_5$)$_3$ (M) calcd. 755.16. found 756.22. UV (10 mM sodium phosphate buffer pH 7.0) λmax=288 nm (ε 21, 300), 373 nm (ε 9, 600).

(15) Synthesis of Bza6-dPnTP (15-1) Synthesis of Bza6 Linker

Dichloromethane (30 ml) was added to 7-octyn-1-ol (2.60 g, 20 mmol) and triphenylphosphine (7.87 g, 30 mmol), and the mixture was cooled to 0° C. Then, carbon tetrabromide (9.95 g, 30 mmol) dissolved in dichloromethane (10 ml) was added thereto. The solution was brought back to room temperature and then separated into aqueous and organic layers by the addition of dichloromethane and a 5% aqueous sodium bicarbonate solution. The organic layer was dried over sodium sulfate, filtered, and then concentrated. This residue was purified by silica gel column chromatography (crude, 20 mmol). This crude (20 mmol) was added to 4-hydroxybenzaldehyde (2.44 g, 20 mmol), potassium carbonate (2.76 g, 20 mmol), and potassium iodide (332 mg, 2 mmol) dissolved in DMF (10 ml), and the mixture was stirred overnight at 70° C. The reaction solution was separated into aqueous and organic layers by the addition of ethyl acetate, water, and a few drops of hydrochloric acid. The organic layer was dried over sodium sulfate, filtered, and then concentrated. This residue was purified by silica gel column chromatography to obtain Bza6 linker (729 mg, 3.17 mmol, 16%).

(15-2) Synthesis of Bza6-dPn

DMF (5 ml) was added to 1-(2-deoxy-β-D-ribofuranosyl)-4-iodo-2-nitropyrrole (354 mg, 1 mmol), copper iodide (31 mg, 0.16 mmol), and Pd(PPh$_3$)$_4$ (58 mg, 0.05 mmol). After dissolution of 1-(2-deoxy-β-D-ribofuranosyl)-4-iodo-2-nitropyrrole, triethylamine (208 μl, 1.5 mmol) and Bza6 linker (276 mg, 1.2 mmol) were added thereto, and the mixture was reacted at room temperature for 14 hours. The reaction solution was concentrated. Then, the residue was purified by silica gel column chromatography and HPLC to obtain Bza6-dPn (138 mg, 0.30 mmol, 30%).

(15-3) Synthesis of Bza6-dPnTP

After azeotropy of Bza6-dPn (46 mg, 0.1 mmol) twice with pyridine and once with toluene, proton sponge (33 mg, 0.15 mmol) was added to the residue, and the mixture was dissolved in trimethyl phosphate (500 μl). Then, the solution was cooled to 0° C. Phosphoryl chloride (13 μl, 0.13 mmol) was added thereto, and the mixture was stirred at 0° C. for 1 hour. Tri-n-butylamine (120 μl) and bis-tri-n-butylammonium pyrophosphate (1.0 ml, 0.5 M DMF solution) were added thereto, and the mixture was stirred at 0° C. for 30 minutes. Further, 0.5 M TBAF (0.5 ml) and water (5.0 ml) were added thereto, and the mixture was stirred at 0° C. for 30 minutes. Then, the reaction solution was freeze-dried. This residue was purified by DEAE Sephadex A-25 ion-exchange column chromatography and HPLC to obtain Bza6-dPnTP (27 μmol, 27%).

(15-4) Physical Property of Compound (15-4-1) Bza6 Linker $^1$H NMR (300 MHz, DMSO-d6) δ 9.85 (s, 1H), 7.86-7.83 (m, 2H), 7.12-7.09 (m, 2H), 4.07 (t, 2H, J=6.4 Hz), 2.73 (t, 2H, J=2.6 Hz), 2.17-2.12 (m, 2H), 1.48-1.42 (m, 8H)

(15-4-2) Bza6-dPn $^1$H NMR (300 MHz, DMSO-d6) 9.84 (s, 1H), 7.89 (d, 1H, J=2.1 Hz), 7.86-7.81 (m, 2H), 7.24 (d, 1H, J=2.2 Hz), 7.12-7.08 (m, 2H), 6.53 (t, 1H, J=5.6 Hz), 5.28 (d, 1H, J=3.8 Hz), 5.10 (t, 1H, J=5.3 Hz), 4.22 (m, 1H), 4.08 (t, 2H, J=6.4 Hz), 3.85-3.81 (m, 1H), 3.66-3.53 (m, 2H), 2.46-2.17 (m, 4H), 1.77-1.73 (m, 2H), 1.55-1.44 (m, 6H).

(15-4-3) Bza6-dPnTP $^1$H NMR (300 MHz, D$_2$O) δ 9.71 (s, 1H), 7.85-7.82 (m, 2H), 7.63 (d, 1H, J=2.1 Hz), 7.14 (d, 1H, J=2.1 Hz), 7.11-7.07 (m, 2H), 6.65 (t, 1H, J=6.0 Hz), 4.60-4.58 (m, 1H), 4.25-4.17 (m, 5H), 3.20 (q, 18H, J=7.3 Hz), 2.63-2.57 (m, 1H), 2.44-2.38 (m, 3H), 1.88-1.84 (m, 2H), 1.63-1.54 (m, 6H), 1.28 (t, 27H, J=7.3 Hz). $^{31}$P NMR (121 MHz, D$_2$O) δ −10.25 (d, 1P, J=19.4 Hz), −10.68 (d, 1P, J=19.8 Hz), −22.62

(t, 1P, J=19.8 Hz). MS (ESI-Tof) for $C_{24}H_{31}N_2O_{16}P_3$—N$(C_2H_5)_3$ (M) calcd. 797.21. found 798.24. UV (10 mM sodium phosphatebuffer pH 7.0) λmax=289 nm (ε 20, 500), 374 nm (ε 8, 900).

(16) Synthesis of Tripeptide-Bound dPnTP (16-1) Synthesis of Tripeptide

Fmoc solid-phase synthesis was performed in a 5-mL column tube (made of PP) equipped with a filter. A 2-chlorotrityl chloride resin (1.58 mmol/mg, 250 mg, 0.4 mmol) was weighed into a tube, to which 2 mL of methylene chloride (DCM) was then added. The tube was shaken for 20 minutes in a shaker to swell the resin (×2). For coupling of the first amino acid residue to the resin, Fmoc-amino acid (1.5 equiv.) and DIPEA (2.5 equiv.) were dissolved in DCM (1.5 mL), and the solution was added to the resin-containing column tube and stirred at room temperature for 2 hours to couple the amino acid to the resin. After the reaction, 1 mL of MeOH was added thereto, and the mixture was stirred for 15 minutes. Then, the reaction solution was removed, and the resin was washed with DCM (2 mL)×4, DMF (2 mL)×4, DCM (2 mL)×2, DMF:MeOH=1:1 (v/v)×2, DCM:MeOH=1:1 (v/v)×2, and MeOH×2. After sufficient drying in a vacuum line, the mass of the resin was weighed, and the amount of the first residue introduced was examined from the pre- and post-reaction masses of the resin. The equivalents of the materials for coupling of the second or later residues were used in reaction with reference to the value. The resin was swollen again under the above conditions. Then, 1.5 mL of a 20% solution of piperidine in DMF was added thereto, and the mixture was stirred for 20 minutes to remove the Fmoc group. The resin was fully washed with DMF until the smell of piperidine disappeared (2 mL×approximately 8 to 10) (this Fmoc removal operation was repeated twice). Fmoc-amino acid (2.5 equiv.), HOBt (2.5 equiv.), and N,N'-diisopropyl-carbodiimide (2.5 equiv.) were dissolved in DMF (1.5 mL). The solution was added to the column and stirred at room temperature for 1 hour for reaction. The reaction solution was removed, and the resin was then washed with DMF (2 mL)×5, DCM (2 mL)×5, and DMF (2 mL)×5. These reactions were repeated to extend the strand to tripeptide. For subsequent excision of the tripeptide from the resin, 2 mL of 20% hexafluoroisopropanol/DCM (or 1% TFA/DCM) was added thereto, and the mixture was stirred at room temperature for 10 minutes and filtered to recover a filtrate containing the peptide (this operation was repeated three times). The filtrates were concentrated to dryness by evaporation to obtain tripeptide.

(16-2) Synthesis of Fmoc-Leu-Leu-Leu N-Succinimidyl Ester

Fmoc-Leu-Leu-Leu (292.5 mg, 0.5 mmol) was dissolved in DMF (5 mL). To the solution, N-hydroxysuccinimide (89.3 mg, 0.75 mmol) and 1-ethyl-3-(3-dimethylaminopropyl) carbodiimide hydrochloride (143.7 mg, 0.75 mmol) were added, and the mixture was reacted at room temperature for 1 hour. The reaction solution was added dropwise into cold water to form a white precipitate, which was then suction-filtered. The crystals were washed with water and then dried in a vacuum line to obtain a white powder of the compound of interest (255.8 mg, 76%).

(16-3) Synthesis of Fmoc-Pro-Phe-Trp N-Succinimidyl Ester

Fmoc-Pro-Phe-Trp (202 mg, 0.3 mmol) was dissolved in DMF (3 mL). To the solution, N-hydroxysuccinimide (53 mg, 0.45 mmol) and 1-ethyl-3-(3-dimethylaminopropyl) carbodiimide hydrochloride (86 mg, 0.45 mmol) were added, and the mixture was reacted at room temperature for 1 hour. The reaction solution was added dropwise into cold water to form a white precipitate, which was then suction-filtered. The crystals were washed with water and then dried in a vacuum line to obtain a white powder of the compound of interest (163 mg, 95%).

(16-4) Synthesis of Leu-Leu-Leu-hx-dPnTP $NH_2$-hx-dPnTP (196 mol) was dissolved in DMF (4 mL). Fmoc-Leu-Leu-Leu N-succinimidyl ester dissolved in DMF (4 mL) was added to the reaction solution, and the mixture was reacted at room temperature. After 22 hours, piperidine (500 μl) was added to the reaction solution, and the mixture was stirred for 10 minutes to remove the Fmoc group. The reaction solution was subjected to extraction with ethyl acetate and water. The aqueous phase was washed twice with ethyl acetate and then freeze-dried. Crude crystals were dissolved in 50 mM TEAB, and the solution was charged into a DEAE resin swollen with 50 mM TEAB, and DEAE-purified (resin: DEAE Sephadex A-25 column, gradient: 50 mM to 1 M TEAB isogradient). The fraction containing the compound of interest was freeze-dried and purified by HPLC (0 to 10 min: 10 to 100% linear gradient of $CH_3CN$ in 100 mM TEAA, pH 7.0) to obtain the compound of interest (34.7 μmol, 18%).

(16-5) Synthesis of Pro-Phe-Trp-hx-dPnTP $NH_2$-hx-dPnTP (30 μmol) was dissolved in DMF (800 μL). Fmoc-Pro-Phe-Trp N-succinimidyl ester (56.3 mg, 73 mol) dissolved in DMF (800 μL) was added to the reaction solution, and the mixture was reacted at room temperature. After 20 hours, piperidine (100 μl) was added to the reaction solution, and the mixture was stirred for 10 minutes to remove the Fmoc group. The reaction solution was subjected to extraction with ethyl acetate and water. The aqueous phase was washed twice with ethyl acetate and then freeze-dried. Crude crystals were dissolved in 50 mM TEAB, and the solution was charged into a DEAE resin swollen with 50 mM TEAB, and DEAE-purified (resin: DEAE Sephadex A-25 column, gradient: 50 mM to 1 M TEAB isogradient). The fraction containing the compound of interest was freeze-dried and purified by HPLC (0 to 10 min: 10 to 100% linear gradient of $CH_3CN$ in 100 mM TEAA, pH 7.0) to obtain the compound of interest (8.5 μmol, 28%).

(16-6) Physical Property of Compound (16-6-1) Fmoc-Leu-Leu-Leu N-succinimidyl ester: $^1H$ NMR (300 MHz, DMSO-d6) δ 8.56 (d, 1H, J=7.6 Hz), 7.94 (d, 1H, J=8.1 Hz), 7.88 (d, 2H, J=7.4 Hz), 7.70 (d, 2H, J=7.1 Hz), 7.48-7.28 (m, 5H), 4.61 (m, 1H), 4.38-4.17 (m, 4H), 4.04 (m, 1H), 2.79 (s, 4H), 1.76-1.37 (m, 9H), 0.92-0.79 (m, 18H) $^{13}C$ NMR (75 MHz, DMSO-d6) δ172.71, 172.33, 172.05, 169.88, 168.43, 155.79, 143.88, 143.69, 140.67, 127.01, 125.25, 120.06, 65.49, 52.94, 50.46, 48.31, 46.66, 25.42, 25.19, 24.11, 23.99, 23.03, 22.87, 22.59, 21.43, 20.97.

(16-6-2) Fmoc-Pro-Phe-Trp N-succinimidyl ester: $^1H$ NMR (300 MHz, DMSO-d6) δ 10.94 (s, 1H), 8.23 (d, 1H, J=8.7 Hz), 8.04-7.85 (m, 5H), 7.64-7.43 (m, 4H), 7.40-6.79 (m, 24H), 4.67 (m, 1H), 4.52 (m, 1H), 4.33-4.05 (m, 5H), 3.84 (m, 2H), 3.31-3.14 (m, 2H, superimposed by $H_2O$ signal), 2.26-2.08 (m, 1H), 3.00 (m, 2H), 2.88-2.72 (m, 9H), 2.17 (m, 1H), 1.92 (m, 1H), 1.67 (m, 5H).

(16-6-3) Leu-Leu-Leu-hx-dPnTP: $^1$H NMR (300 MHz, D$_2$O) δ 7.81 (d, 1H, J=2.1 Hz), 7.39 (d, 1H, J=2.1 Hz), 6.75 (t, 1H, J=6.0 Hz), 4.61 (m, 1H), 4.42 (t, 1H, J=7.5 Hz), 4.26 (m, 4H), 4.14 (s, 2H), 4.01 (t, 1H, J=7.4 Hz), 3.20 (q, 17H, J=7.3 Hz), 2.69-2.60 (m, 1H), 2.51-2.43 (m, 1H), 2.28 (t, 1H, J=7.3 Hz), 1.74-1.46 (m, 13H), 1.28 (t, 24H, J=7.3 Hz), 1.06-0.85 (m, 18H). $^{13}$C NMR (75 MHz, DMSO-d6) δ176.66, 173.83, 173.31, 170.28, 136.03, 129.83, 118.60, 104.72, 88.14, 85.73, 85.59, 75.16, 69.71, 64.95, 52.53, 52.36, 51.71, 46.64, 40.48, 39.99, 39.76, 39.70, 38.98, 35.45, 29.47, 27.89, 25.30, 24.79, 24.30, 24.27, 23.88, 22.05, 21.82, 21.56, 21.50, 21.35, 20.89, 8.21. $^{31}$P NMR (121 MHz, D$_2$O) δ −9.14 (d, 1P, J=20.0 Hz), −10.72 (d, 1P, J=20.0 Hz), −22.35 (t, 1P, J=20.1 Hz). MS (ESI) for C$_{36}$H$_{62}$N$_7$O$_{18}$P$_3$ (M−H)$^−$ calcd. 972.34. found 972.12. UV (10 mM sodium phosphate buffer, pH 7.0) λmax=365 nm (ϵ 10700.

(16-6-4) Pro-Phe-Trp-hx-dPnTP: $^1$H NMR (300 MHz, D$_2$O) δ 7.67 (s, 1H), 7.46-7.40 (m, 2H), 7.33-7.06 (m, 9H), 6.55 (t, 1H, J=5.9 Hz), 4.54-4.22 (m, 3H), 4.37-4.31 (m, 1H), 4.21-4.07 (m, 5H), 3.38-3.25 (m, 3H), 3.20 (q, 19H, J=7.3 Hz), 3.02-2.80 (m, 6H), 2.57-2.48 (m, 1H), 2.28-2.15 (m, 4H), 1.99-1.93 (m, 1H), 1.91-1.75 (m, 1H), 1.58-1.46 (m, 3H), 1.28 (t, 29H, J=7.3 Hz), 1.22-1.19 (m, 2H), 1.09-1.00 (m, 3H). $^{31}$P NMR (121 MHz, D$_2$O) δ −9.21 (d, 1P, J=19.6 Hz), −10.68 (d, 1P, J=19.6 Hz), −22.27 (t, 1P, J=20.0 Hz). MS (ESI) for C$_{43}$H$_{55}$N$_8$O$_{18}$P$_3$ (M−H)$^−$ calcd. 1064.28. found 1063.82. UV (10 mM sodium phosphate buffer, pH7.0) λmax=281 nm (ϵ 8,600), 287 nm (ϵ 8,200), 366 nm (ϵ=10, 500).

(17) Synthesis of Succinimide Ester

[Formula 7]

(7)

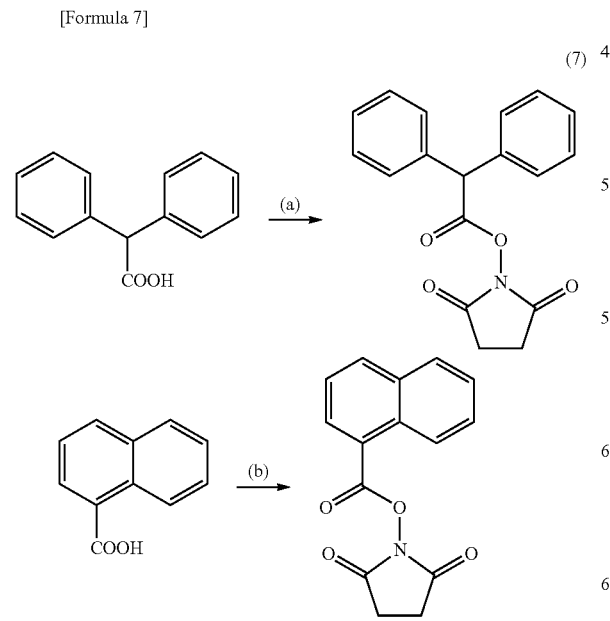

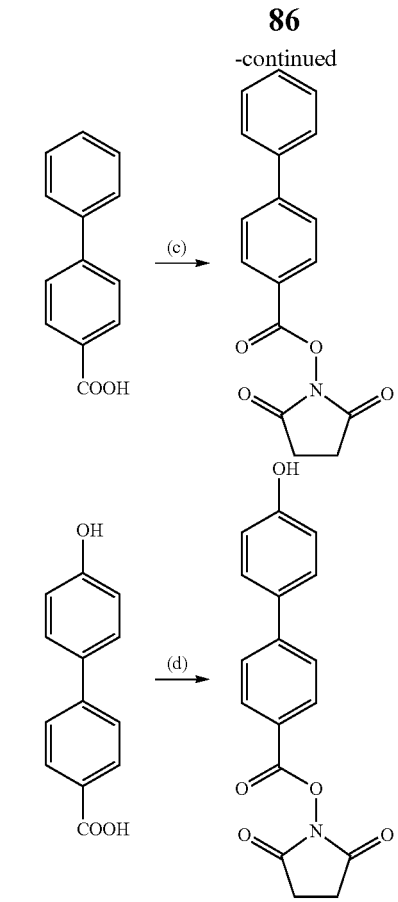

Conditions. (a)(b)(c) N-hydroxysuccinimide, 1-(3-dimethylaminopropyl)-3-ethylcarbodiimide hydrochloride, CH$_2$Cl$_2$, rt. (d) N-hydroxysuccinimide, 1-(3-dimethylaminopropyl)-3-ethylcarbodiimide hydrochloride, THF, DMF, rt.

(17-1) Synthesis of Diphenylacetic Acid N-Hydroxysuccinimide Ester

Diphenylacetic acid (216 mg, 1.02 mmol), N-hydroxysuccinimide (177 mg, 1.53 mmol), and 1-(3-dimethylaminopropyl)-3-ethylcarbodiimide hydrochloride (290 mg, 1.51 mmol) were dissolved in dehydrated methylene chloride (5 ml), and the solution was stirred at room temperature for 7 hours. The reaction solution was diluted with methylene chloride (20 ml) and then washed with a saturated aqueous solution of sodium bicarbonate (10 ml) and subsequently with saturated saline (10 ml). The organic layer was dried over sodium sulfate and concentrated under reduced pressure. The residue was purified by preparative medium-pressure liquid chromatography (eluted with methylene chloride-methanol gradient using AI-580 apparatus and Hi-Flash Column (silica gel) (both from Yamazen Corp.)) to obtain the compound of interest (156 mg, 0.50 mmol, 49%) as a white solid.

<<Known compound>> Ref. J. Med. Chem. 2000, 51, 8168.

(17-2) Physical Property of Diphenylacetic Acid N-Hydroxysuccinimide Ester $^1$H NMR (300 MHz, CDCl$_3$) δ 7.38-7.29 (m, 10H), 5.35 (s, 1H), 2.82 (s, 4H).

(18) Synthesis of 1-Naphthoic Acid N-Hydroxysuccinimide Ester

18-1

1-Naphthoic acid (176 mg, 1.02 mmol), N-hydroxysuccinimide (174 mg, 1.51 mmol), and 1-(3-dimethylaminopropyl)-3-ethylcarbodiimide hydrochloride (288 mg, 1.50 mmol) were dissolved in dehydrated methylene chloride (5 ml), and the solution was stirred at room temperature for 18 hours. The reaction solution was diluted with methylene chloride (10 ml) and then washed with a saturated aqueous solution of sodium bicarbonate (10 ml) and subsequently with saturated saline (10 ml). The organic layer was dried over sodium sulfate and concentrated under reduced pressure. The residue was purified by preparative medium-pressure liquid chromatography (eluted with methylene chloride-methanol gradient using AI-580 apparatus and Hi-Flash Column (silica gel) (both from Yamazen Corp.)) to obtain the compound of interest (131 mg, 0.48 mmol, 48%) as a white solid.
<<Known compound>> Ref. Tetrahedron Letters 2003, 44 (12) 2477-2480 (synthesis method is different from that described herein).

(18-2) Physical Property of 1-Naphthoic Acid N-Hydroxysuccinimide Ester $^1$H NMR (300 MHz, DMSO-$d_6$) δ 8.62 (dd, 1H, J=7.7, 1.0 Hz), 8.40-8.35 (m, 4H), 8.13 (dd, 1H, J=7.9, 0.7 Hz), 7.79-7.66 (m, 3H), 2.94 (s, 4H).

(19) Synthesis of 4-Biphenylcarboxylic Acid N-Hydroxysuccinimide Ester

19-1

4-Biphenylcarboxylic acid (200 mg, 1.00 mmol), N-hydroxysuccinimide (178 mg, 1.55 mmol), and 1-(3-dimethylaminopropyl)-3-ethylcarbodiimide hydrochloride (287 mg, 1.50 mmol) were dissolved in dehydrated methylene chloride (5 ml), and the solution was stirred at room temperature for 21 hours. The reaction solution was diluted with methylene chloride (20 ml) and then washed with a saturated aqueous solution of sodium bicarbonate (10 ml) and subsequently with saturated saline (10 ml). The organic layer was dried over sodium sulfate and concentrated under reduced pressure. The residue was purified by preparative medium-pressure liquid chromatography (eluted with methylene chloride-methanol gradient using AI-580 apparatus and Hi-Flash Column (silica gel) (both from Yamazen Corp.)) and dissolved in DMF (2.5 ml). This solution was added to water (50 ml) for reprecipitation to obtain the compound of interest (139 mg, 0.47 mmol, 47%) as a white solid.
<<Known compound>> Ref. Russ. J. Bioorg. Chem. 2009, 35, 342 (synthesis method is different from that described herein).

(19-2) Physical Property of 4-Biphenylcarboxylic Acid N-Hydroxysuccinimide Ester $^1$H NMR (300 MHz, DMSO-$d_6$) δ 8.18 (d, 2H, J=8.6 Hz), 7.97 (d, 2H, J=8.6 Hz), 7.82-7.78 (m, 2H), 7.57-7.44 (m, 3H), 2.91 (s, 4H).

(20) Synthesis of 4'-Hydroxy-4-Biphenylcarboxylic Acid N-Hydroxysuccinimide Ester

20-1

4'-Hydroxy-4-biphenylcarboxylic acid (214 mg, 1.00 mmol), N-hydroxysuccinimide (174 mg, 1.50 mmol), and 1-(3-dimethylaminopropyl)-3-ethylcarbodiimide hydrochloride (288 mg, 1.50 mmol) were dissolved in dehydrated THF (10 ml) and dehydrated DMF (4 ml), and the solution was stirred at room temperature for 5 hours. The reaction solution was poured into water (50 ml). The resulting precipitate was collected by filtration, washed with hexane, and then dried in vacuum to obtain the compound of interest (207 mg, 0.67 mmol, 67%) as a white solid.
<<Known compound>> Ref. J. Med. Chem. 2008, 51, 6665-6681 (synthesis method is neither described nor cited therein).

(20-2) Physical Property of 4'-Hydroxy-4-Biphenylcarboxylic Acid N-Hydroxysuccinimide Ester $^1$H NMR (300 MHz, DMSO-$d_6$) δ 9.84 (s, 1H), 8.11 (dd, 2H, J=6.8, 1.8 Hz), 7.88 (dd, 2H, J=6.8, 1.8 Hz), 7.68-7.64 (m, 2H), 6.93-6.88 (m, 2H), 2.90 (s, 4H).

(21) Synthesis of 9-Anthracenecarboxylic Acid N-Hydroxysuccinimide Ester

21-1

9-Anthracenecarboxylic acid (220 mg, 0.99 mmol), di(N-succinimidyl) carbonate (357 mg, 1.39 mmol), and triethylamine (220 μl, 1.60 mmol) were dissolved in dehydrated methylene chloride (10 ml), and the solution was stirred at room temperature for 24 hours. The reaction solution was diluted with methylene chloride (10 ml) and then washed with a saturated aqueous solution of sodium bicarbonate (20 ml) and subsequently with saturated saline (20 ml). The organic layer was dried over sodium sulfate and concentrated under reduced pressure. The residue was purified by preparative medium-pressure liquid chromatography (eluted with methylene chloride-methanol gradient using AI-580 apparatus and Hi-Flash Column (silica gel) (both from Yamazen Corp.)) to obtain the compound of interest (66 mg, 0.20 mmol, 20%) as a white solid.

(21-2) Physical Property of 9-Anthracenecarboxylic Acid N-Hydroxysuccinimide Ester $^1$H NMR (300 MHz, DMSO-$d_6$, 40° C.) δ 8.97 (s, 1H), 8.32-8.24 (m, 4H), 7.78-7.63 (m, 4H), 3.02 (s, 4H).

(22) Synthesis of Modified dPnTP (R-hx-dPnTP)

[Formula 8]

(8)

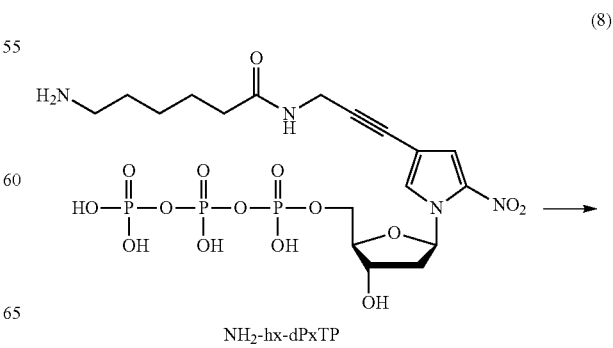

NH$_2$-hx-dPxTP

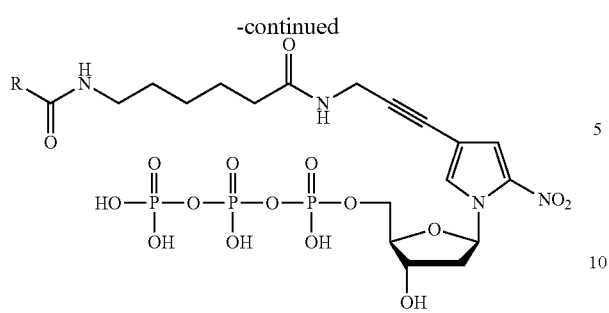
R-hx-dPxTP
Condition: N-hydroxysuccinimide ester, triethylamine, 70%/DMF-H₂O, rt.
[Formula 9]
(9)
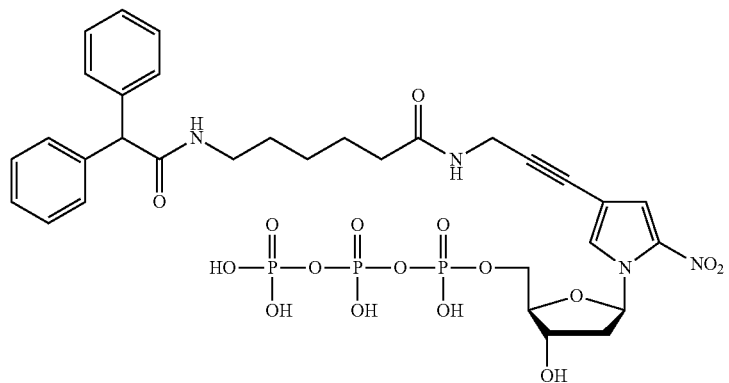
DPM-hx-dPxTP
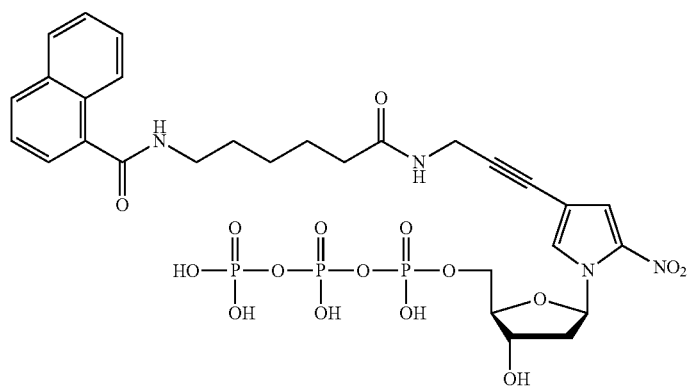
NAP-hx-dPxTP
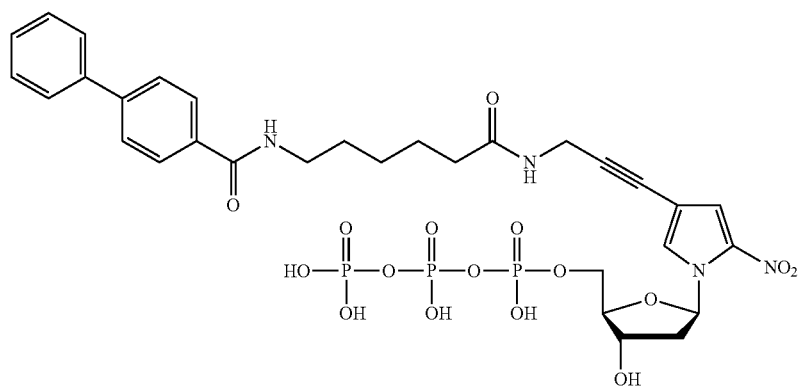
BPH-hx-dPxTP

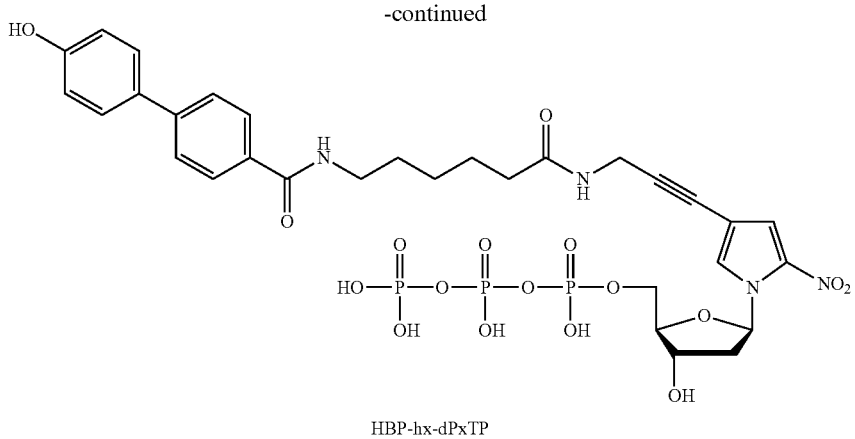

HBP-hx-dPxTP

(22-1) Synthesis of Diphenylmethane-Modified dPnTP (DPM-hx-dPnTP)

A DMF solution (3.0 ml) of diphenylacetic acid succinimide ester (120 µmol) and triethylamine (6.2 µl) were added to a 40% aqueous DMF solution (3.0 ml) of 3-(β-D-ribofuranosyl)-4-[3-(6-aminohexanamido)-1-propynyl]-2-nitropyrrole 5'-triphosphate (30 µmol), and the mixture was left standing at room temperature for 24 hours. Water (18 ml) was added to the reaction solution, and the resulting white precipitate was filtered off through Steriflip (Millipore Corp.). The filtrate was freeze-dried and then dissolved in a 100 mM triethylamine acetate buffer solution (2.0 ml). The solution was filtered through Ultrafree (0.22 µm, Millipore Corp.). The filtrate was purified on a C18 column (Nacalai Tesque, Inc., COSMOSIL 140C19-OPN; eluted with 0%4 to 30% acetonitrile linear gradient in a 100 mM triethylamine acetate buffer solution) and by C8 HPLC (Shiseido CAPCELL PAK C8; eluted with 25% to 50% acetonitrile linear gradient in a 100 mM triethylamine acetate buffer solution over 13 minutes) to obtain DPM-hx-dPnTP (yield: 15.4 µmol (51%)).

(22-2) Synthesis of Naphthalene-Modified dPnTP (NAP-hx-dPnTP)

A DMF solution (3.0 ml) of 1-naphthoic acid succinimide ester (120 µmol) and triethylamine (6.2 µl) were added to a 40% aqueous DMF solution (3.0 ml) of 3-(β-D-ribofuranosyl)-4-[3-(6-aminohexanamido)-1-propynyl]-2-nitropyrrole 5'-triphosphate (30 µmol), and the mixture was left standing at room temperature for 66 hours. Water (18 ml) was added to the reaction solution, and the resulting white precipitate was filtered off through Steriflip (Millipore Corp.). The filtrate was freeze-dried and then dissolved in a 100 mM triethylamine acetate buffer solution (3.0 ml). The solution was filtered through Ultrafree (0.22 µm, Millipore Corp.). The filtrate was purified on a C18 column (Nacalai Tesque, Inc., COSMOSIL 140C19-OPN; eluted with 0% to 30% acetonitrile linear gradient in a 100 mM triethylamine acetate buffer solution) and by C18 HPLC (Shiseido CAPCELL PAK C18; eluted with 15% to 50% acetonitrile linear gradient in a 100 mM triethylamine acetate buffer solution over 13 minutes) to obtain NAP-hx-dPnTP (yield: 16.4 µmol (55%)).

(22-3) Synthesis of Biphenyl-Modified dPnTP (BPH-hx-dPnTP)

A DMF solution (3.0 ml) of 4-biphenylcarboxylic acid succinimide ester (120 µmol) and triethylamine (6.2 µl) were added to a 40% aqueous DMF solution (3.0 ml) of 3-(β-D-ribofuranosyl)-4-[3-(6-aminohexanamido)-1-propynyl]-2-nitropyrrole 5'-triphosphate (30 µmol), and the mixture was left standing at room temperature for 51 hours. Water (18 µm) was added to the reaction solution, and the resulting white precipitate was filtered off through Steriflip (Millipore Corp.). The filtrate was freeze-dried and then dissolved in a 100 mM triethylamine acetate buffer solution (2.0 ml). The solution was filtered through Ultrafree (0.22 µm, Millipore Corp.). The filtrate was purified on a C18 column (Nacalai Tesque, Inc., COSMOSIL 140C19-OPN; eluted with 0% to 30% acetonitrile linear gradient in a 100 mM triethylamine acetate buffer solution) and by C1 HPLC (Shiseido CAPCELL PAK C1; eluted with 20% to 50% acetonitrile linear gradient in a 100 mM triethylamine acetate buffer solution over 13 minutes) to obtain BPH-hx-dPnTP (yield: 10.0 µmol (33%)).

(22-4) Synthesis of 4-Hydroxybiphenyl-Modified dPnTP (HBP-hx-dPnTP)

A DMF solution (3.0 ml) of 4'-hydroxy-4-biphenylcarboxylic acid succinimide ester (120 µmol) and triethylamine (6.2 µl) were added to a 40% aqueous DMF solution (3.0 ml) of 3-(β-D-ribofuranosyl)-4-[3-(6-aminohexanamido)-1-propynyl]-2-nitropyrrole 5'-triphosphate (30 µmol), and the mixture was left standing at room temperature for 45 hours. Water (18 ml) was added to the reaction solution, and the resulting white precipitate was filtered off through Steriflip (Millipore Corp.). The filtrate was freeze-dried and then dissolved in a 100 mM triethylamine acetate buffer solution (2.0 ml). The solution was filtered through Ultrafree (0.22 µm, Millipore Corp.). The filtrate was purified on a C18 column (Nacalai Tesque, Inc., COSMOSIL 140C19-OPN; eluted with 0% to 30% acetonitrile linear gradient in a 100 mM triethylamine acetate buffer solution) and by C8 HPLC (Shiseido CAPCELL PAK C8; eluted with 15% to 50% acetonitrile linear gradient in a 100 mM triethylamine acetate buffer solution over 13 minutes) to obtain HBP-hx-dPnTP (yield: 13.9 µmol (46%)).

(22-5) Physical Property of Modified dPnTP (R-hx-dPnTP)

(22-5-1) Physical Property of DPM-hx-dPnTP $^1$H NMR (300 MHz, $D_2O$) δ 7.72 (d, 1H, J=2.1 Hz), 7.43-7.33 (m, 6H), 7.26-7.21 (m, 5H), 6.64 (t, 1H, J=5.9

Hz), 5.01 (s, 1H), 4.53 (m, 1H), 4.20 (m, 3H), 4.14 (m, 2H), 2.23-3.16 (m, 1H and (CH$_3$CH$_2$)$_3$N), 2.54 (m, 1H), 2.36 (m, 1H), 2.26 (t, 1H, J=7.0 Hz), 1.63-1.58 (m, 2H), 1.53-1.49 (m, 2H), 1.30-1.35 (m, 1H and (CH$_3$CH$_2$)$_3$N). $^{31}$P NMR (121 MHz, D$_2$O), δ −9.47 (d, 1P, J=15.5 Hz), −10.70 (d, 1P, J=19.8 Hz), −22.47 (t, 1P, J=20.0 Hz).

ESI-MS for [M−H]− (C$_{32}$H$_{38}$N$_4$O$_{16}$P$_3$): calcd. 827.16. found: 827.02.

$l_{max}$=369 nm, $e_{260}$=2.40×10$^3$, $e_{369}$=1.07×10$^4$.

(22-5-2) Physical Property of NAP-hx-dPnTP $^1$H NMR (300 MHz, D$_2$O) δ 8.02-7.93 (m, 3H), 7.65-7.48 (m, 5H), 6.98 (d, 1H, J=2.1 Hz), 6.50 (t, 1H, J=5.9 Hz), 4.53 (m, 1H), 4.18 (m, 3H), 4.10 (s, 2H), 3.49 (t, 1H, J=6.4 Hz), 2.58-2.49 (m, 1H), 2.37-2.26 (m, 3H), 1.79-1.67 (m, 4H), 1.54-1.46 (m, 2H).
$^{31}$P NMR (121 MHz, D$_2$O), δ 9.91 (d, 1P, J=19.4 Hz), −10.77 (d, 1P, J=20.0 Hz), −22.56 (t, 1P, J=20.0 Hz).
$l_{max}$=369 nm, $e_{260}$=4.90×10$^3$, $e_{369}$=9.35×10$^3$.

(22-5-3) Physical Property of BPH-hx-dPnTP $^1$H NMR (300 MHz, D$_2$O) δ 7.76-7.68 (m, 7H), 7.61 (d, 1H, J=2.1 Hz), 7.55-7.7.45 (m, 3H), 7.04 (d, 1H, J=2.1 Hz), 6.38 (t, 1H, J=5.9 Hz), 4.45 (m, 1H), 4.16-4.10 (m, 5H), 3.39 (t, 2H, J=6.6 Hz), 2.42 (m, 1H), 2.32 (t, 1H, J=6.5 Hz), 2.19 (m, 1H), 1.74-1.62 (m, 4H), 1.45 (m, 1H).
$^{31}$P NMR (121 MHz, D$_2$O), δ −10.33 (d, 1P, J=19.7 Hz), −10.84 (d, 1P, J=19.7 Hz), −22.75 (t, 1P, J=19.8 Hz).
$l_{max}$=368 nm, $e_{260}$=2.46×10$^4$, $e_{368}$=1.04×10$^4$.

(22-5-4) Physical Property of HBP-hx-dPnTP $^1$H NMR (300 MHz, D$_2$O) δ 7.71 (d, 2H, J=8.4 Hz), 7.62-7.56 (m, 5H), 6.99 (d, 2H, J=7.5 Hz), 6.97 (s, 1H), 6.36 (t, 1H, J=5.9 Hz), 4.44 (m, 1H), 4.15-4.09 (m, 5H), 3.39 (t, 2H, J=6.5 Hz), 2.46-2.38 (m, 1H), 2.32 (t, 2H, J=6.3 Hz), 2.18-2.12 (m, 1H), 1.73-1.61 (m, 4H), 1.29-1.24 (m, 2H).
$^{31}$P NMR (121 MHz, D$_2$O), δ −9.86 (d, 1P, J=19.6 Hz), −10.75 (d, 1P, J=19.8 Hz), −22.55 (t, 1P, J=19.9 Hz).
$l_{max}$=368 nm, $e_{260}$=1.41×10$^4$, $e_{368}$=1.02×10$^4$.

Example 8

Production of DNA Aptamer Binding to VEGF-165—(2)

DNA aptamers more strongly binding to VEGF-165 were produced using a modification of a method based on the method described in Example 1.
(1) Preparation of Library of Single-Stranded DNAs Each Comprising Artificial Base Ds at Particular Site of Central Region Each single-stranded DNA library prepared in Example 1 was used.
(2) Production of VEGF-165-Binding Single-Stranded DNA Aptamer Comprising Ds The basic method followed the method described in Example 1. Hereinafter, points different from Example 1 will be particularly described, so that the description about overlapping portions will be omitted, as a rule.
A. Operation of 1 Selection Round
(i) Binding Between Target Protein and DNA Library In order to form a conformation in the DNA molecules, folding treatment (95° C. for 3 min→room temperature for 10 min→on ice for 5 min→9 room temperature) was performed. Then, the library solution was mixed with a PBS solution containing Nonidet P-40 to adjust the final concentration of Nonidet P-40 to 0.005%. The resulting nucleic acid solution was mixed with streptavidin-coupled magnetic beads, and the mixture was inverted and mixed at 25° C. for 30 minutes. A supernatant obtained using centrifugation operation and a magnetic stand was mixed with VEGF-165 to form DNA-protein complexes.
(ii) Screening for DNA Sequence Bound with Target Protein A N-hydroxysuccinimide ester (NHS)-biotinylating reagent was added to the mixed solution thus obtained, for protein biotinylation. Then, unreacted biotinylating reagents were removed by ultrafiltration. The resulting solution was mixed with streptavidin-coupled magnetic beads at room temperature to immobilize the DNA-protein complexes onto the magnetic beads. Then, the operation of suspending the magnetic beads in 1.0 ml of a PBS solution containing 0.005% Nonidet P-40 (buffer solution A), and incubating the suspension at 25° C. for 5 minutes was repeated 5 times.

In the final round (round 7), the operation of inverting and mixing using buffer solution A (1.0 ml, 25° C. for 5 min) containing 3 M urea was performed 3 times, followed by two additional operations of inverting and mixing using buffer solution A (1.0 ml, 25° C. for 5 min) to render the washing conditions further stricter. To the magnetic beads thus washed, 200 μl of an eluting solution (50 mM NaOH) was added, and the mixture was incubated at 25° C. for 5 minutes. Then, the resulting solution was recovered and neutralized using an ion-exchange resin. DNAs in the recovered solution were used as PCR templates in library preparation for the subsequent selection round.
(iii) Preparation (Amplification) of Single-Stranded DNA Library Each single-stranded DNA library for use in the subsequent round was prepared using the template DNAs obtained by the preceding selection round. Specifically, PCR amplification was performed on the basis of the approach of Bartel et al. (Nucleic Acids Res. 1995, 23: 4220-1). The Ds-containing single-stranded DNA library thus amplified was separated using a 10% polyaramide denaturing gel containing 7 M urea, then eluted and recovered from the gel, and used as a library for the subsequent round. The following primer set was used as primers for single-stranded DNA library preparation:

```
5'-primer:
                                    (SEQ ID NO: 151)
5'-TTCTGTCAATCGATCGTATCAGTCCAC-3'

3'-primer:
                                    (SEQ ID NO: 152)
5'-TTTTTTTTTTTTTTT-(CH2)12-

AAGTAGTCACTAATCCGTTCGAGTCATGC-3'
```

PCR was performed (volume: 400 to 600 μl) using AccuPrime Pfx DNA polymerase (Invitrogen Corp.). The reaction composition used was 1× AccuPrime Pfx reaction mix (containing 0.3 mM dNTPs and 1 mM MgSO$_4$) further supplemented with 0.1 mM dNTPs (N=A, G, C, and T, final concentration: 0.4 mM each dNTP) and 0.5 mM MgSO$_4$ (final concentration: 1.5 mM), 1 μM 5'-primer, 1 μM 3'-primer, 50 μM dDsTP, 50 μM Diol1-dPxTP, and 0.05 U/μl AccuPrime Pfx DNA polymerase. The PCR cycle conditions involved (94° C. for 30 sec→65° C. for 2.5 min)×12 to 26 cycles.

B. Condition of Selection Round in Repetitive Step

Seven selection rounds were performed. The selection conditions of each round are shown in Table 7.

TABLE 7

| Round | [DNA] (nM) | [Protein] (nM) | [Competitor] (nM) | Volume (ml)$^a$ | Number of washes | | PCR cycles | |
|---|---|---|---|---|---|---|---|---|
| | | | | | Without urea | With 3M urea | VEGF-165 | IFN-γ |
| 1 | 50 | 25 | — | 6 | 5 | — | 12 | 22 |
| 2 | 25 | 10 | — | 1 | 5 | — | 20 | 21 |
| 3 | 5 | 5 | — | 1 | 5 | — | 21 | 21 |
| 4 | 1 | 1 | — | 3 | 5 | — | 30 | 26 |
| 5 | 1 | 1 | 100 | 3 | 5 | — | 26 | 20 |
| 6 | 1 | 1 | 500 | 3 | 5 | — | 21 | 20 |
| 7 | 1 | 1 | 500 | 3 | 2 | 3 | 23 | 25 |

In order to render the protein-DNA complex formation conditions stricter, protein and DNA concentrations were gradually decreased, while an excessive amount of a DNA fragment previously reported as a DNA aptamer binding to the target protein was added as a competitive inhibiting DNA molecule (Competitor) during protein-DNA library mixing in rounds 5 to 7. The nucleotide sequence of the DNA fragment used is as follows:

```
ContVG (28-mer):
                                     (SEQ ID NO: 153)
5'-GCCCGTCTTCCAGACAAGAGTGCAGGGC-3'
```

(3) Identification of DNA Aptamer Sequence Obtained by Selection

The DNA aptamer sequences were identified using a method described below. First, aliquots of the single-stranded DNAs recovered after the completion of 7 rounds of in vitro selection were used as templates in PCR to replace the artificial base site with a natural base without the addition of artificial base substrates. The obtained double-stranded DNA library was sequenced using a third-generation sequencer (Life Technologies Corp.; Ion Torrent The Personal Genome Machine™ (PGM™)) without the operation of conventional cloning using E. coli. By use of the property of Ds of being replaced with A or T in most clones, the position of Ds was identified, and the sequence groups of interest were extracted. The obtained DNA aptamers were sequenced. Specifically, PCR (volume: 100 pd) was performed using 1 μM each of 5'-primer (5'-TTCTGTCAATC-GATCGTATCAGTCCAC-3'; SEQ ID NO: 151 above) and 3'-primer (5'-AAGTAGTCACTAATCCGTTTCGAGT-CATGC-3'; SEQ ID NO: 154) with the reaction composition of 0.3 mM dNTPs (N=A, G, C, and T), 50 μM dPa'TP, and 1× Titanium Taq in 1× Titanium Taq PCR buffer (Clontech Laboratories, Inc.). The PCR cycle conditions involved (94° C. for 30 sec→68° C. for 2 min)×20 to 25 cycles.

The obtained PCR products were purified through a silica gel membrane column. Then, a library was prepared therefrom using Ion Fragment Library Kit (Life Technologies Corp.) according to a method described in the manual attached thereto. The obtained DNA library was quantified using Ion Library Quantification Kit (Life Technologies Corp.), diluted to a predetermined concentration, and then treated with Ion OneTouch™ Template Kit (Life Technologies Corp.) to prepare template DNAs for analysis with The Personal Genome Machine™ (PGM™) from Life Technologies Corp. Ion Torrent The Personal Genome Machine™ sequencing was performed using Ion Sequencing Kit v2.0 (Life Technologies Corp.). The total number of reads thus obtained was analyzed using CLC Genomics Workbench (version 4.7.2) from CLC bio Japan, Inc. Specifically, the Ds-containing library sequences were screened for analyte sequences consecutively comprising 27-base 5'-primer—tag sequence (varying)—43-base sequence—6-base partial sequence (GCATGA) of the 3'-primer, while complementary sequences of the Ds-containing library sequences were screened for analyte sequences consecutively comprising the 29-base sequence of the 3'-primer except for the linker and poly-T regions—43-base sequence—tag sequence (varying)—6-base partial sequence (GTGGAC) of the 5'-primer. Then, the sequences were screened according to the position of Ds for each tag sequence. Finally, a total of 92613 read sequences were analyzed. Among them, DNA aptamers with a large number of clones (=a large number of reads) are DNA aptamers having particularly high binding ability against the target substance. Table 8 shows sequences with the number of clones of 100 or more.

TABLE 8

| Target | Selected clones | Counts* | Recognition tag-N$_{43}$ sequences (n = Ds or A) | SEQ ID NO. |
|---|---|---|---|---|
| VEGF-165 | Total | 150,364 | | |
| | Extracted | 92,613 | | |
| | N43Ds-02 | 43,717 | at-N$_{28}$-n-N$_{14}$ | |
| | VG02a | 10,570 | atCGAGCGTGAGGTCCGAAAGGCGACTCTTnTAACATCAAGTAAT | 155 |
| | VG02b | 1,299 | atACGCGGGGTGTTGAAGGGTTAGTCGGAnGTAGTGTGTACAGA | 156 |
| | N43Ds-01 | 36,833 | aa-N$_{13}$-n-N$_{29}$ | |
| | VG01 | 16,555 | aaAGTGCTGGGTCCGnATGGCGGGGGGTTAGGCCTCTTTGGGGCG | 157 |
| | | 640 | aaTCGCGGTTCCGTGnTGGCGGGTGAAGGTTATGGTTTGGTGTGG | 158 |

TABLE 8-continued

| Selected Target clones | Counts* | Recognition tag-$N_{43}$ sequences (n = Ds or A) | SEQ ID NO. |
|---|---|---|---|
| N43Ds-20 VG20 | 9,017 | ggt-$N_{19}$-n-$N_8$-n-$N_{14}$ | |
| | 7,385 | ggtAAACTGAGTCCGAAGGGGCnTGCAGTGAnCCCGAATGGGTCCG | 159 |
| | 226 | ggtGAATCCGGCAGAGATCACTnTACGCTTGnTGCCTCTTTAATTC | 160 |
| | 121 | ggtTTAGGCGTCTTTAGGGGGTnGAGGTCGGnTTTTACCGCGGTGT | 161 |
| N43Ds-08 VG08 | 1,463 | ga-$N_{18}$-n-$N_9$-n-$N_6$-n-$N_7$ | |
| | 563 | gaGATGGATGGTAGTGGCCGnACGGGGGGGnTGGAGAnGCTGGCT | 162 |
| N43Ds-21 | 830 | cga-$N_{18}$-n-$N_9$-n-$N_{14}$ | |
| | 504 | cgaTTCCTTATCCTAGGACTTnTTTCCGCGCnCACGTGCTCAGATT | 163 |
| | 130 | cgaTTTGGGGGTGGGGCGGGnCCGTGATGGnGATGAAGGTGGGCG | 164 |
| N43Ds-13 | 168 | cat-$N_9$-n-$N_6$-n-$N_6$-n-$N_{19}$ | |
| | 166 | catGGAGGGCCGnATGGCCnGACACTnGACCGTGCGAGATGGTTGG | 165 |
| N43Ds-15 | 120 | tta-$N_{16}$-n-$N_6$-n-$N_9$-n-$N_9$ | |
| | 107 | ttaTGCGGGTGGGAGCACCnTCGACAnTTGCGTCCGnATGGCCAGA | 166 |

*Total counts: the total number of reads obtained by sequence analysis using a next-generation sequencer.

Extracted counts: analyte sequences were extracted from the total number of reads.

Example 9

Binding Analysis of DNA Aptamer Binding to VFGF-165—(2)

Five types of sequences were selected from the sequences shown in Table 8 and analyzed for their VEGF-165-binding ability by surface plasmon resonance (SPR) assay using BIACORE 3000 (GE Healthcare Japan Corp.) and 57-mer DNA fragments (Table 9) truncated at a primer region. A previously reported 57-mer DNA fragment comprising the DNA sequence of VEGF-165 was also prepared and analyzed as a control.

SPR assay conditions: flow rate: 20 μl/min, assay temperature: 25° C., injection time of VEGF-165 (10 nM): 480 sec, and monitoring time of dissociation: 480 sec.

The basic method followed the method described in Example 2. Hereinafter, conditions different from Example 2 will be particularly described, so that the description about overlapping portions will be omitted, as a rule.

For the immobilization of each DNA fragment onto an SA chip (GE Healthcare Japan Corp.), a DNA solution diluted with a PBS solution to 25 nM was subjected to folding treatment (95° C. for 3 min→room temperature for 10 min→on ice for 5 min→room temperature), and Nonidet P-40 was then added thereto at a final concentration of 0.005%. The resulting DNA solution (5 μl; corresponding to

TABLE 9

| Name | Sequence | SEQ ID NO. | Bound* |
|---|---|---|---|
| VG02aDs-57 | 5'-atcagtccacatCGAGCGTGAGGTCCGAAAGGCGACTCTTDsTAACATCAAGTAATG-3' | 175 | 0.15 |
| VG02aA-57 | 5'-atcagtccacatCGAGCGTGAGGTCCGAAAGGCGACTCTTATAACATCAAGTAATG-3' | 176 | 0.01 |
| VG02bDs-57 | 5'-atcagtccacatACGCGGGGGTGTTGAAGGGTTAGTCGGADsGTAGTGTGTACAGAG-3' | 177 | 0.39 |
| VG02bA-57 | 5'-atcagtccacatACGCGGGGGTGTTGAAGGGTTAGTCGGAAGTAGTGTGTACAGAG-3' | 178 | 0.31 |
| VG01Ds-57 | 5'-atcagtccacaaAGTGCTGGGTCCGDsATGGCGGGGGGTTAGGCCTCTTTGGGGCGG-3' | 179 | 0.20 |
| VG01A-57 | 5'-atcagtccacaaAGTGCTGGGTCCGAATGGCGGGGGGTTAGGCCTCTTTGGGGCGG-3' | 180 | 0.37 |
| VG20Ds-57 | 5'-tcagtccacggtAAACTGAGTCCGAAGGGGCDsTGCAGTGADsCCCGAATGGGTCCGG-3' | 181 | 0.66 |
| VG20A-57 | 5'-tcagtccacggtAAACTGAGTCCGAAGGGGCATGCAGTGAACCCGAATGGGTCCGG-3' | 182 | 0.37 |
| VG08Ds-57 | 5'-atcagtccacgaGATGGATGGTAGTGGCCGDsACGGGGGGGDsTGGAGADsGCTGGCTG-3' | 183 | 0.21 |
| VG08A-57 | 5'-atcagtccacgaGATGGATGGTAGTGGCCGAACGGGGGGGATGGAGAAGCTGGCTG-3' | 184 | 0.01 |
| contVG-57 | 5'-TCTGTCAATCGATCGTATCAGTCCACAA*GCCCGTCTTCCAGACAAGAGTGCAGGGC*-3' | 185 | |

*Bound = [Resonance units after 930 seconds from the start of protein injection]/[Resonance units of the immobilized DNA] × [Molecular weight of the immobilized DNA]/[Molecular weight of the protein].

1 min) was injected to the SA chip at a flow rate of 5 μl/min to achieve the immobilization. After the immobilization, DNA fragments nonspecifically adsorbed on the SA chip were washed off. The interaction between the immobilized DNA fragment and VEGF-165 was detected under monitoring by the injection of 2.5 nM, 5 nM, and 10 nM VEGF-165 solutions at the Kinetic Injection mode. The assay conditions involved a flow rate of 20 μl/min and protein injection for 8 minutes. Sensorgrams obtained by the examination of binding to VEGF-165 are shown in FIG. 15.

The results of this assay demonstrated that, of the DNA fragments used in the assay, VG20Ds-57 particularly strongly binds to VEGF-165. The replacement of Ds in these DNA fragments with the natural base A was also found to weaken the binding of the resulting DNA fragments to the target protein.

The DNA fragments used in the assay were subjected to curve fitting using BiaEvaluation software attached to Biacore 3000 and reaction models of Langmuir with mass transfer. As a result, VG20Ds-57 was shown to have a dissociation constant (Kd) of 5.9 μM, which was lower than the dissociation constant (46 μM) of the existing aptamer (contVG-57). The sequence VG20A-57 derived from VG20Ds-57 by the replacement of the Ds base with the natural base A had a dissociation constant of 0.22 nM, demonstrating that the binding of VG20Ds-57 to VEGF-165 depends on the Ds base.

Example 10

Doped Selection Based on Sequence of VG20Ds-57

The tag and random region sequences of VG20Ds-57 found to strongly bind to the target protein were mutated. The optimization of the aptamer and the prediction of the secondary structure were performed by selection.

Each DNA library for doped selection was prepared in the same way as in Example 3 on the basis of the sequence of VG20Ds-57. Each DNA library used in doped selection was prepared by chemical synthesis and gel purification so that primer regions, Ds bases, and one base of the 3-base tag sequence were fixed while the other portions constituted by natural nucleotide sequences including the remaining portion of the tag sequence contained 55% of the original bases and 45% of bases different from the original bases (15% each of 3 types of bases). The sequences are as follows:

```
                                       (SEQ ID NO: 330)
5'-CTGTCAATCGATCGTATCAGTCCACGgtaaactgagtccgaagggc DstgcagtgaDscccgaatgggtccgGCATGACTCGAACGGATTAGTGAC
T-3'
(upper-case letter: fixed sequence, lower-case
letter: doped sequence)
``` a=A: 55%; G: 15%; C: 15%, T: 15% g=A: 15%; G: 55%; C: 15%, T: 15% c=A: 15%; G: 15%; C: 55%, T: 15% t=A: 15%; G: 15%; C: 15%, T: 55%

DNA aptamers binding to the target protein were selected by the procedures as in Example 1(2) using this library. The selection conditions are shown in Table 10.

TABLE 10

| Round | [DNA] (nM) | [Protein] (nM) | [Competitor] (nM) | Volume (ml)[a] | Number of washes | | PCR Cycles | |
|---|---|---|---|---|---|---|---|---|
| | | | | | Without urea | With 3M urea | VEGF-165 | IFN-γ |
| 1 | 50 | 25 | — | 6 | 5 | — | 12 | 19 |
| 2 | 5 | 5 | — | 1 | 5 | — | 23 | 20 |
| 3 | 1 | 1 | 100 | 3 | 5 | — | 14 | 17 |
| 4 | 1 | 1 | 500 | 3 | 2 | 3 | 19 | 20 |

Figure 16A:
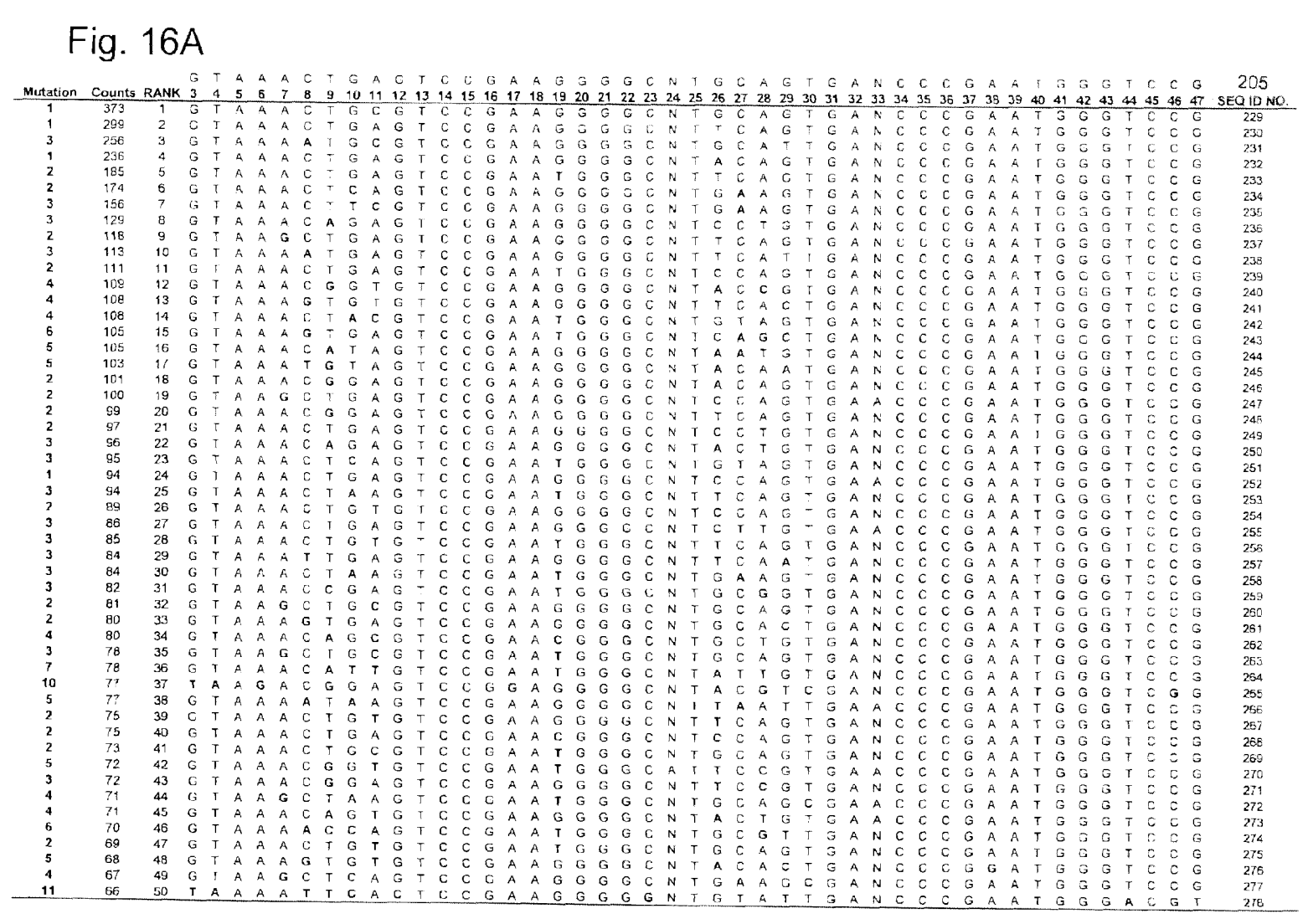
Figure 16B:
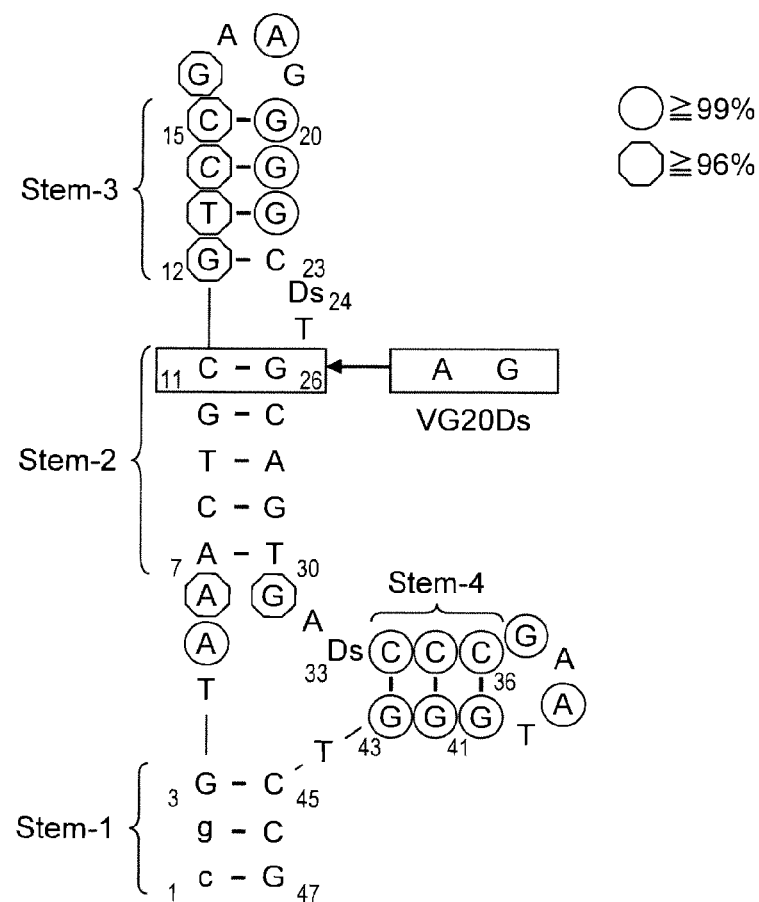
FIG. 16B shows the sequence and predicted secondary structure of VGd1-2Ds-47 (SEQ ID NO: 198). Bases exhibiting 99% or more and 96% or more rates of retention in a doped sequence portion except for artificial bases in a sequence obtained by 4 rounds of doped selection are indicated with a circle and an octagon, respectively. The lower-case letter represents a base derived from a primer region sequence during selection.
Figure 17A:
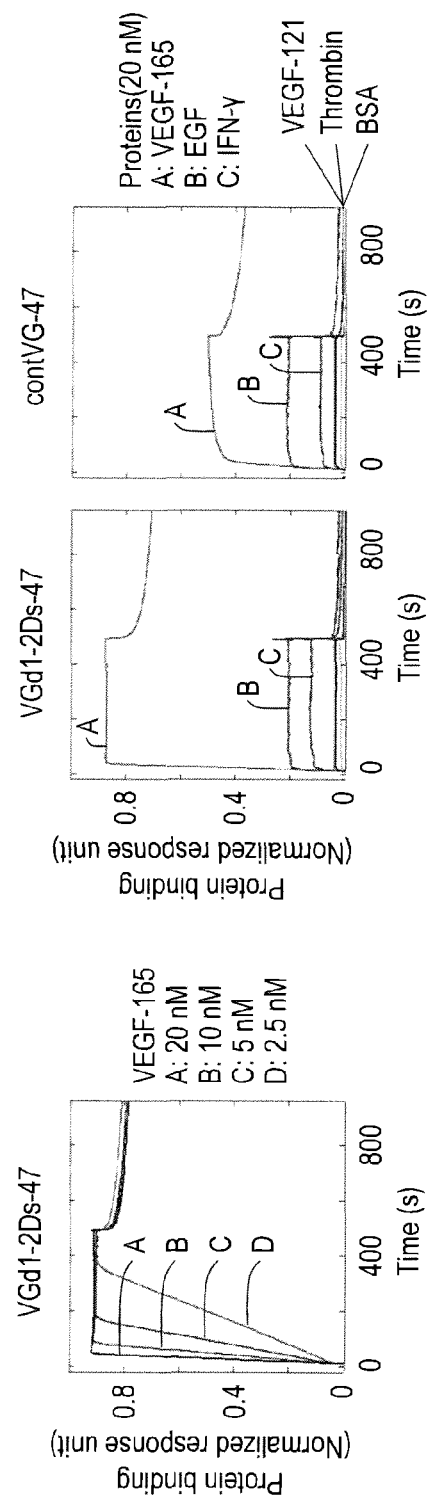
FIG. 17A shows SPR analysis results of the binding of VGd1-2Ds-47 and an existing anti-VEGF-165 aptamer to each protein.
Figure 17B:
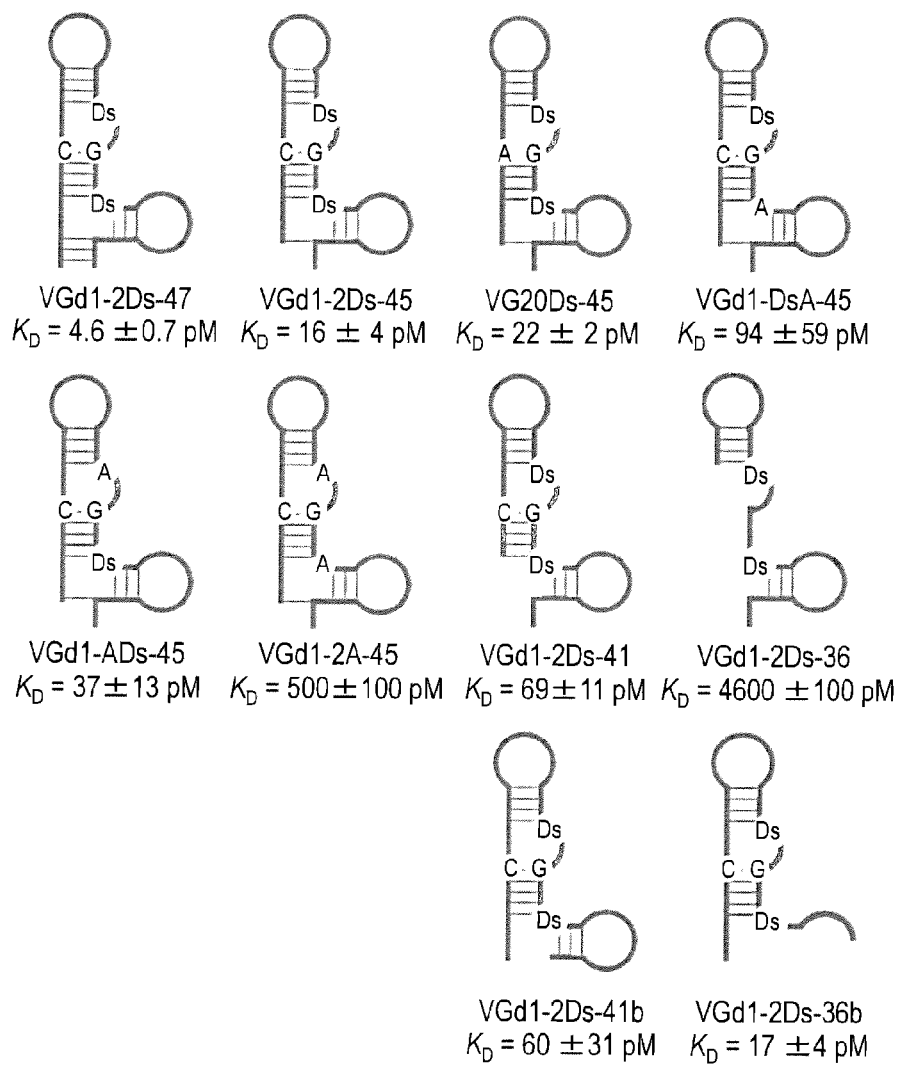
FIG. 17B shows the position of Ds in the predicted secondary structures of various VGd1-2Ds-47 variants and their binding ability ($K_D$) against VEGF-165.

The aptamers obtained by selection after 4 rounds were sequenced in the same way as the method described in Example 8(3) to analyze a total of 43719 read sequences. From the sequencing results, regions having a high rate of retention and regions with co-variation were identified. Their secondary structures were predicted from the obtained information (FIGS. 16A and 16B). As a result, a single-base mutation stabilizing the predicted structure, for example, the mutation of A11 to C11, was confirmed in VG20Ds-57. A 47-mer truncated VEGF-165-binding DNA fragment (VGd1-2Ds-47; SEQ ID NO: 198) (FIG. 17A) comprising this single-base mutation was used in binding analysis by the same SPR procedures as in Example 9 (FIGS. 17B and 18). As a result, VGd1-2Ds-47 had Kd of 4.6 pM, which was one order of magnitude less than the Kd 44 μM of the existing DNA aptamer (contVG-47; SEQ ID NO: 200) constituted only by natural bases. This indicates that VGd1-2Ds-47 can bind to the target protein with approximately 10 times the intensity of the existing DNA aptamer. As a result of examining the binding of VGd1-2Ds-47 to non-target proteins (VEGF-121 (PeproTech, Inc.), EGF (PeproTech, Inc.), thrombin (Enzyme Research laboratories Ltd.), and BSA (Sigma-Aldrich Corp.)), VGd1-2Ds-47 was shown to selectively bind to the target protein (FIG. 17B).

Each of various truncated variants of the aptamer or substitution variants with the replacement of the Ds base with A was further produced as shown in Table 11.

TABLE 11

| Name | Sequence [a] | SEQ ID NO. | $K_D$ [b] | | Bound [b] |
|---|---|---|---|---|---|
| VGd1-2Ds-47 | 5'-CGGTAAACTGCGTCCGAAGGGGCDsTGCAGTGADsCCCGAATGGGTCCG-3' | 198 | 4.6 ± 0.7 | pM | 0.79 |
| VGd1-2A-47 | 5'-CGGTAAACTGCGTCCGAAGGGGCATGCAGTGAACCCGAATGGGTCCG-3' | 199 | 0.2 ± 0.1 | nM | 0.50 |
| contVG-47 | 5'-CGATCGTATCAGTCCACAA*GCCCGTCTTCCAGACAAGAGTGCAGGGC*-3' | 200 | 44 ± 1 | pM | 0.39 |
| VGd1-2Ds-49 | 5'-CCGGTAAACTGCGTCCGAAGGGGCDsTGCAGTGADsCCCGAATGGGTCCGG-3' | 201 | 4.6 ± 1.4 | pM | 1.03 |
| VGd1-2Ds-45 | 5'-GTAAACTGCGTCCGAAGGGGCDsTGCAGTGADsCCCGAATGGGTCCG-3' | 202 | 16 ± 4 | pM | 0.71 |
| VGd1-2A-45 | 5'-GTAAACTGCGTCCGAAGGGGCATGCAGTGAACCCGAATGGGTCCG-3' | 203 | 0.5 ± 0.1 | nM | 0.46 |
| contVG-45 | 5'-ATCGTATCAGTCCACAA*GCCCGTCTTCCAGACAAGAGTGCAGGGC*-3' | 204 | 81 ± 2 | pM | 0.39 |
| VG20Ds-45 | 5'-GTAAACTGAGTCCGAAGGGGCDsTGCAGTGADsCCCGAATGGGTCCG-3' | 205 | 22 ± 2 | pM | 0.67 |
| VGd1-DsA-45 | 5'-GTAAACTGCGTCCGAAGGGGCDsTGCAGTGAACCCGAATGGGTCCG-3' | 206 | 94 ± 59 | pM | 0.54 |
| VGd1-ADs-45 | 5'-GTAAACTGCGTCCGAAGGGGCATGCAGTGADsCCCGAATGGGTCCG-3' | 207 | 37 ± 13 | pM | 0.89 |
| VGd1-2Ds-50 | 5'-TTTTTGTAAACTGCGTCCGAAGGGGCDsTGCAGTGADsCCCGAATGGGTCCG-3' | 208 | 17 ± 4 | pM | 0.96 |
| VGd1-2Ds-41 | 5'-ACTGCGTCCGAAGGGGCDsTGCAGTGADsCCCGAATGGGTCCG-3' | 209 | 69 ± 11 | pM | 0.64 |
| VGd1-2Ds-36 | 5'-GTCCGAAGGGGCDsTGCAGTGADsCCCGAATGGGTCCG-3' | 210 | 4.6 ± 0.1 | nM | 0.02 |
| VGd1-2Ds-41b | 5'-GTAAACTGCGTCCGAAGGGGCDsTGCAGTGADsCCCGAATGGG-3' | 211 | 60 ± 31 | pM | 0.71 |
| VGd1-2Ds-36b | 5'-GTAAACTGCGTCCGAAGGGGCDsTGCAGTGADsCCCGA-3' | 212 | 17 ± 4 | pM | 0.49 |
| Random-45 | 5'-ATGCTAGAGCATTGCGTAGAAGCTTGATATGTTGCTGGCCCGGAC-3' | 213 | – | | 0.01 |

Sequences of anti-VEGF-165 aptamer (VGd1-2Ds-47) and its variants and analysis results of VEGF-165-binding ability of each DNA fragment determined by SPR
[a] The sequence of contVG is indicated in underlined italic.
[b] Bound = [Resonance units after 930 seconds from the start of protein injection]/[Resonance units of the immobilized DNA] × [Molecular weight of the immobilized DNA]/[Molecular weight of VEGF-165].

SPR assay conditions: flow rate: 20 μl/min, assay temperature: 25° C., injection time of VEGF-165 (10 nM): 480 sec, and monitoring time of dissociation: 480 sec.

The sensorgrams are shown in FIG. 18. The dissociation constants were calculated by global fitting.

As a result of examining binding to the target protein, a 45-mer variant truncated at the 5'-terminal primer region (VGd1-2Ds-45; SEQ ID NO: 202) had a Kd value of 16 μM (FIG. 17B and Table 11). The binding analysis results about a variant (VGd1-2A-45; SEQ ID NO: 203) derived from this 45-mer DNA fragment by the replacement of the Ds base with A revealed that in VGd1-2Ds-45, two Ds bases, i.e., Ds22 and Ds33, are strongly involved in the binding. In VGd1-2Ds-47, Stem-2 flanked by two Ds bases was further found to be particularly largely involved in the binding. Also, a 36-mer variant (VGd1-2Ds-36b; SEQ ID NO: 212) had a Kd value of 17 μM (FIG. 17B and Table 11). These results demonstrated that among the anti-VEGF-165 aptamers having a nucleotide sequence related to VGd1-2Ds-47, the DNA aptamer comprising the nucleotide sequence represented by SEQ ID NO: 212 has VEGF-165-binding activity.

In the nucleic acid aptamer of the present invention, a non-natural nucleotide does not base-pair with a natural nucleotide, as a rule. Thus, the presence of one or more, preferably two or more non-natural nucleotides (e.g., Ds) in the nucleotide sequence of the nucleic acid aptamer leads to the exclusion of some candidates of the predicted secondary structure. Specifically, according to the nucleic acid aptamer of the present invention, the predicted secondary structure can be narrowed down to obtain a more accurate secondary structure, compared with conventional nucleic acid aptamers. Thus, according to the nucleic acid aptamer of the present invention, which permits more accurate prediction of the secondary structure, other nucleic acid aptamer derivatives having an arbitrary nucleotide sequence may be constructed on the basis of the secondary structure of the nucleic acid aptamer.

Example 11

Production of DNA Aptamer Binding to IFN-γ

DNA aptamers strongly binding to IFN-γ were produced in the same way as in Example 8. The method of this Example was basically the same as that in Example 8 and was performed according thereto.

(1) Preparation of Library of Single-Stranded DNAs Each Comprising Artificial Base Ds at Particular Site of Central Region Each single-stranded DNA library prepared in Example 1 was used.

(2) Production of IFN-γ-Binding Single-Stranded DNA Aptamer Comprising Ds

The basic procedures, etc. followed the method described in Example 8. Hereinafter, points different from Example 8 will be particularly described, so that the description about overlapping portions will be omitted, as a rule.

A. Operation of 1 Selection Round (i) Binding Between Target Protein and DNA Library In order to form a conformation in the DNA molecules, folding treatment was performed. Then, the library solution was mixed with a PBS solution containing Nonidet P-40 to adjust the final concentration of Nonidet P-40 to 0.005%. The resulting nucleic acid solution was mixed with streptavidin-coupled magnetic beads. A supernatant was mixed with IFN-γ (PeproTech, Inc.) to form DNA-protein complexes.

(ii) Screening for DNA Sequence Bound with Target Protein

The procedures were performed according to the method described in Example 8.

(iii) Preparation (Amplification) of Single-Stranded DNA Library

The procedures were performed according to the method described in Example 8. The number of selection rounds was set to 7. The conditions of each selection round are shown in Table 7 above. In order to render the protein-DNA complex formation conditions stricter, an excessive amount of a DNA fragment having the following nucleotide sequence was added as a competitive inhibiting molecule (Competitor):

```
                                             (SEQ ID NO: 228)
ContIF (26-mer):  5'-GGGGTTGGTTGTGTTGGGTGTTGTGT-3'
```

(3) Identification of DNA Aptamer Sequence Obtained by Selection

The DNA aptamer sequences were identified according to the method described in Example 8. Finally, a total of 21242 read sequences were analyzed. Among them, DNA aptamers with a large number of clones (=a large number of reads) are DNA aptamers having particularly high binding ability against the target substance. Table 12 shows sequences with the number of clones of 100 or more.

TABLE 12

| Target | Selected clones | Counts* | Recognition tag-$N_{43}$ sequences (n = Ds or A) | SEQ ID NO. |
|---|---|---|---|---|
| IFN-γ | Total | 51,461 | | |
| | Extracted | 21,242 | | |
| | N43Ds-07 | 13,768 | tc-$N_{10}$-n-$N_{10}$-n-$N_{10}$-n-$N_{10}$ | |
| | IF07a | 5,688 | tcCTTCTGTCATnGGGCAGGCGCnTTTGGTGTAGnGTTTATCTTG | 167 |
| | IF07b | 4,965 | tcGGGTCGTTTAnTAATGTAGGTnTGGGCTAGGCnGCTAGTGGAT | 168 |
| | N43Ds-11 | 5,195 | ct-$N_{11}$-n-$N_{13}$-n-$N_9$-n-$N_7$ | |
| | IF11 | 4,508 | ctATGTGGGTTGGnTGGGGTGTATGTTnGTAGGGCTAnGGAGGTG | 169 |
| | N43Ds-02 | 793 | at-$N_{28}$-n-$N_{14}$ | |
| | IF02 | 682 | atTGGACTTAGCCCAGCAAGACAATCTACGnTATGCCAGAAGTTG | 170 |
| | N43Ds-01 | 648 | aa-$N_{13}$-n-$N_{29}$ | |
| | | 357 | aaAGTTAGGGACTGAnCCCTTTCCGTGAAGCGTGGAGGGACGATA | 171 |
| | | 160 | aaTGCGAGGTACGAGnAGGGTTTGGGTTGGCGGGGCCATTGTAGT | 172 |
| | N43Ds-04 | 600 | ta-$N_{10}$-n-$N_{15}$-n-$N_{16}$ | |
| | IF04 | 386 | taATCAGGAAGAnGATAGGGTTTGTCTTnTGTTGCCACGCTGGGA | 173 |
| | N43Ds-03 | 177 | ag-$N_{16}$-n-$N_{15}$-n-$N_{10}$ | |
| | | 108 | agGCTATCATTCGCGTTCnGGTTTGATTGGTTCTnGGAGGGGTGG | 174 |

*Total counts: the total number of reads obtained by sequence analysis using a next-generation sequencer Extracted counts: analyte sequences were extracted from the total number of reads.

Example 12

Binding Analysis of DNA Aptamer Binding to IFN-γ

Five types of sequences were selected from the sequences shown in Table 12 and analyzed for their IFN-γ-binding ability by surface plasmon resonance assay and 57-mer DNA fragments (Table 13) truncated at a primer region. A previously reported 57-mer DNA fragment comprising the DNA sequence of IFN-γ was also prepared and analyzed as a control.

TABLE 13

| Name | Sequence | SEQ ID NO. | Bound* |
|---|---|---|---|
| IF07aDs-57 | 5'-atcagtccactcCTTCTGTCATDsGGGCAGGCGCDsTTTGGTGTAGDsGTTTATCTTGg-3' | 186 | 0.07 |
| IF07aA-57 | 5'-atcagtccactcCTTCTGTCATAGGGCAGGCGCATTTGGTGTAGAGTTTATCTTGg-3' | 187 | 0.19 |
| IF07bDs-57 | 5'-atcagtccactcGGGTCGTTTADsTAATGTAGGTDsTGGGCTAGGCDsGCTAGTGGATg-3' | 188 | 0.72 |
| IF07bA-57 | 5'-atcagtccactcGGGTCGTTTAATAATGTAGGTATGGGCTAGGCAGCTAGTGGATg-3' | 189 | 0.05 |
| IF11Ds-57 | 5'-atcagtccacctATGTGGGTTGGDsTGGGGTGTATGTTDsGTAGGGCTADsGGAGGTGg-3' | 190 | 0.66 |
| IF11A-57 | 5'-atcagtccacctATGTGGGTTGGATGGGGTGTATGTTAGTAGGGCTAAGGAGGTGg-3' | 191 | 0.46 |
| IF02Ds-57 | 5'-atcagtccacatTGGACTTAGCCCAGCAAGACAATCTACGDsTATGCCAGAAGTTGg-3' | 192 | 0.03 |
| IF02A-57 | 5'-atcagtccacatTGGACTTAGCCCAGCAAGACAATCTACGATATGCCAGAAGTTGg-3' | 193 | 0.03 |
| IF04Ds-57 | 5'-atcagtccactaATCAGGAAGADsGATAGGGTTTGTCTTDsTGTTGCCACGCTGGGAg-3' | 194 | 0.10 |
| IF04A-57 | 5'-atcagtccactaATCAGGAAGAAGATAGGGTTTGTCTTATGTTGCCACGCTGGGAg-3' | 195 | 0.08 |
| contIF-57 | 5'-TTCTGTCAATCGATCGTATCAGTCCACAAT*GGGGTTGGTTGTGTTGGGTGTTGTGT*-3' | 196 | |
| Random-57 | 5'-ATCAGTCCACAATGCTAGAGCATTGCGTAGAAGCTTGATATGTTGCTGGCCCGGAC-3' | 197 | |

*Bound = [Resonance units after 930 seconds from the start of protein injection]/[Resonance units of the immobilized DNA] × [Molecular weight of the immobilized DNA]/[Molecular weight of the protein].

SPR assay conditions: flow rate: 20 μl/min, assay temperature: 25° C., injection time of IFN-γ (150 nM): 480 sec, and monitoring time of dissociation: 480 sec.

The basic method followed the method described in Example 9. Hereinafter, conditions different from Example 9 will be particularly described, so that the description about overlapping portions will be omitted, as a rule. Sensorgrams obtained by the examination of binding to IFN-γ are shown in FIG. 19.

The results of this assay demonstrated that, of the DNA fragments used in the assay, IF07b-57 most strongly binds to IFN-γ. The replacement of Ds in these DNA fragments with the natural base A was also found to weaken the binding of the resulting DNA fragments to the target protein.

The DNA fragments used in the assay were subjected to curve fitting in the same way as in Example 9. As a result, IF07b-57 was shown to have a dissociation constant (Kd) of 2 nM, which was lower than the dissociation constant (67 nM) of the existing aptamer (contIF-57) constituted only by natural bases, demonstrating the strong binding of this aptamer to the target protein.

Example 13

Doped Selection Based on Sequence of IF07b-57

As in Example 10, the tag and random region sequences of IF07b-57 found to strongly bind to the target protein were mutated. The optimization of the aptamer and the prediction of the secondary structure were performed by selection. The basic operation was performed according to the method described in Example 10. DNA aptamer selection in each round was performed under the conditions shown in Table 10 above.

Figure 20A:
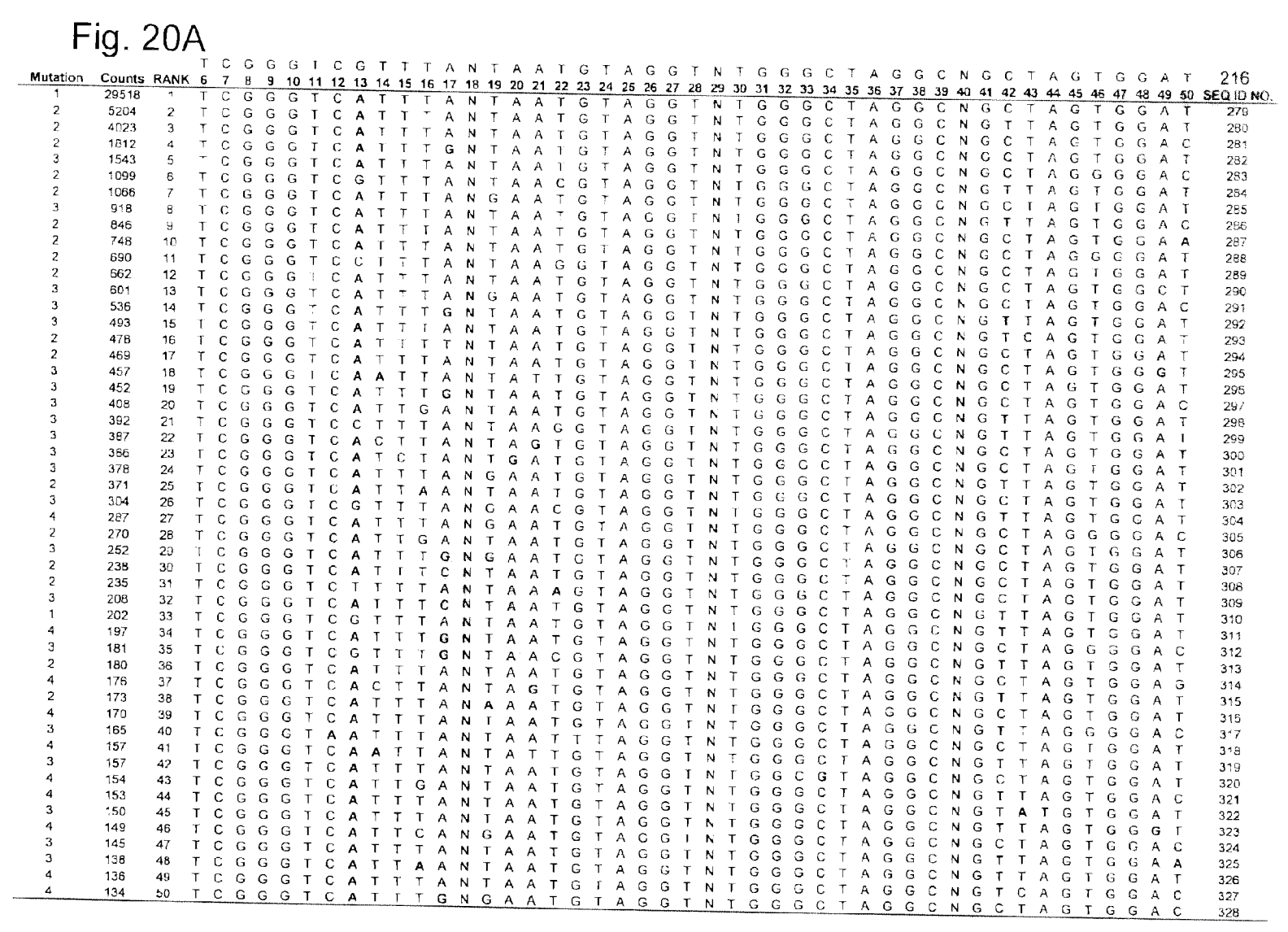
Figure 20B:
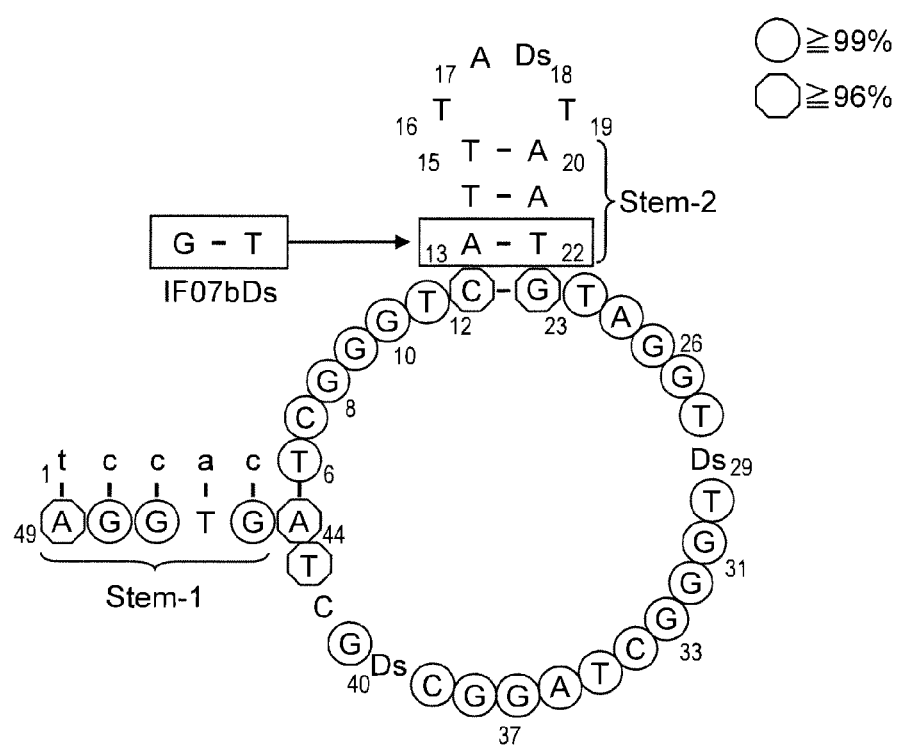
FIG. 20B shows the sequence and predicted secondary structure of IFd1-3Ds-49 (SEQ ID NO: 214). Bases exhibiting 99% or more and 96% or more rates of retention in a doped sequence portion except for artificial bases in a sequence obtained by 4 rounds of doped selection are indicated with a circle and an octagon, respectively. The lower-case letter represents a base derived from a primer region sequence during selection.

The aptamers obtained by selection after 4 rounds were sequenced to analyze 73918 read sequences. From the sequencing results, regions having a high rate of retention and regions with co-variation were identified. Their secondary structures were predicted from the obtained information (FIGS. 20A and 20B).

Figure 21A:
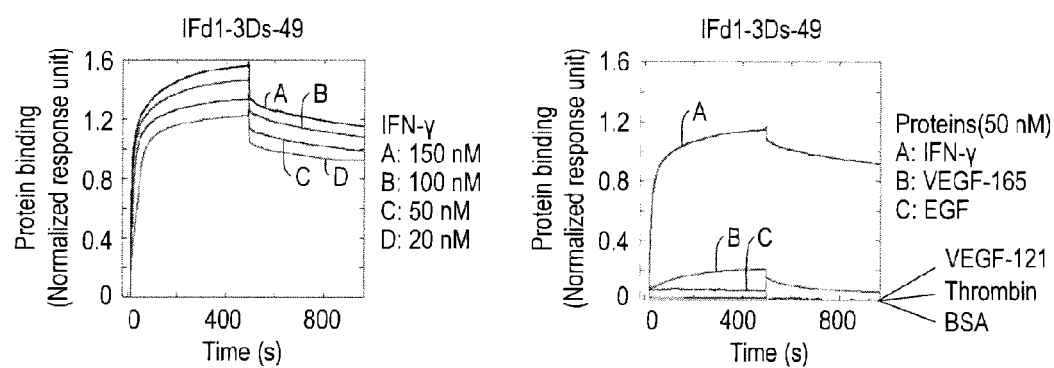
FIG. 21A shows SPR analysis results of the binding of IFd1-3Ds-49 and an existing anti-IFN-γ aptamer to each protein.
Figure 21B:
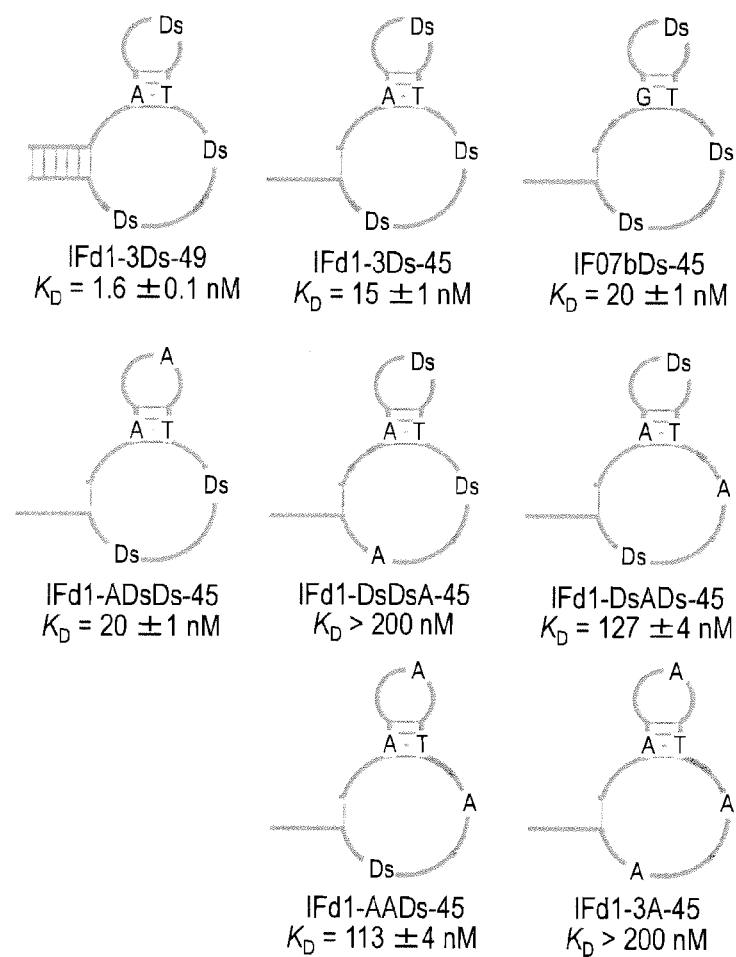
FIG. 21B shows the position of Ds in the predicted secondary structures of various IFd1-3Ds-49 variants and their binding ability ($K_D$) against IFN-γ.
Figure 22:
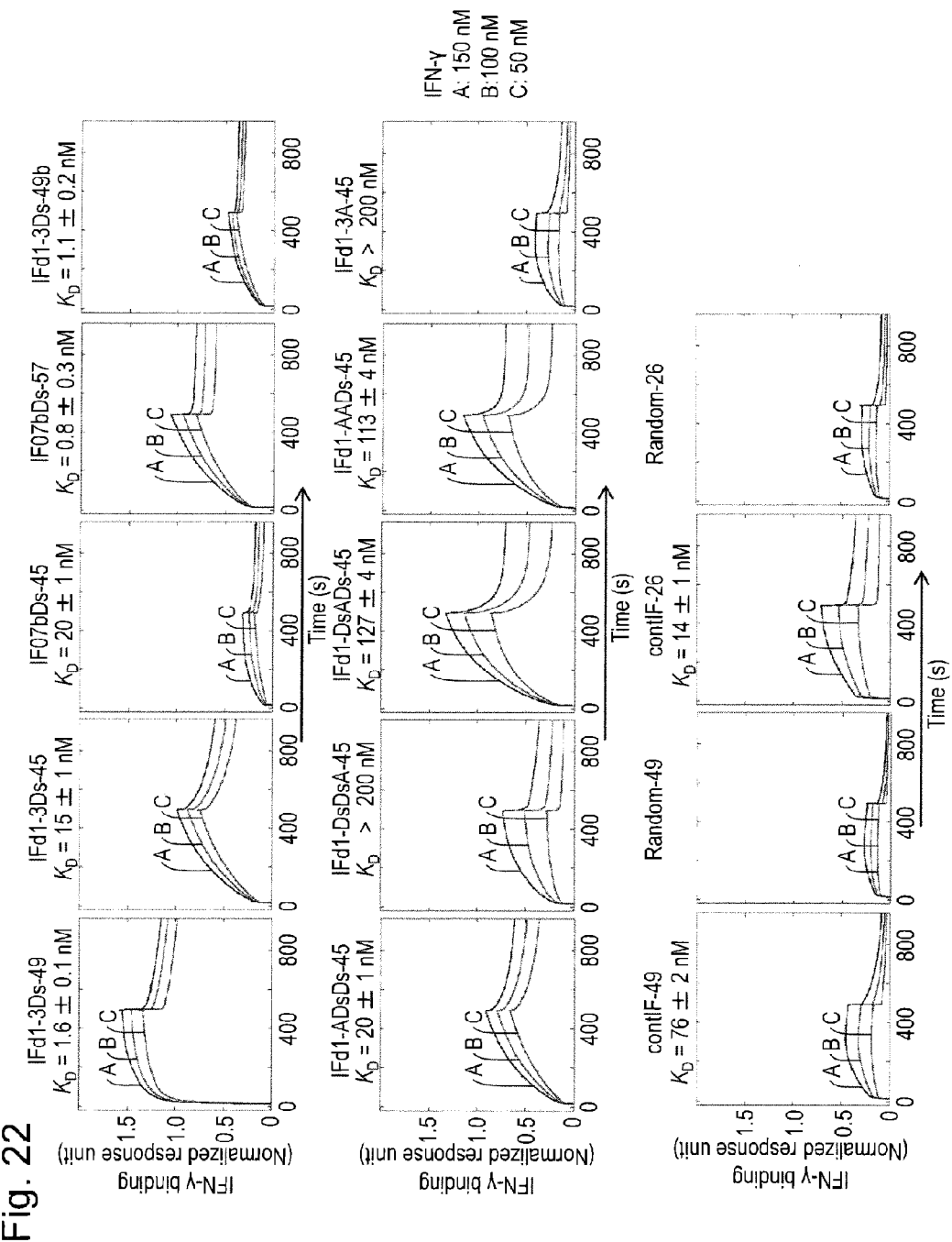
FIG. 22 shows SPR sensorgrams showing the IFN-γ binding of various IFd1-3Ds-49 variants, wherein 50 nM (A), 100 nM (B), or 150 nM (C) IFN-γ was injected.

As a result, a single-base mutation stabilizing the predicted structure, for example, the mutation of G13 to A13, was confirmed in IF07b-57. A 47-mer truncated IFN-γ-binding DNA fragment (IFd1-3Ds-49; SEQ ID NO: 214) (FIG. 21A) comprising this single-base mutation was used in binding analysis by SPR. As a result, IFd1-3Ds-49 had Kd of 1.6 nM, which was higher than the Kd 76 nM of the existing DNA aptamer (contIF-49; SEQ ID NO: 224) constituted only by natural bases (FIGS. 21B and 22). This indicates that IFd1-3Ds-49 can bind to the target protein with 40 or more times the intensity of the existing DNA aptamer. As a result of examining the binding of IFd1-3Ds-49 to non-target proteins (VEGF-121 (PeproTech, Inc.), EGF (PeproTech, Inc.), thrombin (Enzyme Research laboratories Ltd.), and BSA (Sigma-Aldrich Corp.)), IFd1-3Ds-49 was shown to selectively bind to the target protein IFN-γ (FIG. 21A). Each of various truncated variants of the aptamer or substitution variants with the replacement of the Ds base with A was further produced as shown in Table 14.

TABLE 14

| Name | Sequence[a] | SEQ ID NO. | $K_D$ (nM)[b] | Bound[b] |
|---|---|---|---|---|
| IFd1-3Ds-49 | 5'-TCCACTCGGGTCATTTADsTAATGTAGGTDsTGGGCTAGGCDsGCTAGTGGA-3' | 214 | 1.6 ± 0.1 | 1.16 |
| IFd1-3Ds-45 | 5'-TCGGGTCATTTADsTAATGTAGGTDsTGGGCTAGGCDsGCTAGTGGAT-3' | 215 | 15 ± 1 | 0.60 |

TABLE 14-continued

| Name | Sequence a) | SEQ ID NO. | $K_D$ (nM) b) | Bound b) |
|---|---|---|---|---|
| IF07bDs-45 | 5'-TCGGGTCGTTTADsTAATGTAGGTDsTGGGCTAGGCDsGCTAGTGGAT-3' | 216 | 20 ± 1 | 0.18 |
| IF07bDs-57 | 5'-ATCAGTCCACTCGGGTCGTTTADsTAATGTAGGTDsTGGGCTAGGCDsGCTAGTGGATG-3' | 217 | 0.8 ± 0.3 | 0.81 |
| IFd1-3Ds-49b | 5'-TGACCTCGGGTCATTTADsTAATGTAGGTDsTGGGCTAGGCDsGCTAGGTCA | 218 | 1.1 ± 0.2 | 0.37 |
| IFd1-A2Ds-45 | 5'-TCGGGTCATTTAATAATGTAGGTDsTGGGCTAGGCDsGCTAGTGGAT-3' | 219 | 20 ± 1 | 0.61 |
| IFd1-DsDsA-45 | 5'-TCGGGTCATTTADsTAATGTAGGTDsTGGGCTAGGCAGCTAGTGGAT-3' | 220 | >200 | 0.36 |
| IFd1-DsADs-45 | 5'-TCGGGTCATTTADsTAATGTAGGTATGGGCTAGGCDsGCTAGTGGAT-3' | 221 | 127 ± 4 | 0.71 |
| IFd1-AADs-45 | 5'-TCGGGTCATTTAATAATGTAGGTATGGGCTAGGCDsGCTAGTGGAT-3' | 222 | 113 ± 4 | 0.72 |
| IFd1-3A-45 | 5'-TCGGGTCATTTAATAATGTAGGTATGGGCTAGGCAGCTAGTGGAT-3' | 223 | >200 | 0.14 |
| contIF-49 | 5'-AATCGATCGTATCAGTCCACAAT_GGGGTTGGTTGTGTTGGGTGTTGTGT_-3' | 224 | 76 ± 2 c) | 0.09 |
| Random-49 | 5'-CACAATGCTAGAGCATTGCGTAGAAGCTTGATATGTTGCTGGCCCGGAC-3' | 225 | — | 0.06 |
| contIF-26 | 5'-_GGGGTTGGTTGTGTTGGGTGTTGTGT_-3' | 226 | 14 ± 1 c) | 0.36 |
| Random-26 | 5'-GGGTGTGGTGTGTGTGTGTGTTGT-3' | 227 | — | 0.09 |

Sequences of anti-IFN-γ aptamer (IFd1-3Ds-49) and its variants and analysis results of IFN-γ-binding ability of each DNA fragment determined by SPR
a) The sequence of contIF is indicated in underlined italic.
b) Bound = [Resonance units after 930 seconds from the start of protein injection]/[Resonance units of the immobilized DNA] × [Molecular weight of the immobilized DNA]/[Molecular weight of IFN-γ].

SPR assay conditions: flow rate: 20 μl/min, assay temperature: 25° C., injection time of IFN-γ (150 nM): 480 sec, and monitoring time of dissociation: 480 sec. Assay buffer: 1 mM $KH_2PO_4$, 3 mM $Na_2HPO_4$, and 205 mM NaCl, pH 7.4.

The sensorgrams are shown in FIG. 22. The dissociation constants were calculated by global fitting.

c) Nonspecific adsorption was confirmed from these dissociation constants. Thus, Rmax was determined by local fitting, and the other values were calculated by global fitting.

As a result of examining binding to the target protein, a 45-mer variant truncated at the 5'-terminal primer region (IFd1-3Ds-45; SEQ ID NO: 215) had a Kd value of 15 nM (FIGS. 21B and 22). This result indicates that Stem-1 is not essential for the IFN-γ-binding activity of IFd1-3Ds-49 shown in FIG. 20B. The binding analysis results about variants (IFd1-A2Ds-45; SEQ ID NO: 219, IFd1-2DsA-45; SEQ ID NO: 220, IFd1-DsADs-45; SEQ ID NO: 221, IFd1-2ADs-45; SEQ ID NO: 222, and IFd1-3A-45; SEQ ID NO: 223) derived from this 45-mer DNA fragment by the replacement of the Ds base with A revealed that in IFd1-3Ds-45, two Ds bases, i.e., Ds29 and Ds40, are strongly involved in the binding. These results, however, also revealed that any one of these Ds bases Ds29 or Ds40 suffices for the binding. On the other hand, Ds18 was found not essential for the binding. Although structural information is unknown about IFd1-3Ds-49 except for Stem-1 and Stem-2, four G-tracts appear in highly conservative regions, suggesting the possible formation of a G-quartet structure. The G-quartet structure is an important motif for various existing DNA aptamers or protein interactions. This suggested that the introduction of the Ds base can also enhance the diversity of specific motifs such as a G-quartet structure.

All publications, patents, and patent applications cited herein are incorporated herein by reference in their entirety.

The invention claimed is:

1. A transcribable or replicable nucleic acid aptamer comprising:
   natural nucleotides and
   non-natural nucleotides having an artificial base-pairable artificial base,
   wherein the artificial base is selected from the group consisting of 7-(2-thienyl)-3H-imidazo[4,5-b]pyridin-3-yl, 2-nitropyrrol-1-yl, and 2-formyl-1H-pyrrol-1-yl, and wherein the nucleic acid aptamer is directed against interferon γ as a target substance,
      wherein the nucleic acid aptamer comprises any one nucleotide sequence selected from the group consisting of SEQ ID NOs: 167 to 174 (provided that "n" in the sequences represents 7-(2-thienyl)-3H-imidazo[4,5-b]pyridin-3-yl), 186, 188, 190, 192, 194, 214 to 222, and 279 to 328.

2. The nucleic acid aptamer according to claim 1, wherein the artificial base includes an artificial base-pairable derivative of the artificial base.

3. The nucleic acid aptamer according to claim 1, wherein the content of the non-natural nucleotide is 20% or less of the total number of nucleotides.

4. The nucleic acid aptamer according to claim 1, wherein the nucleic acid is a DNA or an RNA.

5. The nucleic acid aptamer according to claim 1, wherein the nucleic acid aptamer consists of any one nucleotide sequence according to claim 1 that is 5' flanked by the nucleotide sequence represented by SEQ ID NO: 1 and 3' flanked by the nucleotide sequence represented by SEQ ID NO: 2.

6. A pharmaceutical composition which comprises a nucleic acid aptamer according to claim 1 as an active ingredient and functionally inhibits a target substance of the nucleic acid aptamer.

7. A pharmaceutical composition for functional inhibition of interferon γ, comprising a nucleic acid aptamer according to claim 1 as an active ingredient.

* * * * *

SEQUENCE LISTING

<160> NUMBER OF SEQ ID NOS: 337

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ctgtcaatcg atcgtatcag tccac                           25

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
gcatgactcg aacggattag tgactac                                          27

<210> SEQ ID NO 3
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (28)..(40)
<223> OTHER INFORMATION: a, c, g, or t
<220> FEATURE:
<221> NAME/KEY: modified_base
<222> LOCATION: (41)..(41)
<223> OTHER INFORMATION: Ds(7-(2-thienyl)imidazo[4,5-b]pyridine)
<220> FEATURE:
<221> NAME/KEY: modified_base
<222> LOCATION: (42)..(70)
<223> OTHER INFORMATION: a, c, g, or t

<400> SEQUENCE: 3
ctgtcaatcg atcgtatcag tccacaannn nnnnnnnnnn nnnnnnnnnn nnnnnnnnnn      60
nnnnnnnnnn gcatgactcg aacggattag tgactac                              97

<210> SEQ ID NO 4
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (28)..(55)
<223> OTHER INFORMATION: a, c, g, or t
<220> FEATURE:
<221> NAME/KEY: modified_base
<222> LOCATION: (56)..(56)
<223> OTHER INFORMATION: Ds(7-(2-thienyl)imidazo[4,5-b]pyridine)
<220> FEATURE:
<221> NAME/KEY: modified_base
<222> LOCATION: (57)..(70)
<223> OTHER INFORMATION: a, c, g, or t

<400> SEQUENCE: 4
ctgtcaatcg atcgtatcag tccacatnnn nnnnnnnnnn nnnnnnnnnn nnnnnnnnnn      60
nnnnnnnnnn gcatgactcg aacggattag tgactac                              97

<210> SEQ ID NO 5
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (28)..(43)
<223> OTHER INFORMATION: a, c, g, or t
<220> FEATURE:

```
<221> NAME/KEY: modified_base
<222> LOCATION: (44)..(44)
<223> OTHER INFORMATION: Ds(7-(2-thienyl)imidazo[4,5-b]pyridine)
<220> FEATURE:
<221> NAME/KEY: modified_base
<222> LOCATION: (45)..(59)
<223> OTHER INFORMATION: a, c, g, or t
<220> FEATURE:
<221> NAME/KEY: modified_base
<222> LOCATION: (60)..(60)
<223> OTHER INFORMATION: Ds(7-(2-thienyl)imidazo[4,5-b]pyridine)
<220> FEATURE:
<221> NAME/KEY: modified_base
<222> LOCATION: (61)..(70)
<223> OTHER INFORMATION: a, c, g, or t

<400> SEQUENCE: 5
ctgtcaatcg atcgtatcag tccacagnnn nnnnnnnnn nnnnnnnnn nnnnnnnnn      60 nnnnnnnnnn gcatgactcg aacggattag tgactac                            97

<210> SEQ ID NO 6
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(37)
<223> OTHER INFORMATION: a, c, g, or t
<220> FEATURE:
<221> NAME/KEY: modified_base
<222> LOCATION: (38)..(38)
<223> OTHER INFORMATION: Ds(7-(2-thienyl)imidazo[4,5-b]pyridine)
<220> FEATURE:
<221> NAME/KEY: modified_base
<222> LOCATION: (39)..(53)
<223> OTHER INFORMATION: a, c, g, or t
<220> FEATURE:
<221> NAME/KEY: modified_base
<222> LOCATION: (54)..(54)
<223> OTHER INFORMATION: Ds(7-(2-thienyl)imidazo[4,5-b]pyridine)
<220> FEATURE:
<221> NAME/KEY: modified_base
<222> LOCATION: (55)..(70)
<223> OTHER INFORMATION: a, c, g, or t

<400> SEQUENCE: 6
ctgtcaatcg atcgtatcag tccactannn nnnnnnnnn nnnnnnnnn nnnnnnnnn      60 nnnnnnnnnn gcatgactcg aacggattag tgactac                            97

<210> SEQ ID NO 7
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(37)
<223> OTHER INFORMATION: a, c, g, or t
<220> FEATURE:
<221> NAME/KEY: modified_base
<222> LOCATION: (38)..(38)
<223> OTHER INFORMATION: Ds(7-(2-thienyl)imidazo[4,5-b]pyridine)
<220> FEATURE:
<221> NAME/KEY: modified_base
<222> LOCATION: (39)..(45)
<223> OTHER INFORMATION: a, c, g, or t
<220> FEATURE:
<221> NAME/KEY: modified_base
```

<222> LOCATION: (46)..(46)
<223> OTHER INFORMATION: Ds(7-(2-thienyl)imidazo[4,5-b]pyridine)
<220> FEATURE:
<221> NAME/KEY: modified_base
<222> LOCATION: (47)..(70)
<223> OTHER INFORMATION: a, c, g, or t

<400> SEQUENCE: 7
ctgtcaatcg atcgtatcag tccacttnnn nnnnnnnnn nnnnnnnnnn nnnnnnnnn    60 nnnnnnnnnn gcatgactcg aacggattag tgactac                          97

<210> SEQ ID NO 8
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(51)
<223> OTHER INFORMATION: a, c, g, or t
<220> FEATURE:
<221> NAME/KEY: modified_base
<222> LOCATION: (52)..(52)
<223> OTHER INFORMATION: Ds(7-(2-thienyl)imidazo[4,5-b]pyridine)
<220> FEATURE:
<221> NAME/KEY: modified_base
<222> LOCATION: (53)..(59)
<223> OTHER INFORMATION: a, c, g, or t
<220> FEATURE:
<221> NAME/KEY: modified_base
<222> LOCATION: (60)..(60)
<223> OTHER INFORMATION: Ds(7-(2-thienyl)imidazo[4,5-b]pyridine)
<220> FEATURE:
<221> NAME/KEY: modified_base
<222> LOCATION: (61)..(70)
<223> OTHER INFORMATION: a, c, g, or t

<400> SEQUENCE: 8
ctgtcaatcg atcgtatcag tccactgnnn nnnnnnnnn nnnnnnnnnn nnnnnnnnn    60 nnnnnnnnnn gcatgactcg aacggattag tgactac                          97

<210> SEQ ID NO 9
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(37)
<223> OTHER INFORMATION: a, c, g, or t
<220> FEATURE:
<221> NAME/KEY: modified_base
<222> LOCATION: (38)..(38)
<223> OTHER INFORMATION: Ds(7-(2-thienyl)imidazo[4,5-b]pyridine)
<220> FEATURE:
<221> NAME/KEY: modified_base
<222> LOCATION: (39)..(48)
<223> OTHER INFORMATION: a, c, g, or t
<220> FEATURE:
<221> NAME/KEY: modified_base
<222> LOCATION: (49)..(49)
<223> OTHER INFORMATION: Ds(7-(2-thienyl)imidazo[4,5-b]pyridine)
<220> FEATURE:
<221> NAME/KEY: modified_base
<222> LOCATION: (50)..(59)
<223> OTHER INFORMATION: a, c, g, or t
<220> FEATURE:
<221> NAME/KEY: modified_base
<222> LOCATION: (60)..(60)

<223> OTHER INFORMATION: Ds(7-(2-thienyl)imidazo[4,5-b]pyridine)
<220> FEATURE:
<221> NAME/KEY: modified_base
<222> LOCATION: (61)..(70)
<223> OTHER INFORMATION: a, c, g, or t

<400> SEQUENCE: 9
ctgtcaatcg atcgtatcag tccactcnnn nnnnnnnnn nnnnnnnnn nnnnnnnnn    60 nnnnnnnnnn gcatgactcg aacggattag tgactac                          97

<210> SEQ ID NO 10
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(45)
<223> OTHER INFORMATION: a, c, g, or t
<220> FEATURE:
<221> NAME/KEY: modified_base
<222> LOCATION: (46)..(46)
<223> OTHER INFORMATION: Ds(7-(2-thienyl)imidazo[4,5-b]pyridine)
<220> FEATURE:
<221> NAME/KEY: modified_base
<222> LOCATION: (47)..(55)
<223> OTHER INFORMATION: a, c, g, or t
<220> FEATURE:
<221> NAME/KEY: modified_base
<222> LOCATION: (56)..(56)
<223> OTHER INFORMATION: Ds(7-(2-thienyl)imidazo[4,5-b]pyridine)
<220> FEATURE:
<221> NAME/KEY: modified_base
<222> LOCATION: (57)..(62)
<223> OTHER INFORMATION: a, c, g, or t
<220> FEATURE:
<221> NAME/KEY: modified_base
<222> LOCATION: (63)..(63)
<223> OTHER INFORMATION: Ds(7-(2-thienyl)imidazo[4,5-b]pyridine)
<220> FEATURE:
<221> NAME/KEY: modified_base
<222> LOCATION: (64)..(70)
<223> OTHER INFORMATION: a, c, g, or t

<400> SEQUENCE: 10
ctgtcaatcg atcgtatcag tccacgannn nnnnnnnnn nnnnnnnnn nnnnnnnnn    60 nnnnnnnnnn gcatgactcg aacggattag tgactac                          97

<210> SEQ ID NO 11
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(34)
<223> OTHER INFORMATION: a, c, g, or t
<220> FEATURE:
<221> NAME/KEY: modified_base
<222> LOCATION: (35)..(35)
<223> OTHER INFORMATION: Ds(7-(2-thienyl)imidazo[4,5-b]pyridine)
<220> FEATURE:
<221> NAME/KEY: modified_base
<222> LOCATION: (36)..(41)
<223> OTHER INFORMATION: a, c, g, or t
<220> FEATURE:
<221> NAME/KEY: modified_base
<222> LOCATION: (42)..(42)
<223> OTHER INFORMATION: Ds(7-(2-thienyl)imidazo[4,5-b]pyridine)

```
<220> FEATURE:
<221> NAME/KEY: modified_base
<222> LOCATION: (43)..(51)
<223> OTHER INFORMATION: a, c, g, or t
<220> FEATURE:
<221> NAME/KEY: modified_base
<222> LOCATION: (52)..(52)
<223> OTHER INFORMATION: Ds(7-(2-thienyl)imidazo[4,5-b]pyridine)
<220> FEATURE:
<221> NAME/KEY: modified_base
<222> LOCATION: (53)..(70)
<223> OTHER INFORMATION: a, c, g, or t

<400> SEQUENCE: 11
ctgtcaatcg atcgtatcag tccacgtnnn nnnnnnnnn nnnnnnnnnn nnnnnnnnnn      60
nnnnnnnnnn gcatgactcg aacggattag tgactac                              97

<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(38)
<223> OTHER INFORMATION: a, c, g, or t
<220> FEATURE:
<221> NAME/KEY: modified_base
<222> LOCATION: (39)..(39)
<223> OTHER INFORMATION: Ds(7-(2-thienyl)imidazo[4,5-b]pyridine)
<220> FEATURE:
<221> NAME/KEY: modified_base
<222> LOCATION: (40)..(48)
<223> OTHER INFORMATION: a, c, g, or t
<220> FEATURE:
<221> NAME/KEY: modified_base
<222> LOCATION: (49)..(49)
<223> OTHER INFORMATION: Ds(7-(2-thienyl)imidazo[4,5-b]pyridine)
<220> FEATURE:
<221> NAME/KEY: modified_base
<222> LOCATION: (50)..(62)
<223> OTHER INFORMATION: a, c, g, or t
<220> FEATURE:
<221> NAME/KEY: modified_base
<222> LOCATION: (63)..(63)
<223> OTHER INFORMATION: Ds(7-(2-thienyl)imidazo[4,5-b]pyridine)
<220> FEATURE:
<221> NAME/KEY: modified_base
<222> LOCATION: (64)..(70)
<223> OTHER INFORMATION: a, c, g, or t

<400> SEQUENCE: 12
ctgtcaatcg atcgtatcag tccaccannn nnnnnnnnn nnnnnnnnnn nnnnnnnnnn      60
nnnnnnnnnn gcatgactcg aacggattag tgactac                              97

<210> SEQ ID NO 13
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(38)
<223> OTHER INFORMATION: a, c, g, or t
<220> FEATURE:
<221> NAME/KEY: modified_base
<222> LOCATION: (39)..(39)
<223> OTHER INFORMATION: Ds(7-(2-thienyl)imidazo[4,5-b]pyridine)
<220> FEATURE:
```

<221> NAME/KEY: modified_base
<222> LOCATION: (40)..(52)
<223> OTHER INFORMATION: a, c, g, or t
<220> FEATURE:
<221> NAME/KEY: modified_base
<222> LOCATION: (53)..(53)
<223> OTHER INFORMATION: Ds(7-(2-thienyl)imidazo[4,5-b]pyridine)
<220> FEATURE:
<221> NAME/KEY: modified_base
<222> LOCATION: (54)..(62)
<223> OTHER INFORMATION: a, c, g, or t
<220> FEATURE:
<221> NAME/KEY: modified_base
<222> LOCATION: (63)..(63)
<223> OTHER INFORMATION: Ds(7-(2-thienyl)imidazo[4,5-b]pyridine)
<220> FEATURE:
<221> NAME/KEY: modified_base
<222> LOCATION: (64)..(70)
<223> OTHER INFORMATION: a, c, g, or t

<400> SEQUENCE: 13
ctgtcaatcg atcgtatcag tccacctnnn nnnnnnnnn nnnnnnnnnn nnnnnnnnnn    60
nnnnnnnnnn gcatgactcg aacggattag tgactac                            97

<210> SEQ ID NO 14
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(37)
<223> OTHER INFORMATION: a, c, g, or t
<220> FEATURE:
<221> NAME/KEY: modified_base
<222> LOCATION: (38)..(38)
<223> OTHER INFORMATION: Ds(7-(2-thienyl)imidazo[4,5-b]pyridine)
<220> FEATURE:
<221> NAME/KEY: modified_base
<222> LOCATION: (39)..(54)
<223> OTHER INFORMATION: a, c, g, or t
<220> FEATURE:
<221> NAME/KEY: modified_base
<222> LOCATION: (55)..(55)
<223> OTHER INFORMATION: Ds(7-(2-thienyl)imidazo[4,5-b]pyridine)
<220> FEATURE:
<221> NAME/KEY: modified_base
<222> LOCATION: (56)..(61)
<223> OTHER INFORMATION: a, c, g, or t
<220> FEATURE:
<221> NAME/KEY: modified_base
<222> LOCATION: (62)..(62)
<223> OTHER INFORMATION: Ds(7-(2-thienyl)imidazo[4,5-b]pyridine)
<220> FEATURE:
<221> NAME/KEY: modified_base
<222> LOCATION: (63)..(71)
<223> OTHER INFORMATION: a, c, g, or t

<400> SEQUENCE: 14
ctgtcaatcg atcgtatcag tccaccagnn nnnnnnnnn nnnnnnnnnn nnnnnnnnnn     60
nnnnnnnnnn ngcatgactc gaacggatta gtgactac                            98

<210> SEQ ID NO 15
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (29)..(37)
<223> OTHER INFORMATION: a, c, g, or t
<220> FEATURE:
<221> NAME/KEY: modified_base
<222> LOCATION: (38)..(38)
<223> OTHER INFORMATION: Ds(7-(2-thienyl)imidazo[4,5-b]pyridine)
<220> FEATURE:
<221> NAME/KEY: modified_base
<222> LOCATION: (39)..(44)
<223> OTHER INFORMATION: a, c, g, or t
<220> FEATURE:
<221> NAME/KEY: modified_base
<222> LOCATION: (45)..(45)
<223> OTHER INFORMATION: Ds(7-(2-thienyl)imidazo[4,5-b]pyridine)
<220> FEATURE:
<221> NAME/KEY: modified_base
<222> LOCATION: (46)..(51)
<223> OTHER INFORMATION: a, c, g, or t
<220> FEATURE:
<221> NAME/KEY: modified_base
<222> LOCATION: (52)..(52)
<223> OTHER INFORMATION: Ds(7-(2-thienyl)imidazo[4,5-b]pyridine)
<220> FEATURE:
<221> NAME/KEY: modified_base
<222> LOCATION: (53)..(71)
<223> OTHER INFORMATION: a, c, g, or t

<400> SEQUENCE: 15
ctgtcaatcg atcgtatcag tccaccatnn nnnnnnnnn nnnnnnnnn nnnnnnnnn      60 nnnnnnnnnn ngcatgactc gaacggatta gtgactac                           98

<210> SEQ ID NO 16
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(44)
<223> OTHER INFORMATION: a, c, g, or t
<220> FEATURE:
<221> NAME/KEY: modified_base
<222> LOCATION: (45)..(45)
<223> OTHER INFORMATION: Ds(7-(2-thienyl)imidazo[4,5-b]pyridine)
<220> FEATURE:
<221> NAME/KEY: modified_base
<222> LOCATION: (46)..(51)
<223> OTHER INFORMATION: a, c, g, or t
<220> FEATURE:
<221> NAME/KEY: modified_base
<222> LOCATION: (52)..(52)
<223> OTHER INFORMATION: Ds(7-(2-thienyl)imidazo[4,5-b]pyridine)
<220> FEATURE:
<221> NAME/KEY: modified_base
<222> LOCATION: (53)..(58)
<223> OTHER INFORMATION: a, c, g, or t
<220> FEATURE:
<221> NAME/KEY: modified_base
<222> LOCATION: (59)..(59)
<223> OTHER INFORMATION: Ds(7-(2-thienyl)imidazo[4,5-b]pyridine)
<220> FEATURE:
<221> NAME/KEY: modified_base
<222> LOCATION: (60)..(71)
<223> OTHER INFORMATION: a, c, g, or t

<400> SEQUENCE: 16
ctgtcaatcg atcgtatcag tccactatnn nnnnnnnnn nnnnnnnnn nnnnnnnnn      60 nnnnnnnnnn ngcatgactc gaacggatta gtgactac                           98

<210> SEQ ID NO 17
<211> LENGTH: 98
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(44)
<223> OTHER INFORMATION: a, c, g, or t
<220> FEATURE:
<221> NAME/KEY: modified_base
<222> LOCATION: (45)..(45)
<223> OTHER INFORMATION: Ds(7-(2-thienyl)imidazo[4,5-b]pyridine)
<220> FEATURE:
<221> NAME/KEY: modified_base
<222> LOCATION: (46)..(51)
<223> OTHER INFORMATION: a, c, g, or t
<220> FEATURE:
<221> NAME/KEY: modified_base
<222> LOCATION: (52)..(52)
<223> OTHER INFORMATION: Ds(7-(2-thienyl)imidazo[4,5-b]pyridine)
<220> FEATURE:
<221> NAME/KEY: modified_base
<222> LOCATION: (53)..(61)
<223> OTHER INFORMATION: a, c, g, or t
<220> FEATURE:
<221> NAME/KEY: modified_base
<222> LOCATION: (62)..(62)
<223> OTHER INFORMATION: Ds(7-(2-thienyl)imidazo[4,5-b]pyridine)
<220> FEATURE:
<221> NAME/KEY: modified_base
<222> LOCATION: (63)..(71)
<223> OTHER INFORMATION: a, c, g, or t

<400> SEQUENCE: 17
ctgtcaatcg atcgtatcag tccacttann nnnnnnnnnn nnnnnnnnnn nnnnnnnnn      60 nnnnnnnnnn ngcatgactc gaacggatta gtgactac                             98

<210> SEQ ID NO 18
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(51)
<223> OTHER INFORMATION: a, c, g, or t
<220> FEATURE:
<221> NAME/KEY: modified_base
<222> LOCATION: (52)..(52)
<223> OTHER INFORMATION: Ds(7-(2-thienyl)imidazo[4,5-b]pyridine)
<220> FEATURE:
<221> NAME/KEY: modified_base
<222> LOCATION: (53)..(56)
<223> OTHER INFORMATION: a, c, g, or t
<220> FEATURE:
<221> NAME/KEY: modified_base
<222> LOCATION: (57)..(57)
<223> OTHER INFORMATION: Ds(7-(2-thienyl)imidazo[4,5-b]pyridine)
<220> FEATURE:
<221> NAME/KEY: modified_base
<222> LOCATION: (58)..(71)
<223> OTHER INFORMATION: a, c, g, or t

<400> SEQUENCE: 18
ctgtcaatcg atcgtatcag tccacgctnn nnnnnnnnnn nnnnnnnnnn nnnnnnnnn      60 nnnnnnnnnn ngcatgactc gaacggatta gtgactac                             98

<210> SEQ ID NO 19
<211> LENGTH: 98
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(50)
<223> OTHER INFORMATION: a, c, g, or t
<220> FEATURE:
<221> NAME/KEY: modified_base
<222> LOCATION: (51)..(51)
<223> OTHER INFORMATION: Ds(7-(2-thienyl)imidazo[4,5-b]pyridine)
<220> FEATURE:
<221> NAME/KEY: modified_base
<222> LOCATION: (52)..(56)
<223> OTHER INFORMATION: a, c, g, or t
<220> FEATURE:
<221> NAME/KEY: modified_base
<222> LOCATION: (57)..(57)
<223> OTHER INFORMATION: Ds(7-(2-thienyl)imidazo[4,5-b]pyridine)
<220> FEATURE:
<221> NAME/KEY: modified_base
<222> LOCATION: (58)..(71)
<223> OTHER INFORMATION: a, c, g, or t

<400> SEQUENCE: 19
ctgtcaatcg atcgtatcag tccacccann nnnnnnnnnn nnnnnnnnnn nnnnnnnnnn    60
nnnnnnnnnn ngcatgactc gaacggatta gtgactac                            98

<210> SEQ ID NO 20
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(49)
<223> OTHER INFORMATION: a, c, g, or t
<220> FEATURE:
<221> NAME/KEY: modified_base
<222> LOCATION: (50)..(50)
<223> OTHER INFORMATION: Ds(7-(2-thienyl)imidazo[4,5-b]pyridine)
<220> FEATURE:
<221> NAME/KEY: modified_base
<222> LOCATION: (51)..(56)
<223> OTHER INFORMATION: a, c, g, or t
<220> FEATURE:
<221> NAME/KEY: modified_base
<222> LOCATION: (57)..(57)
<223> OTHER INFORMATION: Ds(7-(2-thienyl)imidazo[4,5-b]pyridine)
<220> FEATURE:
<221> NAME/KEY: modified_base
<222> LOCATION: (58)..(71)
<223> OTHER INFORMATION: a, c, g, or t

<400> SEQUENCE: 20
ctgtcaatcg atcgtatcag tccaccctnn nnnnnnnnn nnnnnnnnnn nnnnnnnnnn     60
nnnnnnnnnn ngcatgactc gaacggatta gtgactac                            98

<210> SEQ ID NO 21
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(48)
<223> OTHER INFORMATION: a, c, g, or t
<220> FEATURE:

```
<221> NAME/KEY: modified_base
<222> LOCATION: (49)..(49)
<223> OTHER INFORMATION: Ds(7-(2-thienyl)imidazo[4,5-b]pyridine)
<220> FEATURE:
<221> NAME/KEY: modified_base
<222> LOCATION: (50)..(56)
<223> OTHER INFORMATION: a, c, g, or t
<220> FEATURE:
<221> NAME/KEY: modified_base
<222> LOCATION: (57)..(57)
<223> OTHER INFORMATION: Ds(7-(2-thienyl)imidazo[4,5-b]pyridine)
<220> FEATURE:
<221> NAME/KEY: modified_base
<222> LOCATION: (58)..(71)
<223> OTHER INFORMATION: a, c, g, or t

<400> SEQUENCE: 21
ctgtcaatcg atcgtatcag tccacggann nnnnnnnnnn nnnnnnnnnn nnnnnnnnnn    60
nnnnnnnnnn ngcatgactc gaacggatta gtgactac                           98

<210> SEQ ID NO 22
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(47)
<223> OTHER INFORMATION: a, c, g, or t
<220> FEATURE:
<221> NAME/KEY: modified_base
<222> LOCATION: (48)..(48)
<223> OTHER INFORMATION: Ds(7-(2-thienyl)imidazo[4,5-b]pyridine)
<220> FEATURE:
<221> NAME/KEY: modified_base
<222> LOCATION: (49)..(56)
<223> OTHER INFORMATION: a, c, g, or t
<220> FEATURE:
<221> NAME/KEY: modified_base
<222> LOCATION: (57)..(57)
<223> OTHER INFORMATION: Ds(7-(2-thienyl)imidazo[4,5-b]pyridine)
<220> FEATURE:
<221> NAME/KEY: modified_base
<222> LOCATION: (58)..(71)
<223> OTHER INFORMATION: a, c, g, or t

<400> SEQUENCE: 22
ctgtcaatcg atcgtatcag tccacggtnn nnnnnnnnnn nnnnnnnnnn nnnnnnnnnn    60
nnnnnnnnnn ngcatgactc gaacggatta gtgactac                           98

<210> SEQ ID NO 23
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(46)
<223> OTHER INFORMATION: a, c, g, or t
<220> FEATURE:
<221> NAME/KEY: modified_base
<222> LOCATION: (47)..(47)
<223> OTHER INFORMATION: Ds(7-(2-thienyl)imidazo[4,5-b]pyridine)
<220> FEATURE:
<221> NAME/KEY: modified_base
<222> LOCATION: (48)..(56)
<223> OTHER INFORMATION: a, c, g, or t
<220> FEATURE:
<221> NAME/KEY: modified_base
```

```
<222> LOCATION: (57)..(57)
<223> OTHER INFORMATION: Ds(7-(2-thienyl)imidazo[4,5-b]pyridine)
<220> FEATURE:
<221> NAME/KEY: modified_base
<222> LOCATION: (58)..(71)
<223> OTHER INFORMATION: a, c, g, or t

<400> SEQUENCE: 23
ctgtcaatcg atcgtatcag tccaccgann nnnnnnnnnn nnnnnnnnnn nnnnnnnnn      60 nnnnnnnnnn ngcatgactc gaacggatta gtgactac                            98

<210> SEQ ID NO 24
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(46)
<223> OTHER INFORMATION: a, c, g, or t
<220> FEATURE:
<221> NAME/KEY: modified_base
<222> LOCATION: (47)..(47)
<223> OTHER INFORMATION: Ds(7-(2-thienyl)imidazo[4,5-b]pyridine)
<220> FEATURE:
<221> NAME/KEY: modified_base
<222> LOCATION: (48)..(57)
<223> OTHER INFORMATION: a, c, g, or t
<220> FEATURE:
<221> NAME/KEY: modified_base
<222> LOCATION: (58)..(58)
<223> OTHER INFORMATION: Ds(7-(2-thienyl)imidazo[4,5-b]pyridine)
<220> FEATURE:
<221> NAME/KEY: modified_base
<222> LOCATION: (59)..(71)
<223> OTHER INFORMATION: a, c, g, or t

<400> SEQUENCE: 24
ctgtcaatcg atcgtatcag tccaccgtnn nnnnnnnnn nnnnnnnnnn nnnnnnnnnn      60
nnnnnnnnnn ngcatgactc gaacggatta gtgactac                            98

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Ds(7-(2-thienyl)imidazo[4,5-b]pyridine)

<400> SEQUENCE: 25
aagtgttctg gagacnctta ggatgtcgcg gagggtgcg gcctt                     45

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Ds(7-(2-thienyl)imidazo[4,5-b]pyridine)

<400> SEQUENCE: 26
```
aaaaatgcga gggtcngtgg cgtaggttcg gaaattttgt tatgt                45

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Ds(7-(2-thienyl)imidazo[4,5-b]pyridine)

<400> SEQUENCE: 27
aaaaatgcgg gggtcngtgg cgtaggttcg gaaattttgt tatgt                45

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Ds(7-(2-thienyl)imidazo[4,5-b]pyridine)

<400> SEQUENCE: 28
atggaattgt ggggccggaa tctgttatgt ntgccaggaa ggagc                45

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Ds(7-(2-thienyl)imidazo[4,5-b]pyridine)

<400> SEQUENCE: 29
atggaaatgt ggggccggaa tctgttatgt ntgccaggaa ggagc                45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Ds(7-(2-thienyl)imidazo[4,5-b]pyridine)

<400> SEQUENCE: 30
atcttgcacg cgggggggttc tggtgtagga ncggagggaa agtgc                45

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (21)..(21)
<223> OTHER INFORMATION: Ds(7-(2-thienyl)imidazo[4,5-b]pyridine)
<220> FEATURE:
<221> NAME/KEY: modified_base
<222> LOCATION: (31)..(31)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 31
gaggaatgtc cagcgctggg nttggagggg ngtcggantg ggctc            45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Ds(7-(2-thienyl)imidazo[4,5-b]pyridine)
<220> FEATURE:
<221> NAME/KEY: modified_base
<222> LOCATION: (31)..(31)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 32
gagggcggct taaacaaggg nttgggggggg ngtcggtngt aaggc            45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Ds(7-(2-thienyl)imidazo[4,5-b]pyridine)
<220> FEATURE:
<221> NAME/KEY: modified_base
<222> LOCATION: (31)..(31)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 33
gatgaagagg gtggcgtccg nacggggggg naggtatnca cgtag            45

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
```

```
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 34
gtctaagtan ggtgggnttg gcggggntgt cggatatact ttgac            45

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Ds(7-(2-thienyl)imidazo[4,5-b]pyridine)
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 35
cacaatattc gggnttggag gggngtcggg tggatagntg gtgct            45

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 36
ggtagggtaa gtaggtattg ccngtcgtag cntggatggc gtgccg           46

<210> SEQ ID NO 37
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 37
cgattcctta tcctaggact tntttccgcg cncacgtgct cagatt           46
```

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 38
cgattccttt tcctaggact tntttccgcg cncacgtgct cagatt                46

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Ds(7-(2-thienyl)imidazo[4,5-b]pyridine)

<400> SEQUENCE: 39
aacgggcggt gggcgncggg cagtattggg tcccgttgtg gggcc                 45

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Ds(7-(2-thienyl)imidazo[4,5-b]pyridine)

<400> SEQUENCE: 40
aaggtctggg ggatancgta gctagggtcg aggtgtcacc ttggg                 45

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Ds(7-(2-thienyl)imidazo[4,5-b]pyridine)

<400> SEQUENCE: 41
atcttcacta taacgtacgt tcgctcatct ntggtggtcg gtgga                 45

<210> SEQ ID NO 42
<211> LENGTH: 45
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Ds(7-(2-thienyl)imidazo[4,5-b]pyridine)
<220> FEATURE:
<221> NAME/KEY: modified_base
<222> LOCATION: (35)..(35)
<223> OTHER INFORMATION: Ds(7-(2-thienyl)imidazo[4,5-b]pyridine)

<400> SEQUENCE: 42
aggcgcgggg gttttgggng caggcaacgg agccngggggg caaca            45

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: Ds(7-(2-thienyl)imidazo[4,5-b]pyridine)
<220> FEATURE:
<221> NAME/KEY: modified_base
<222> LOCATION: (29)..(29)
<223> OTHER INFORMATION: Ds(7-(2-thienyl)imidazo[4,5-b]pyridine)

<400> SEQUENCE: 43
taatgaggca gcngagtccc aggatgana atagcggtgt tgctt               45

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: Ds(7-(2-thienyl)imidazo[4,5-b]pyridine)
<220> FEATURE:
<221> NAME/KEY: modified_base
<222> LOCATION: (21)..(21)
<223> OTHER INFORMATION: Ds(7-(2-thienyl)imidazo[4,5-b]pyridine)

<400> SEQUENCE: 44
ttatattttc cangccagaa ncgggattgg tggggagtcg gcggg              45

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: Ds(7-(2-thienyl)imidazo[4,5-b]pyridine)
<220> FEATURE:
<221> NAME/KEY: modified_base
<222> LOCATION: (35)..(35)
<223> OTHER INFORMATION: Ds(7-(2-thienyl)imidazo[4,5-b]pyridine)

<400> SEQUENCE: 45
tggcgcgggg gttttgggtg caggcancgg agccngggggg caaca            45
```

```
<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: Ds(7-(2-thienyl)imidazo[4,5-b]pyridine)
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
<221> NAME/KEY: modified_base
<222> LOCATION: (35)..(35)
<223> OTHER INFORMATION: Ds(7-(2-thienyl)imidazo[4,5-b]pyridine)

<400> SEQUENCE: 46
tctttcgtag ggnttaggcg gggntgtatc ggtgntgggg agagg            45

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Ds(7-(2-thienyl)imidazo[4,5-b]pyridine)
<220> FEATURE:
<221> NAME/KEY: modified_base
<222> LOCATION: (31)..(31)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 47
gacagattat gtggactcca ntcagaggat ntccccgnat gggcc            45

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Ds(7-(2-thienyl)imidazo[4,5-b]pyridine)
<220> FEATURE:
<221> NAME/KEY: modified_base
<222> LOCATION: (31)..(31)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 48
gagggagcag gtgctaaggg nctggtgggg ngtcggtntc aagca            45

<210> SEQ ID NO 49
<211> LENGTH: 45
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Ds(7-(2-thienyl)imidazo[4,5-b]pyridine)
<220> FEATURE:
<221> NAME/KEY: modified_base
<222> LOCATION: (31)..(31)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 49
gagatggatg gtagtggccg nacgggggggg ntggagangc tggct            45

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Ds(7-(2-thienyl)imidazo[4,5-b]pyridine)
<220> FEATURE:
<221> NAME/KEY: modified_base
<222> LOCATION: (31)..(31)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 50
gaggcagtga tcgctatggg nttggtgggg ngtcggangg ctgtc            45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 51
gtgagtaaan ttagggnttg gagggngtc ggtagtagga tactc            45

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 52
gtatggccan tcagggnttg gcggggngtc ggtagtggtc tagag                45

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 53
gtagagagcn gtggggnttg gaggggngtc gggcgcgacg cagtg                45

<210> SEQ ID NO 54
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 54
gttgttatgn gaggggnttg gtggggngtc ggctagcatc aatgg                45

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
```

```
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 55
gtttatagcn tatgggnttg gggggngtc ggatactcta ccgtg          45

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Ds(7-(2-thienyl)imidazo[4,5-b]pyridine)
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 56
cagcgcaggg gggnttggag gggngtcggc tgctgtgnga tggtg          45

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Ds(7-(2-thienyl)imidazo[4,5-b]pyridine)
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 57
cagattgccg gggnttggag gggngtcggc cagctganta tctgc          45

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Ds(7-(2-thienyl)imidazo[4,5-b]pyridine)
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
```

```
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 58
cataatatta gggnttggag gggngtcggt attctctntg gatgg            45

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Ds(7-(2-thienyl)imidazo[4,5-b]pyridine)
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 59
catgatcatt gggnttggag gggngtcgga agatgcantg gtggc            45

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Ds(7-(2-thienyl)imidazo[4,5-b]pyridine)
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)

<400> SEQUENCE: 60
catggttctg gggnttgggg gggngtcggc tttactanta tggtg            45

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Ds(7-(2-thienyl)imidazo[4,5-b]pyridine)
<220> FEATURE:
<221> NAME/KEY: modified_base
<222> LOCATION: (28)..(28)
<223> OTHER INFORMATION: Ds(7-(2-thienyl)imidazo[4,5-b]pyridine)
<220> FEATURE:
<221> NAME/KEY: modified_base
<222> LOCATION: (38)..(38)
<223> OTHER INFORMATION: Ds(7-(2-thienyl)imidazo[4,5-b]pyridine)
```

<400> SEQUENCE: 61
ctatagttgg tccnagtcgt gtgtgggntt ggagggngt cggga                45

<210> SEQ ID NO 62
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: Ds(7-(2-thienyl)imidazo[4,5-b]pyridine)
<220> FEATURE:
<221> NAME/KEY: modified_base
<222> LOCATION: (30)..(30)
<223> OTHER INFORMATION: Ds(7-(2-thienyl)imidazo[4,5-b]pyridine)
<220> FEATURE:
<221> NAME/KEY: modified_base
<222> LOCATION: (37)..(37)
<223> OTHER INFORMATION: Ds(7-(2-thienyl)imidazo[4,5-b]pyridine)

<400> SEQUENCE: 62
cagcgggggg tangggtgta gggtgcggan tggaggnacg ttaggc              46

<210> SEQ ID NO 63
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)
<220> FEATURE:
<221> NAME/KEY: modified_base
<222> LOCATION: (37)..(37)
<223> OTHER INFORMATION: Ds(7-(2-thienyl)imidazo[4,5-b]pyridine)

<400> SEQUENCE: 63
ttatattttc catgccagan tcggggnttg gtgggngtc ggcggg               46

<210> SEQ ID NO 64
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)
<220> FEATURE:
<221> NAME/KEY: modified_base
<222> LOCATION: (37)..(37)
<223> OTHER INFORMATION: Ds(7-(2-thienyl)imidazo[4,5-b]pyridine)

<400> SEQUENCE: 64
ttaaaacgtc gagtcagacn ggagggnttg gaggggngtc ggggcg              46

```
<210> SEQ ID NO 65
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)
<220> FEATURE:
<221> NAME/KEY: modified_base
<222> LOCATION: (37)..(37)
<223> OTHER INFORMATION: Ds(7-(2-thienyl)imidazo[4,5-b]pyridine)

<400> SEQUENCE: 65
ttatggctgc gggatgtgcn atggggnttg gggggngcc ggctat                46

<210> SEQ ID NO 66
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 66
cctgtgagct ctggtatggt ctggngtaag gngatagcgc acacaa             46

<210> SEQ ID NO 67
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 67
ggaggctgcg ctattttcgc ctangccgcg gngggtgcg gccagg              46

<210> SEQ ID NO 68
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: Ds(7-(2-thienyl)imidazo[4,5-b]pyridine)
```

```
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 68
ggaggtcgct ggtagtggct tggngtatgg gntgcaggcc ggcgcg                46

<210> SEQ ID NO 69
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 69
ggtggggagc ggccagctga ttnacgttaa gnttaattag cgcggg                46

<210> SEQ ID NO 70
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 70
cgaggagtct gctgcgcggg gnttggaggg gngccggcga aaagca                46

<210> SEQ ID NO 71
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 71
cgatatggta gggttgtagg gnttggtggg gngccggtgg aaaccc                46

<210> SEQ ID NO 72
<211> LENGTH: 46
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (22)..(22)
<223> OTHER INFORMATION: Ds(7-(2-thienyl)imidazo[4,5-b]pyridine)
<220> FEATURE:
<221> NAME/KEY: modified_base
<222> LOCATION: (32)..(32)
<223> OTHER INFORMATION: Ds(7-(2-thienyl)imidazo[4,5-b]pyridine)

<400> SEQUENCE: 72
cgagtttggt tagtggtctg gnttagggag ancctcggtg aaatga          46

<210> SEQ ID NO 73
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: Ds(7-(2-thienyl)imidazo[4,5-b]pyridine)
<220> FEATURE:
<221> NAME/KEY: modified_base
<222> LOCATION: (33)..(33)
<223> OTHER INFORMATION: Ds(7-(2-thienyl)imidazo[4,5-b]pyridine)

<400> SEQUENCE: 73
cgtcggccgg aatctggcag tntgccgcga ccnttcacct gtaagt          46

<210> SEQ ID NO 74
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tctgtcaatc gatcgtatca gtccacgagg aatgtccagc gctgggattg gaggggtgtc     60
ggaatgggct cgcatgactc gaacggatta gtgactac                             98

<210> SEQ ID NO 75
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tctgtcaatc gatcgtatca gtccacgtct aagtaaggtg ggtttggcgg ggatgtcgga     60
tatactttga cgcatgactc gaacggatta gtgactac                             98

<210> SEQ ID NO 76
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tctgtcaatc gatcgtatca gtccacgtct aagtagggtg gggttggcgg gggtgtcgga     60
tatactttga cgcatgactc gaacggatta gtgactac                             98

<210> SEQ ID NO 77
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tctgtcaatc gatcgtatca gtccacggta gggtaagtag gtattgccag tcgtagcatg      60
gatggcgtgc cggcatgact cgaacggatt agtgactac                            99

<210> SEQ ID NO 78
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tctgtcaatc gatcgtatca gtccaccgat tccttatcct aggactttt tccgcgcaca      60 cgtgctcaga ttgcatgact cgaacggatt agtgactac                            99

<210> SEQ ID NO 79
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tataccagtc tattcaattg cactctgtgg gggtggacgg gccgggtaga tagtatgtgc      60
aatc                                                                  64

<210> SEQ ID NO 80
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 80
gtctaagtan ggtgggnttg gaggggntgt cggatgaact ttgac                     45

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 81
gtataagtan ggtgggnttg gcggggntgt cggatatact tgtac            45

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 82
gtcaaagaan tgtgggnttg gagggntgt cggatatact ttgac            45

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 83
gactaagtan tgtgggnttg gagggntgt cggatatgct ttgtc            45

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
```

```
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 84
gtcaaagtan ggtgggnttg gggggntgt cggagatact ttggg                45

<210> SEQ ID NO 85
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 85
gtcgaaggan tgtgggnttg gagggntgt cggatgtact ttgac                45

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 86
ggttaagtan tgtgggnttg gggggntgt cggagatact ttgaa                45

<210> SEQ ID NO 87
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
```

```
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 87
ggctaagtan tgtgggnttg gagggngtgt cggaggtact tagac        45

<210> SEQ ID NO 88
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 88
gttaaagtan catgggnttg gagggngtgt cggatatact ttgat        45

<210> SEQ ID NO 89
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 89
gtctgagtan ggtgggnttg gggggngtgt cggatacact ctgcg        45

<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)
```

<400> SEQUENCE: 90
gtctaaatan tgtgggnttg gaggggntgt cggaggtatt ttgac        45

<210> SEQ ID NO 91
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 91
gtctaagtan tgtgggnttg gaggggncgt cggaagtact ttgat        45

<210> SEQ ID NO 92
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 92
ggcagagtan gttgggnttg gaggggntgt cggatttact atgac        45

<210> SEQ ID NO 93
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 93
gtcgaagtan tatgggnttg gaggggntgt cggaagtact ttgat        45

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 94
gctttagtan gggggggnttg gagggggntgt cgggtctact ttggc            45

<210> SEQ ID NO 95
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 95
gtattagtan tgggggnttg gtgggggntgt cggagatact atgtc            45

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 96
ggcggagtan tgagggnttg gagggggntgt cggttatact gggac            45

<210> SEQ ID NO 97
<211> LENGTH: 45

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 97
gcctaaatan tatgggnttg gagggggntgt cggaggtagt ttggc            45

<210> SEQ ID NO 98
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 98
gtcaaagtan caagggnttg gagggggntgt cggtaattct ttgag            45

<210> SEQ ID NO 99
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 99
gtctaattan tatgggnttg gggggggntgt cggaaataat gggat            45

<210> SEQ ID NO 100
<211> LENGTH: 45
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 100
atgggagtan tatgggnttg gcggggntgt cggagatact tcaat            45

<210> SEQ ID NO 101
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 101
ttcgaaggan catgggnttg gcggggntgt cggagagcct tagaa            45

<210> SEQ ID NO 102
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 102
gcggaggtan tatgggnttg gggggntgt cggaaatact tatgc             45

<210> SEQ ID NO 103
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
```

<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 103
atgcaagaan ttagggnttg gagggggntgt cggttatatt ttaaa                45

<210> SEQ ID NO 104
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ds(7-(2-thienyl)imidazo[4,5-b]pyridine)
<220> FEATURE:
<221> NAME/KEY: modified_base
<222> LOCATION: (17)..(17)
<223> OTHER INFORMATION: Ds(7-(2-thienyl)imidazo[4,5-b]pyridine)
<220> FEATURE:
<221> NAME/KEY: modified_base
<222> LOCATION: (27)..(27)
<223> OTHER INFORMATION: Ds(7-(2-thienyl)imidazo[4,5-b]pyridine)

<400> SEQUENCE: 104
gtgttaatan tatgggnttg gggggggntgt cggaaatgtt aagcc                45

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Ds(7-(2-thienyl)imidazo[4,5-b]pyridine)
<220> FEATURE:
<221> NAME/KEY: modified_base
<222> LOCATION: (9)..(9)
<223> OTHER INFORMATION: a, c, g, or t
<220> FEATURE:
<221> NAME/KEY: modified_base
<222> LOCATION: (14)..(14)
<223> OTHER INFORMATION: Ds(7-(2-thienyl)imidazo[4,5-b]pyridine)

<400> SEQUENCE: 105
gggnttggng gggntgtcgg                                             20

<210> SEQ ID NO 106
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: Ds(7-(2-thienyl)imidazo[4,5-b]pyridine)
<220> FEATURE:
<221> NAME/KEY: modified_base
<222> LOCATION: (18)..(18)

```
<223> OTHER INFORMATION: Ds(7-(2-thienyl)imidazo[4,5-b]pyridine)
<220> FEATURE:
<221> NAME/KEY: modified_base
<222> LOCATION: (28)..(28)
<223> OTHER INFORMATION: Ds(7-(2-thienyl)imidazo[4,5-b]pyridine)

<400> SEQUENCE: 106
tgtctaagta nggtgggntt ggcggggntg tcgga                              35

<210> SEQ ID NO 107
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Ds(7-(2-thienyl)imidazo[4,5-b]pyridine)
<220> FEATURE:
<221> NAME/KEY: modified_base
<222> LOCATION: (28)..(28)
<223> OTHER INFORMATION: Ds(7-(2-thienyl)imidazo[4,5-b]pyridine)

<400> SEQUENCE: 107
tgtctaagta aggtgggntt ggcggggntg tcgga                              35

<210> SEQ ID NO 108
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: Ds(7-(2-thienyl)imidazo[4,5-b]pyridine)
<220> FEATURE:
<221> NAME/KEY: modified_base
<222> LOCATION: (28)..(28)
<223> OTHER INFORMATION: Ds(7-(2-thienyl)imidazo[4,5-b]pyridine)

<400> SEQUENCE: 108
tgtctaagta nggtgggatt ggcggggntg tcgga                              35

<210> SEQ ID NO 109
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: Ds(7-(2-thienyl)imidazo[4,5-b]pyridine)
<220> FEATURE:
<221> NAME/KEY: modified_base
<222> LOCATION: (18)..(18)
<223> OTHER INFORMATION: Ds(7-(2-thienyl)imidazo[4,5-b]pyridine)

<400> SEQUENCE: 109
tgtctaagta nggtgggntt ggcggggatg tcgga                              35

<210> SEQ ID NO 110
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 110
tgtctaagta aggtgggatt ggcggggatg tcgga                              35

<210> SEQ ID NO 111
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: Ds(7-(2-thienyl)imidazo[4,5-b]pyridine)
<220> FEATURE:
<221> NAME/KEY: modified_base
<222> LOCATION: (18)..(18)
<223> OTHER INFORMATION: Ds(7-(2-thienyl)imidazo[4,5-b]pyridine)
<220> FEATURE:
<221> NAME/KEY: modified_base
<222> LOCATION: (28)..(28)
<223> OTHER INFORMATION: Ds(7-(2-thienyl)imidazo[4,5-b]pyridine)

<400> SEQUENCE: 111
tgtctaagta ntgtgggntt ggaggggntg tcgga                              35

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
acgcatgaac aaacttgctt g                                             21

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acaatgaaac ttctgcgtac tcc                                           23

<210> SEQ ID NO 114
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(66)
<223> OTHER INFORMATION: a, c, g, t, or Ds(7-(2-thienyl)imidazo
      [4,5-b]pyridine)

<400> SEQUENCE: 114
acgcatgaac aaacttgctt gnnnnnnnnn nnnnnnnnnn nnnnnnnnnn nnnnnnnnn     60 nnnnnnggag tacgcagaag tttcattgt                                     89
```

```
<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgaatctgaa atccaatgtt ccca                                          24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
taccagccac gttgcggttc caag                                          24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
acctcattgt tttaaccctt caag                                          24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gtactctgta agtatgttca caag                                          24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gtaccaacac attatcaact caag                                          24

<210> SEQ ID NO 120
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
acgcatgaac aaacttgctt gcgtacgcgg aggggggcgg cctgggaaca ttggatttca   60
gattcaggag tacgcagaag tttcattgt                                     89
```

<210> SEQ ID NO 121
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
acgcatgaac aaacttgctt gcgtacgcgg tgggggcgg cctgggaaca ttggatttca      60
gattcaggag tacgcagaag tttcattgt                                       89

<210> SEQ ID NO 122
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
acgcatgaac aaacttgctt gcgtacgcgg tgggggcgg cctgggaaca ttggatttca      60
gattccggag tacgcagaag tttcattgt                                       89

<210> SEQ ID NO 123
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
acgcatgaac aaacttgctt ggaaccgcat cgtggctggt agtggccgaa tgggggtgg      60 tgagcgggag tacgcagaag tttcattgt                                       89

<210> SEQ ID NO 124
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
acgcatgaac aaacttgctt ggaaccgcaa cgtggctggt agcggccgaa tgggggtgg      60 tgagcgggag tacgcagaag tttcattgt                                       89

<210> SEQ ID NO 125
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
acgcatgaac aaacttgctt ggaaccgcaa cgtggctggt agtggccgaa tgggggtgg      60 tgagcgggag tacgcagaag tttcattgt                                       89

<210> SEQ ID NO 126
<211> LENGTH: 89
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 126
acgcatgaac aaacttgctt gaagggttaa acaatgagg tacgcggggg ggtgggtgta      60
ggtgtcggag tacgcagaag tttcattgt                                       89

<210> SEQ ID NO 127
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
acgcatgaac aaacttgctt gaagggttaa aactatgagg tacgcggggg ggtgggtgta     60
ggtgtcggag tacgcagaag tttcattgt                                       89

<210> SEQ ID NO 128
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
acgcatgaac aaacttgctt gaagggttga aactatgagg tacgcggggg ggtgggtgta     60
ggtgtcggag tacgcagaag tttcattgt                                       89

<210> SEQ ID NO 129
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
acgcatgaac aaacttgctt ggagggttaa aactatgagg tacgcggggg ggtgggtgta     60
ggtgtcggag tacgcagaag tttcattgt                                       89

<210> SEQ ID NO 130
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
acgcatgaac aaacttgctt gtgaacatgc ttactgagta cgcgggggtc ggtgggtgta     60
ggtggcggag tacgcagaag tttcattgt                                       89

<210> SEQ ID NO 131
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 131
acgcatgaac aaacttgctt gtgaacatgc ttactgagta cgcggggggtc ggagggtgta     60 ggtggcggag tacgcagaag tttcattgt                                        89

<210> SEQ ID NO 132
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
acgcatgaac aaacttgctt gtgaacatgc ttacagagta cgcggggggtc ggtgggtgta     60 ggtggcggag tacgcagaag tttcattgt                                        89

<210> SEQ ID NO 133
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
acgcatgaac aaacttgctt gtgaacatgc ttacagagta cgcggggggtc ggagggtgta     60 ggtggcggag tacgcagaag tttcattgt                                        89

<210> SEQ ID NO 134
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
acgcatgaac aaacttgctt gtgaacattc ttacagagta cgcggggggtc ggagggtgta     60 ggtggcagag tacgcagaag tttcattgt                                        89

<210> SEQ ID NO 135
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
acgcatgaac aaacttgctt gagttgataa tgtgttggta cgcgggggggg ttgaggtgta     60 ggtttcggag tacgcagaag tttcattgt                                        89

<210> SEQ ID NO 136
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
acgcatgaac aaacttgctt gagttgatta tgtgttggta cgcgggggggg tggaggtgta     60

```
ggtttcggag tacgcagaag tttcattgt                                      89
```

<210> SEQ ID NO 137
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

```
acgcatgaac aaacttgctt gatactaaga taaccgcggg ggggggagg tgtagtcgga     60 gggatcggag tacgcagaag tttcattgt                                      89
```

<210> SEQ ID NO 138
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138

```
acgcatgaac aaacttgctt gcatgttgac ttcaaaagta cgcgggggtt tcgggctgca    60
ggtggcggag tacgcagaag tttcattgt                                      89
```

<210> SEQ ID NO 139
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139

```
acgcatgaac aaacttgctt gcatgttgac ttcaaaagta cgcgggggg tggaggtgta     60 ggtttcggag tacgcagaag tttcattgt                                      89
```

<210> SEQ ID NO 140
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140

```
acgcatgaac aaacttgctt gtaactacat gatacactag tacgcggggg gtggggtgt     60 aggtgcggag tacgcagaag tttcattgt                                      89
```

<210> SEQ ID NO 141
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141

```
acgcatgaac aaacttgctt gcaatcggtg aacttaagtt acgcggggt atagggtgta     60 ggttacggag tacgcagaag tttcattgt                                      89
```

<210> SEQ ID NO 142
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
acgcatgaac aaacttgctt gctacattgg gtggtgtccg gcggggggggg taagtatgta    60 gggattggag tacgcagaag tttcattgt                                       89

<210> SEQ ID NO 143
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
acgcatgaac aaacttgctt gtggacgggc aagggtggg gtccgaaagg gggggcagga     60
tgcgttggag tacgcagaag tttcattgt                                       89

<210> SEQ ID NO 144
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
acgcatgaac aaacttgctt gtagtcccgc tttgcggggg gtttgggtgc aggttgcgga    60
taagtgggag tacgcagaag tttcattgt                                       89

<210> SEQ ID NO 145
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
acgcatgaac aaacttgctt ggatggtagt ggccggaagg ggggtaatat attaagttgg    60
ggattgggag tacgcagaag tttcattgt                                       89

<210> SEQ ID NO 146
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
acgcatgaac aaacttgctt gaggggcatt tacgcggggg ggtgggtgca ggtatcggat    60
gtgaatggag tacgcagaag tttcattgt                                       89

<210> SEQ ID NO 147
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 147 tgtggggtg gacgggccgg gtaga                                          25

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: biotinylated thymine

<400> SEQUENCE: 148
tgtagtcact aatccgttcg agtcatgc                                      28

<210> SEQ ID NO 149
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gtagtcacta atccgttcga gtcatgc                                       27

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: biotinylated thymine

<400> SEQUENCE: 150
tacaatgaaa cttctgcgta ctcc                                          24

<210> SEQ ID NO 151
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ttctgtcaat cgatcgtatc agtccac                                       27

<210> SEQ ID NO 152
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (15)..(16)
```

```
<223> OTHER INFORMATION: Linker between positions consisting of alkylen
      group;-(CH2)12-, not a base, and not a nucleotide

<400> SEQUENCE: 152
tttttttttt tttttaagta gtcactaatc cgttcgagtc atgc                    44

<210> SEQ ID NO 153
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcccgtcttc cagacaagag tgcagggc                                     28

<210> SEQ ID NO 154
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
aagtagtcac taatccgttc gagtcatgc                                    29

<210> SEQ ID NO 155
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 155
atcgagcgtg aggtccgaaa ggcgactctt ntaacatcaa gtaat                  45

<210> SEQ ID NO 156
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 156
atacgcgggg gtgttgaagg gttagtcgga ngtagtgtgt acaga                  45

<210> SEQ ID NO 157
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a or Ds(7-(2-thienyl)imidazo[4,5-b]pyridine)
```

<400> SEQUENCE: 157
aaagtgctgg gtccgnatgg cgggggggtta ggcctctttg gggcg        45

<210> SEQ ID NO 158
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a or Ds(7-(2-thienyl)imidazo[4,5-b]pyridine)

<400> SEQUENCE: 158
aatcgcggtt ccgtgntggc gggtgaaggt tatggtttgg tgtgg        45

<210> SEQ ID NO 159
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a or Ds(7-(2-thienyl)imidazo[4,5-b]pyridine)
<220> FEATURE:
<221> NAME/KEY: modified_base
<222> LOCATION: (32)..(32)
<223> OTHER INFORMATION: a or Ds(7-(2-thienyl)imidazo[4,5-b]pyridine)

<400> SEQUENCE: 159
ggtaaactga gtccgaaggg gcntgcagtg anccgaatg ggtccg        46

<210> SEQ ID NO 160
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a or Ds(7-(2-thienyl)imidazo[4,5-b]pyridine)
<220> FEATURE:
<221> NAME/KEY: modified_base
<222> LOCATION: (32)..(32)
<223> OTHER INFORMATION: a or Ds(7-(2-thienyl)imidazo[4,5-b]pyridine)

<400> SEQUENCE: 160
ggtgaatccg gcagagatca ctntacgctt gntgcctctt taattc        46

<210> SEQ ID NO 161
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a or Ds(7-(2-thienyl)imidazo[4,5-b]pyridine)
<220> FEATURE:
<221> NAME/KEY: modified_base
<222> LOCATION: (32)..(32)

<223> OTHER INFORMATION: a or Ds(7-(2-thienyl)imidazo[4,5-b]pyridine)

<400> SEQUENCE: 161
ggtttaggcg tctttagggg gtngaggtcg gnttttaccg cggtgt                46

<210> SEQ ID NO 162
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)
<220> FEATURE:
<221> NAME/KEY: modified_base
<222> LOCATION: (38)..(38)
<223> OTHER INFORMATION: a or Ds(7-(2-thienyl)imidazo[4,5-b]pyridine)

<400> SEQUENCE: 162
gagatggatg gtagtggccg nacgggggggg ntggagangc tggct                45

<210> SEQ ID NO 163
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (32)..(32)
<223> OTHER INFORMATION: a or Ds(7-(2-thienyl)imidazo[4,5-b]pyridine)

<400> SEQUENCE: 163
cgattcctta tcctaggact tntttccgcg cncacgtgct cagatt                46

<210> SEQ ID NO 164
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (32)..(32)
<223> OTHER INFORMATION: a or Ds(7-(2-thienyl)imidazo[4,5-b]pyridine)

<400> SEQUENCE: 164
cgatttgggg gtggggcggg gnccgtgatg gngatgaagg tgggcg                46

<210> SEQ ID NO 165
<211> LENGTH: 46
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (20)..(20)
<223> OTHER INFORMATION: a or Ds(7-(2-thienyl)imidazo[4,5-b]pyridine)
<220> FEATURE:
<221> NAME/KEY: modified_base
<222> LOCATION: (27)..(27)
<223> OTHER INFORMATION: a or Ds(7-(2-thienyl)imidazo[4,5-b]pyridine)

<400> SEQUENCE: 165
catggagggc cgnatggccn gacactngac cgtgcgagat ggttgg              46

<210> SEQ ID NO 166
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a or Ds(7-(2-thienyl)imidazo[4,5-b]pyridine)
<220> FEATURE:
<221> NAME/KEY: modified_base
<222> LOCATION: (27)..(27)
<223> OTHER INFORMATION: a or Ds(7-(2-thienyl)imidazo[4,5-b]pyridine)
<220> FEATURE:
<221> NAME/KEY: modified_base
<222> LOCATION: (37)..(37)
<223> OTHER INFORMATION: a or Ds(7-(2-thienyl)imidazo[4,5-b]pyridine)

<400> SEQUENCE: 166
ttatgcgggt gggagcaccn tcgacanttg cgtccgnatg gccaga             46

<210> SEQ ID NO 167
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 167
tccttctgtc atngggcagg cgcntttggt gtagngttta tcttg              45

<210> SEQ ID NO 168
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 168
tcgggtcgtt tantaatgta ggtntgggct aggcngctag tggat            45

<210> SEQ ID NO 169
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a or Ds(7-(2-thienyl)imidazo[4,5-b]pyridine)
<220> FEATURE:
<221> NAME/KEY: modified_base
<222> LOCATION: (28)..(28)
<223> OTHER INFORMATION: a or Ds(7-(2-thienyl)imidazo[4,5-b]pyridine)
<220> FEATURE:
<221> NAME/KEY: modified_base
<222> LOCATION: (38)..(38)
<223> OTHER INFORMATION: a or Ds(7-(2-thienyl)imidazo[4,5-b]pyridine)

<400> SEQUENCE: 169
ctatgtgggt tggntggggt gtatgttngt agggctangg aggtg            45

<210> SEQ ID NO 170
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 170
attggactta gcccagcaag acaatctacg ntatgccaga agttg            45

<210> SEQ ID NO 171
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a or Ds(7-(2-thienyl)imidazo[4,5-b]pyridine)

<400> SEQUENCE: 171
aaagttaggg actganccct ttccgtgaag cgtggaggga cgata            45

<210> SEQ ID NO 172
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a or Ds(7-(2-thienyl)imidazo[4,5-b]pyridine)

<400> SEQUENCE: 172
aatgcgaggt acgagnaggg tttggttgg cggggccatt gtagt                45

<210> SEQ ID NO 173
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (29)..(29)
<223> OTHER INFORMATION: a or Ds(7-(2-thienyl)imidazo[4,5-b]pyridine)

<400> SEQUENCE: 173
taatcaggaa gangataggg tttgtcttnt gttgccacgc tggga                45

<210> SEQ ID NO 174
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 174
aggctatcat tcgcgttcng gtttgattgg ttctnggagg ggtgg                45

<210> SEQ ID NO 175
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: a or Ds(7-(2-thienyl)imidazo[4,5-b]pyridine)

<400> SEQUENCE: 175
atcagtccac atcgagcgtg aggtccgaaa ggcgactctt ntaacatcaa gtaatg      56

<210> SEQ ID NO 176
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
atcagtccac atcgagcgtg aggtccgaaa ggcgactctt ataacatcaa gtaatg      56

<210> SEQ ID NO 177
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: a or Ds(7-(2-thienyl)imidazo[4,5-b]pyridine)

<400> SEQUENCE: 177
atcagtccac atacgcgggg gtgttgaagg gttagtcgga ngtagtgtgt acagag      56

<210> SEQ ID NO 178
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
atcagtccac atacgcgggg gtgttgaagg gttagtcgga agtagtgtgt acagag      56

<210> SEQ ID NO 179
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a or Ds(7-(2-thienyl)imidazo[4,5-b]pyridine)

<400> SEQUENCE: 179
atcagtccac aaagtgctgg gtccgnatgg cgggggtta ggcctctttg gggcgg      56

<210> SEQ ID NO 180
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
atcagtccac aaagtgctgg gtccgaatgg cgggggtta ggcctctttg gggcgg      56

<210> SEQ ID NO 181
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a or Ds(7-(2-thienyl)imidazo[4,5-b]pyridine)
<220> FEATURE:
<221> NAME/KEY: modified_base

```
<222> LOCATION: (41)..(41)
<223> OTHER INFORMATION: a or Ds(7-(2-thienyl)imidazo[4,5-b]pyridine)

<400> SEQUENCE: 181
tcagtccacg gtaaactgag tccgaagggg cntgcagtga ncccgaatgg gtccgg          56

<210> SEQ ID NO 182
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tcagtccacg gtaaactgag tccgaagggg catgcagtga acccgaatgg gtccgg          56

<210> SEQ ID NO 183
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)
<220> FEATURE:
<221> NAME/KEY: modified_base
<222> LOCATION: (41)..(41)
<223> OTHER INFORMATION: a or Ds(7-(2-thienyl)imidazo[4,5-b]pyridine)
<220> FEATURE:
<221> NAME/KEY: modified_base
<222> LOCATION: (48)..(48)
<223> OTHER INFORMATION: a or Ds(7-(2-thienyl)imidazo[4,5-b]pyridine)

<400> SEQUENCE: 183
atcagtccac gagatggatg gtagtggccg nacgggnggg ntggagangc tggctg          56

<210> SEQ ID NO 184
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
atcagtccac gagatggatg gtagtggccg aacgggnggg atggagaagc tggctg          56

<210> SEQ ID NO 185
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tctgtcaatc gatcgtatca gtccacaagc ccgtcttcca gacaagagtg cagggc          56

<210> SEQ ID NO 186
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (23)..(23)
<223> OTHER INFORMATION: a or Ds(7-(2-thienyl)imidazo[4,5-b]pyridine)
<220> FEATURE:
<221> NAME/KEY: modified_base
<222> LOCATION: (34)..(34)
<223> OTHER INFORMATION: a or Ds(7-(2-thienyl)imidazo[4,5-b]pyridine)
<220> FEATURE:
<221> NAME/KEY: modified_base
<222> LOCATION: (45)..(45)
<223> OTHER INFORMATION: a or Ds(7-(2-thienyl)imidazo[4,5-b]pyridine)

<400> SEQUENCE: 186
atcagtccac tccttctgtc atngggcagg cgcntttggt gtagngttta tcttgg       56

<210> SEQ ID NO 187
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
atcagtccac tccttctgtc atagggcagg cgcatttggt gtagagttta tcttgg       56

<210> SEQ ID NO 188
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a or Ds(7-(2-thienyl)imidazo[4,5-b]pyridine)
<220> FEATURE:
<221> NAME/KEY: modified_base
<222> LOCATION: (34)..(34)
<223> OTHER INFORMATION: a or Ds(7-(2-thienyl)imidazo[4,5-b]pyridine)
<220> FEATURE:
<221> NAME/KEY: modified_base
<222> LOCATION: (45)..(45)
<223> OTHER INFORMATION: a or Ds(7-(2-thienyl)imidazo[4,5-b]pyridine)

<400> SEQUENCE: 188
atcagtccac tcgggtcgtt tantaatgta ggtntgggct aggcngctag tggatg       56

<210> SEQ ID NO 189
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
atcagtccac tcgggtcgtt taataatgta ggtatgggct aggcagctag tggatg       56

<210> SEQ ID NO 190
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
```

<223> OTHER INFORMATION: a or Ds(7-(2-thienyl)imidazo[4,5-b]pyridine)
<220> FEATURE:
<221> NAME/KEY: modified_base
<222> LOCATION: (38)..(38)
<223> OTHER INFORMATION: a or Ds(7-(2-thienyl)imidazo[4,5-b]pyridine)
<220> FEATURE:
<221> NAME/KEY: modified_base
<222> LOCATION: (48)..(48)
<223> OTHER INFORMATION: a or Ds(7-(2-thienyl)imidazo[4,5-b]pyridine)

<400> SEQUENCE: 190
atcagtccac ctatgtgggt tggntggggt gtatgttngt agggctangg aggtgg    56

<210> SEQ ID NO 191
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
atcagtccac ctatgtgggt tggatggggt gtatgttagt agggctaagg aggtgg    56

<210> SEQ ID NO 192
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: a or Ds(7-(2-thienyl)imidazo[4,5-b]pyridine)

<400> SEQUENCE: 192
atcagtccac attggactta gcccagcaag acaatctacg ntatgccaga agttgg    56

<210> SEQ ID NO 193
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
atcagtccac attggactta gcccagcaag acaatctacg atatgccaga agttgg    56

<210> SEQ ID NO 194
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a or Ds(7-(2-thienyl)imidazo[4,5-b]pyridine)
<220> FEATURE:
<221> NAME/KEY: modified_base
<222> LOCATION: (39)..(39)
<223> OTHER INFORMATION: a or Ds(7-(2-thienyl)imidazo[4,5-b]pyridine)

<400> SEQUENCE: 194
atcagtccac taatcaggaa gangataggg tttgtcttnt gttgccacgc tgggag    56

```
<210> SEQ ID NO 195
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
atcagtccac taatcaggaa gaagataggg tttgtcttat gttgccacgc tgggag        56

<210> SEQ ID NO 196
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ttctgtcaat cgatcgtatc agtccacaat ggggttggtt gtgttgggtg ttgtgt        56

<210> SEQ ID NO 197
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
atcagtccac aatgctagag cattgcgtag aagcttgata tgttgctggc ccggac        56

<210> SEQ ID NO 198
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (33)..(33)
<223> OTHER INFORMATION: a or Ds(7-(2-thienyl)imidazo[4,5-b]pyridine)

<400> SEQUENCE: 198
cggtaaactg cgtccgaagg ggcntgcagt gancccgaat gggtccg              47

<210> SEQ ID NO 199
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cggtaaactg cgtccgaagg ggcatgcagt gaacccgaat gggtccg               47

<210> SEQ ID NO 200
<211> LENGTH: 47
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 200
cgatcgtatc agtccacaag cccgtcttcc agacaagagt gcagggc                47

<210> SEQ ID NO 201
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: a or Ds(7-(2-thienyl)imidazo[4,5-b]pyridine)
<220> FEATURE:
<221> NAME/KEY: modified_base
<222> LOCATION: (34)..(34)
<223> OTHER INFORMATION: a or Ds(7-(2-thienyl)imidazo[4,5-b]pyridine)

<400> SEQUENCE: 201
ccggtaaact gcgtccgaag gggcntgcag tgancccgaa tgggtccgg              49

<210> SEQ ID NO 202
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 202
gtaaactgcg tccgaagggg cntgcagtga ncccgaatgg gtccg                  45

<210> SEQ ID NO 203
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gtaaactgcg tccgaagggg catgcagtga acccgaatgg gtccg                  45

<210> SEQ ID NO 204
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
atcgtatcag tccacaagcc cgtcttccag acaagagtgc agggc                  45

<210> SEQ ID NO 205
<211> LENGTH: 45
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 205
gtaaactgag tccgaagggg cntgcagtga ncccgaatgg gtccg            45

<210> SEQ ID NO 206
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)

<400> SEQUENCE: 206
gtaaactgcg tccgaagggg cntgcagtga acccgaatgg gtccg            45

<210> SEQ ID NO 207
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 207
gtaaactgcg tccgaagggg catgcagtga ncccgaatgg gtccg            45

<210> SEQ ID NO 208
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: a or Ds(7-(2-thienyl)imidazo[4,5-b]pyridine)
<220> FEATURE:
<221> NAME/KEY: modified_base
<222> LOCATION: (36)..(36)
<223> OTHER INFORMATION: a or Ds(7-(2-thienyl)imidazo[4,5-b]pyridine)

<400> SEQUENCE: 208
tttttgtaaa ctgcgtccga aggggcntgc agtgancccg aatgggtccg       50

<210> SEQ ID NO 209
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (18)..(18)
<223> OTHER INFORMATION: a or Ds(7-(2-thienyl)imidazo[4,5-b]pyridine)
<220> FEATURE:
<221> NAME/KEY: modified_base
<222> LOCATION: (27)..(27)
<223> OTHER INFORMATION: a or Ds(7-(2-thienyl)imidazo[4,5-b]pyridine)

<400> SEQUENCE: 209
actgcgtccg aagggcntg cagtganccc gaatgggtcc g                    41

<210> SEQ ID NO 210
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)

<400> SEQUENCE: 210
gtccgaaggg gcntgcagtg ancccgaatg ggtccg                        36

<210> SEQ ID NO 211
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 211
gtaaactgcg tccgaagggg cntgcagtga ncccgaatgg g                  41

<210> SEQ ID NO 212
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 212
gtaaactgcg tccgaagggg cntgcagtga ncccga                        36

<210> SEQ ID NO 213
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
atgctagagc attgcgtaga agcttgatat gttgctggcc cggac                    45

<210> SEQ ID NO 214
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a or Ds(7-(2-thienyl)imidazo[4,5-b]pyridine)
<220> FEATURE:
<221> NAME/KEY: modified_base
<222> LOCATION: (29)..(29)
<223> OTHER INFORMATION: a or Ds(7-(2-thienyl)imidazo[4,5-b]pyridine)
<220> FEATURE:
<221> NAME/KEY: modified_base
<222> LOCATION: (40)..(40)
<223> OTHER INFORMATION: a or Ds(7-(2-thienyl)imidazo[4,5-b]pyridine)

<400> SEQUENCE: 214
tccactcggg tcatttanta atgtaggtnt gggctaggcn gctagtgga               49

<210> SEQ ID NO 215
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 215
tcgggtcatt tantaatgta ggtntgggct aggcngctag tggat                    45

<210> SEQ ID NO 216
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
```

<223> OTHER INFORMATION: a or Ds(7-(2-thienyl)imidazo[4,5-b]pyridine)

<400> SEQUENCE: 216
tcgggtcgtt tantaatgta ggtntgggct aggcngctag tggat         45

<210> SEQ ID NO 217
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a or Ds(7-(2-thienyl)imidazo[4,5-b]pyridine)
<220> FEATURE:
<221> NAME/KEY: modified_base
<222> LOCATION: (34)..(34)
<223> OTHER INFORMATION: a or Ds(7-(2-thienyl)imidazo[4,5-b]pyridine)
<220> FEATURE:
<221> NAME/KEY: modified_base
<222> LOCATION: (45)..(45)
<223> OTHER INFORMATION: a or Ds(7-(2-thienyl)imidazo[4,5-b]pyridine)

<400> SEQUENCE: 217
atcagtccac tcgggtcgtt tantaatgta ggtntgggct aggcngctag tggatg         56

<210> SEQ ID NO 218
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a or Ds(7-(2-thienyl)imidazo[4,5-b]pyridine)
<220> FEATURE:
<221> NAME/KEY: modified_base
<222> LOCATION: (29)..(29)
<223> OTHER INFORMATION: a or Ds(7-(2-thienyl)imidazo[4,5-b]pyridine)
<220> FEATURE:
<221> NAME/KEY: modified_base
<222> LOCATION: (40)..(40)
<223> OTHER INFORMATION: a or Ds(7-(2-thienyl)imidazo[4,5-b]pyridine)

<400> SEQUENCE: 218
tgacctcggg tcatttanta atgtaggtnt gggctaggcn gctaggtca         49

<210> SEQ ID NO 219
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 219
tcgggtcatt taataatgta ggtntgggct aggcngctag tggat         45

<210> SEQ ID NO 220

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)

<400> SEQUENCE: 220
tcgggtcatt tantaatgta ggtntgggct aggcagctag tggat            45

<210> SEQ ID NO 221
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 221
tcgggtcatt tantaatgta ggtatgggct aggcngctag tggat            45

<210> SEQ ID NO 222
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 222
tcgggtcatt taataatgta ggtatgggct aggcngctag tggat            45

<210> SEQ ID NO 223
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tcgggtcatt taataatgta ggtatgggct aggcagctag tggat            45

<210> SEQ ID NO 224
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 224
aatcgatcgt atcagtccac aatggggttg gttgtgttgg gtgttgtgt         49

<210> SEQ ID NO 225
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
cacaatgcta gagcattgcg tagaagcttg atatgttgct ggcccggac         49

<210> SEQ ID NO 226
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ggggttggtt gtgttgggtg ttgtgt                                  26

<210> SEQ ID NO 227
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gggtgtggtg tgtgtgtgtg tgttgt                                  26

<210> SEQ ID NO 228
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ggggttggtt gtgttgggtg ttgtgt                                  26

<210> SEQ ID NO 229
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 229
gtaaactgcg tccgaagggg cntgcagtga ncccgaatgg gtccg             45

<210> SEQ ID NO 230

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 230
gtaaactgag tccgaagggg cnttcagtga ncccgaatgg gtccg            45

<210> SEQ ID NO 231
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 231
gtaaaatgcg tccgaagggg cntgcattga ncccgaatgg gtccg            45

<210> SEQ ID NO 232
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 232
gtaaactgag tccgaagggg cntacagtga ncccgaatgg gtccg            45

<210> SEQ ID NO 233
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 233
```
gtaaactgag tccgaatggg cnttcagtga ncccgaatgg gtccg                                45

<210> SEQ ID NO 234
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 234
gtaaactcag tccgaagggg cntgaagtga ncccgaatgg gtccg                                45

<210> SEQ ID NO 235
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 235
gtaaacttcg tccgaagggg cntgaagtga ncccgaatgg gtccg                                45

<210> SEQ ID NO 236
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 236
gtaaacagag tccgaagggg cntcctgtga ncccgaatgg gtccg                                45

<210> SEQ ID NO 237
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:

```
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 237
gtaagctgag tccgaagggg cnttcagtga ncccgaatgg gtccg          45

<210> SEQ ID NO 238
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 238
gtaaaatgag tccgaagggg cnttcattga ncccgaatgg gtccg          45

<210> SEQ ID NO 239
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 239
gtaaactgag tccgaatggg cntccagtga ncccgaatgg gtccg          45

<210> SEQ ID NO 240
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 240
gtaaacggtg tccgaagggg cntaccgtga ncccgaatgg gtccg          45

<210> SEQ ID NO 241
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 241
gtaaagtgtg tccgaagggg cnttcactga ncccgaatgg gtccg              45

<210> SEQ ID NO 242
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 242
gtaaactacg tccgaatggg cntgtagtga ncccgaatgg gtccg              45

<210> SEQ ID NO 243
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 243
gtaaagtgag tccgaatggg cntcagctga ncccgaatgg gtccg              45

<210> SEQ ID NO 244
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 244
gtaaacatag tccgaagggg cntaatgtga ncccgaatgg gtccg              45

<210> SEQ ID NO 245
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 245
gtaaatgtag tccgaagggg cntacaatga ncccgaatgg gtccg            45

<210> SEQ ID NO 246
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 246
gtaaacggag tccgaagggg cntacagtga ncccgaatgg gtccg            45

<210> SEQ ID NO 247
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 247
gtaagctgag tccgaagggg cntccagtga ncccgaatgg gtccg            45

<210> SEQ ID NO 248
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 248
```
gtaaacggag tccgaagggg cnttcagtga ncccgaatgg gtccg            45

<210> SEQ ID NO 249
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 249
gtaaactgag tccgaagggg cntcctgtga ncccgaatgg gtccg            45

<210> SEQ ID NO 250
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 250
gtaaacagag tccgaagggg cntactgtga ncccgaatgg gtccg            45

<210> SEQ ID NO 251
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 251
gtaaactcag tccgaatggg cntgtagtga ncccgaatgg gtccg            45

<210> SEQ ID NO 252
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 252
gtaaactgag tccgaagggg cntccagtga ncccgaatgg gtccg          45

<210> SEQ ID NO 253
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 253
gtaaactaag tccgaatggg cnttcagtga ncccgaatgg gtccg          45

<210> SEQ ID NO 254
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 254
gtaaactgtg tccgaagggg cntccagtga ncccgaatgg gtccg          45

<210> SEQ ID NO 255
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 255
gtaaactgag tccgaagggg cntcttgtga ncccgaatgg gtccg          45

<210> SEQ ID NO 256
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 256
gtaaactgtg tccgaatggg cnttcagtga ncccgaatgg gtccg          45

<210> SEQ ID NO 257
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 257
gtaaattgag tccgaagggg cnttcaatga ncccgaatgg gtccg          45

<210> SEQ ID NO 258
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 258
gtaaactaag tccgaatggg cntgaagtga ncccgaatgg gtccg          45

<210> SEQ ID NO 259
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 259
gtaaaccgag tccgaatggg cntgcggtga ncccgaatgg gtccg          45

<210> SEQ ID NO 260
<211> LENGTH: 45
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 260
gtaagctgcg tccgaagggg cntgcagtga ncccgaatgg gtccg          45

<210> SEQ ID NO 261
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 261
gtaaagtgag tccgaagggg cntgcactga ncccgaatgg gtccg          45

<210> SEQ ID NO 262
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 262
gtaaacagcg tccgaacggg cntgctgtga ncccgaatgg gtccg          45

<210> SEQ ID NO 263
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 263
gtaagctgcg tccgaatggg cntgcagtga ncccgaatgg gtccg          45
```

```
<210> SEQ ID NO 264
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 264
gtaaacattg tccgaatggg cntattgtga ncccgaatgg gtccg              45

<210> SEQ ID NO 265
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 265
taagacggag tccggagggg cntacgtcga ncccgaatgg gtcgg              45

<210> SEQ ID NO 266
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 266
gtaaaataag tccgaagggg cnttaattga ncccgaatgg gtccg              45

<210> SEQ ID NO 267
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
```

<223> OTHER INFORMATION: a or Ds(7-(2-thienyl)imidazo[4,5-b]pyridine)

<400> SEQUENCE: 267
gtaaactgtg tccgaagggg cnttcagtga ncccgaatgg gtccg    45

<210> SEQ ID NO 268
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 268
gtaaactgag tccgaacggg cntccagtga ncccgaatgg gtccg    45

<210> SEQ ID NO 269
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 269
gtaaactgcg tccgaatggg cntgcagtga ncccgaatgg gtccg    45

<210> SEQ ID NO 270
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)

<400> SEQUENCE: 270
gtaaacggtg tccgaatggg cattccgtga acccgaatgg gtccg    45

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 271
gtaaacggag tccgaagggg cnttccgtga ncccgaatgg gtccg    45

<210> SEQ ID NO 272
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 272
gtaagctaag tccgaatggg cntgcagcga ncccgaatgg gtccg    45

<210> SEQ ID NO 273
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 273
gtaaacagtg tccgaagggg cntactgtga ncccgaatgg gtccg    45

<210> SEQ ID NO 274
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 274
gtaaaaccag tccgaatggg cntgcgttga ncccgaatgg gtccg    45

<210> SEQ ID NO 275
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 275
gtaaactgtg tccgaatggg cntgcagtga ncccgaatgg gtccg          45

<210> SEQ ID NO 276
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 276
gtaaagtgtg tccgaagggg cntacactga ncccggatgg gtccg          45

<210> SEQ ID NO 277
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 277
gtaagctcag tccgaagggg cntgaagcga ncccgaatgg gtccg          45

<210> SEQ ID NO 278
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a or Ds(7-(2-thienyl)imidazo[4,5-b]pyridine)
<220> FEATURE:
<221> NAME/KEY: modified_base
<222> LOCATION: (31)..(31)
<223> OTHER INFORMATION: a or Ds(7-(2-thienyl)imidazo[4,5-b]pyridine)

<400> SEQUENCE: 278
taaaattcac tccgaagggg gntgtattga ncccgaatgg gacgt          45

<210> SEQ ID NO 279
<211> LENGTH: 45
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 279
tcgggtcatt tantaatgta ggtntgggct aggcngctag tggat             45

<210> SEQ ID NO 280
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 280
tcgggtcatt tantaatgta ggtntgggct aggcngttag tggat             45

<210> SEQ ID NO 281
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 281
tcgggtcatt tantaatgta ggtntgggct aggcngctag tggac             45

<210> SEQ ID NO 282
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 282
tcgggtcatt tgntaatgta ggtntgggct aggcngctag tggat              45

<210> SEQ ID NO 283
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 283
tcgggtcatt tantaatgta ggtntgggct aggcngctag gggac              45

<210> SEQ ID NO 284
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 284
tcgggtcgtt tantaacgta ggtntgggct aggcngttag tggat              45

<210> SEQ ID NO 285
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
```

```
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 285
tcgggtcatt tangaatgta ggtntgggct aggcngctag tggat          45

<210> SEQ ID NO 286
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 286
tcgggtcatt tantaatgta ggtntgggct aggcngttag tggac          45

<210> SEQ ID NO 287
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 287
tcgggtcatt tantaatgta ggtntgggct aggcngctag tggaa          45

<210> SEQ ID NO 288
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
```

-continued

```
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 288
tcgggtcatt tantaatgta ggtntgggct aggcngctag gggat          45

<210> SEQ ID NO 289
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 289
tcgggtcctt tantaaggta ggtntgggct aggcngctag tggat          45

<210> SEQ ID NO 290
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 290
tcgggtcatt tantaatgta ggtntgggct aggcngctag tggct          45

<210> SEQ ID NO 291
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)
```

<400> SEQUENCE: 291
tcgggtcatt tangaatgta ggtntgggct aggcngctag tggac                45

<210> SEQ ID NO 292
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 292
tcgggtcatt tgntaatgta ggtntgggct aggcngttag tggat                45

<210> SEQ ID NO 293
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 293
tcgggtcatt tantaatgta ggtntgggct aggcngtcag tggat                45

<210> SEQ ID NO 294
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 294
tcgggtcatt ttntaatgta ggtntgggct aggcngctag tggat                45

<210> SEQ ID NO 295
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 295
tcgggtcatt tantaatgta ggtntgggct aggcngctag tgggt           45

<210> SEQ ID NO 296
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 296
tcgggtcaat tantattgta ggtntgggct aggcngctag tggat           45

<210> SEQ ID NO 297
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 297
tcgggtcatt tgntaatgta ggtntgggct aggcngctag tggac           45

<210> SEQ ID NO 298
<211> LENGTH: 45

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 298
tcgggtcatt gantaatgta ggtntgggct aggcngttag tggat            45

<210> SEQ ID NO 299
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 299
tcgggtcctt tantaaggta ggtntgggct aggcngttag tggat            45

<210> SEQ ID NO 300
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 300
tcgggtcact tantagtgta ggtntgggct aggcngctag tggat            45

<210> SEQ ID NO 301
<211> LENGTH: 45
<212> TYPE: DNA
<213> ORGANISM: Artificial Sequence
<220> FEATURE:
<223> OTHER INFORMATION: Description of Artificial Sequence: Synthetic
```

```
         oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 301
tcgggtcatc tantgatgta ggtntgggct aggcngctag tggat            45

<210> SEQ ID NO 302
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 302
tcgggtcatt tangaatgta ggtntgggct aggcngttag tggat            45

<210> SEQ ID NO 303
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 303
tcgggtcatt aantaatgta ggtntgggct aggcngctag tggat            45

<210> SEQ ID NO 304
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
```

<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 304
tcgggtcgtt tangaacgta ggtntgggct aggcngttag tggat           45

<210> SEQ ID NO 305
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 305
tcgggtcatt tangaatgta ggtntgggct aggcngctag gggac           45

<210> SEQ ID NO 306
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 306
tcgggtcatt gantaatgta ggtntgggct aggcngctag tggat           45

<210> SEQ ID NO 307
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)

```
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 307
tcgggtcatt tgngaatgta ggtntgggct aggcngctag tggat          45

<210> SEQ ID NO 308
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 308
tcgggtcatt tcntaatgta ggtntgggct aggcngctag tggat          45

<210> SEQ ID NO 309
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 309
tcgggtcttt tantaaagta ggtntgggct aggcngctag tggat          45

<210> SEQ ID NO 310
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
```

<223> OTHER INFORMATION: a or Ds(7-(2-thienyl)imidazo[4,5-b]pyridine)

<400> SEQUENCE: 310
tcgggtcatt tcntaatgta ggtntgggct aggcngttag tggat                45

<210> SEQ ID NO 311
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 311
tcgggtcgtt tantaatgta ggtntgggct aggcngttag tggat                45

<210> SEQ ID NO 312
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 312
tcgggtcatt tgntaatgta ggtntgggct aggcngctag gggac                45

<210> SEQ ID NO 313
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 313
tcgggtcgtt tgntaacgta ggtntgggct aggcngttag tggat            45

<210> SEQ ID NO 314
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 314
tcgggtcatt tantaatgta ggtntgggct aggcngctag tggag            45

<210> SEQ ID NO 315
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 315
tcgggtcact tantagtgta ggtntgggct aggcngttag tggat            45

<210> SEQ ID NO 316
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 316
tcgggtcatt tanaaatgta ggtntgggct aggcngctag tggat            45

<210> SEQ ID NO 317

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 317
tcgggtcatt tantaatgta ggtntgggct aggcngttag gggac            45

<210> SEQ ID NO 318
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 318
tcgggtaatt tantaattta ggtntgggct aggcngctag tggat            45

<210> SEQ ID NO 319
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 319
tcgggtcaat tantattgta ggtntgggct aggcngttag tggat            45

<210> SEQ ID NO 320
<211> LENGTH: 45
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 320
tcgggtcatt tantaatgta ggtntggcgt aggcngctag tggat            45

<210> SEQ ID NO 321
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 321
tcgggtcatt gantaatgta ggtntgggct aggcngttag tggac            45

<210> SEQ ID NO 322
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 322
tcgggtcatt tantaatgta ggtntgggct aggcngtatg tggat            45

<210> SEQ ID NO 323
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base -continued

```
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 323
tcgggtcatt tantaatgta ggtntgggct aggcngttag tgggt            45

<210> SEQ ID NO 324
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 324
tcgggtcatt cangaatgta ggtntgggct aggcngctag tggac            45

<210> SEQ ID NO 325
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 325
tcgggtcatt tantaatgta ggtntgggct aggcngttag tggaa            45

<210> SEQ ID NO 326
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
```

```
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 326
tcgggtcatt aantaatgta ggtntgggct aggcngttag tggat              45

<210> SEQ ID NO 327
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 327
tcgggtcatt tantaatgta ggtntgggct aggcngtcag tggac              45

<210> SEQ ID NO 328
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a or Ds(7-(2-thienyl)imidazo[4,5-b]pyridine)
<220> FEATURE:
<221> NAME/KEY: modified_base
<222> LOCATION: (24)..(24)
<223> OTHER INFORMATION: a or Ds(7-(2-thienyl)imidazo[4,5-b]pyridine)
<220> FEATURE:
<221> NAME/KEY: modified_base
<222> LOCATION: (35)..(35)
<223> OTHER INFORMATION: a or Ds(7-(2-thienyl)imidazo[4,5-b]pyridine)

<400> SEQUENCE: 328
tcgggtcatt tgngaatgta ggtntgggct aggcngctag tggac              45

<210> SEQ ID NO 329
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ttgcactctg tgggggtgga cgggccgggt agata                         35

<210> SEQ ID NO 330
<211> LENGTH: 96
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (48)..(48)
<223> OTHER INFORMATION: Ds(7-(2-thienyl)imidazo[4,5-b]pyridine)
<220> FEATURE:
<221> NAME/KEY: modified_base
<222> LOCATION: (57)..(57)
<223> OTHER INFORMATION: Ds(7-(2-thienyl)imidazo[4,5-b]pyridine)

<400> SEQUENCE: 330
ctgtcaatcg atcgtatcag tccacggtaa actgagtccg aaggggcntg cagtganccc      60
gaatgggtcc ggcatgactc gaacggatta gtgact                               96

<210> SEQ ID NO 331
<211> LENGTH: 98
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (47)..(47)
<223> OTHER INFORMATION: Ds(7-(2-thienyl)imidazo[4,5-b]pyridine)
<220> FEATURE:
<221> NAME/KEY: modified_base
<222> LOCATION: (57)..(57)
<223> OTHER INFORMATION: Ds(7-(2-thienyl)imidazo[4,5-b]pyridine)
<220> FEATURE:
<221> NAME/KEY: modified_base
<222> LOCATION: (64)..(64)
<223> OTHER INFORMATION: Ds(7-(2-thienyl)imidazo[4,5-b]pyridine)

<400> SEQUENCE: 331
tctgtcaatc gatcgtatca gtccacgagg aatgtccagc gctgggnttg gagggngtc       60 ggantgggct cgcatgactc gaacggatta gtgactac                             98

<210> SEQ ID NO 332
<211> LENGTH: 98
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (36)..(36)
<223> OTHER INFORMATION: Ds(7-(2-thienyl)imidazo[4,5-b]pyridine)
<220> FEATURE:
<221> NAME/KEY: modified_base
<222> LOCATION: (43)..(43)
<223> OTHER INFORMATION: Ds(7-(2-thienyl)imidazo[4,5-b]pyridine)
<220> FEATURE:
<221> NAME/KEY: modified_base
<222> LOCATION: (53)..(53)
<223> OTHER INFORMATION: Ds(7-(2-thienyl)imidazo[4,5-b]pyridine)

<400> SEQUENCE: 332
tctgtcaatc gatcgtatca gtccacgtct aagtanggtg ggnttggcgg ggntgtcgga     60
tatactttga cgcatgactc gaacggatta gtgactac                             98

<210> SEQ ID NO 333
<211> LENGTH: 99
<212> TYPE: DNA
<213> ORGANISM: Artificial Sequence
<220> FEATURE:
<223> OTHER INFORMATION: Description of Artificial Sequence: Synthetic
```

```
      polynucleotide
<220> FEATURE:
<221> NAME/KEY: modified_base
<222> LOCATION: (49)..(49)
<223> OTHER INFORMATION: Ds(7-(2-thienyl)imidazo[4,5-b]pyridine)
<220> FEATURE:
<221> NAME/KEY: modified_base
<222> LOCATION: (58)..(58)
<223> OTHER INFORMATION: Ds(7-(2-thienyl)imidazo[4,5-b]pyridine)

<400> SEQUENCE: 333
tctgtcaatc gatcgtatca gtccacggta gggtaagtag gtattgccng tcgtagcntg      60
gatggcgtgc cggcatgact cgaacggatt agtgactac                            99

<210> SEQ ID NO 334
<211> LENGTH: 99
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(48)
<223> OTHER INFORMATION: Ds(7-(2-thienyl)imidazo[4,5-b]pyridine)
<220> FEATURE:
<221> NAME/KEY: modified_base
<222> LOCATION: (58)..(58)
<223> OTHER INFORMATION: Ds(7-(2-thienyl)imidazo[4,5-b]pyridine)

<400> SEQUENCE: 334
tctgtcaatc gatcgtatca gtccaccgat tccttatcct aggacttntt tccgcgcnca      60
cgtgctcaga ttgcatgact cgaacggatt agtgactac                            99

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Ds(7-(2-thienyl)imidazo[4,5-b]pyridine)
<220> FEATURE:
<221> NAME/KEY: modified_base
<222> LOCATION: (9)..(9)
<223> OTHER INFORMATION: a, c, g, or t
<220> FEATURE:
<221> NAME/KEY: modified_base
<222> LOCATION: (14)..(14)
<223> OTHER INFORMATION: Ds(7-(2-thienyl)imidazo[4,5-b]pyridine)

<400> SEQUENCE: 335
gggnttggng gggngtcgg                                                  19

<210> SEQ ID NO 336
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Ds(7-(2-thienyl)imidazo[4,5-b]pyridine)
<220> FEATURE:
<221> NAME/KEY: modified_base
<222> LOCATION: (14)..(14)
```

```
<223> OTHER INFORMATION: Ds(7-(2-thienyl)imidazo[4,5-b]pyridine)

<400> SEQUENCE: 336
gggnttggag gggngtcgg                                                    19

<210> SEQ ID NO 337
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(35)
<223> OTHER INFORMATION: Ds(7-(2-thienyl)imidazo[4,5-b]pyridine)
<220> FEATURE:
<221> NAME/KEY: modified_base
<222> LOCATION: (42)..(42)
<223> OTHER INFORMATION: Ds(7-(2-thienyl)imidazo[4,5-b]pyridine)
<220> FEATURE:
<221> NAME/KEY: modified_base
<222> LOCATION: (52)..(52)
<223> OTHER INFORMATION: Ds(7-(2-thienyl)imidazo[4,5-b]pyridine)

<400> SEQUENCE: 337
ctgtcaatcg atcgtatcag tccacgtcta agtanggtgg gnttggcggg gntgtcggat       60
atactttgac gcatgactcg aacggattag tgactac                                97
```